(12) United States Patent
Liao et al.

(10) Patent No.: US 12,215,173 B2
(45) Date of Patent: *Feb. 4, 2025

(54) KAPPA OPIOID RECEPTOR PEPTIDE AMIDE LIGANDS

(71) Applicant: Humanwell Pharmaceutical US, Ballwin, MO (US)

(72) Inventors: Subo Liao, Ballwin, MO (US); Jun Yang, Ballwin, MO (US); Jinliang Lv, Yichang (CN); Zongquan Liao, Yichang (CN); Hao Zhou, Yichang (CN); Jueyuan Gao, Yichang (CN); Tianpeng Xie, Yichang (CN); Quanli Yang, Yichang (CN); Lei Wang, Wuhan (CN); Zejian Ding, Wuhan (CN)

(73) Assignees: Humanwell Pharmaceutical US, Inc., Ballwin, MO (US); Yichang Humanwell Pharmaceuticals Co. Ltd., Yichang (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/988,229

(22) Filed: Aug. 7, 2020

(65) Prior Publication Data

US 2021/0040150 A1 Feb. 11, 2021

Related U.S. Application Data

(60) Provisional application No. 62/883,916, filed on Aug. 7, 2019.

(51) Int. Cl.
  *C07K 5/107* (2006.01)
  *A61K 38/00* (2006.01)

(52) U.S. Cl.
  CPC ............ *C07K 5/1016* (2013.01); *A61K 38/00* (2013.01)

(58) Field of Classification Search
  None
  See application file for complete search history.

(56) References Cited

U.S. PATENT DOCUMENTS

| | | |
|---|---|---|
| 4,406,202 A | 9/1983 | Salje et al. |
| 5,492,894 A | 2/1996 | Bascom et al. |
| 5,965,701 A | 10/1999 | Junien et al. |
| 7,402,564 B1 | 7/2008 | Schteingart et al. |
| 7,713,937 B2 | 5/2010 | Schteingart et al. |
| 7,727,963 B2 | 6/2010 | Schteingart et al. |
| 7,842,662 B2 | 11/2010 | Schteingart et al. |
| 8,217,007 B1 | 7/2012 | Schteingart et al. |
| 8,236,766 B2 | 8/2012 | Schteingart et al. |
| 8,486,894 B2 | 7/2013 | Schteingart et al. |
| 8,507,649 B2 | 8/2013 | Lintner et al. |
| 8,536,131 B2 | 9/2013 | Schteingart et al. |
| 8,906,859 B2 | 12/2014 | Schteingart et al. |
| 8,951,970 B2 | 2/2015 | Schteingart et al. |
| 9,321,810 B2 | 4/2016 | Schteingart et al. |
| 9,334,305 B2 | 5/2016 | Schteingart et al. |
| 9,359,399 B2 | 6/2016 | Schteingart et al. |
| 10,004,749 B2 | 6/2018 | Hsu |
| 10,017,536 B2 | 7/2018 | Schteingart et al. |
| 10,035,767 B2 | 7/2018 | Murayama et al. |
| 10,138,270 B2 | 11/2018 | Schteingart et al. |
| 10,653,700 B2 | 5/2020 | Hsu |
| 10,766,925 B2 | 9/2020 | Vardanyan et al. |
| 2004/0162242 A1 | 8/2004 | Olson et al. |
| 2009/0156508 A1 | 6/2009 | Schteingart et al. |
| 2010/0075910 A1 | 3/2010 | Schteingart et al. |
| 2011/0212882 A1* | 9/2011 | Schteingart ............ A61K 38/07 514/1.4 |
| 2015/0150935 A1 | 6/2015 | Chalmers et al. |
| 2016/0250277 A1 | 9/2016 | Chalmers et al. |
| 2017/0183307 A1 | 6/2017 | Murayama et al. |
| 2017/0231979 A1 | 8/2017 | Steiner et al. |
| 2018/0028594 A1 | 2/2018 | Chalmers et al. |
| 2018/0078605 A1 | 3/2018 | Spencer et al. |
| 2019/0076400 A1* | 3/2019 | Anandan ................ A61P 29/00 |
| 2019/0144499 A1 | 5/2019 | Li et al. |
| 2020/0054594 A1 | 2/2020 | Niu et al. |
| 2020/0085961 A1 | 3/2020 | Wilson et al. |
| 2020/0109166 A1 | 4/2020 | Cai et al. |

FOREIGN PATENT DOCUMENTS

| | | |
|---|---|---|
| CN | 101535336 A | 9/2009 |
| CN | 101627049 A | 1/2010 |
| CN | 107098871 A | 8/2017 |
| CN | 107098876 A | 8/2017 |
| CN | 109280075 A | 1/2019 |
| CN | 109280076 A | 1/2019 |

(Continued)

OTHER PUBLICATIONS

Pommie et al. ('IMGT standardized criteria for statistical analysis of immunoglobulin V-REGION amino acid properties' Journal of Molecular Recognition v17 2004 pp. 17-32) (Year: 2004).*
Roberts et al. ('Kappa agonist CovX-Bodies' Bioorganic & Medicinal Chemistry Letters v22 2012 pp. 4173-4178) (Year: 2012).*
Barber A., et al., "Novel Developments with Selective Non-Peptidic Kappa-Opioid Receptor Agonists," Expert Opinion Investigational Drugs, 1997, vol. 6, No. 10, pp. 1351-1368.
Dehaven-Hudkins D.L., et al., "Peripherally Restricted Opioid Agonists as Novel Analgesic Agents," Current Pharmaceutical Design, 2004, vol. 10, pp. 743-757.
Final Office Action for U.S. Appl. No. 16/911,701 mailed Jan. 20, 2022, 7 Pages.
Fishbane S., et al., "A Phase 3 Trial of Difelikefalin in Hemodialysis Patients with Pruritus," The New England Journal of Medicine, 2020, vol. 382, No. 3, pp. 222-232.
Hesselink J.M.K., "CR845 (Difelikefalin), A Kappa Receptors Agonist in Phase III by CARA Therapeutics: A Case of Spin' in Scientific Writing?," Journal of Pharmacology & Clinical Research, Mar. 10, 2017, vol. 2, No. 3, pp. 001-010.

(Continued)

*Primary Examiner* — Ronald T Niebauer
(74) *Attorney, Agent, or Firm* — POLSINELLI PC

(57) ABSTRACT

The present invention provides kappa opioid receptor peptide agonists, methods for preparing these compounds, compositions comprising these kappa opioid receptor peptide agonists, and methods of using the kappa opioid receptor peptide agonists to treat pain or other conditions.

2 Claims, No Drawings

(56) References Cited

FOREIGN PATENT DOCUMENTS

| | | | |
|---|---|---|---|
| CN | 109422798 A | 3/2019 | |
| CN | 109879934 A | 6/2019 | |
| CN | 109563133 B | 9/2020 | |
| JP | 5807140 B1 | 11/2015 | |
| WO | 9932510 A1 | 7/1999 | |
| WO | 0110890 A2 | 2/2001 | |
| WO | 02060432 A1 | 8/2002 | |
| WO | 03105677 A2 | 12/2003 | |
| WO | 2007120614 A2 | 10/2007 | |
| WO | 2007139826 A2 | 12/2007 | |
| WO | 2007139921 A2 | 12/2007 | |
| WO | 2008057608 A2 | 5/2008 | |
| WO | 2010057961 A1 | 5/2010 | |
| WO | 2012092367 A1 | 7/2012 | |
| WO | 2012118780 A2 | 9/2012 | |
| WO | 2016073443 A2 | 5/2016 | |
| WO | 2016181408 A2 | 11/2016 | |
| WO | 2017151866 A1 | 9/2017 | |
| WO | 2017180535 A1 | 10/2017 | |
| WO | 2017180659 A1 | 10/2017 | |
| WO | 2017201433 A1 | 11/2017 | |
| WO | 2017210668 A1 | 12/2017 | |
| WO | 2017211272 A1 | 12/2017 | |
| WO | 2017216177 A1 | 12/2017 | |
| WO | 2018059331 A1 | 4/2018 | |
| WO | 2018103624 A1 | 6/2018 | |
| WO | 2018188641 A1 | 10/2018 | |
| WO | 2019109934 A1 | 6/2019 | |
| WO | 2019109937 A1 | 6/2019 | |
| WO | 2019134510 A1 | 7/2019 | |
| WO | 2019148047 A1 | 8/2019 | |
| WO | 2019219019 A1 | 11/2019 | |
| WO | 2020034912 A1 | 2/2020 | |

OTHER PUBLICATIONS

Inan S., et al., "Kappa Opioid Agonists Suppress Chloroquine-Induced Scratching in Mice," European Journal of Pharmacology, 2004, vol. 502, pp. 233-237.

International Preliminary Report on Patentability for International Application No. PCT/US2020/045482, mailed Feb. 17, 2022, 9 Pages.

International Search Report and Written Opinion for International Application No. PCT/US2020/039581, mailed Nov. 20, 2020, 12 pages.

International Search Report and Written Opinion for International Application No. PCT/US2020/045482, mailed Nov. 23, 2020, 9 Pages.

Jordan, et al., "Opioids and Their Complicated Receptor Complexes," Neuropsychopharmacology, Oct. 2000, vol. 23, pp. S5-S18, especially p. S6, col. 1, para 3.

Law P-Y., et al., "Molecular Mechanisms and Regulation of Opioid Receptor Signaling," Annual Review of Pharmacology and Toxicology, 2000, vol. 40, pp. 389-430.

Mannekens, et al., "Synthesis of the Diastereomers of Beta-Me-Tyr and Beta-Me-Phe and their Effect on the Biological Properties of the Delta Opioid receptor antagonist TIPP," Letters in Peptide Science, 1995, vol. 2, pp. 190-192.

Negus S.S., et al., "Effects of Peripherally Restricted Kappa Opioid Receptor Agonists on Pain-Related Stimulation and Depression of Behavior in Rats," The Journal of Pharmacology And Experimental Therapeutics, 2012, vol. 340, No. 3, pp. 501-509.

Non-Final Office Action for U.S. Appl. No. 16/911,701 dated Sep. 27, 2021, 16 pages.

PubChem CID: 10877239, Create Date: Oct. 26, 2006 (Oct. 26, 2006), p. 2 Formula.

PubChem CID 11029875, Create Date: Oct. 26, 2006 (Oct. 26, 2006), p. 2, Formula.

Schrier A.J., et al., "New Chemical Entities Entering Phase III Trials in 2015," Chapter 24, Medicinal Chemistry Reviews, 2016, vol. 51, pp. 419-436.

Wadenberg M-L.G., "A Review of the Properties of Spiradoline: A Potent and Selective K-Opioid Receptor Agonist," CNS Drug Reviews, Summer, 2003, vol. 9, No. 2, pp. 187-198.

Walsh S.L., et al., "Enadoline, A Selective Kappa Opioid Agonist: Comparison with Butorphanol and Hydromorphone in Humans," Psychopharmacology, 2001, vol. 157, pp. 151-162.

First Office Action for Chinese Patent Application No. 202080070432.3, mailed Jun. 7, 2023, 27 pages.

Second Office Action for Chinese Patent Application No. 202080070432.3, mailed on Dec. 20, 2023, 21 pages.

Decision on Rejection (Final Rejection) for Chinese Patent Application No. 202080070432.3, mailed on Mar. 26, 2024, 30 pages.

* cited by examiner

KAPPA OPIOID RECEPTOR PEPTIDE AMIDE LIGANDS

CROSS-REFERENCE TO RELATED APPLICATION

This application claims benefit of U.S. Provisional Patent Application No. 62/883,916, which was filed in the U.S. Patent and Trademark Office on Aug. 7, 2019, the entire contents of which are incorporated herein by reference for all purposes.

FIELD OF THE INVENTION

The present disclosure generally relates to kappa opioid receptor peptide agonists, methods for preparing these compounds, compositions comprising these kappa opioid receptor peptide agonists, and methods of use of the kappa opioid receptor peptide agonists.

BACKGROUND OF THE INVENTION

Opioid kappa receptors (KORs) exist in many parts of the body such as the brain, the spinal cord, and on central and peripheral nerve terminals. KORs play important roles in signal transduction to maintain many physiological functions of the body. Like opioid mu receptors (MORs) and delta receptors (DORs), agonist-induced activation of KORs leads to the inhibition of adenylyl cyclase and calcium channel activity and stimulation of the potassium channel activities (Law et al., Annu Rev Pharmacol Toxicol 2000; 40: 389-430; Al-Hasani and Bruchas, Anesthesiology, 2011, 115(6), 1363-1381).

A variety of physiological processes are related to the activation of KORs such as analgesia, anti-pruritic activity (Inan et al., Eur J. Pharmacol 2004; 502, 233-7), diuresis (Barber et al., Exp Opinion Investigational Drugs 1997; 6: 1351-68; DeHaven-Hudkins et al., Curr Pharm Des 2004; 10:743-57), mood modulation (Bailey and Husbands; Neuronal Signaling, 2018, 2, NS20170145), inflammation, and immune system modulation. Thus, there is a great potential for using KOR selective ligands to treat medical disorders such as pain, mood disorders, autoimmune disorders, and/or neurological diseases.

Many KOR selective agonists have been designed as potential analgesics to avoid of side effects associated with traditional opioid analgesics such as respiratory depression, dependence, addiction, and constipation. A few of these agents have been tested in clinical trial but failed due to side effects like diuresis, sedation, and dysphoria, or lack of efficacy. Examples of such KOR ligands include spiradoline mesylate (U62,066E) (Wadenberg, CNS Drug Rev. 2003, 9(2): 187-98), enadoline (Walsh et al., Psychopharmacology 2001, 157, 151-162), and ADL-10-0101 (Eisenach et al., Pain 2003, 101(1-2): 89-95). Nalfurafine was originally developed as a potential analgesic but achieved success as anti-pruritic reagent and attained regulatory approval in Japan.

Highly selective opioid kappa-receptor and potent D-amino acids tetrapeptide agonists were reported by Ferring (U.S. Pat. No. 5,965,701). The lead tetrapeptide compound CR-845 is currently under development by Cara therapeutics in the clinical trials as an analgesic and anti-pruritic agent (Hesselink, J. Pharm & Clinical Res. 2017; 2(3): 555588. DOI: 10.19080/JPCR.2017.02.555588). Encouraged by the progress of CR-845 in clinical trial, several pharmaceutical companies have actively engaged in the discovery of peptide-based KOR selective agonist ligands by modifying the structure of CR-845 with the goal of finding new analgesics and potential anti-pruritus agents without the conventional side effects of morphinan analgesics (see, e.g., CN107098871, WO2017211272A1, WO2018103624A1, WO2017210668A1, WO2018059331A1).

In addition, KOR agonists have also been developed for other indications. For example, such fedotozine and asimadoline have been developed as potential therapeutics for the treatment of irritable bowel syndrome and dyspepsia.

What is needed are additional selective peptide based KOR agonists which exhibit analgesic and anti-pruritus effects without the conventional side effects associated with morphinan analgesics.

SUMMARY OF THE INVENTION

In one aspect, disclosed herein, are kappa opioid receptor peptide agonists of Formula (I) or a salt thereof:

$$A_1\text{-}A_2\text{-}A_3\text{-}A_4\text{-}B \qquad \text{Formula (I)}$$

wherein:

$A_1$ and $A_2$ independently selected from a group consisting of D-phenylalanine, alpha-methyl-D-phenylalanine, 4-$R_1$-D-phenylalanine, D-tetrahydro-isoquinoline-3-carboxylic acid, 2-aminoindane-2-carboxilic acid, (2R)-2-aminotetralin-2-carboxylic acid, (2S)-2-aminotetralin-2-carboxylic acid, D-2-amino-2-benzyl-butanoic acid, D-homophenylalanine, cyclohexylglycine, cyclohexylalanine;

$A_3$ is D-leucine, D-isoleucine, D-norleucine, D-phenylalanine, alpha-methyl-D-leucine, D-homoleucine, D-valine, D-2-amino-3-cyclopropyl-propanoic acid, D-methionine, 2-amino-3,3-dimethyl-butanoic acid, or D-proline;

$A_4$ is D-lysine, alpha-methyl-D-lysine, omega-$R_2$-lysine, D-homolysine, D-arginine, D-norarginine, D-ornithine, D-histamine, D-aminohexanoic acid, or (2R)-2-amino-3-(2-aminopyrimidin-5-yl)propanoic acid;

B is selected from a group consisting of:

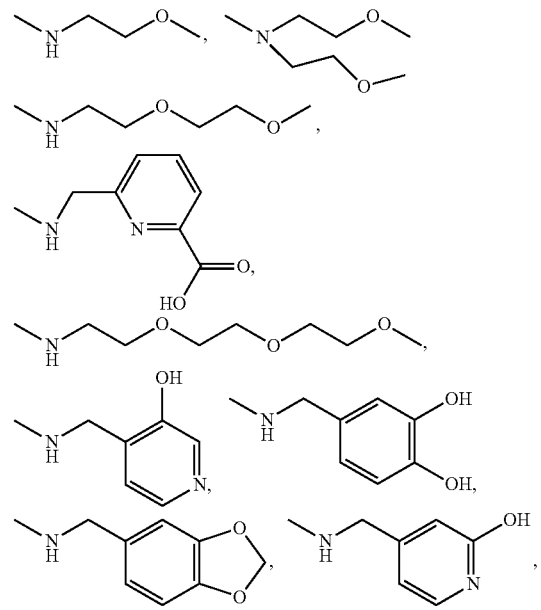

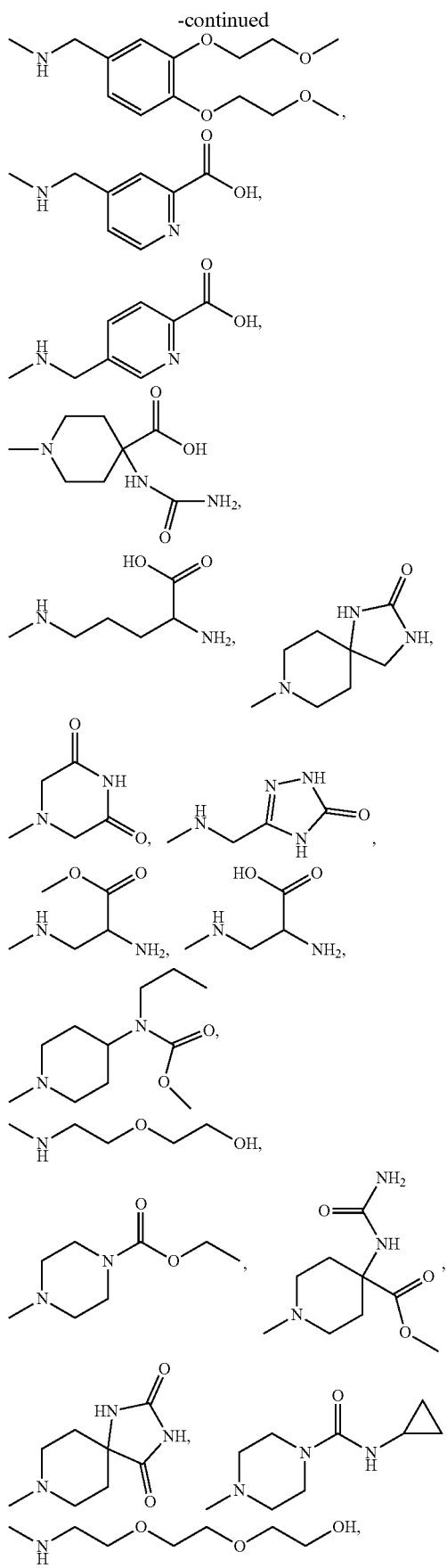
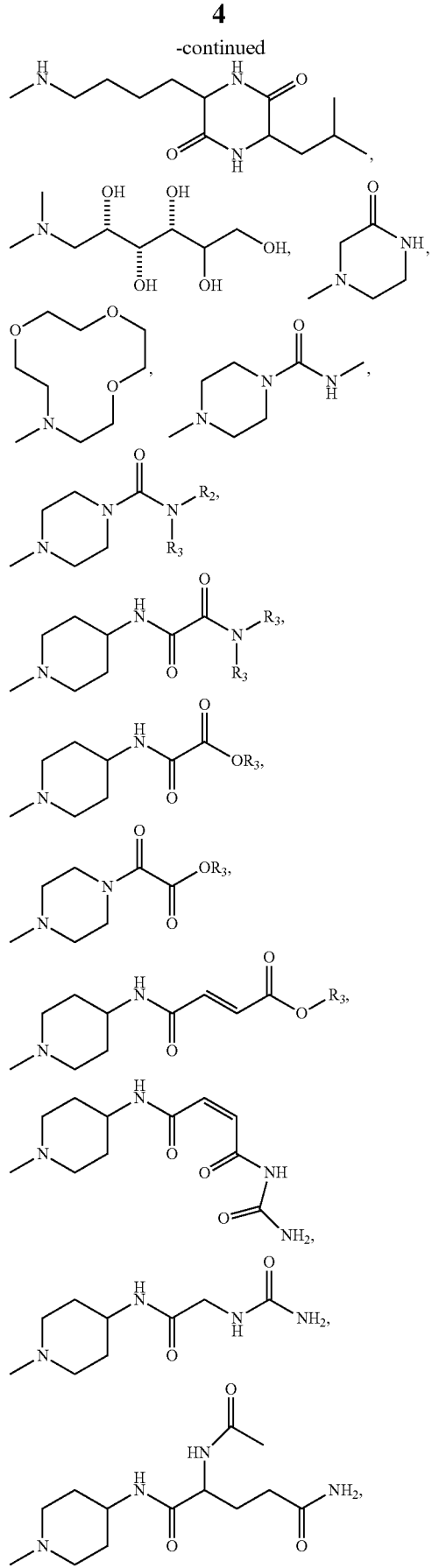

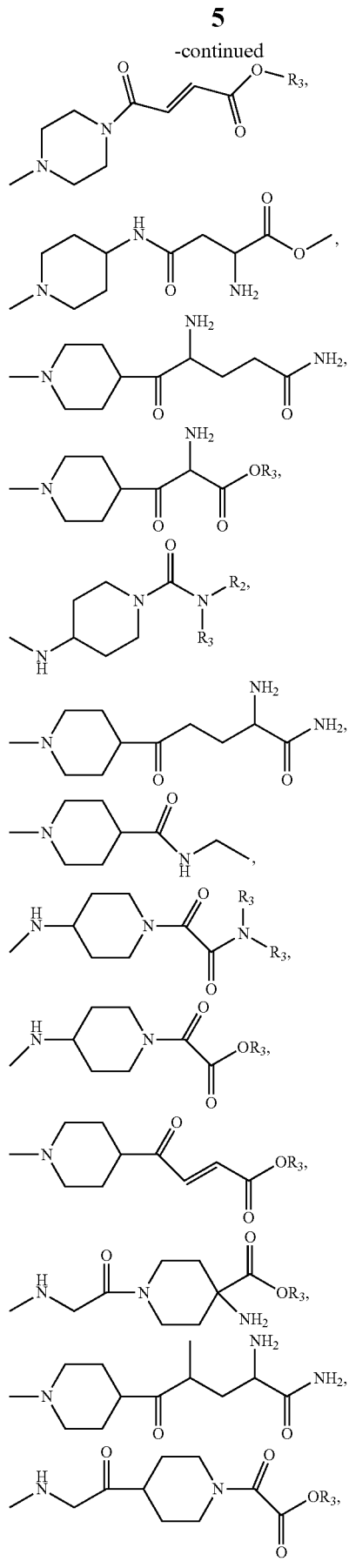

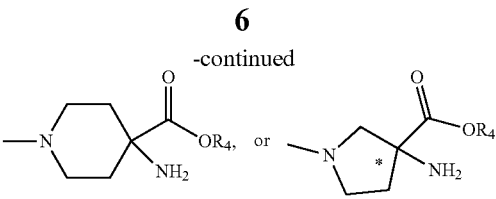

wherein $R_1$ is halo, cyano, C1-C8 unsubstituted alkyl, C1-C8 substituted alkyl, C3-C8 unsubstituted cycloalkyl, C3-C8 substituted cycloalkyl, $CFH_2$, $CF_2H$, $CF_3$, OH, $OCH_3$, $OCF_3$, or $CONH_2$;

$R_2$ is H, C1-C8 unsubstituted alkyl, C1-C8 substituted alkyl, C3-C8 unsubstituted cycloalkyl, C3-C8 substituted cycloalkyl, unsubstituted heterocyclic, substituted heterocyclic, $(OCH_2CH_2O)_{1-6}$—OH), or $(OCH_2CH_2O)_{1-6}$—OMe);

$R_3$ is H, methyl, ethyl, iso-propyl, C3-C8 unsubstituted cycloalkyl, C3-C8 substituted cycloalkyl, unsubstituted heterocyclic, or substituted heterocyclic;

$R_4$ is methyl, ethyl, iso-propyl, C3-C8 unsubstituted cycloalkyl, C3-C8 substituted cycloalkyl, unsubstituted heterocyclic, substituted heterocyclic; $(OCH_2CH_2O)_{1-6}$—OH, or $(OCH_2CH_2O)_{1-6}$—OMe); and * is a (R) stereocenter or a (S) stereocenter.

In another aspect, disclosed herein, are processes to prepare the kappa opioid receptor peptide agonists.

In yet another aspect, disclosed herein are compositions comprising the kappa opioid receptor peptide agonist of Formula (I) and at least one pharmaceutically acceptable excipient.

In still another aspect, disclosed herein are methods for treating a kappa opioid receptor-related disease or disorder, the method comprising administering a pharmaceutically effective amount of the pharmaceutical composition comprising the kappa opioid receptor peptide agonist of Formula (I) to a subject in need thereof Other features and iterations of the invention are described in more detail below.

DETAILED DESCRIPTION OF THE INVENTION

Disclosed herein are kappa opioid receptor peptide agonists, methods for preparing these compounds, compositions comprising these kappa opioid receptor peptide agonists, and methods of using of the kappa opioid receptor peptide agonists to treat pain or other suitable conditions.

These compounds and compositions have been shown to be highly effective therapeutics for treating many conditions, such as pain, pruritis, irritable bowel syndrome, and dyspepsia.

(I) Compounds Comprising Formula (I) or Salt Thereof

One aspect of the present disclosure encompasses A kappa opioid receptor peptide agonist of Formula (I) or a salt thereof:

$$A_1\text{-}A_2\text{-}A_3\text{-}A_4\text{-}B \qquad \text{Formula (I)}$$

wherein:

$A_1$ and $A_2$ independently selected from a group consisting of D-phenylalanine, alpha-methyl-D-phenylalanine, 4-$R_1$-D-phenylalanine, D-tetrahydro-isoquinoline-3-carboxylic acid, 2-aminoindane-2-carboxilic acid, (2R)-2-aminotetralin-2-carboxylic acid, (2S)-2-aminotetralin-2-carboxylic acid, D-2-amino-2-benzyl-butanoic acid, D-homophenylalanine, cyclohexylglycine, or cyclohexylalanine;

A₃ is D-leucine, D-isoleucine, D-norleucine, D-phenylalanine, alpha-methyl-D-leucine, D-homoleucine, D-valine, D-2-amino-3-cyclopropyl-propanoic acid, D-methionine, 2-amino-3,3-dimethyl-butanoic acid, D-2-aminohexanoic acid, or D-proline;

A₄ is D-lysine, alpha-methyl-D-lysine, omega-R₂-lysine, D-homolysine, D-arginine, D-norarginine, D-ornithine, D-histamine, or (2R)-2-amino-3-(2-aminopyrimidin-5-yl)propanoic acid;

B is selected from a group consisting of:

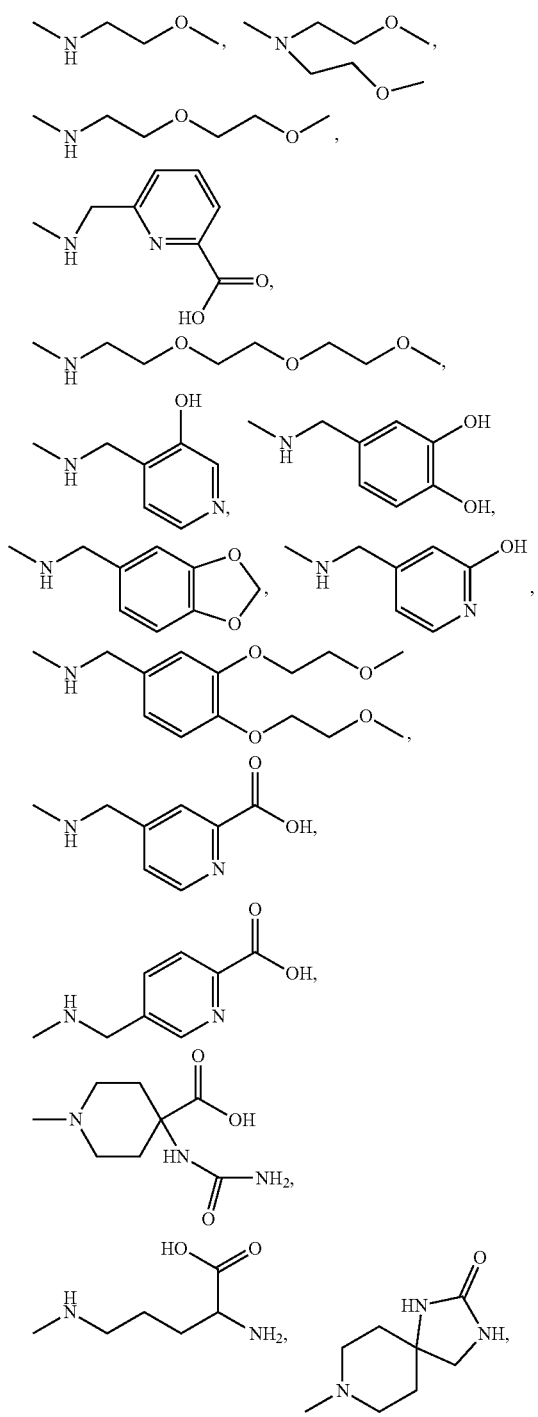
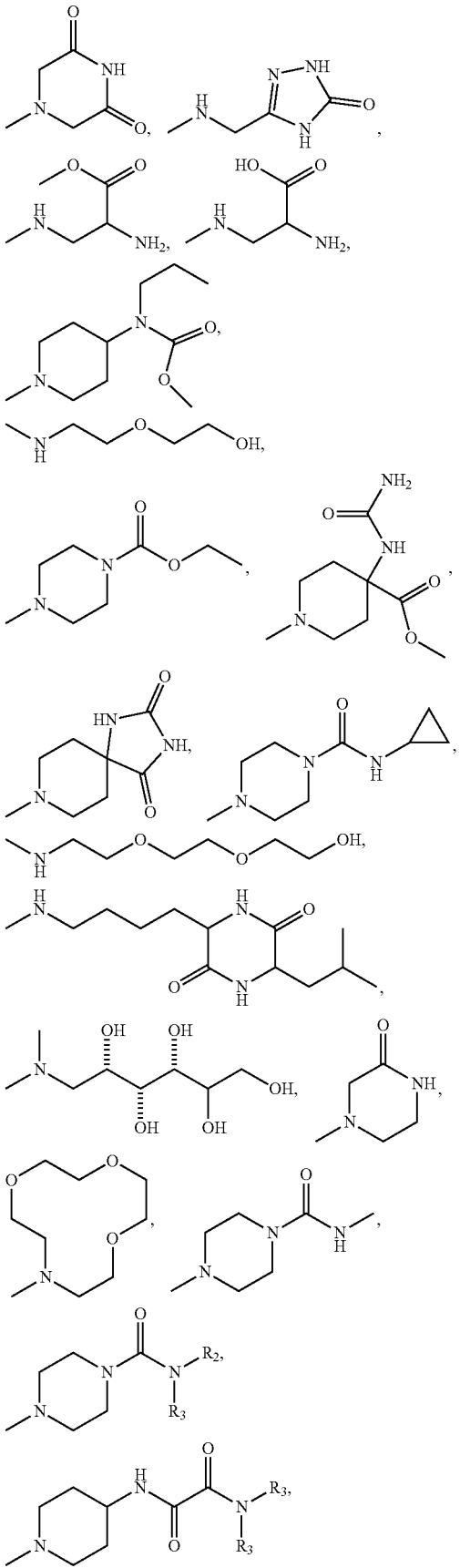

-continued

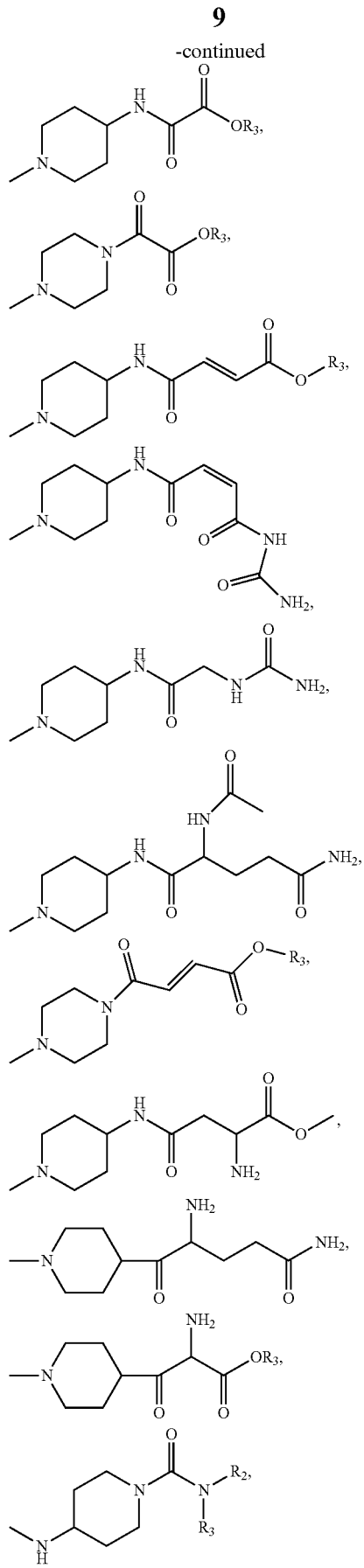

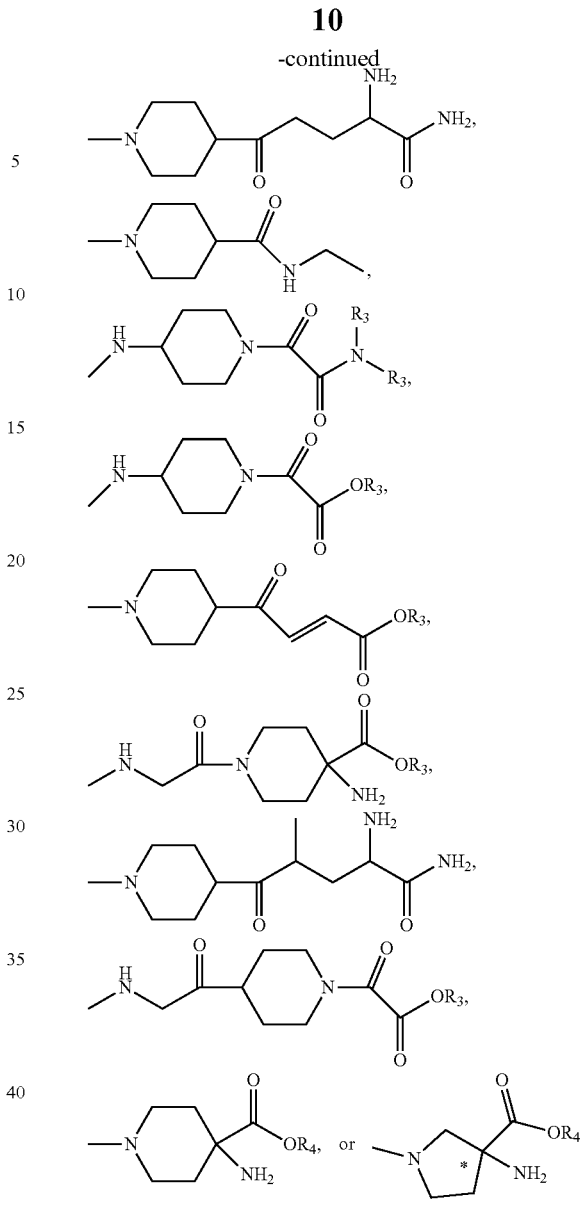

wherein R₁ is halo, cyano, C1-C8 unsubstituted alkyl, C1-C8 substituted alkyl, C3-C8 unsubstituted cycloalkyl, C3-C8 substituted cycloalkyl, $CFH_2$, $CF_2H$, $CF_3$, OH, $OCH_3$, $OCF_3$, or $CONH_2$;

R₂ is H, C1-C8 unsubstituted alkyl, C1-C8 substituted alkyl, C3-C8 unsubstituted cycloalkyl, C3-C8 substituted cycloalkyl, unsubstituted heterocyclic, substituted heterocyclic, $(OCH_2CH_2O)_{1-6}$—OH), or $(OCH_2CH_2O)_{1-6}$—OMe);

R₃ is H, methyl, ethyl, iso-propyl, C3-C8 unsubstituted cycloalkyl, C3-C8 substituted cycloalkyl, unsubstituted heterocyclic, or substituted heterocyclic;

R₄ is methyl, ethyl, iso-propyl, C3-C8 unsubstituted cycloalkyl, C3-C8 substituted cycloalkyl, unsubstituted heterocyclic, substituted heterocyclic; $(OCH_2CH_2O)_{1-6}$—OH, or $(OCH_2CH_2O)_{1-6}$—OMe); and * is a (R) stereocenter or a (S) stereocenter.

Generally, A₁ and A₂ independently may be D-phenylalanine, alpha-methyl-D-phenylalanine, 4-R₁-D-phenylalanine, D-tetrahydro-isoquinoline-3-carboxylic acid, 2-aminoindane-2-carboxylic acid, (2R)-2-aminotetralin-2- carboxylic acid, (2S)-2-aminotetralin-2-carboxylic acid, D-2-amino-2-benzyl-butanoic acid, D-homophenylalanine, cyclohexylglycine, or cyclohexylalanine. In various embodiments, $A_1$ and $A_2$ independently may be D-phenylalanine, alpha-methyl-D-phenylalanine, D-tetrahydro-isoquinoline-3-carboxylic acid, 2-aminoindane-2-carboxylic acid or 4-$R_1$-D-phenylalanine. In other embodiments, $A_1$ and $A_2$ independently may be D-phenylalanine, alpha-methyl-D-phenylalanine, D-tetrahydro-isoquinoline-3-carboxylic acid, 2-aminoindane-2-carboxylic acid, or 4-$R_1$-D-phenylalanine. In specific embodiments, $A_1$ and $A_2$ may be independently selected from a group consisting of 4-F-D-phenylalanine, 4-$CF_3$-D-phenylalanine, D-phenylalanine, D-tetrahydro-isoquinoline-3-carboxylic acid, 2-aminoindane-2-carboxylic acid, or D-tetrahydro-isoquinoline-3-carboxylic acid.

In general, $A_3$ may be is D-leucine, D-isoleucine, D-norleucine, D-phenylalanine, alpha-methyl-D-leucine, D-homoleucine, D-valine, D-2-amino-3-cyclopropyl-propanoic acid, D-methionine, 2-amino-3,3-dimethyl-butanoic acid, 2-aminohexanoic acid, or D-proline. In various embodiments, $A_3$ may be D-leucine, D-isoleucine, D-norleucine, alpha-methyl-D-leucine, D-2-amino-3-cyclopropyl-propanoic acid, D-2-aminohexanoic acid, D-proline, or D-homoleucine. In other embodiments, $A^3$ is D-leucine, D-isoleucine, D-norleucine, alpha-methyl-D-leucine, D-2-amino-3-cyclopropyl-propanoic acid, D-proline, D-2-aminohexanoic acid, 2-amino-3,3-dimethyl-butanoic acid, or D-homoleucine. In specific embodiments, $A_3$ may be D-leucine, D-proline, D-2-aminohexanoic acid, or D-2-amino-3-cyclopropyl-propanoic acid.

Generally, $A_4$ may be D-lysine, alpha-methyl-D-lysine, omega-$R_2$-lysine, D-homolysine, D-arginine, D-norarginine, D-ornithine, D-histamine, or (2R)-2-amino-3-(2-aminopyrimidin-5-yl)propanoic acid. In various embodiments, $A_4$ may, D-lysine, alpha-methyl-D-lysine, omega-$R^2$-lysine, D-homolysine, or (2R)-2-amino-3-(2-aminopyrimidin-5-yl) propanoic acid. In other embodiments, $A_4$ may be D-lysine, alpha-methyl-D-lysine, omega-$R^2$-lysine, D-homolysine, D-arginine, or (2R)-2-amino-3-(2-aminopyrimidin-5-yl) propanoic acid. In specific embodiments, $A_4$ may be D-lysine, D-(2R)-2-amino-3-(2-aminopyrimidin-5-yl) propanoic acid, or D-arginine.

In general, $R_1$ may be halo, cyano, C1-C8 unsubstituted alkyl, C1-C8 substituted alkyl, C3-C8 unsubstituted cycloalkyl, C3-C8 substituted cycloalkyl, $CFH_2$, $CF_2H$, $CF_3$, OH, $OCH_3$, $OCF_3$, or $CONH_2$. In various embodiments, $R_1$ may be halo, cyano, C1-C4 unsubstituted alkyl, C3-C6 unsubstituted cycloalkyl, $CFH_2$, $CF_2H$, $CF_3$, OH, $OCH_3$, $OCF_3$, or $CONH_2$. In specific embodiments, $R_1$ may be F, methyl, ethyl, iso-propyl, cyclopropyl, $CFH_2$, $CF_2H$, $CF_3$, OH, $OCH_3$, $OCF_3$, or $CONH_2$.

Generally, $R_2$ may be H, C1-C8 unsubstituted alkyl, C1-C8 substituted alkyl, C3-C8 unsubstituted cycloalkyl, C3-C8 substituted cycloalkyl, unsubstituted heterocyclic, substituted heterocyclic, $(OCH_2CH_2O)_{1-6}$—OH), or $(OCH_2CH_2O)_{1-6}$—OMe). In various embodiments, $R_2$ may be H, C1-C4 unsubstituted alkyl or C1-C4 substituted alkyl. In specific embodiments, $R_2$ may be H, C1-C4 unsubstituted alkyl, or C1-C4 substituted alkyl.

In general, $R_3$ may be H, methyl, ethyl, iso-propyl, C3-C8 unsubstituted cycloalkyl, C3-C8 substituted cycloalkyl, unsubstituted heterocyclic, or substituted heterocyclic. In various embodiments, $R_3$ may be H, methyl, ethyl, iso-propyl, C3-C8 unsubstituted cycloalkyl, C3-C8 substituted cycloalkyl, unsubstituted heterocyclic, or substituted heterocyclic. In specific embodiments, $R_3$ may be H.

Generally, $R_4$ may be methyl, ethyl, iso-propyl, C3-C8 unsubstituted cycloalkyl, C3-C8 substituted cycloalkyl, unsubstituted heterocyclic, substituted heterocyclic; $(OCH_2CH_2O)_{1-6}$—OH, or $(OCH_2CH_2O)_{1-6}$—OMe). In various embodiments, $R_4$ may be methyl, ethyl, iso-propyl, C3-C8 unsubstituted cycloalkyl, C3-C8 substituted cycloalkyl, unsubstituted heterocyclic, substituted heterocyclic; $(OCH_2CH_2O)_{1-6}$—OH, or $(OCH_2CH_2O)_{1-6}$—OMe). In specific embodiments, $R_4$ may be methyl, ethyl, iso-propyl, C3-C8 unsubstituted cycloalkyl, C3-C8 substituted cycloalkyl, unsubstituted heterocyclic, substituted heterocyclic; $(OCH_2CH_2O)_{1-6}$—OH, or $(OCH_2CH_2O)_{1-6}$—OMe).

In general, * is a (R) stereocenter or a (S) stereocenter.

In exemplary embodiments, $A_1$ may be D-phenylalanine, $A_2$ may be D-phenylalanine, $A_3$ may be D-leucine, and $A_4$ may be D-lysine. In another exemplary embodiment, $A_1$ is D-phenylalanine, $A_2$ is D-phenylalanine, $A_3$ is D-proline, $A_4$ is D-lysine. In yet another exemplary embodiment, $A_1$ is D-phenylalanine $A_2$ is D-phenylalanine, $A_3$ is D-2-aminohexanoic acid, $A_4$ is D-(2R)-2-amino-3-(2-aminopyrimidin-5-yl) propanoic acid. In still another exemplary embodiment, D-phenylalanine, $A_2$ is D-phenylalanine, $A_3$ is D-2-amino-3-cyclopropyl-propanoic acid, and $A_4$ is D-lysine. In yet another exemplary embodiment, $A_1$ is D-phenylalanine, $A_2$ is D-tetrahydro-isoquinoline-3-carboxylic acid, $A_3$ is D-leucine, $A_4$ is D-lysine. In still another exemplary embodiment, $A_1$ is 2-aminoindane-2-carboxylic acid, $A_2$ is D-phenylalanine, $A_3$ is D-leucine, $A_4$ is D-lysine. In another embodiment, $A_1$ is D-tetrahydro-isoquinoline-3-carboxylic acid, $A_2$ is D-phenylalanine, $A_3$ is D-leucine, $A_4$ is D-lysine. In still yet another embodiment, $A_1$ is 4-F-D-phenylalanine, $A_2$ is D-phenylalanine, $A_3$ is D-leucine, $A_4$ is D-lysine. In yet another exemplary embodiment, $A_1$ is 4-$CF_3$-D-phenylalanine, $A_2$ is D-phenylalanine, $A_3$ is D-leucine, $A_4$ is D-lysine.

In various embodiments, B is selected from a group consisting of:

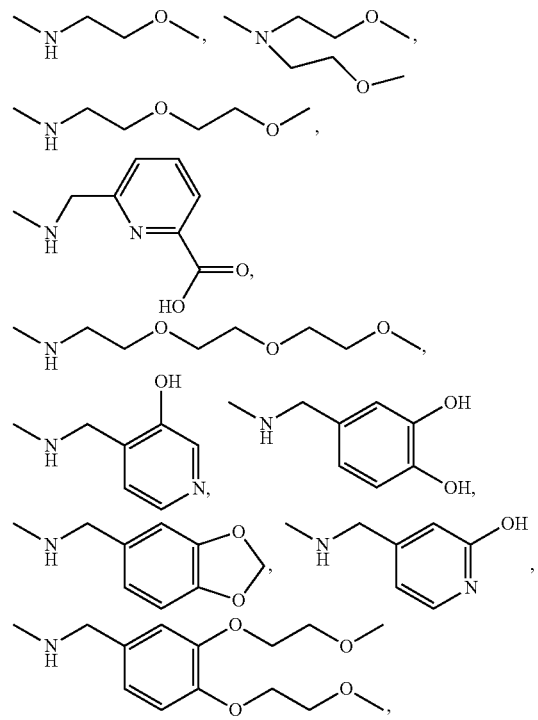

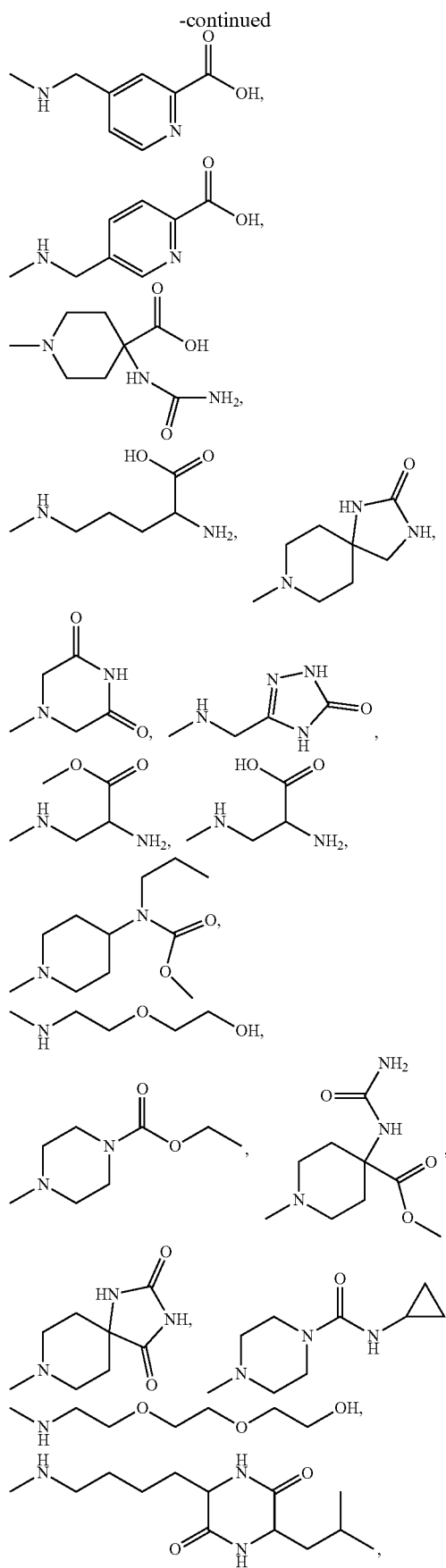
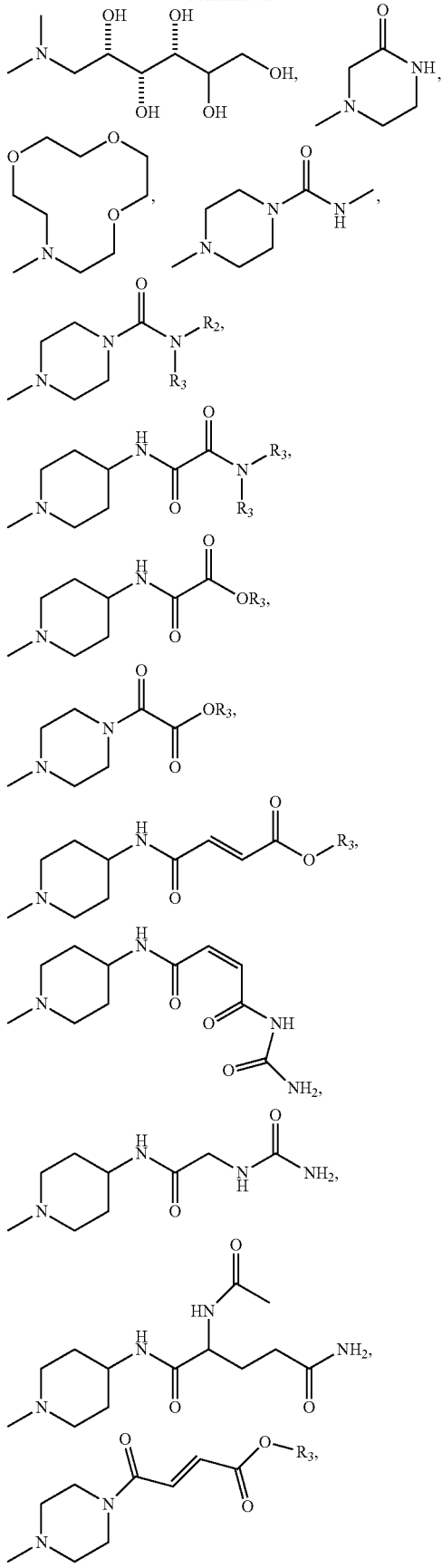

-continued

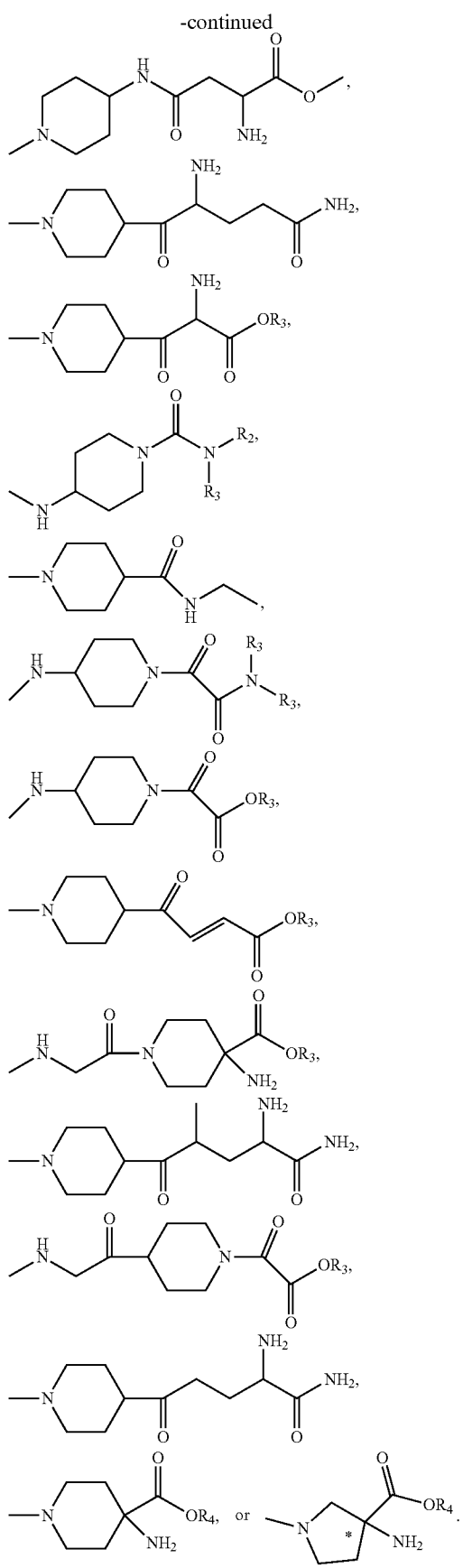

(II) Processes for Preparing Compounds Having Formula (I)

Still another aspect of the present disclosure encompasses process for preparing compounds of Formula (I). The processes comprise preparing the tetrapeptide utilizing known peptide coupling methods. The processes may either be sequential or convergent.

Common to coupling-type chemical synthesis of peptides is the protection of any labile side chain of an amino acid being coupled, and usually the protection also of the N-amino group. Thus, the addition takes place at the carboxyl group of the individual amino acid or dipeptide or tripeptide that is being added. Such protecting groups and methods for deprotecting these groups are well known in the art. Suitable protecting groups and methods for deprotecting these groups can be found in "Protective Groups in Organic Synthesis" by T. W. Greene, John Wiley & Sons, 2006. In specific embodiments, preferred nitrogen protecting groups are tert-butyloxycarbonyl (Boc), and 9-fluorenylmethoxycarbonyl (Fmoc). The preferred carboxylic acid protecting groups are esters, especially the methyl ester.

The final step of preparing the kappa opioid receptor peptide agonist comprises coupling the tetrapeptide with the B group using an acyl coupling reaction, thereby forming an amide. Various methods of conducting this coupling are known in the art. The tetrapeptide may be protected on the amino end before the acyl coupling occurs. Various useful nitrogen protecting groups are described above. Finally, the nitrogen protecting group is removed using standard protocols forming the kappa opioid receptor peptide amide agonist of Formula (I). A pharmaceutically acceptable salt thereof may be prepared from the kappa opioid receptor agonist of Formula (I). List of pharmaceutically acceptable salts are known in the arts.

(III) Compositions Comprising Compounds of Formula (I)

In still another aspect of the present disclosure encompasses compositions comprising the compound of Formula (I). These compositions comprise the kappa opioid receptor peptide of Formula (I) and at least one pharmaceutically acceptable excipient. In various embodiments, the composition is a dosage formulation.

(a). The Kappa Opioid Receptor Peptide of Formula (I).

The kappa opioid receptor peptide agonist of Formula (I) are described in more detail above in Section (I).

(b) At Least One Pharmaceutically Acceptable Excipient.

A composition as disclosed herein further comprises at least one pharmaceutically acceptable excipient. Non-limiting examples of pharmaceutically acceptable excipients are carriers, diluents, binders, fillers, buffering agents, pH modifiers, disintegrants, dispersants, preservatives, lubricants, sweetening agents, taste masking agents, flavoring agents, thickening agents, or combinations thereof. These excipients do not deleteriously react with the kappa opioid receptor peptide agonist of Formula (I).

A carrier may be aqueous, organic, inorganic, or any combination thereof. Non-limiting examples of a carrier are water, polyethylene glycol, propylene glycol, ethanol, corn oil, cottonseed oil, peanut oil, sesame oil, benzyl alcohol, protein carriers, lipids, aqueous sodium chloride, agar, agaropectin, xanthan gum, guar gum, liposomes, niosomes, transferosomes, glycerin, and/or various buffers.

In one aspect, an excipient may be a diluent. A diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated (phosphorylated) corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another aspect, an excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

In another aspect, an excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another aspect, an excipient may be a buffering agent. Representative examples of suitable buffering agents include, but are not limited to phosphates, carbonates, citrates, tris buffers, and buffered saline salts (e.g., Tris buffered saline or phosphate buffered saline).

In various aspects, an excipient may be a pH modifier, to adjust pH of the formulation to a desired level. As will be appreciated, the pH of the liquid dosage formulation can have an impact on the taste and stability of the liquid dosage formulation. Basic liquid formulations do not exhibit improved taste, while acidic liquid formulations do exhibit improved taste. Additionally, in any formulation containing one or more preservatives, pH can have an impact on efficacy of the preservative(s). By way of non-limiting example, the pH modifying agent may be sodium carbonate, sodium bicarbonate, sodium citrate, citric acid, trisodium citrate, or phosphoric acid. In general, the pH of the formulation considering the stability of ANAVEX2-73 may be either basic or acidic. For example, the liquid dosage formulation may be acidic, generally in the range of about pH 3.0 to about 6.5. In various examples, the pH of the oral dosage formulation is about 4.2, about 4.6, or about 6.0. In another aspect, the formulations disclosed herein encompass any formulation containing sodium benzoate as a preservative, optionally in addition to a formulation containing a buffer system such as citrate/citric acid, and the pH is adjusted to about pH 3.0 to about 5.0, or to about 4.2, or about 4.6.

In a further aspect, an excipient may be a disintegrant. The disintegrant may be non-effervescent or effervescent. Suitable examples of non-effervescent disintegrants include, but are not limited to starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

In yet another aspect, an excipient may be a dispersant or dispersing enhancing agent. Suitable dispersants include, but are not limited to starch, alginic acid, polyvinylpyrrolidones, guar gum, kaolin, bentonite, purified wood cellulose, sodium starch glycolate, isoamorphous silicate, and microcrystalline cellulose.

In still another aspect, an excipient may be a preservative. Non-limiting examples of suitable preservatives include antioxidants, such as BHA, BHT, vitamin A, vitamin C, vitamin E, or retinyl palmitate, sodium benzoate, trisodium citrate, citric acid, sodium citrate; chelators such as EDTA or EGTA; and antimicrobials, such as parabens, chlorobutanol, or phenol. The preservative in the liquid dosage formulation is citric acid, sodium citrate, sodium benzoate, or combinations thereof.

In a further aspect, an excipient may be a lubricant. Non-limiting examples of suitable lubricants include minerals such as talc or silica; and fats such as vegetable stearin, magnesium stearate or stearic acid.

In another aspect, an excipient may be a sweetening agent. Non-limiting examples of sweetening agent may sucralose, saccharin, aspartame, mannitol, sorbitol, sucrose, maltose, fructose, lactose, xylitol, or combinations thereof. In one aspect, the sweetening agent is sucralose.

In yet another aspect, an excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; citric acid; and combinations thereof.

In an alternate aspect, an excipient may be a flavoring agent or bitterness masking agent. A flavoring agent may be chosen from synthetic flavor oils and flavoring aromatics and/or natural oils, extracts from plants, leaves, flowers, fruits, maltodextrin, hydroxypropyl, and combinations thereof. In one aspect, a flavoring agent is one that appeals to children, such as a fruit flavor. Non-limiting exemplary flavors are orange, lemon, lime, lemon-lime, lemonade, cherry (including sour cherry and black cherry), passion fruit, strawberry, blueberry, raspberry, mixed berry, and grape.

In another aspect, an excipient may be a thickening agent. Non-limiting examples of these components are xanthan gum, guar gum, poloxamer, pectin, agar, gelatin, salts of alginic acid, carrageenan locust bean gum, and any combination thereof. By way of non-limiting example, a thickening agent is xanthan gum.

In still a further aspect, an excipient may be a coloring agent. Suitable color additives include, but are not limited to, food, drug and cosmetic colors (FD&C), drug and cosmetic colors (D&C), or external drug and cosmetic colors (Ext. D&C).

A dosage formulation comprising a therapeutic amount of the kappa opioid receptor peptide of Formula (I) may be administered to a subject in need thereof by various methods.

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2% or less, or about 1% or less of the total weight of the composition.

The composition may be formulated into various dosage forms and administered by a number of different means that will deliver a therapeutically effective amount of the active ingredient. Such compositions may be administered orally, parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Gennaro, A. R., Remington's Pharmaceutical Sciences, Mack Publishing Co., Easton, Pa. (18th ed, 1995), and Liberman, H. A. and Lachman, L., Eds., Pharmaceutical Dosage Forms, Marcel Dekker Inc., New York, N.Y. (1980). In a specific embodiment, a composition may be a food supplement or a composition may be a cosmetic.

Solid dosage forms for oral administration may include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

For parenteral administration (including subcutaneous, intradermal, intravenous, intramuscular, and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules, and tablets.

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols, or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles, and mouth washes. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition comprising Formula (I) or a pharmaceutically acceptable salt of the compound comprising Formula (I) is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers, and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of a composition comprising Formula (I) or a pharmaceutically acceptable salt of the compound comprising Formula (I) in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, the composition comprising at least one anti-viral therapeutic may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying a composition comprising the compound comprising Formula (I) may be prepared by any known method of preparing liposomes for drug delivery, such as, for example, detailed in U.S. Pat. Nos. 4,241,046, 4,394,448, 4,529,561, 4,755,388, 4,828,837, 4,925,661, 4,954,345, 4,957,735, 5,043,164, 5,064,655, 5,077,211, and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar liposomes.

As would be apparent to one of ordinary skill, all of the parameters that govern liposome formation may be varied. These parameters include, but are not limited to, temperature, pH, concentration of methionine compound, concentration, and composition of lipid, concentration of multivalent cations, rate of mixing, presence of and concentration of solvent.

In another embodiment, a composition of the disclosure may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. A composition comprising at least one anti-viral therapeutic derivative may be encapsulated in a microemulsion by any method generally known in the art.

In yet another embodiment, the composition comprising Formula (I) or a pharmaceutically acceptable salt of the compound comprising Formula (I) may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

(c) Dosage Forms

The composition comprising the compound of Formula (I) can be formulated into various dosage forms and administered by a number of different means that will deliver a therapeutically effective amount of the active ingredient. Such compositions can be administered orally, parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Gennaro, A. R., Remington's Pharmaceutical Sciences, Mack Publishing Co., Easton, Pa. (18th ed, 1995), and Liberman, H. A. and Lachman, L., Eds., Pharmaceutical Dosage Forms, Marcel Dekker Inc., New York, N.Y. (1980).

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

For parenteral administration (including subcutaneous, intradermal, intravenous, intramuscular, and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil.

Non-limiting methods of administration are oral, topical, transmucosal, transdermal, buccal, sublingual, intravenous, and parental.

(IV) Methods of Use

Another aspect of the disclosure provides methods for treating pain, pruritis, irritable bowel syndrome, dyspepsia, and mood disorders. In general, the methods comprise administering to a subject in need thereof a therapeutically effective amount of the kappa opioid receptor peptide agonist of Formula (I). The kappa opioid receptor-related disease or disorder is pain, pruritis, addiction, depression, stress, anxiety, autoimmune disorders, mycocardial infarction, inflammation, edemia, emetic, or neurological diseases, irritable bowel syndrome, or dyspepsia. Persons of skill in the art are familiar with means for determining effective amounts of pharmaceutical compositions.

(a) Composition and Dosage Forms.

Compositions and dosage forms are described in more detail above in Section (III).

Such compositions can be administered orally, parenterally, by inhalation spray, rectally, intradermally, transdermally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques.

For parenteral administration (including subcutaneous, intradermal, intravenous, intramuscular, and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil.

For topical (e.g., transdermal or transmucosal) administration, penetrants appropriate to the barrier to be permeated are generally included in the preparation. Transmucosal administration may be accomplished through the use of nasal sprays, aerosol sprays, tablets, or suppositories, and transdermal administration may be via ointments, salves, gels, patches, or creams as generally known in the art.

The amount of agent that is administered to the subject can and will vary depending upon the type of agent, the subject, and the particular mode of administration. Those skilled in the art will appreciate that dosages may also be determined with guidance from Goodman & Goldman's The Pharmacological Basis of Therapeutics, Tenth Edition (2001), Appendix II, pp. 475-493, and the Physicians' Desk Reference.

(b) Subjects

A suitable subject includes a human, a livestock animal, a companion animal, a lab animal, or a zoological animal. In one embodiment, the subject may be a rodent, e.g., a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a specific embodiment, the animal is a laboratory animal. Non-limiting examples of a laboratory animal may include rodents, canines, felines, and non-human primates. In certain embodiments, the animal is a rodent. Non-limiting examples of rodents may include mice, rats, guinea pigs, etc. In preferred embodiments, the subject is a human.

Routes of administration are described above. Suitable subjects include mammals especially humans.

Definitions

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

Having described the invention in detail, it will be apparent that modifications and variations are possible without departing from the scope of the invention defined in the appended claims.

EXAMPLES

The following examples illustrate various embodiments of the invention.

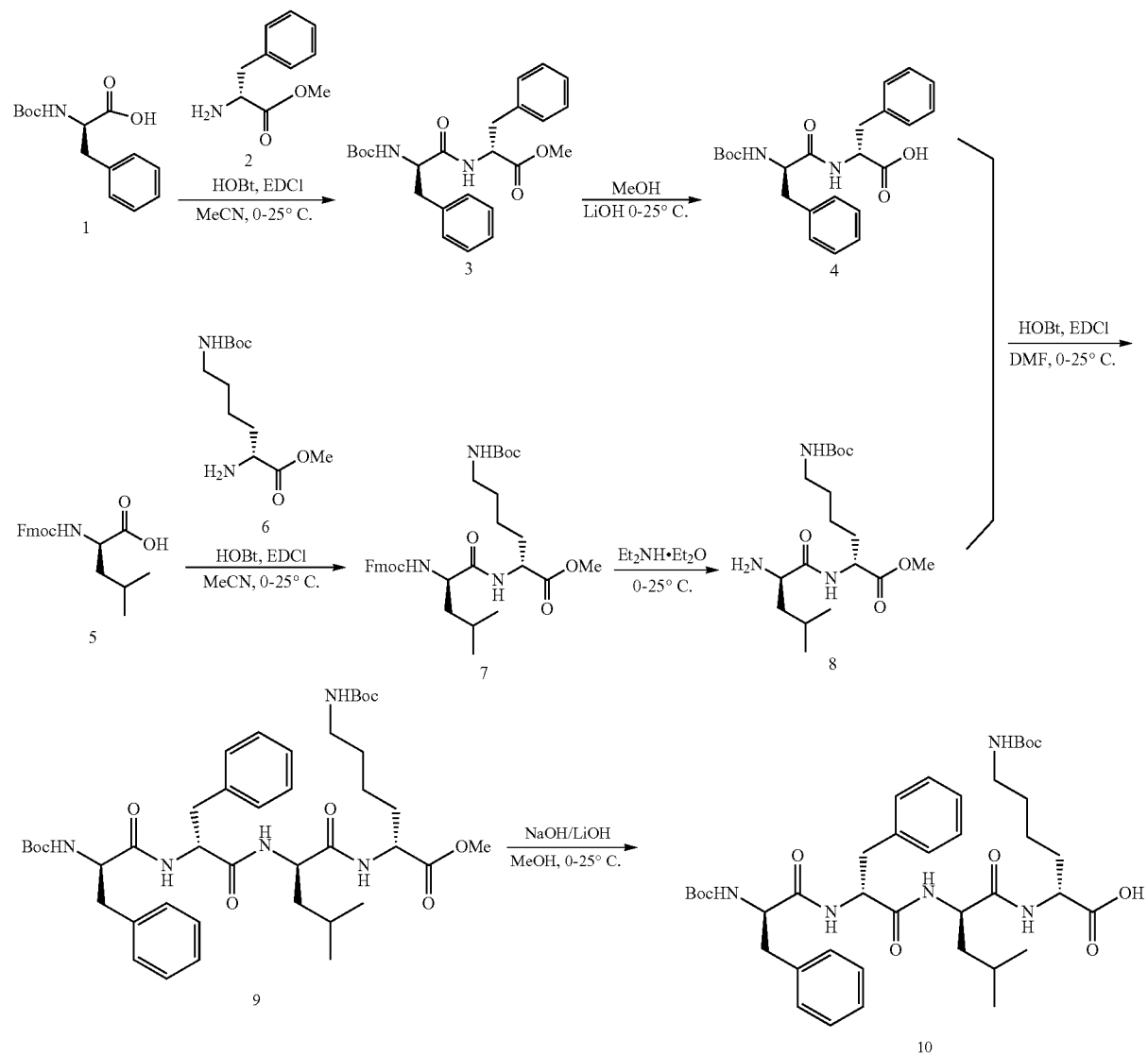

Reaction Scheme 1

Example 1: Synthesis of Compound 3

To the cooled solution of Boc-D-Phe-OH 1 (0.265 g, 1.0 mmol, 1.0 eq) in acetonitrile (8.0 mL) at 0° C. was added HOBt·H$_2$O (0.182 g, 1.1 mmol, 1.1 eq) and EDCI (0.259 g, 1.1 mmol, 1.1 eq). The reaction was stirred at 0° C. for 30 min, then to the resulting solution was added H-D-Phe- OMe·HCl 2 (0.358 g, 1.1 mmol, 1.1 eq) was added dropwise N-methylmorpholine (0.261 g, 2.1 mmol, 2.1 eq). After the addition was completed, the resulting mixture was stirred at room temperature 25° C. for 6 hours. At that time, the reaction was deemed complete as monitored by TLC and HPLC. Then, water (16.0 mL) was added to the reaction under slowing stirring. A white product formed and stood at room temperature until the crystallization was complete. The white solid was collected by filtration, washed with water (16.0 mL), and the filtering cake was dried in vacuum overnight. The crude material was further purified on silica gel column eluting with a gradient from 100:1 DCM/MeOH to 20:1 DCM/MeOH. After evaporating the desired fractions, the product 1 was isolated a white solid, 0.402 g, yield=94.4%, purity>95% (HPLC), $^1$H NMR (400 MHz, CDCl$_3$) δ 7.42-7.10 (m, 8H), 7.10-6.92 (m, 2H), 6.31 (d, J=7.5 Hz, 1H), 4.97 (d, J=8.0 Hz, 1H), 4.78 (q, J=6.4 Hz, 1H), 4.48-4.11 (m, 1H), 3.67 (s, 3H), 3.25-2.86 (m, 4H), 1.40 (s, 9H). $^{13}$C NMR (100 MHz, CDCl$_3$) δ 171.5, 170.9, 155.4, 136.6, 135.7, 129.5, 129.3, 128.8, 128.7, 127.2, 127.1, 80.3, 77.5, 77.2, 76.8, 53.4, 52.4, 38.4, 38.1, 28.3. LC-MS: [M+H]$^+$=472.2.

Example 2: Synthesis of Compound 4

To the solution of dipeptide intermediate 3 (0.426 g, 1.0 mmol, 1.0 eq) in 5 mL of methanol was added water (10 mL). The resulting solution was cooled in a 0° C. bath, then LiOH·H$_2$O (0.419 g, 1.0 mmol, 1.0 eq) was added in one portion. The resulting mixture was warmed to room temperature (25° C.) and was stirred at room temperature for 4 hours. The reaction was complete as indicated by TLC and HPLC. To the reaction mixture was added 2N HCl dropwise until the pH reached 3-4 where a white solid formed. Then the temperature was cooled to 0° C. for further crystallization. After one hour, the solid was collected by filtration and washed with water and then dried in vacuum overnight. The crude product was further purified on silica gel column eluting with a gradient from 100:1 DCM/MeOH to 20:1 DCM/MeOH. The product 4 (0.40 g) was obtained as a white solid with a yield of 96.4% and a purity>95% (HPLC). LC-MS: [M+H]$^+$=413.2.

Example 3: Synthesis of Compound 7

To the cooled solution of Fmoc-D-Leu-OH 5 (0.353 g, 1.0 mmol, 1.0 eq) in acetonitrile (10.5 mL) maintained at 0° C. was added HOBt·H$_2$O (0.148 g, 1.1 mmol, 1.1 eq) and EDCI (0.211 g, 1.1 mmol, 1.1 eq). The reaction was stirred at 0° C. for 30 minutes; then to the reaction was added H-D-Lys (Boc)-OMe·HCl 6 (0.326 g, 1.1 mmol, 1.1 eq) followed by adding dropwise N-methylmorpholine (0.212 g, 2.1 mmol, 2.1 eq). Then, the reaction was warmed to room temperature and stirred at room temperature until HPLC analysis indicated the reaction was done. To the reaction was added water (21.0 mL) with slowing stirring. Solids formed and the mixture was stirred for an additional 30 minutes and then stood for one hour. The solid was collected by filtration and washed with water (21.0 mL). The solids were then dried in vacuum at 30° C. overnight. The crude material was purified on silica gel column eluting with a gradient from 100:1 DCM/MeOH to 20:1 DCM/MeOH. The product was obtained as a white solid, 0.548 g, 91.9% yield; LC-MS: [M+H]$^+$=596.3.

Example 4: Synthesis of Compound 8

To the cooled flask containing dipeptide intermediate 7 (0.060 g, 0.1 mmol, 1.0 eq) in 0° C. ice bath was added diethylamine (0.36 mL). The resulting mixture was stirred in ice bath for 5 minute, then at 20-25° C. until HPLC indicated the reaction was completed. The reaction solution was concentrated on rotavapor in 30-35° C. bath to remove volatiles, and then to the oil residue was added diethyl ether (0.36 mL) under vigorous stirring where white solids formed. The solid was collected by filtration and washed with diethyl ether (0.18 mL) maintained at 0° C. The product was further dried in vacuum and used for next reaction without further purification. Yield=53.4%, purity>95% by HPLC.

Example 5: Synthesis of Compound 9

To the cooled solution of dipeptide intermediate 4 (0.412 g, 1.0 mmol, 1.0 eq) in DMF (8.0 mL) at 0° C. was added HOBt·H$_2$O (0.148 g, 1.1 mmol, 1.1 eq) and EDCI (0.211 g, 1.1 mmol, 1.1 eq). The resulting solution was stirred at 0° C. for 30 minutes, then the dipeptide intermediate 8 (0.373 g, 1.1 mmol, 1.1 eq) was added followed by a dropwise addition of N-methylmorpholine (0.111 g, 1.1 mmol, 1.1 eq). The resulting mixture was warmed to room temperature and stirred at 25° C. until the reaction was deemed complete by HPLC analysis. Then, water (25.0 mL) was added to the reaction mixture to the reaction and a white solid formed. The resulting mixture stood for one hour. Then, the solid was collected by vacuum filtration, washed with water (25.0 mL), and then dried in vacuum at 30° C. overnight. The crude material was further purified on silica gel column eluting with a gradient from 100:1 DCM/MeOH to 20:1 DCM/MeOH. The purified product was obtained as a white solid, 0.695 g, 90.6% yield, purity>95% on HPLC. $^{13}$C NMR (100 MHz, DMSO) δ 173.16, 171.77, 171.52, 155.49, 138.55, 137.89, 129.81, 129.59, 128.46, 126.75, 126.60, 78.57, 56.35, 53.72, 52.34, 50.72, 40.64, 40.43, 40.22, 40.01, 39.80, 39.59, 39.39, 38.23, 37.96, 28.56, 28.20, 24.64, 23.23, 21.74. LC-MS: [M+H]$^+$=768.5.

Example 6: Synthesis of Compound 10

To the solution of tetrapeptide intermediate 9 (0.768 g, 0.1 mmol, 1.0 eq) in 30 mL methanol was added water (15 mL). The resulting solution was cooled to 0° C., where a white solid formed. To the cooled mixture was added LiOH·H$_2$O (0.419 g, 1.0 mmol, 1.0 eq). The resulting mixture was warmed to room temperature (25° C.) and stirred at 25° C. for four hours. HPLC analysis indicated the reaction was completed. The reaction pH was adjusted with 2N HCl to pH 3-4. The mixture stood for one hour; the solid was collected by filtration, and washed with water. The crude product was further purified on silica gel column eluting with a gradient from 100:1 DCM/MeOH to 20:1 DCM/MeOH. The purified product was obtained as white solid, 0.718 g, 95% yield. LC-MS: [M+H]$^+$=754.4.

II. Linear Synthesis of Compound 9

The linear synthesis of the tetrapeptide intermediate 9 is prepared according to the reaction scheme below:

Reaction Scheme 2

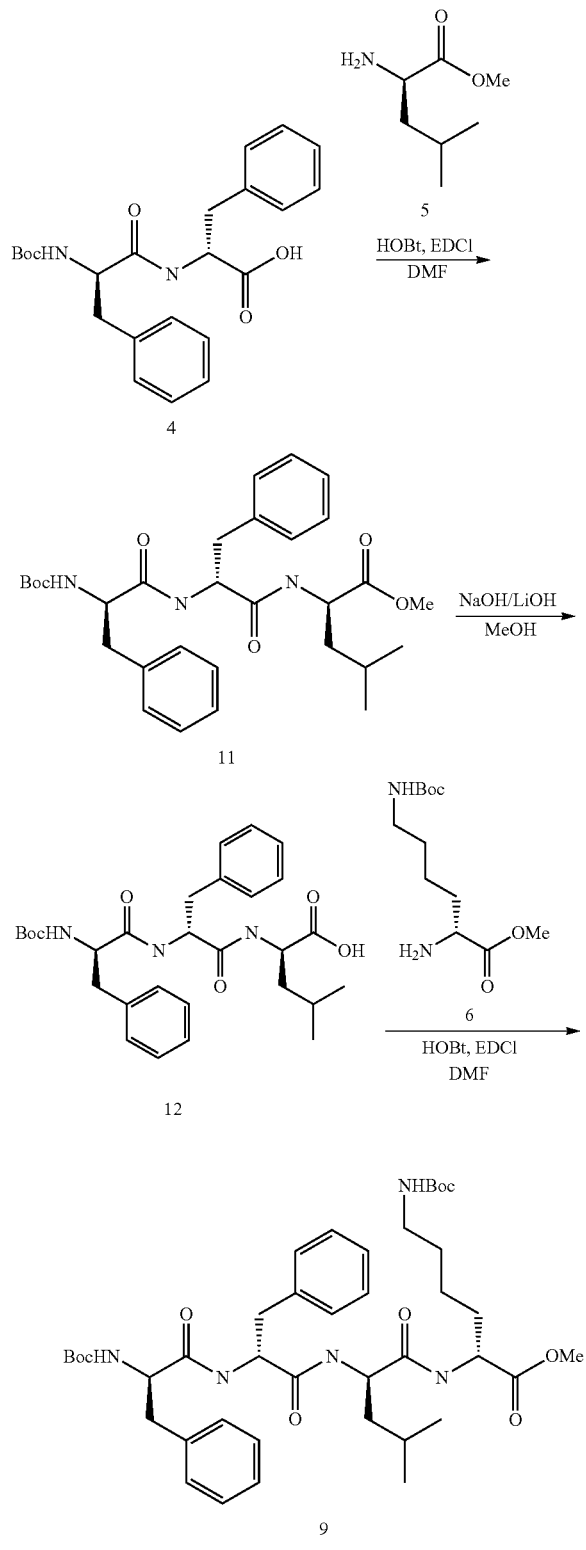

Example 7: Synthesis of Compound 11

To the cooled solution of dipeptide intermediate 4 (0.412 g, 1.0 mmol, 1.0 eq) in DMF (8.25 mL) at 0° C. was added HOBt·H$_2$O (0.148 g, 1.1 mmol, 1.1 eq) and EDCI (0.211 g, 1.1 mmol, 1.1 eq). The resulting mixture was stirred at 0° C. for 30 minutes, then to the reaction was added H-D-Leu-OMe·HCl 5 (1.1 mmol, 1.1 eq), followed by dropwise addition of N-methylmorpholine (0.261 g, 2.1 mmol, 2.1 eq). The reaction was then stirred at room temperature (25° C.) until HPLC analysis indicated the reaction was completed. To the reaction was dropwise added water (25.0 mL); then the reaction was standing for one hour. The white solid was collected by vacuum filtration, washed with water (25.0 mL), and then dried in vacuum overnight. The crude material was purified on silica gel column eluting with a gradient from 100:1 DCM/MeOH to 20:1 DCM/MeOH. The purified product was obtained as white solid, 0.514 g, 95.2%. LC-MS: [M+H]$^+$=540.3.

Example 8: Synthesis of Compound 12

To the solution of tripeptide intermediate 11 (0.539 g, 1.0 mmol, 1.0 eq) in 30 mL methanol was added 15 mL water. The resulting mixture was cooled to 0° C.; to the cooled mixture was added LiOH·H$_2$O (0.539 g, 1.0 mmol, 1.0 eq). Then, the resulting mixture was warmed to room temperature and stirred at room temperature for four hours. After HPLC analysis indicated the reaction was completed, the pH of reaction was adjusted to 3-4 with 2M HCl where a white solid was precipitated. The mixture stood for one hour before the white was collected by filtration. The collected white solid was dried in vacuum at 37° C. overnight. The crude product was purified on silica gel column eluting with a gradient from 100:1 DCM/MeOH to 20:1 DCM/MeOH. The purified product was obtained as white solid, 0.506 g, yield=96.3%. LC-MS: [M+H]$^+$=526.3.

Example 9: Synthesis of Compound 9

To the cooled solution of tripeptide intermediate 12 (0.526 g, 1.0 mmol, 1.0 eq) in DMF (10.5 mL) at 0° C. was added HOBt·H$_2$O (0.148 g, 1.1 mmol, 1.1 eq) and EDCI (0.211 g, 1.1 mmol, 1.1 eq). The resulting mixture was stirred at 0° C. for 30 minutes, then to the reaction was added H-D-Lys(Boc)-OMe·HCl 6 (0.326 g, 1.1 mmol, 1.1 eq), followed by dropwise addition of N-methylmorpholine (0.212 g, 2.1 mmol, 2.1 eq). The resulting mixture was stirred at room temperature (25° C.) until HPLC analysis indicated the reaction was completed. To the reaction was added dropwise water (31.5 mL) where a white solid precipitated. The reaction stood for one hour without stirring, then the white solid was collected by filtration, washed with water (31.5 mL), and then dried in vacuum at 30° C. overnight. The crude material was purified on silica gel column eluting with a gradient from 100:1 DCM/MeOH to 20:1 DCM/MeOH. LC-MS: [M+H]$^+$=768.5.

III. Demonstrated Below are the Preparations for the Peptide Mimics for Medical Products: Compound 13 Series

Example 10: Synthesis of Compound 13-1

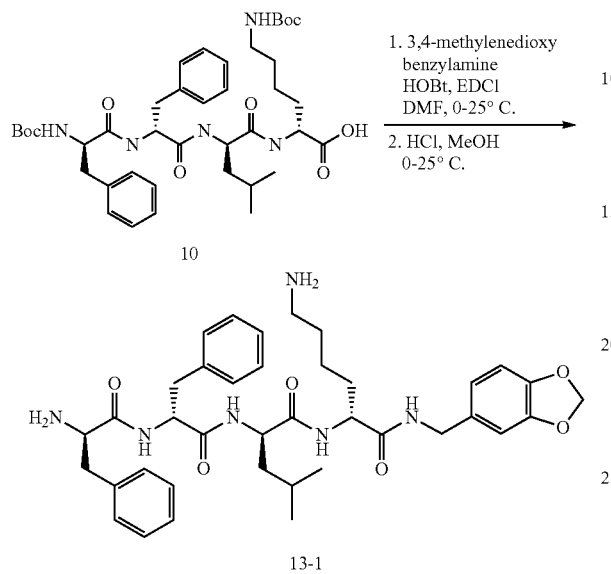

To the cooled solution of tetrapeptide intermediate 10 (0.200 g, 0.26 mmol, 1.0 eq) in DMF (4.0 mL) at 0° C. was added HOBt·H$_2$O (0.043 g, 0.32 mmol, 1.1 eq) and EDCI (0.032 g, 0.32 mmol, 1.1 eq). The resulting mixture was stirred at 0° C. for 30 minutes, then to the reaction was added 3,4-methylenedioxybenzylamine (0.048 g, 0.32 mmol, 1.2 eq), followed by dropwise addition of N-methyl morpholine (0.032 g, 0.32 mmol, 1.2 eq). The resulting mixture was stirred at room temperature (25° C.) until HPLC analysis indicated the reaction was done. To the reaction was added water (12.0 mL) dropwise where a white solid precipitated. The mixture stood for one hour, then the white solid was collected by filtration, washed with water (12 mL), and dried in vacuum at 30° C. overnight. The crude product was further purified on silica gel column eluting with a gradient from 100:1 DCM/MeOH to 20:1 DCM/MeOH. The ester of product 13A was obtained as white solid, 0.222 g, yield=94.3%. LC-MS: [M+H]$^+$=887.5.

The white solid obtained above was dissolved in 10 mL methanol; the resulting solution was cooled to 0° C.; to the cooled solution was added approximately one equivalent of a HCl methanol solution while the solution was stirred. The reaction was deemed complete as monitored by HPLC. The solvent was then removed in vacuum; the residue was purified on Prep LC eluting with 0.02% TFA aqueous solution/acetonitrile mixture from 95% to 20% as mobile phase. The collected fractions were evaporated to remove organic solvent on rotavapor and the remained aqueous solution was lyophilized as white solid, 52.7 mg, yield=30.6% in two steps. $^1$H NMR (400 MHz, D$_2$O) δ 7.44-7.25 (m, 6H), 7.25-7.12 (m, 4H), 6.83 (d, J=7.9 Hz, 1H), 6.80-6.74 (m, 2H), 5.90 (dd, J=5.5, 1.0 Hz, 2H), 4.60 (t, J=7.5 Hz, 1H), 4.31 (d, J=14.9 Hz, 1H), 4.27-4.18 (m, 3H), 4.14 (t, J=7.3 Hz, 1H), 3.15 (d, J=7.0 Hz, 2H), 2.95 (td, J=7.4, 4.1 Hz, 4H), 1.87-1.57 (m, 4H), 1.52-1.26 (m, 6H), 0.85 (dd, J=18.5, 5.7 Hz, 6H). $^{13}$C NMR (100 MHz, D$_2$O) δ 173.37, 173.24, 171.54, 168.58, 147.32, 146.37, 135.95, 133.56, 131.78, 129.38, 129.18, 128.75, 128.07, 127.23, 121.08, 108.55, 108.09, 101.12, 54.71, 54.08, 52.08, 42.78, 40.14, 39.19, 37.28, 36.85, 30.20, 26.40, 24.26, 22.24, 21.87, 21.38. LC-MS: [M+H]$^+$=687.4.

Example 11: Synthesis of Compound 13-2

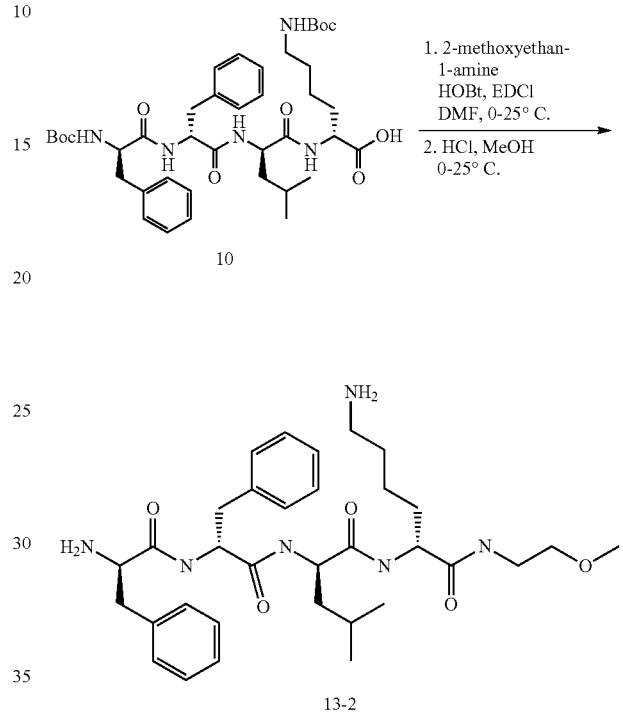

To the cooled solution of tetrapeptide intermediate 10 (0.200 g, 0.26 mmol, 1.0 eq) in DMF (4.0 mL) at 0° C. was added (HOBt·H$_2$O, 0.043 g, 0.32 mmol, 1.1 eq) and EDCI (0.032 g, 0.32 mmol, 1.1 eq). The resulting mixture was stirred at 0° C. for 30 minutes, then to the reaction was added 2-methoxyethan-1-amine (0.024 g, 0.32 mmol, 1.2 eq), followed by dropwise addition of N-methyl morpholine (0.032 g, 0.32 mmol, 1.2 eq). The resulting mixture was stirred at room temperature (25° C.) until HPLC analysis indicated the reaction was done. To the reaction was added dropwise water (12.0 mL) where a white solid precipitated. The mixture stood for one hour, then the white solid was collected by filtration, washed with water (12.0 mL), and dried in vacuum at 30° C. overnight. The crude product was further purified on silica gel column eluting with a gradient from 100:1 DCM/MeOH to 20:1 DCM/MeOH. The white solid obtained above from column chromatography was dissolved in 10 mL methanol; the resulting solution was cooled to 0° C.; to the cooled solution was added one equivalent of a HCl methanol solution under stirring; the reaction was monitored with HPLC until it completed. The solvent was then removed in vacuum; the residue was purified on Prep LC with 0.02% TFA aqueous solution/acetonitrile mixture from 95% to 20% as mobile phase. The collected fractions were evaporated to remove organic solvent on rotavapor and the remained aqueous solution was lyophilized as white solid. 34.2 mg, yield=22.6%. LC-MS: [M+H]$^+$=611.4.

Example 12: Synthesis of Compound 13-3

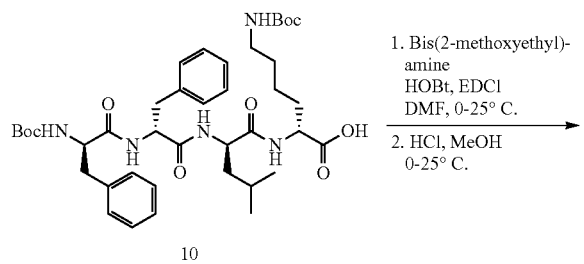

Example 13: Synthesis of Compound 13-4

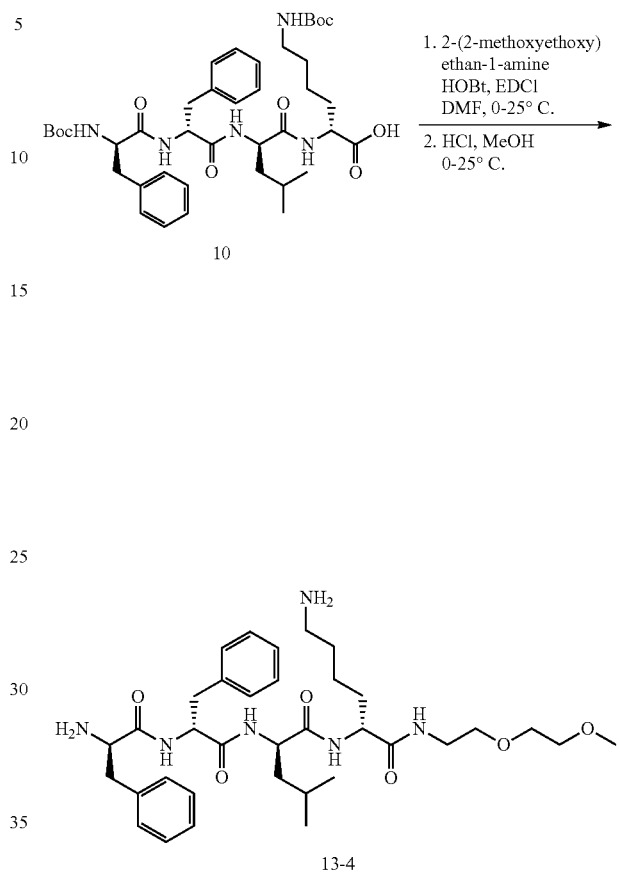

To the cooled solution of tetrapeptide intermediate 10 (0.200 g, 0.26 mmol, 1.0 eq) in DMF (4.0 mL) at 0° C. was added HOBt·H$_2$O (0.043 g, 0.32 mmol, 1.1 eq) and EDCI (0.032 g, 0.32 mmol, 1.1 eq). The resulting mixture was stirred at 0° C. for 30 minutes, then to the reaction was added bis(2-methoxyethyl)amine (0.042 g, 0.32 mmol, 1.2 eq), followed by dropwise addition of N-methyl morpholine (0.032 g, 0.32 mmol, 1.2 eq). The resulting mixture was stirred at room temperature (25° C.) for approximately 6 hours until HPLC analysis indicated the reaction was complete. To the reaction was added dropwise water (12.0 mL) where a white solid precipitated. The mixture stood for one hour, then the white solid was collected by filtration, washed with water (12.0 mL), and dried in vacuum at 30° C. overnight. The crude product was further purified on silica gel column eluting with a gradient from 100:1 DCM/MeOH to 20:1 DCM/MeOH. The white solid obtained above from column chromatography was dissolved in 10 mL methanol; the resulting solution was cooled to 0° C.; to the cooled solution was added approximately one equivalent of a HCl methanol solution under stirring; the reaction was monitored with HPLC until it completed. The solvent was then removed in vacuum; the residue was purified on Prep LC with 0.02% TFA aqueous solution/acetonitrile mixture from 95% to 20% as mobile phase. The collected fractions were evaporated to remove organic solvent on rotavapor and the remained aqueous solution was lyophilized as white solid. 35.3 mg, yield=23.1%. LC-MS: [M+H]$^+$=669.5.

To the cooled solution of tetrapeptide intermediate 10 (0.200 g, 0.26 mmol, 1.0 eq) in DMF (4.0 mL) at 0° C. was added HOBt·H$_2$O (0.043 g, 0.32 mmol, 1.1 eq) and EDCI (0.032 g, 0.32 mmol, 1.1 eq). The resulting mixture was stirred at 0° C. for 30 minutes, then to the reaction was added 2-(2-methoxyethoxy)ethan-1-amine (0.035 g, 0.32 mmol, 1.2 eq), followed by dropwise addition of N-methyl morpholine (0.032 g, 0.32 mmol, 1.2 eq). The resulting mixture was stirred at room temperature (25° C.) until HPLC analysis indicated the reaction was done. To the reaction was added water (12.0 mL) dropwise where a white solid precipitated. The mixture stood for one hour, then the white solid was collected by filtration, washed with water (12.0 mL), dried in vacuum at 30° C. overnight. The crude product was further purified on silica gel column eluting with a gradient from 100:1 DCM/MeOH to 20:1 DCM/MeOH. The white solid obtained above from column chromatography was dissolved in 10 mL methanol; the resulting solution was cooled to 0° C.; to the cooled solution was added approximately one equivalent of a HCl methanol solution under stirring; the reaction was monitored with HPLC until it completed. The solvent was then removed in vacuum; the residue was purified on Prep LC with 0.02% TFA aqueous solution/acetonitrile mixture from 95% to 20% as mobile phase. The collected fractions were evaporated to remove organic solvent on rotavapor and the remained aqueous solution was lyophilized as white solid. 37.0 mg, yield=22.8%. LC-MS: [M+H]$^+$=655.4.

Example 14: Synthesis of Compound 13-5

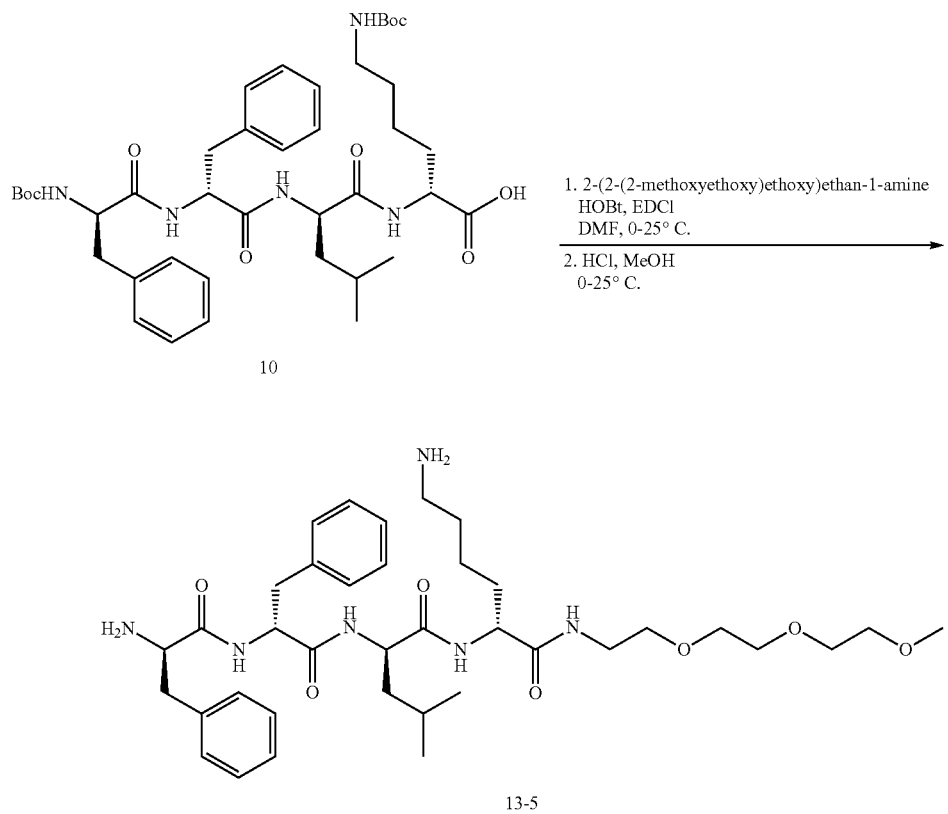

To the cooled solution of tetrapeptide intermediate 10 (0.200 g, 0.26 mmol, 1.0 eq) in DMF (4.0 mL) at 0° C. was added HOBt·H$_2$O (0.043 g, 0.32 mmol, 1.1 eq) and EDCI (0.032 g, 0.32 mmol, 1.1 eq). The resulting mixture was stirred at 0° C. for 30 minutes, then to the reaction was added 2-(2-(2-methoxyethoxy)ethoxy)ethan-1-amine (0.048 g, 0.32 mmol, 1.2 eq), followed by dropwise addition of N-methyl morpholine (0.032 g, 0.32 mmol, 1.2 eq). The resulting mixture was stirred at room temperature (25° C.) until HPLC analysis indicated the reaction was complete. To the reaction was added water (12.0 mL) dropwise where a white solid precipitated. The mixture stood for one hour, then the white solid was collected by filtration, washed with water (12.0 mL), and dried in vacuum at 30° C. overnight. The crude product was further purified on silica gel column eluting with a gradient from 100:1 DCM/MeOH to 20:1 DCM/MeOH. The white solid obtained from column chromatography separation was dissolved in 10 mL methanol; the resulting solution was cooled to 0° C.; to the cooled solution was added HCl methanol solution under stirring. The reaction was monitored with HPLC until completion. The solvent was then removed in vacuum; the residue was purified on Prep LC with 0.02% TFA aqueous solution/acetonitrile mixture from 95% to 20% as mobile phase. The collected fractions were evaporated to remove organic solvent on rotavapor and the remained aqueous solution was lyophilized as white solid. 35.4 mg, yield=20.3%. LC-MS: [M+H]$^+$=699.5.

Example 15: Synthesis of Compound 13-6

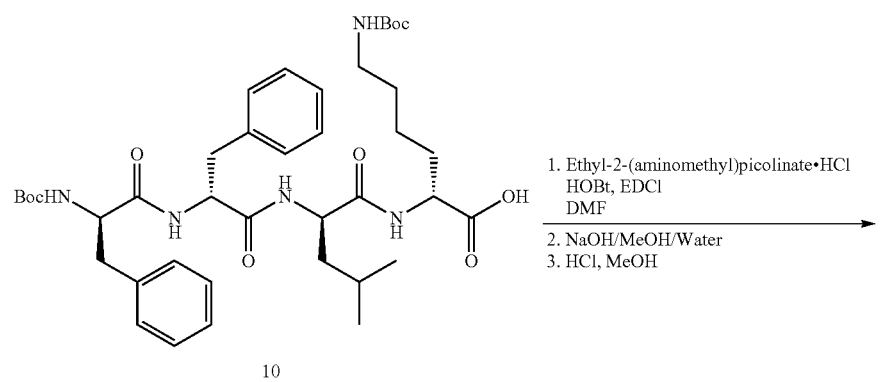

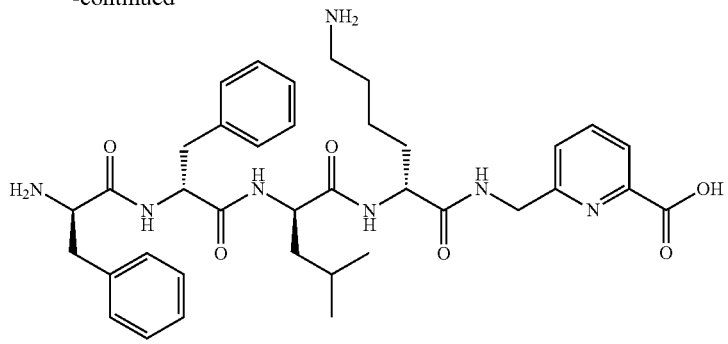

13-6

To the cooled solution of tetrapeptide intermediate 10 (0.200 g, 0.26 mmol, 1.0 eq) in DMF (4.0 mL) at 0° C. was added HOBt·H$_2$O (0.043 g, 0.32 mmol, 1.1 eq) and EDCI (0.032 g, 0.32 mmol, 1.1 eq). The resulting mixture was stirred at 0° C. for 30 minutes, then to the reaction was added ethyl 2-(aminomethyl)picolinate·HCl (0.069 g, 0.32 mmol, 1.2 eq), followed by dropwise addition of N-methyl morpholine (0.086 g, 0.85 mmol, 3.2 eq). The resulting mixture was stirred at room temperature (25° C.) until HPLC analysis indicated the reaction was done. To the reaction was added water (12.0 mL) dropwise where a white solid precipitated. The mixture stood for one hour, and then the white solid was collected by filtration, washed with water (12.0 mL), and dried in vacuum at 30° C. overnight. The crude product was further purified on silica gel eluting with a gradient from 100:1 DCM/MeOH to 20:1 DCM/MeOH. The ester of product 13F was obtained as white solid, 0.231 g, yield=95.1%. LC-MS: [M+H]$^+$=916.5.

The white solid obtained from chromatography separation was dissolved in 30 mL methanol, followed by adding 15 mL water; the resulting solution was cooled to 0° C.; to the cooled reaction added LiOH·H$_2$O (0.964 g, 2.3 mmol, 10.0 eq). The reaction was warmed to room temperature and stirred at room temperature for four hours; HPLC analysis indicated the reaction was completed. The pH of reaction was then adjusted to 3-4 with 2N HCl. Plenty of white solid precipitated; the mixture was standing for one hour; the solid was collected by filtration and washed with water and dried in vacuum overnight. Then, the dried white solid was dissolved in 30 mL of methanol. The resulting solution was cooled to 0° C.; to the cooled solution was added HCl methanol solution under stirring. The reaction was monitored with HPLC until the reaction was completed. The volatiles were removed under vacuum. The residue was purified on Prep LC with 0.02% TFA aqueous solution/acetonitrile mixture from 95% to 20% as mobile phase. The collected fractions were concentrated on rotavapor and then lyophilized as white solid, 60.3 mg, yield=34.8% in two steps. LC-MS: [M+H]$^+$=688.4.

Example 16: Synthesis of Compound 13-7

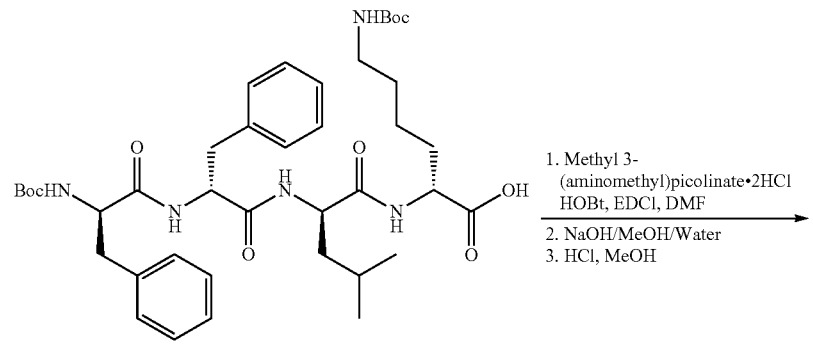

10

1. Methyl 3-(aminomethyl)picolinate·2HCl
HOBt, EDCl, DMF
2. NaOH/MeOH/Water
3. HCl, MeOH

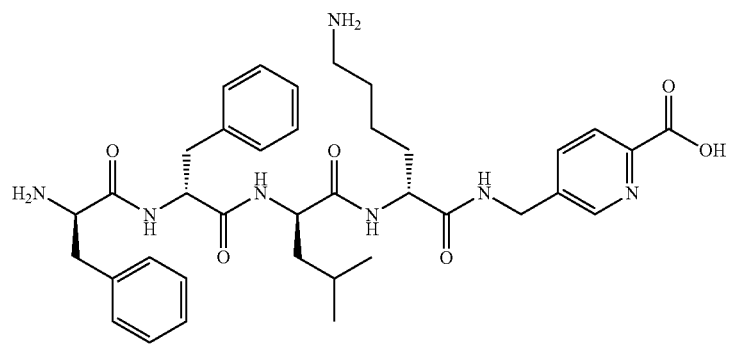

13-7

To the cooled solution of tetrapeptide intermediate 10 (0.200 g, 0.26 mmol, 1.0 eq) in DMF (4.0 mL) at 0° C. was added HOBt·H₂O (0.043 g, 0.32 mmol, 1.1 eq) and EDCI (0.032 g, 0.32 mmol, 1.1 eq). The resulting mixture was stirred at 0° C. for 30 minutes, then to the reaction was added methyl 3-(aminomethyl)picolinate. 2HCl (0.076 g, 0.32 mmol, 1.2 eq) followed by dropwise addition of N-methyl morpholine (0.086 g, 0.85 mmol, 3.2 eq). The resulting mixture was stirred at room temperature (25° C.) until HPLC analysis indicated the reaction was complete. To the reaction was added water (12.0 mL) dropwise where a white solid precipitated. The mixture was standing for one hour, then the white solid was collected by filtration, washed with water (12.0 mL), dried in vacuum at 30° C. overnight. The crude product was further purified on silica gel column eluting with a gradient from 100:1 DCM/MeOH to 20:1 DCM/MeOH. The ester of product 13G was obtained as white solid, 0.234 g, yield=96.3%. LC-MS: [M+H]⁺=902.5.

The white solid obtained from chromatography separation was dissolved in 30 mL methanol, followed by adding 15 mL water; the resulting solution was cooled to 0° C.; to the cooled reaction added LiOH·H₂O (0.964 g, 2.3 mmol, 10.0 eq). The reaction was stirred at room temperature for four hours; HPLC analysis indicated the reaction was completed. The pH of reaction was then adjusted to 3-4 with 2N HCl. Plenty of white solid precipitated; the mixture was standing for one hour; the solid was collected by filtration and washed with water and dried in vacuum overnight. Then the dried white solid was dissolved in 30 mL of methanol. The resulting solution was cooled to 0° C.; to the cooled solution was added HCl methanol solution under stirring. The reaction was monitored with HPLC until the reaction was completed. The volatiles were removed under vacuum; the residue was purified on Prep LC with 0.02% TFA aqueous solution/acetonitrile mixture from 95% to 20% as mobile phase. The collected fractions were concentrated on rotavapor to remove organic solvent and then lyophilized as white solid, 60.1 mg, yield=34.7% in two steps. LC-MS: [M+H]⁺=688.4.

Example 17: Synthesis of Compound 13-8

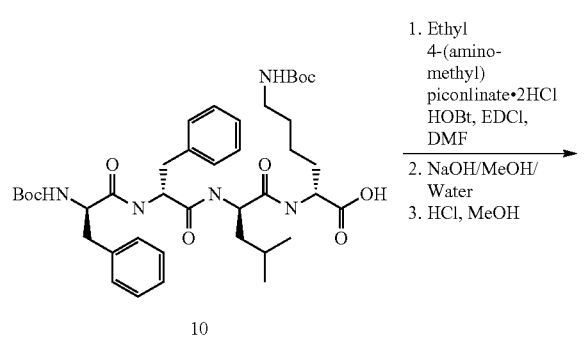

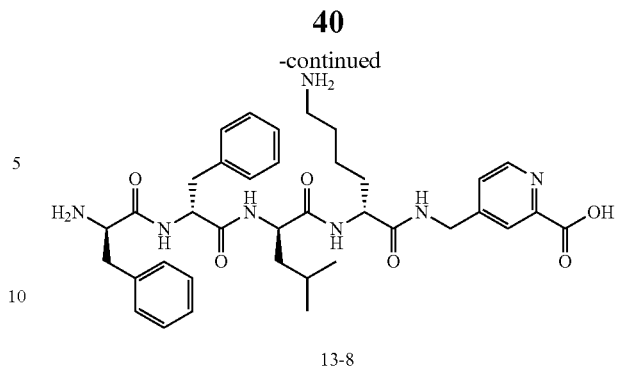

13-8

To the cooled solution of tetrapeptide intermediate 10 (0.200 g, 0.26 mmol, 1.0 eq) in DMF (4.0 mL) at 0° C. was added HOBt·H₂O (0.043 g, 0.32 mmol, 1.1 eq) and EDCI (0.032 g, 0.32 mmol, 1.1 eq). The resulting mixture was stirred at 0° C. for 30 minutes, then to the reaction was added Methyl 4-(aminomethyl)picolinate·2HCl (0.081 g, 0.32 mmol, 1.2 eq), followed by dropwise addition of N-methyl morpholine (0.086 g, 0.85 mmol, 3.2 eq). The resulting mixture was stirred at room temperature (25° C.) until HPLC analysis indicated the reaction was done. To the reaction was added water (12.0 mL) dropwise where a white solid precipitated. The mixture stood for one hour, then the white solid was collected by filtration, washed with water (12.0 mL), and dried in vacuum at 30° C. overnight. The crude product was further purified on silica gel column eluting with a gradient from 100:1 DCM/MeOH to 20:1 DCM/MeOH. The ester of product 13H was obtained as white solid, 0.229 g, yield=94.2%. LC-MS: [M+H]⁺=916.5.

The white solid obtained from chromatography separation was dissolved in 30 mL methanol, followed by adding 15 mL water; the resulting solution was cooled to 0° C.; to the cooled reaction added LiOH·H₂O (0.964 g, 2.3 mmol, 10.0 eq). The reaction was stirred at room temperature for four hours; HPLC analysis indicated the reaction was completed. The pH of reaction was then adjusted to 3-4 with 2N HCl where a white solid precipitated. The mixture stood for one hour; the solid was collected by filtration and washed with water and dried in vacuum overnight. Then, the dried white solid was dissolved in 30 mL of methanol. The resulting solution was cooled to 0° C. To the cooled solution was added HCl methanol solution under stirring. The reaction was monitored with HPLC until the reaction was deemed completed. The volatiles were removed under vacuum. The residue was purified on Prep LC with 0.02% TFA aqueous solution/acetonitrile mixture from 95% to 20% as mobile phase. The collected fractions were concentrated on rotavapor to remove organic solvent and then lyophilized as white solid, 58.5 mg, yield=34.0% in two steps. LC-MS: [M+H]⁺=688.4.

Example 18: Synthesis of Compound 13-9

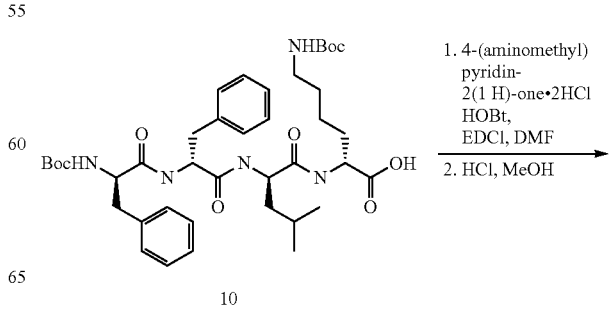

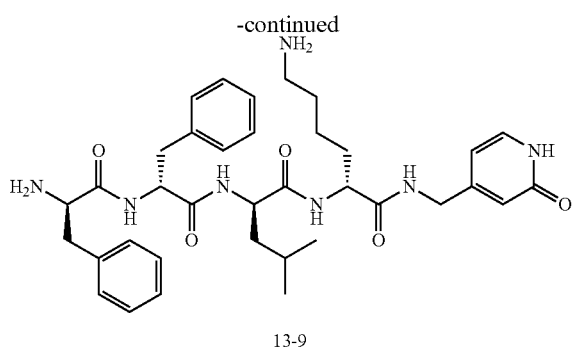

13-9

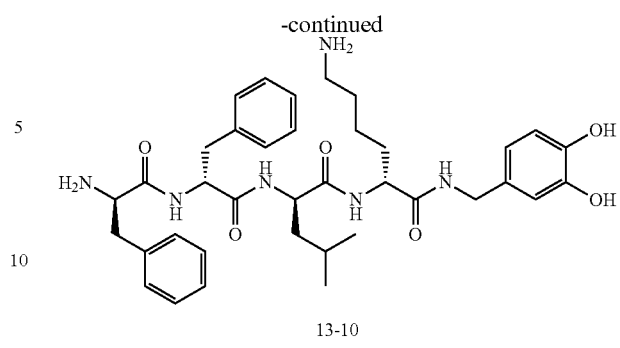

13-10

To the cooled solution of tetrapeptide intermediate 10 (0.200 g, 0.26 mmol, 1.0 eq) in DMF (4.0 mL) at 0° C. was added HOBt·H$_2$O (0.043 g, 0.32 mmol, 1.1 eq) and EDCI (0.032 g, 0.32 mmol, 1.1 eq). The resulting mixture was stirred at 0° C. for 30 minutes, then to the reaction was added 4-(aminoethyl)pyridine-2(1H)-one·2HCl (0.051 g, 0.32 mmol, 1.2 eq), followed by dropwise addition of N-methyl morpholine (0.086 g, 0.85 mmol, 3.2 eq). The resulting mixture was warmed to room temperature and stirred at room temperature (25° C.) until HPLC analysis indicated the reaction was complete. To the reaction was added water (12.0 mL) dropwise where a white solid precipitated. The mixture stood for one hour, then the white solid was collected by filtration, washed with water (12.0 mL), and dried in vacuum at 30° C. overnight. The crude product was further purified on silica gel column eluting with a gradient from 100:1 DCM/MeOH to 20:1 DCM/MeOH. The white solid obtained from column chromatography separation was dissolved in 10 mL methanol; the resulting solution was cooled to 0° C.; to the cooled solution was added HCl methanol solution under stirring; the reaction was monitored with HPLC until was deemed complete. The solvent was then removed in vacuum; the residue was purified on Prep LC with 0.02% TFA aqueous solution/acetonitrile mixture from 95% to 20% as mobile phase. The collected fractions were evaporated to remove organic solvent on rotavapor and the remained aqueous solution was lyophilized as white solid. 51.7 mg, yield=32.2%. LC-MS: [M+H]$^+$=660.4.

Example 19: Synthesis of Compound 13-10

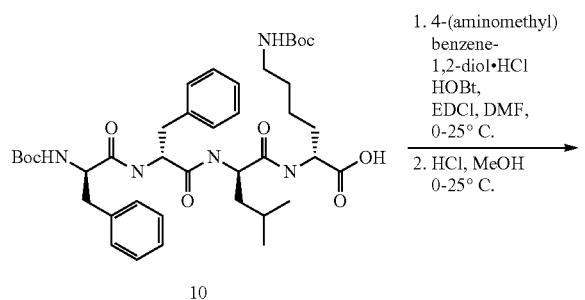

To the cooled solution of tetrapeptide intermediate 10 (0.200 g, 0.26 mmol, 1.0 eq) in DMF (4.0 mL) at 0° C. was added HOBt·H$_2$O (0.043 g, 0.32 mmol, 1.1 eq) and EDCI (0.032 g, 0.32 mmol, 1.1 eq). The resulting mixture was stirred at 0° C. for 30 minutes, then to the reaction was added 4-(aminomethyl)benzene-1,2-diol·2HCl (0.070 g, 0.32 mmol, 1.2 eq), followed by dropwise addition of N-methyl morpholine (0.086 g, 0.85 mmol, 3.2 eq). The resulting mixture was warmed to room temperature and stirred at room temperature (25° C.) until HPLC analysis indicated the reaction was complete. To the reaction was added water (12.0 mL) dropwise where a white solid precipitated. The mixture stood for one hour, then the white solid was collected by filtration, washed with water (12.0 mL), and dried in vacuum at 30° C. overnight. The crude product was further purified on silica gel column eluting with a gradient from 100:1 DCM/MeOH to 20:1 DCM/MeOH. After evaporation, a white solid was obtained. The white solid obtained from column chromatography separation was dissolved in 10 mL methanol; the resulting solution was cooled to 0° C.; to the cooled solution was added HCl methanol solution under stirring; the reaction was monitored with HPLC until the reaction was deemed complete. The solvent was then removed in vacuum; the residue was purified on Prep LC with 0.02% TFA aqueous solution/acetonitrile mixture from 95% to 20% as mobile phase. The collected fractions were evaporated to remove organic solvent on rotavapor and the remained aqueous solution was lyophilized as light yellow solid. 50.3 mg, yield=30.6%. LC-MS: [M+H]$^+$=675.4.

Example 20: Synthesis of Compound 13-11

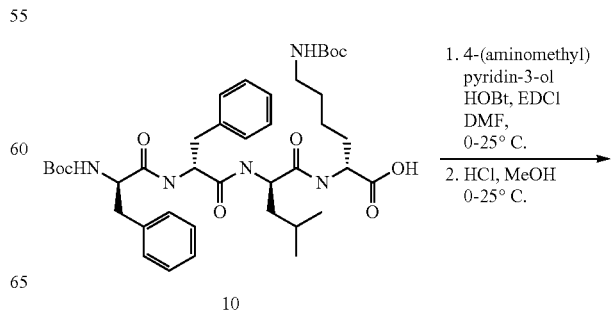

-continued

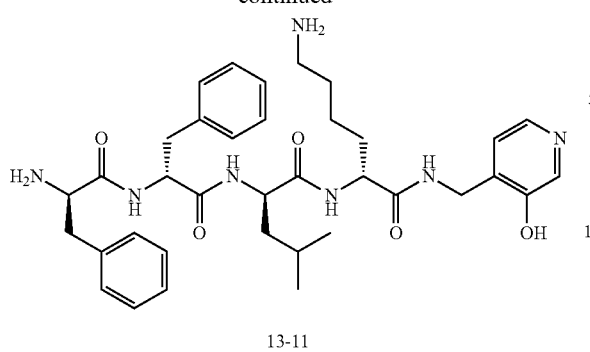

13-11

To the cooled solution of tetrapeptide intermediate 10 (0.200 g, 0.26 mmol, 1.0 eq) in DMF (4.0 mL) at 0° C. was added HOBt·H₂O (0.043 g, 0.32 mmol, 1.1 eq) and EDCI (0.032 g, 0.32 mmol, 1.1 eq). The resulting mixture was stirred at 0° C. for 30 minutes, then to the reaction was added 4-(aminoethyl)pyridine-3-ol (0.040 g, 0.32 mmol, 1.2 eq), followed by dropwise addition of N-methyl morpholine (0.032 g, 0.32 mmol, 1.2 eq). The resulting mixture was stirred at room temperature (25° C.) until HPLC analysis indicated the reaction was deemed complete. To the reaction was added dropwise (12.0 mL) water where a white solid precipitated. The mixture stood for one hour, then the white solid was collected by filtration, washed with water (12.0 mL), and dried in vacuum at 30° C. overnight. The crude product was further purified on silica gel column eluting with a gradient from 100:1 DCM/MeOH to 20:1 DCM/MeOH obtaining a white solid. The white solid obtained from column chromatography was dissolved in 10 mL methanol; the resulting solution was cooled to 0° C.; to the cooled solution was added HCl methanol solution under stirring; the reaction was monitored with HPLC until was deemed complete. The solvent was then removed in vacuum; the residue was purified on Prep LC with 0.02% TFA aqueous solution/acetonitrile mixture from 95% to 20% as mobile phase. The collected fractions were evaporated to remove organic solvent on rotavapor and the remained aqueous solution was lyophilized as white solid. 51.2 mg, yield=30.8%. LC-MS: [M+H]⁺=660.4.

Example 21: Synthesis of Compound 13-12

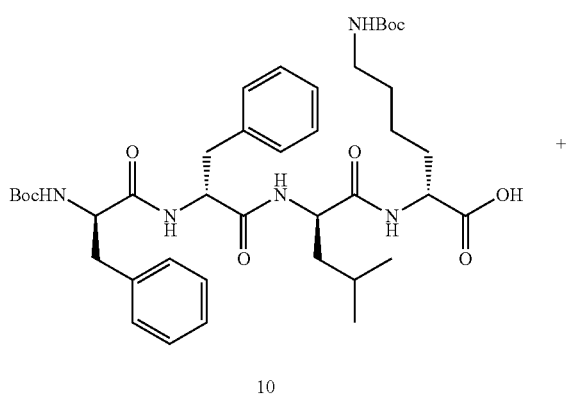

10

-continued

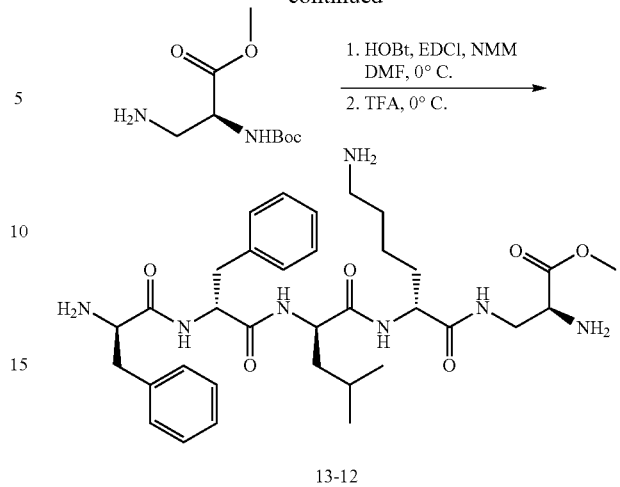

13-12

Into a reaction flask under nitrogen was added compound (10) (0.745 g, 1.0 mmol, 1.0 eq) and DMF (16 mL) under nitrogen. The resulting reaction mixture was cooled to 0° C. in ice bath. To the cooled reaction mixture was added HOBt·H₂O (0.184 g, 1.2 mmol, 1.2 eq) and EDCI (0.23 g, 1.2 mmol, 1.2 eq). After 30 minutes, (S)-Methyl 3-amino-2-((tert-butoxycarbonyl)amino)propanoate (0.262 g, 1.2 mmol, 1.2 eq) and N-methylmorpholine (NMM) (0.121 g, 1.2 mmol 1.2 eq) were added. The reaction mixture was stirred at 0° C. for one hour and then warmed to room temperature until HPLC analysis indicated the reaction was completed. The reaction solution was added dropwise into water (44.7 mL) with stirring. After addition was completed, stirring was stopped and a precipitate formed. The reaction mixture stood for one hour. The precipitate was collected by filtration, washed with water (45 mL×4) and then dried under vacuum (30° C.). The isolated solid intermediate was a white solid, 0.931 g, yield=97.6%. LCMS: m/z=955.1 [M+H]⁺.

The intermediate obtained above was placed into a reaction flask under nitrogen; to the flask was added dichloromethane (48 mL); the resulting solution was cooled in ice bath for 10 minutes; then to the reaction was added a mixture of TFA (12 mL) and dichloromethane (12 mL). The resulting solution was stirred in ice bath for 4 hours and then at room temperature for 2 hours. HPLC analysis indicated the reaction was completed. The volatiles were removed on rotavapor. To the residue was added methanol (12 mL). The resulting solution was evaporated to a residue. The residue was dissolved in water and then lyophilized to a white solid, 0.902 g. LCMS: MS m/z=654.9[M+H]⁺.

Example 22: Synthesis of Compound 13-13

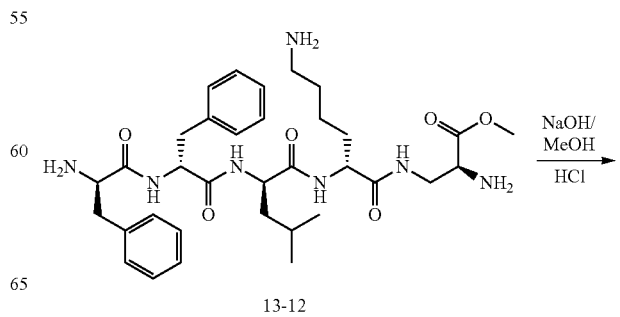

13-12

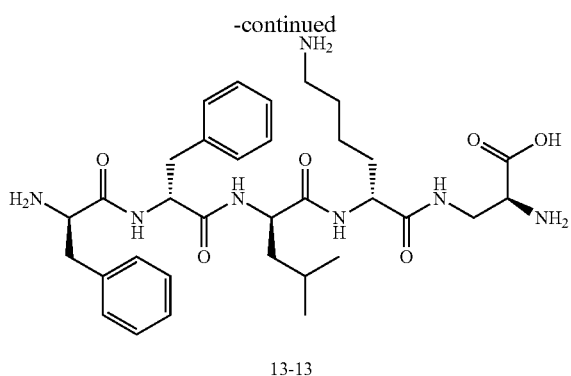

13-13

Compound (13-12) (200 mg, 0.191 mmol, 1.0 eq) was placed into a reaction flask under nitrogen; Into a reaction flask was added methanol (2 mL) under nitrogen. Stirring was initiated and a NaOH solution (0.995 mL, 0.995 mmol, 5.2 eq) was added dropwise. The reaction mixture was stirred at room temperature about 2 hours until HPLC analysis indicated the reaction was completed. Then, an HCl solution (1.0 M) was added dropwise until a pH of 4~5 was achieved. The reaction mixture was purified on reverse phase HPLC; the collected fraction was lyophilized and provided a white solid (13-13), 38 mg, LCMS m/z=640.7 [M+H]$^+$.

Example 23: Synthesis of Compound 13-14

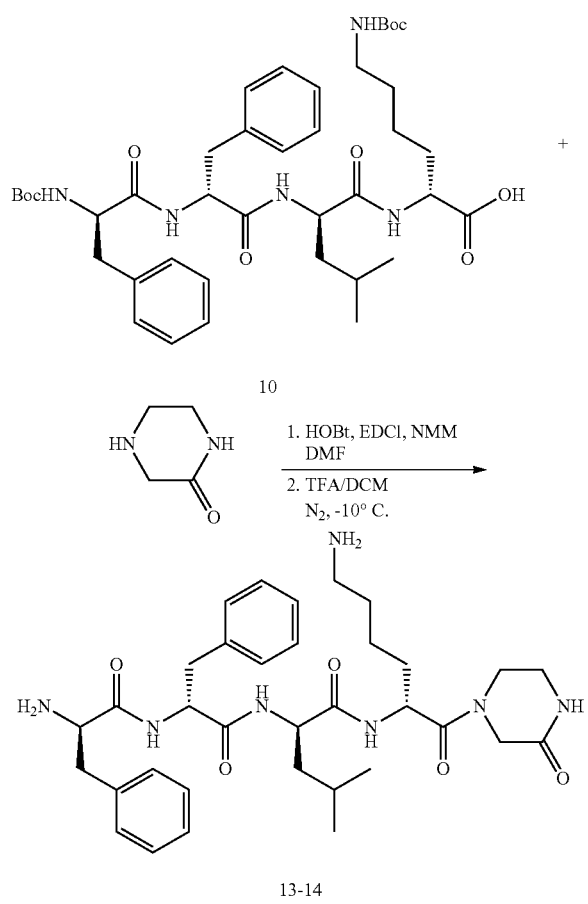

Into a reaction flask under nitrogen was added compound (10) (0.5 g, 0.663 mmol, 1.0 eq) and DMF (10.6 mL) under nitrogen. The resulting reaction mixture was cooled to 0° C. in ice bath. To the cooled reaction mixture was added HOBt. H$_2$O (0.112 g, 0.73 mmol, 1.1 eq) and EDCI (0.140 g, 0.73 mmol, 1.1 eq). After stirring for 30 minutes in ice bath, 2-Oxopiperazine (0.073 g, 0.73 mmol, 1.1 eq) and N-methylmorpholine (NMM) (0.0738 g, 0.73 mmol, 1.1 eq) were added. The reaction mixture was stirred at 0° C. for four hour, HPLC analysis indicated the reaction was completed. The reaction solution was added dropwise into water (30 mL) with stirring. After addition was completed, stirring was stopped and a precipitate formed. The reaction mixture stood for one hour. The precipitate was collected by filtration, washed with water (25 mL×3) and then dried under vacuum (30° C.). The isolated solid intermediate was a white solid, 0.39 g, yield=70.3%. LCMS: m/z=836.5 [M+H]$^+$.

The intermediate obtained above (100 mg, 0.120 mmol, 1.0 eq) was placed into a reaction flask under nitrogen; to the flask was added dichloromethane (2 mL); the resulting solution was cooled to −10° C. for 10 minutes; then to the reaction was added a mixture of TFA (2 mL) and dichloromethane (4 mL). The resulting solution was stirred at −10° C. for 2 hours; HPLC analysis indicated the reaction was completed. The volatiles were removed on rotavapor. To the residue was added dichloromethane (10 mL). The resulting solution was evaporated on rotavapor to a residue. The dichloromethane dissolution/evaporation was repeated three times. Then, the residue was dissolved in methanol (10 mL) and the resulting solution was evaporated to dryness on rotavapor. The residue was dissolved in water and then lyophilized to a white solid (13-13), 0.26 g; LCMS: MS m/z=636.4[M+H]$^+$.

Example 24: Synthesis of Compound 13-15

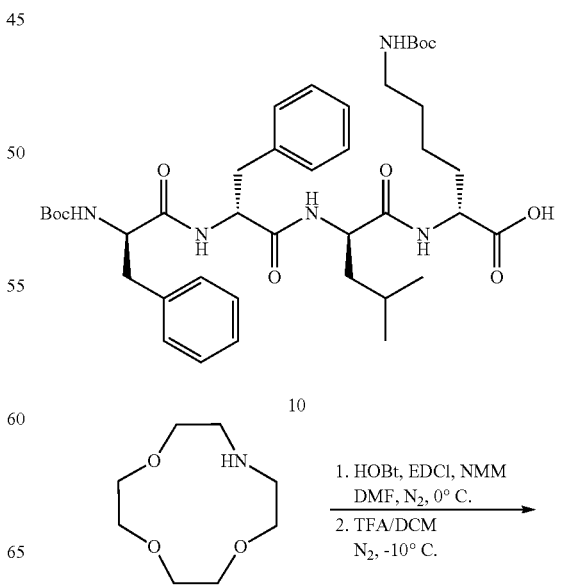

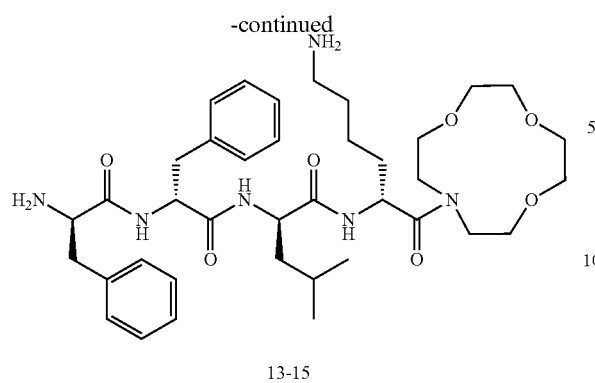

13-15

Example 25: Synthesis of Compound 13-16

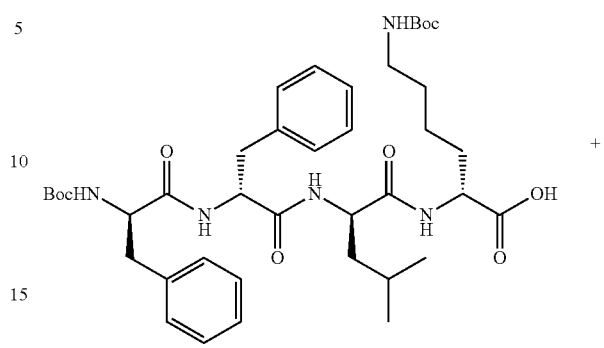

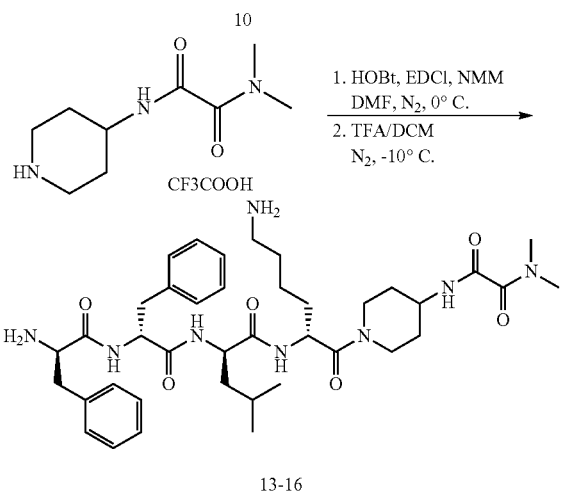

13-16

Into a reaction flask under nitrogen was added compound (10) (0.5 g, 0.663 mmol, 1.0 eq) and DMF (10.6 mL) under nitrogen. The resulting reaction mixture was cooled to 0° C. in ice bath. To the cooled reaction mixture was added HOBt. $H_2O$ (0.112 g, 0.73 mmol, 1.1 eq) and EDCI (0.140 g, 0.73 mmol, 1.1 eq). After stirring for 30 minutes in ice bath, 1-Aza-12-crown-4 (0.1278 g, 0.73 mmol, 1.1 eq) and N-methylmorpholine (NMM) (0.0738 g, 0.73 mmol, 1.1 eq) were added. The reaction mixture was stirred at 0° C. for four hour, HPLC analysis indicated the reaction was completed. The reaction solution was added dropwise into water (30 mL) with stirring. After addition was completed, stirring was stopped and a precipitate formed. The reaction mixture stood for one hour. The precipitate was collected by filtration, washed with water (25 mL) and then dried under vacuum (30° C.). The isolated solid intermediate was a white solid, 0.39 g, yield=64.5%. LCMS: m/z=911.5 [M+H]$^+$.

The intermediate obtained above (100 mg, 0.110 mmol, 1.0 eq) was placed into a reaction flask under nitrogen; to the flask was added dichloromethane (2 mL); the resulting solution was cooled to −10° C. for 10 minutes; then to the cooled reaction was added a mixture of TFA (2 mL) and dichloromethane (4 mL). The resulting solution was stirred at −10° C. for 2 hours; HPLC analysis indicated the reaction was completed. The volatiles were removed on rotavapor. To the residue was added dichloromethane (10 mL). The resulting solution was evaporated on rotavapor to a residue. The dichloromethane dissolution/evaporation was repeated three times. Then, the residue was dissolved in methanol (10 mL) and the resulting solution was evaporated to dryness on rotavapor. The residue was dissolved in water and then lyophilized to a white solid product (13-15), 26 mg, 25.2% yield; LCMS: MS m/z=711.4[M+H]$^+$.

Into a reaction flask under nitrogen was added compound (10) (0.2 g, 0.265 mmol, 1.0 eq) and DMF (4.23 mL) under nitrogen. The resulting reaction mixture was cooled to 0° C. in ice bath. To the cooled reaction mixture was added HOBt. $H_2O$ (0.061 g, 0.40 mmol, 1.5 eq) and EDCI (0.076 g, 0.4 mmol, 1.5 eq). After stirring for 30 minutes in ice bath, N',N'-dimethyl-N-(4-piperidyl)oxamide; 2,2,2-trifluoroacetic acid (0.125 g, 0.4 mmol, 1.5 eq) and N-methylmorpholine (NMM) (0.075 g, 0.74 mmol, 2.8 eq) were added. The reaction mixture was stirred at 0° C. for two hour, HPLC analysis indicated the reaction was completed. The reaction solution was added dropwise into water (12 mL) with stirring. After addition was completed, stirring was stopped and a precipitate formed. The reaction mixture stood for one hour. The precipitate was collected by filtration, washed with water (17 mL×3) and then dried under vacuum (30° C.). The isolated solid intermediate was a white solid, 0.21 g, LCMS: m/z=935.6[M+H]$^+$.

The intermediate obtained above (100 mg, 0.110 mmol, 1.0 eq) was placed into a reaction flask under nitrogen; to the flask was added dichloromethane (2 mL); the resulting solution was cooled to −10° C. for 10 minutes; then to the cooled reaction was added a mixture of TFA (2 mL) and dichloromethane (4 mL). The resulting solution was stirred at −10° C. for 2 hours; HPLC analysis indicated the reaction was completed. The volatiles were removed on rotavapor. To the residue was added dichloromethane (10 mL). The resulting solution was evaporated on rotavapor to a residue. The dichloromethane dissolution/evaporation was repeated three times. Then, the residue was dissolved in methanol (10 mL) and the resulting solution was evaporated to dryness on rotavapor. The residue was dissolved in water and then lyophilized to a white solid product (13-16), 44 mg, 42.7% yield; LCMS: MS m/z=735.5[M+H]$^+$.

Example 26: Synthesis of Compound 13-17

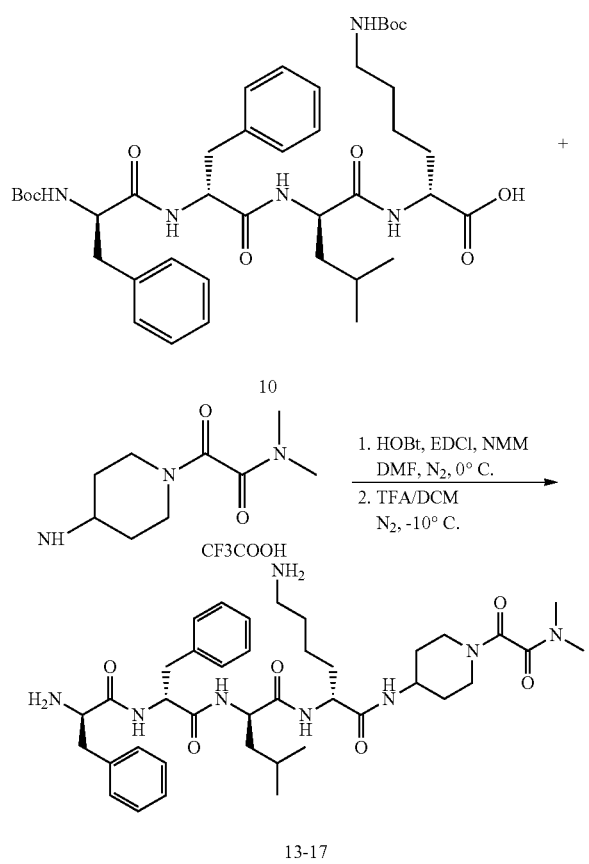

Into a reaction flask under nitrogen was added compound (10) (0.2 g, 0.265 mmol, 1.0 eq) and DMF (4.23 mL) under nitrogen. The resulting reaction mixture was cooled to 0° C. in ice bath. To the cooled reaction mixture was added HOBt.H$_2$O (0.061 g, 0.40 mmol, 1.5 eq) and EDCI (0.076 g, 0.4 mmol, 1.5 eq). After stirring for 30 minutes in ice bath, 2-(4-amino-1-piperidyl)-N,N-dimethyl-2-oxo-acetamide; 2,2,2-trifluoroacetic acid (0.125 g, 0.4 mmol, 1.5 eq) and N-methylmorpholine (NMM) (0.075 g, 0.74 mmol, 2.8 eq) were added. The reaction mixture was stirred at 0° C. for two hour, HPLC analysis indicated the reaction was completed. The reaction solution was added dropwise into water (12 mL) with stirring. After addition was completed, stirring was stopped and a precipitate formed. The reaction mixture stood for one hour. The precipitate was collected by filtration, washed with water (17 mL×3) and then dried under vacuum (30° C.). The isolated solid intermediate was a white solid, 0.19 g, LCMS: m/z=935.6[M+H]$^+$.

The intermediate obtained above (100 mg, 0.11 mmol, 1.0 eq) was placed into a reaction flask under nitrogen; to the flask was added dichloromethane (2 mL); the resulting solution was cooled to −10° C. for 10 minutes; then to the cooled reaction was added a mixture of TFA (2 mL) and dichloromethane (4 mL). The resulting solution was stirred at −10° C. for 2 hours; HPLC analysis indicated the reaction was completed. The volatiles were removed on rotavapor. To the residue was added dichloromethane (10 mL). The resulting solution was evaporated on rotavapor to a residue. The dichloromethane dissolution/evaporation was repeated three times. Then, the residue was dissolved in methanol (10 mL) and the resulting solution was evaporated to dryness on rotavapor. The residue was dissolved in water and then lyophilized to a white solid product (13-17), 78 mg, 75.7% yield; LCMS: MS m/z=735.5[M+H]$^+$.

Example 27: Synthesis of Compound 13-18

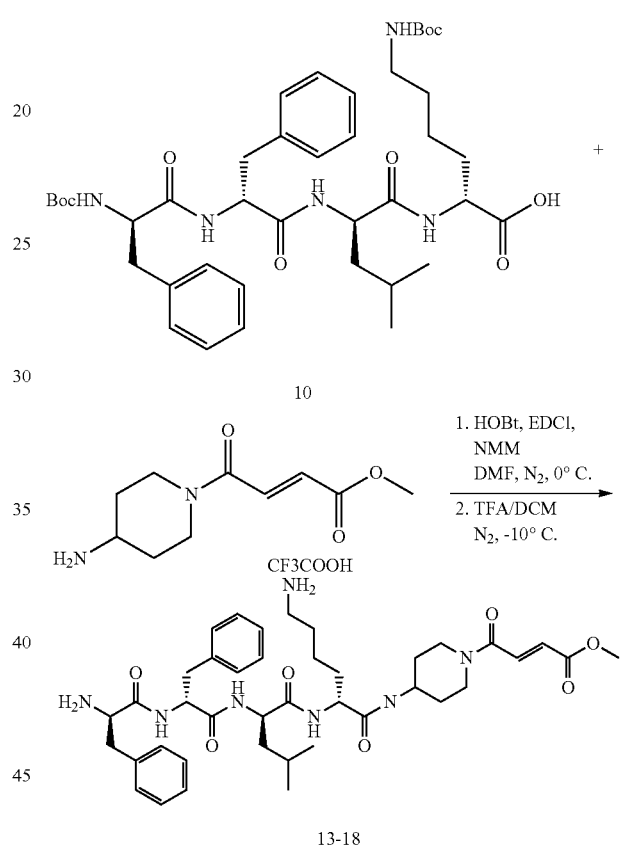

Into a reaction flask under nitrogen was added compound (10) (0.2 g, 0.265 mmol, 1.0 eq) and DMF (4.23 mL) under nitrogen. The resulting reaction mixture was cooled to 0° C. in ice bath. To the cooled reaction mixture was added HOBt.H$_2$O (0.061 g, 0.40 mmol, 1.5 eq) and EDCI (0.076 g, 0.4 mmol, 1.5 eq). After stirring for 30 minutes in ice bath methyl (E)-4-(4-amino-1-piperidyl)-4-oxo-but-2-enoate; 2,2,2-trifluoroacetic acid (0.130 g, 0.4 mmol, 1.5 eq) and N-methylmorpholine (NMM) (0.075 g, 0.74 mmol, 2.8 eq) were added. The reaction mixture was stirred at 0° C. for two hour, HPLC analysis indicated the reaction was completed. The reaction solution was added dropwise into water (12 mL) with stirring. After addition was completed, stirring was stopped and a precipitate formed. The reaction mixture stood for one hour. The precipitate was collected by filtration, washed with water (17 mL×3) and then dried under vacuum (30° C.). The isolated solid intermediate was a white solid, 0.21 g, LCMS: m/z=948.5[M+H]$^+$.

The intermediate obtained above (100 mg, 0.105 mmol, 1.0 eq) was placed into a reaction flask under nitrogen; to the flask was added dichloromethane (2 mL); the resulting solution was cooled to −10° C. for 10 minutes; then to the cooled reaction was added a mixture of TFA (2 mL) and dichloromethane (4 mL). The resulting solution was stirred at −10° C. for 2 hours; HPLC analysis indicated the reaction was completed. The volatiles were removed on rotavapor. To the residue was added dichloromethane (10 mL). The resulting solution was evaporated on rotavapor to a residue. The dichloromethane dissolution/evaporation was repeated three times. Then, the residue was dissolved in methanol (10 mL) and the resulting solution was evaporated to dryness on rotavapor. The residue was dissolved in water and then lyophilized to a white solid product (13-18), 29 mg, 75.7% yield; LCMS: MS m/z=748.4[M+H]$^+$.

Example 28: Synthesis of Compound 13-19

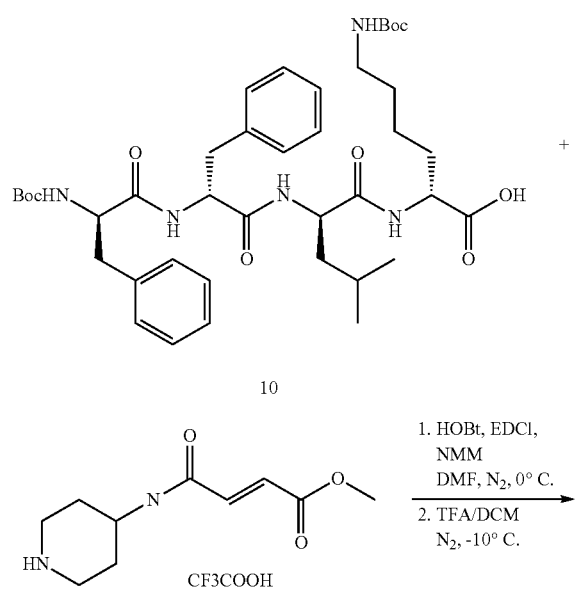

10

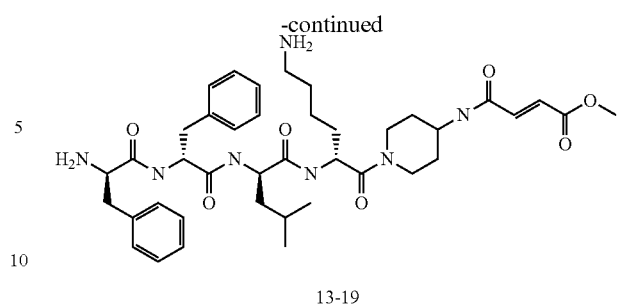

13-19

Into a reaction flask under nitrogen was added compound (10) (0.5 g, 0.663 mmol, 1.0 eq) and DMF (10.6 mL) under nitrogen. The resulting reaction mixture was cooled to 0° C. in ice bath. To the cooled reaction mixture was added HOBt.H$_2$O (0.152 g, 0.995 mmol, 1.5 eq) and EDCI (0.191 g, 0.995 mmol, 1.5 eq). After stirring for 30 minutes in ice bath, methyl (E)-4-oxo-4-(4-piperidylamino)but-2-enoate; 2,2,2-trifluoroacetic acid (0.324 g, 0.995 mmol, 1.5 eq) and N-methylmorpholine (NMM) (0.181 g, 0.995 mmol, 2.7 eq) were added. The reaction mixture was stirred at 0° C. for two hour, HPLC analysis indicated the reaction was completed. The reaction solution was added dropwise into water (30 mL) with stirring. After addition was completed, stirring was stopped and a precipitate formed. The reaction mixture stood for one hour. The precipitate was collected by filtration, washed with water (25 mL×3) and then dried under vacuum (30° C.). The isolated solid intermediate was a white solid, 0.46 g, LCMS: m/z=948.5[M+H]$^+$.

The intermediate obtained above (400 mg, 0.422 mmol, 1.0 eq) was placed into a reaction flask under nitrogen; to the flask was added dichloromethane (8 mL); the resulting solution was cooled to −10° C. for 10 minutes; then to the cooled reaction was added a mixture of TFA (5.3 mL) and dichloromethane (10.6 mL). The resulting solution was stirred at −10° C. for 2 hours; HPLC analysis indicated the reaction was completed. The volatiles were removed on rotavapor. To the residue was added dichloromethane (10 mL). The resulting solution was evaporated on rotavapor to a residue. The dichloromethane dissolution/evaporation was repeated three times. Then, the residue was dissolved in methanol (10 mL) and the resulting solution was evaporated to dryness on rotavapor. The residue was dissolved in water and then lyophilized to a white solid product (13-19), 300 mg, 75.7% yield; LCMS: MS m/z=748.4[M+H]$^+$.

Example 29: Synthesis of Compound 13-20

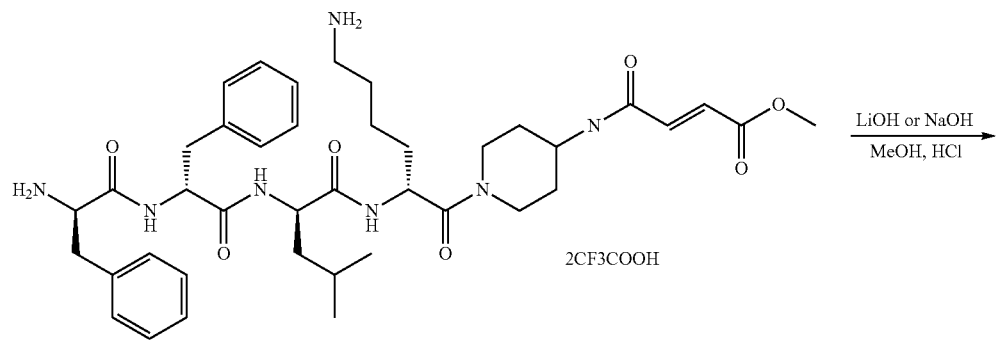

13-19

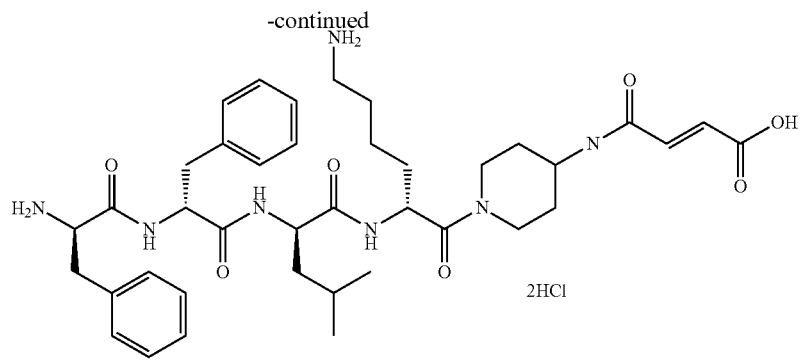

13-20

Into a reaction flask was added compound (13-19) (300 mg, 0.307 mmol, 1 eq) and methanol (6 mL) under nitrogen. To the reaction mixture was added a solution of NaOH (1.5 mL, 1.0 M, 1.5 mmol), 4.9 eq.) dropwise. The reaction mixture was stirred at room temperature for 2 hours until HPLC analysis indicated the reaction was completed. Then, a HCl solution (1.0 M) was added dropwise until pH=~4.5 was achieved. Methanol was removed on a rotoevaporatorator to form a residue. The reside was purified on reverse phase HPLC; the collected fractions were lyophilized to form the product (13-20) as a white solid, 124 mg, yield=50%. LC-MS m/z=734.4 [M+H]$^+$.

Example 30: Synthesis of Compound 13-21

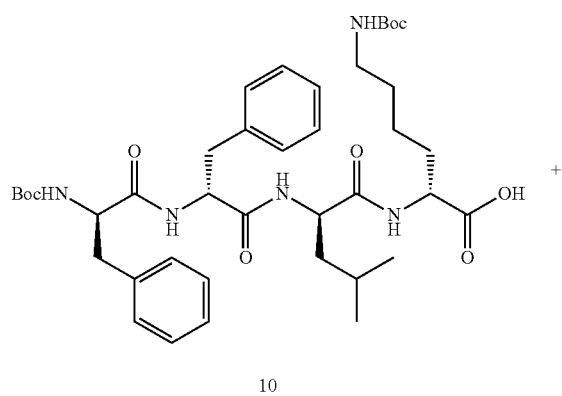

10

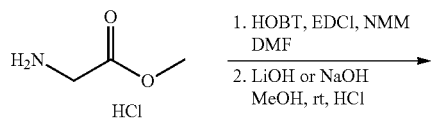

1. HOBT, EDCl, NMM DMF
2. LiOH or NaOH MeOH, rt, HCl

-continued

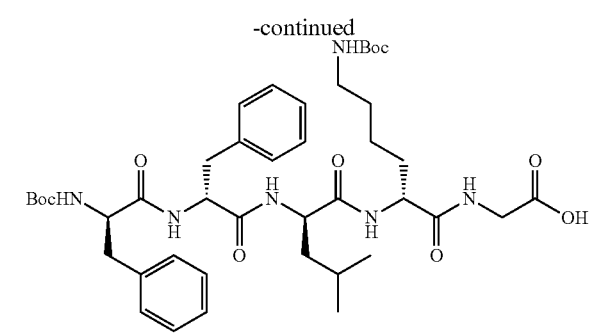

13-21

Into a reaction flask under nitrogen was added compound (10) (1.0 g, 1.33 mmol, 1.0 eq) and DMF (21.2 mL) under nitrogen. The resulting reaction mixture was cooled to 0° C. in ice bath. To the cooled reaction mixture was added HOBt. H$_2$O (0.305 g, 1.99 mmol, 1.5 eq) and EDCI (0.381.4 g, 1.99 mmol, 1.5 eq). After stirring for 30 minutes in ice bath, glycine methyl ester hydrochloride (0.250 g, 1.99 mmol, 1.5 eq) and N-methylmorpholine (NMM) (0.362 g, 3.58 mmol, 2.7 eq) were added. The reaction mixture was stirred at 0° C. for four hour, HPLC analysis indicated the reaction was completed. The reaction solution was added dropwise into water (60 mL) with stirring. After addition was completed, stirring was stopped and a precipitate formed. The reaction mixture stood for one hour. The precipitate was collected by filtration, washed with water (50 mL×3) and then dried under vacuum (30° C.). The isolated solid intermediate was a white solid, 0.92 g, LCMS: m/z=825.5[M+H]$^+$.

The intermediate obtained above (720 mg, 0.872 mmol, 1.0 eq) was placed into a reaction flask under nitrogen, followed by adding methanol (14.4 mL). To the resulting solution was added a solution of NaOH (3.6 mL, 1.0 M, 3.6 mmol), 4.1 eq.) dropwise. The reaction mixture was stirred at room temperature for 2 hours until HPLC analysis indicated the reaction was completed. Then, a HCl solution (1.0 M) was added dropwise until pH=5~6 was achieved. Methanol was removed on a rotoevaporator; the residue was extracted with dichloromethane (170 ml×3). The combined organic extracted was dried and evaporated on rotavaporator, which provided a white solid product (13-21), 413 mg, yield=60%. LC-MS m/z=811.5 [M+H]$^+$.

Example 31: Synthesis of Compound 13-22

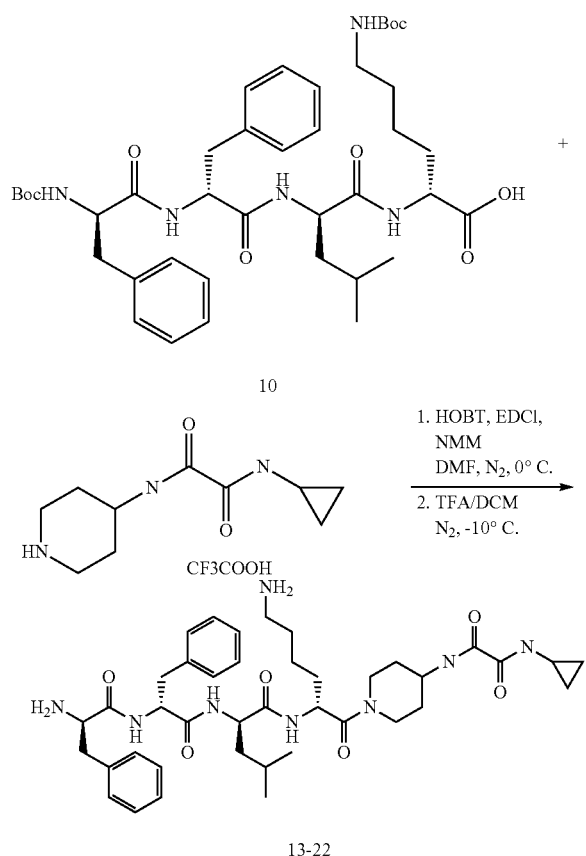

Into a reaction flask under nitrogen was added compound (10) (0.15 g, 0.199 mmol, 1.0 eq) and DMF (3.2 mL) under nitrogen. The resulting reaction mixture was cooled to 0° C. in ice bath. To the cooled reaction mixture was added HOBt. H₂O (45.7 mg, 0.298 mmol, 1.5 eq) and EDCI (57.2 mg, 0.298 mmol, 1.5 eq). After stirring for 30 minutes in ice bath, N-cyclopropyl-N'-(4-piperidyl)oxamide; 2,2,2-trifluoroacetic acid (80 mg, 0.239 mmol, 1.2 eq) and N-methylmorpholine (NMM) (55 mg, 0.537 mmol, 2.7 eq) were added. The reaction mixture was stirred at 0° C. for 4.5 hours, HPLC analysis indicated the reaction was completed. The reaction solution was added dropwise into water (9 mL) with stirring. After addition was completed, stirring was stopped and a precipitate formed. The reaction mixture stood for one hour. The precipitate was collected by filtration, washed with water (25 mL×3) and then dried under vacuum (30° C.). The isolated solid intermediate was a white solid, 0.15 g, LCMS: m/z=947.6[M+H]⁺.

The intermediate obtained above (120 mg, 0.127 mmol, 1.0 eq) was placed into a reaction flask under nitrogen; to the flask was added dichloromethane (2.4 mL); the resulting solution was cooled to −10° C. for 10 minutes; then to the cooled reaction was added a mixture of TFA (2.4 mL) and dichloromethane (4.8 mL). The resulting solution was stirred at −10° C. for 2 hours; HPLC analysis indicated the reaction was completed. The volatiles were removed on rotavapor. To the residue was added dichloromethane (10 mL). The resulting solution was evaporated on rotavapor to a residue again. The dichloromethane dissolution/evaporation was repeated three times. Then, the residue was dissolved in methanol (10 mL) and the resulting solution was evaporated to dryness on rotavapor. The residue was dissolved in water and then lyophilized to a white solid product (13-21), 60 mg, 48.6% yield; LCMS: MS m/z=747.5[M+H]⁺.

Example 32: Synthesis of Compound 13-23

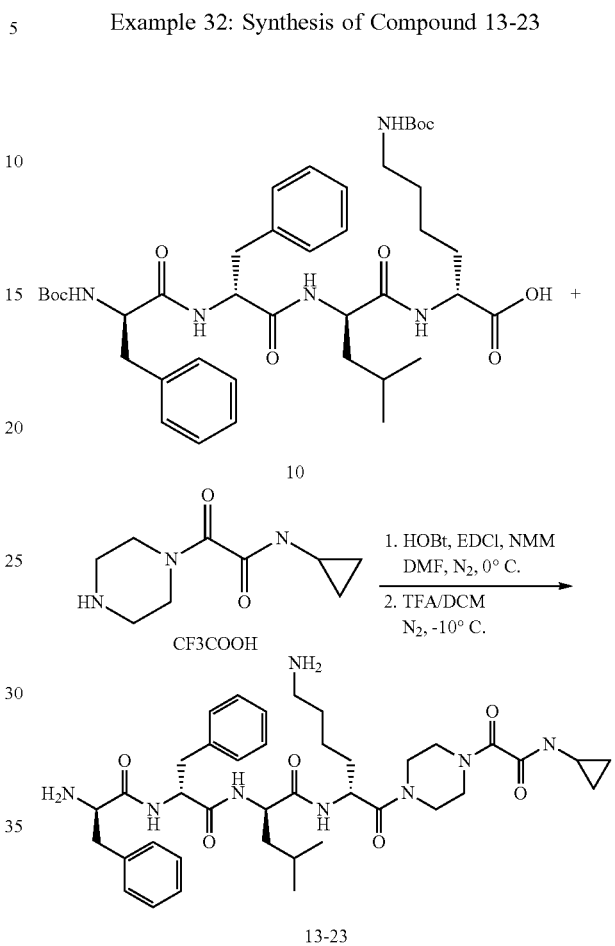

Into a reaction flask under nitrogen was added compound (10) (139 mg, 0.184 mmol, 1.0 eq) and DMF (3.0 mL) under nitrogen. The resulting reaction mixture was cooled to 0° C. in ice bath. To the cooled reaction mixture was added HOBt. H₂O (37.3 mg, 0.276 mmol, 1.5 eq) and EDCI (55 mg, 0.276 mmol, 1.5 eq). After stirring for 30 minutes in ice bath, N-cyclopropyl-2-oxo-2-piperazin-1-yl-acetamide; 2,2,2-trifluoroacetic acid (69 mg, 0.222 mmol, 1.2 eq) and N-methylmorpholine (NMM) (55 mg, 0.515 mmol, 2.8 eq) were added. The reaction mixture was stirred at 0° C. for 4.5 hours, HPLC analysis indicated the reaction was completed. The reaction solution was added dropwise into water (12 mL) with stirring. After addition was completed, stirring was stopped and a precipitate formed. The reaction mixture stood for one hour. The precipitate was collected by filtration, washed with water (20 mL×4) and then dried under vacuum (30° C.). The isolated solid intermediate was a white solid, 0.125 g, LCMS: m/z=933.5[M+H]⁺.

The intermediate obtained above (120 mg, 0.129 mmol, 1.0 eq) was placed into a reaction flask under nitrogen; to the flask was added dichloromethane (2.4 mL); the resulting solution was cooled to −10° C. for 10 minutes; then to the cooled reaction was added a mixture of TFA (2.4 mL) and dichloromethane (4.8 mL). The resulting solution was stirred at −10° C. for 2 hours; HPLC analysis indicated the reaction was completed. The volatiles were removed on rotavapor. To the residue was added dichloromethane (10 mL). The resulting solution was evaporated on rotavapor to a residue again. The dichloromethane dissolution/evaporation was repeated two times. Then, the residue was dissolved in methanol (10 mL) and the resulting solution was evaporated to dryness on rotavapor; repeating the methanol dissolving and evaporating twice, then the residue was dissolved in water and then lyophilized to a white solid product (13-23), 100 mg, 80.9% yield; LCMS: MS m/z=733.4[M+H]$^+$.

Example 33: Synthesis of Compound 13-24

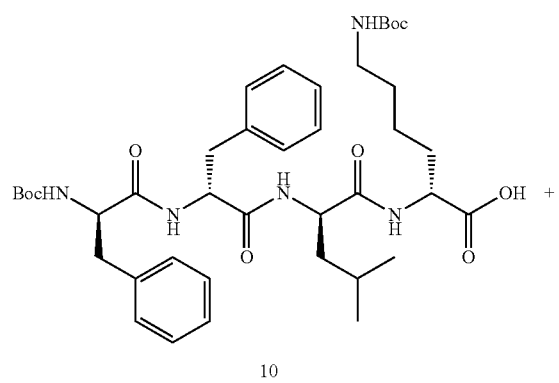

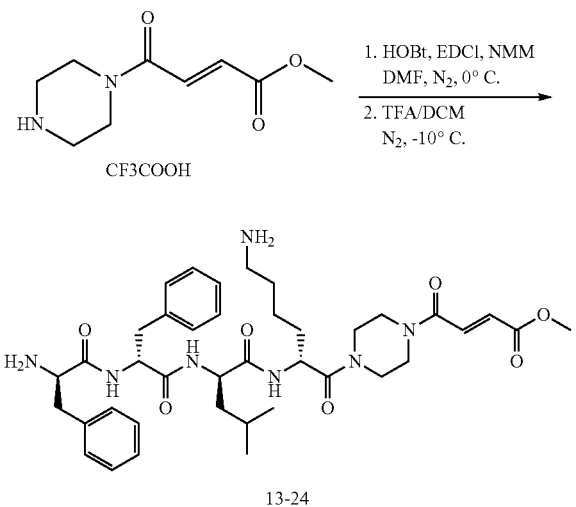

Into a reaction flask under nitrogen was added compound (10) (500 mg, 0.663 mmol, 1.0 eq) and DMF (10.6 mL) under nitrogen. The resulting reaction mixture was cooled to 0° C. in ice bath. To the cooled reaction mixture was added HOBt. H$_2$O (152.2 mg, 0.995 mmol, 1.5 eq) and EDCI (190.70 mg, 0.995 mmol, 1.5 eq). After stirring for 30 minutes in ice bath, methyl (E)-4-oxo-4-piperazin-1-yl-but-2-enoate; 2,2,2-trifluoroacetic acid (310.6 mg, 0.995 mmol, 1.2 eq) and N-methylmorpholine (NMM) (200 mg, 1.98 mmol, 3.0 eq) were added. The reaction mixture was stirred at 0° C. for 10 hours, HPLC analysis indicated the reaction was completed. The reaction solution was added dropwise into water (30 mL) with stirring. After addition was completed, stirring was stopped and a precipitate formed. The reaction mixture stood for one hour. The precipitate was collected by filtration, washed with water (25 mL×3) and then dried under vacuum (30° C.). The isolated solid intermediate was a white solid, 0.42 g, LCMS: m/z=934.5[M+H]$^+$.

The intermediate obtained above (200 mg, 0.214 mmol, 1.0 eq) was placed into a reaction flask under nitrogen; to the flask was added dichloromethane (4 mL); the resulting solution was cooled to −10° C. for 10 minutes; then to the cooled reaction was added a mixture of TFA (4 mL) and dichloromethane (8 mL). The resulting solution was stirred at −10° C. for 2 hours; HPLC analysis indicated the reaction was completed. The volatiles were removed on rotavapor. To the residue was added dichloromethane (10 mL). The resulting solution was evaporated on rotavapor to a residue again. The dichloromethane dissolution/evaporation was repeated three times. Then, the residue was dissolved in methanol (10 mL) and the resulting solution was evaporated to dryness on rotavapor; repeating the methanol dissolving and evaporating twice, then the residue was dissolved in water and then lyophilized to a white solid product (13-24), 150 mg, 72.8% yield; LCMS: MS m/z=734.4[M+H]$^+$.

Example 34: Synthesis of Compound 13-25

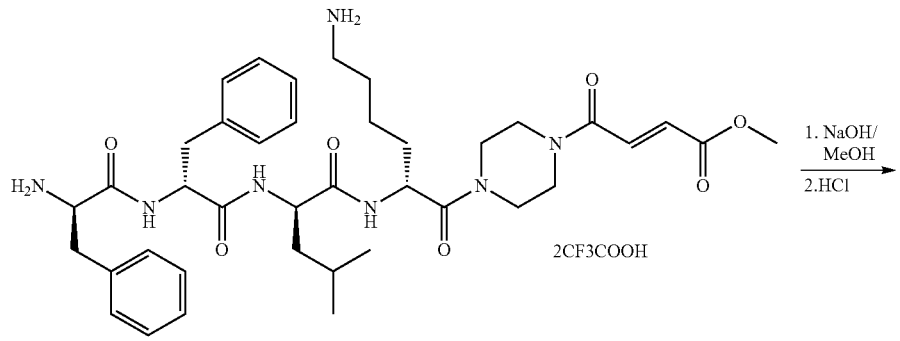

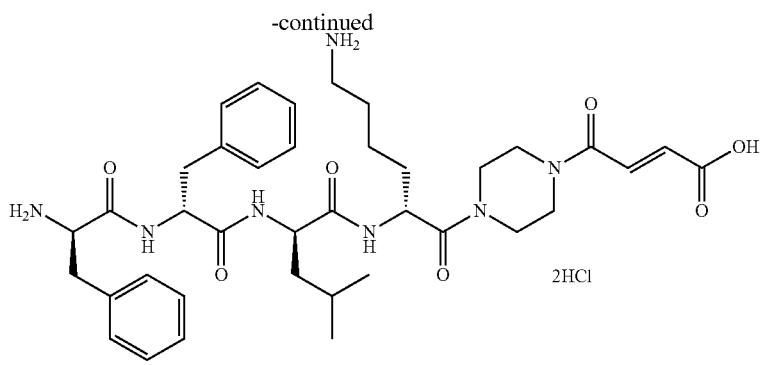

13-25

The compound (13-23) (150 mg, 0.156 mmol, 1.0 eq) was placed into a reaction flask under nitrogen, followed by adding methanol (3 mL). To the resulting solution was added a solution of NaOH (0.75 mL, 1.0 M, 0.75 mmol), 4.8 eq.) dropwise. The reaction mixture was stirred at room temperature for 2 hours until HPLC analysis indicated the reaction was completed. Then, a HCl solution (1.0 M) was added dropwise until pH=4~5 was achieved. The solution was then purified on reverse-phase HPLC, the collection fraction was lyophillized and it provided a white solid product (13-25), 100 mg, yield=80.9%. LC-MS m/z=720.4 [M+H]$^+$.

Example 35: Synthesis of Compound 13-26

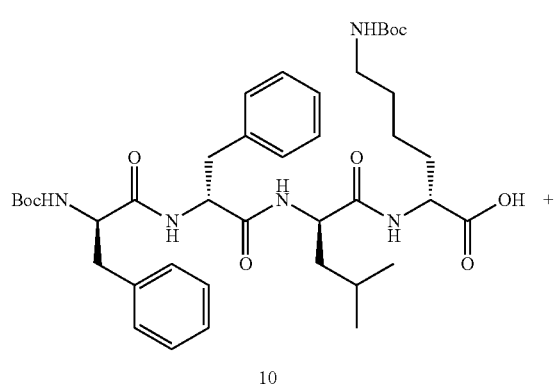

10

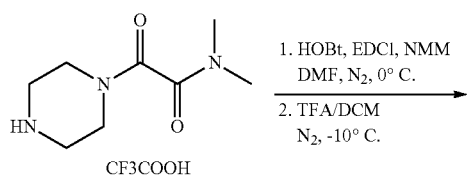

CF3COOH

1. HOBt, EDCl, NMM
DMF, N$_2$, 0° C.
2. TFA/DCM
N$_2$, -10° C.

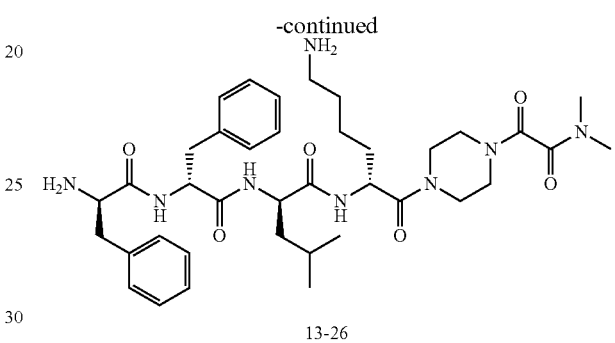

13-26

Into a reaction flask under nitrogen was added compound (10) (200 mg, 0.265 mmol, 1.0 eq) and DMF (4.2 mL) under nitrogen. The resulting reaction mixture was cooled to 0° C. in ice bath. To the cooled reaction mixture was added HOBt. H$_2$O (60.94 mg, 0.398 mmol, 1.5 eq) and EDCI (76.28 mg, 0.398 mmol, 1.5 eq). After stirring for 30 minutes in ice bath, N,N-dimethyl-2-oxo-2-piperazin-1-yl-acetamide; 2,2,2-trifluoroacetic acid (119.07 mg, 0.398 mmol, 1.5 eq) and N-methylmorpholine (NMM) (75.1 mg, 0.743 mmol, 2.8 eq) were added. The reaction mixture was stirred at 0° C. for 8 hours, HPLC analysis indicated the reaction was completed. The reaction solution was added dropwise into water (12 mL) with stirring. After addition was completed, stirring was stopped and a precipitate formed. The reaction mixture stood for one hour. The precipitate was collected by filtration, washed with water (17 mL×3) and then dried under vacuum (30° C.). The isolated solid intermediate was a white solid, 0.151 g, LCMS: m/z=921.5[M+H]$^+$.

The intermediate obtained above (100 mg, 0.109 mmol, 1.0 eq) was placed into a reaction flask under nitrogen; to the flask was added dichloromethane (2 mL); the resulting solution was cooled to -10° C. for 10 minutes; then to the cooled reaction was added a mixture of TFA (2 mL) and dichloromethane (4 mL). The resulting solution was stirred at -10° C. for 2 hours; HPLC analysis indicated the reaction was completed. The volatiles were removed on rotavapor. To the residue was added dichloromethane (10 mL). The resulting solution was evaporated on rotavapor to a residue again. The dichloromethane dissolution/evaporation was repeated three times. Then, the residue was dissolved in methanol (10 mL) and the resulting solution was evaporated to dryness on rotavapor; repeating the methanol dissolving and evaporating twice, then the residue was dissolved in water and then lyophilized to a white solid product (13-26), 74 mg, 71.8% yield; LCMS: MS m/z=721.4[M+H]⁺.

Example 36: Synthesis of Compound 13-27

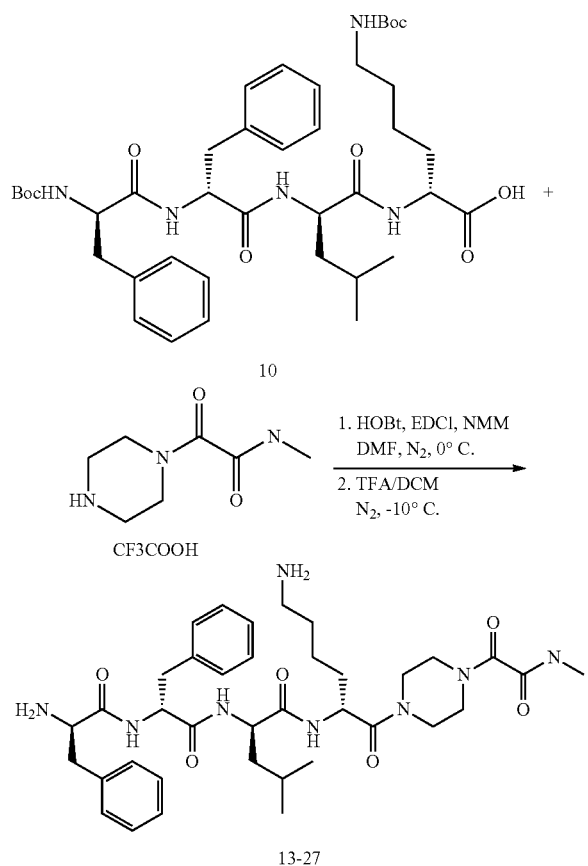

13-27

Into a reaction flask under nitrogen was added compound (10) (200 mg, 0.265 mmol, 1.0 eq) and DMF (4.2 mL) under nitrogen. The resulting reaction mixture was cooled to 0° C. in ice bath. To the cooled reaction mixture was added HOBt. $H_2O$ (60.94 mg, 0.398 mmol, 1.5 eq) and EDCI (76.28 mg, 0.398 mmol, 1.5 eq). After stirring for 30 minutes in ice bath, N-methyl-2-oxo-2-piperazin-1-yl-acetamide; 2,2,2-trifluoroacetic acid (119.0 mg, 0.398 mmol, 1.5 eq) and N-methylmorpholine (NMM) (100 mg, 0.988 mmol, 3.7 eq) were added. The reaction mixture was stirred at 0° C. for 8 hours, HPLC analysis indicated the reaction was completed. The reaction solution was added dropwise into water (12 mL) with stirring. After addition was completed, stirring was stopped and a precipitate formed. The reaction mixture stood for one hour. The precipitate was collected by filtration, washed with water (20 mL×3) and then dried under vacuum (30° C.). The isolated solid intermediate was a white solid, 0.191 g, LCMS: m/z=907.5[M+H]⁺.

The intermediate obtained above (100 mg, 0.11 mmol, 1.0 eq) was placed into a reaction flask under nitrogen; to the flask was added dichloromethane (2 mL); the resulting solution was cooled to −10° C. for 10 minutes; then to the cooled reaction was added a mixture of TFA (2 mL) and dichloromethane (4 mL). The resulting solution was stirred at −10° C. for 2 hours; HPLC analysis indicated the reaction was completed. The volatiles were removed on rotavapor. To the residue was added dichloromethane (10 mL). The resulting solution was evaporated on rotavapor to a residue again. The dichloromethane dissolution/evaporation was repeated three times. Then, the residue was dissolved in methanol (10 mL) and the resulting solution was evaporated to dryness on rotavapor; repeating the methanol dissolving and evaporating twice, then the residue was dissolved in water and then lyophilized to a white solid product (13-27), 86 mg; LCMS: MS m/z=707.4[M+H]⁺.

Example 37: Synthesis of Compound 13-28

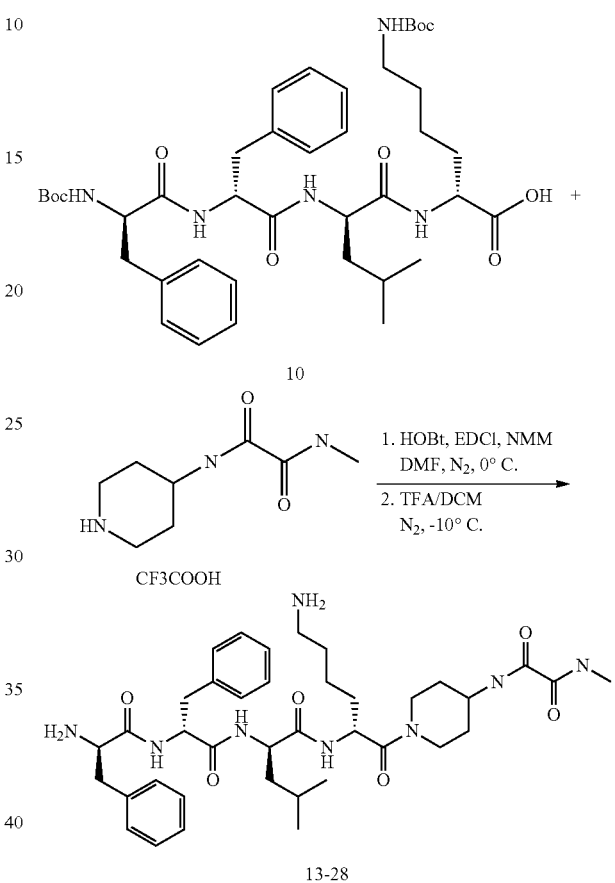

13-28

Into a reaction flask under nitrogen was added compound (10) (200 mg, 0.265 mmol, 1.0 eq) and DMF (4.2 mL) under nitrogen. The resulting reaction mixture was cooled to 0° C. in ice bath. To the cooled reaction mixture was added HOBt. $H_2O$ (60.94 mg, 0.398 mmol, 1.5 eq) and EDCI (76.28 mg, 0.398 mmol, 1.5 eq). After stirring for 30 minutes in ice bath, N-methyl-N'-(4-piperidyl)oxamide; 2,2,2-trifluoroacetic acid (119.0 mg, 0.398 mmol, 1.5 eq) and N-methylmorpholine (NMM) (200 mg, 1.977 mmol, 7.4 eq) were added. The reaction mixture was stirred at 0° C. for 3 hours, HPLC analysis indicated the reaction was completed. The reaction solution was added dropwise into water (15 mL) with stirring. After addition was completed, stirring was stopped and a precipitate formed. The reaction mixture stood for one hour. The precipitate was collected by filtration, washed with water (15 mL×4) and then dried under vacuum (30° C.). The isolated solid intermediate was a white solid, 0.180 g, LCMS: m/z=921.5[M+H]⁺.

The intermediate obtained above (100 mg, 0.109 mmol, 1.0 eq) was placed into a reaction flask under nitrogen; to the flask was added dichloromethane (2 mL); the resulting solution was cooled to −10° C. for 10 minutes; then to the cooled reaction was added a mixture of TFA (2 mL) and dichloromethane (4 mL). The resulting solution was stirred at −10° C. for 2 hours; HPLC analysis indicated the reaction was completed. The volatiles were removed on rotavapor. To the residue was added dichloromethane (10 mL). The resulting solution was evaporated on rotavapor to a residue again. The dichloromethane dissolution/evaporation was repeated three times. Then, the residue was dissolved in methanol (10 mL) and the resulting solution was evaporated to dryness on rotavapor; repeating the methanol dissolving and evaporating twice, then the residue was dissolved in water and then lyophilized to a white solid product (13-28), 94 mg, 91.2% yield; LCMS: MS m/z=721.4[M+H]$^+$.

Example 38: Synthesis of Compound 13-29

Into a reaction flask under nitrogen was added compound (10) (500 mg, 0.663 mmol, 1.0 eq) and DMF (10.6 mL) under nitrogen. The resulting reaction mixture was cooled to 0° C. in ice bath. To the cooled reaction mixture was added HOBt. H$_2$O (152.34 mg, 0.995 mmol, 1.5 eq) and EDCI (190.7 mg, 0.995 mmol, 1.5 eq). After stirring for 30 minutes in ice bath, methyl 2-oxo-2-(4-piperidylamino)acetate; 2,2,2-trifluoroacetic acid (269.0 mg, 0.896 mmol, 1.35 eq) and N-methylmorpholine (NMM) (260 mg, 2.57 mmol, 3.88 eq) were added. The reaction mixture was stirred at 0° C. for 10 hours, HPLC analysis indicated the reaction was completed. The reaction solution was added dropwise into water (30 mL) with stirring. After addition was completed, stirring was stopped and a precipitate formed. The reaction mixture stood for one hour. The precipitate was collected by filtration, washed with water (25 mL×3) and then dried under vacuum (30° C.). The isolated solid intermediate was a white solid, 0.60 g, LCMS: m/z=922.5[M+H]$^+$.

The intermediate obtained above (400 mg, 0.434 mmol, 1.0 eq) was placed into a reaction flask under nitrogen; to the flask was added dichloromethane (8 mL); the resulting solution was cooled to −10° C. for 10 minutes; then to the cooled reaction was added a mixture of TFA (7 mL) and dichloromethane (14 mL). The resulting solution was stirred at −10° C. for 2 hours; HPLC analysis indicated the reaction was completed. The volatiles were removed on rotavapor. To the residue was added dichloromethane (15 mL). The resulting solution was evaporated on rotavapor to a residue again. The dichloromethane dissolution/evaporation was repeated three times. Then, the residue was dissolved in methanol (15 mL) and the resulting solution was evaporated to dryness on rotavapor; repeating the methanol dissolving and evaporating twice, then the residue was dissolved in water and then lyophilized to a white solid product (13-29), 300 mg; LCMS: MS m/z=722.4[M+H]$^+$.

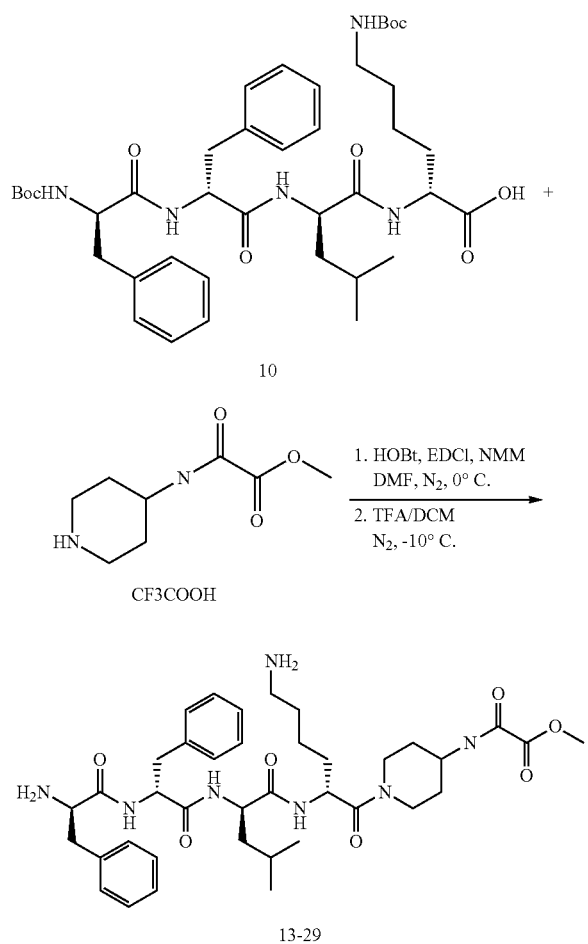

Example 39: Synthesis of Compound 13-30

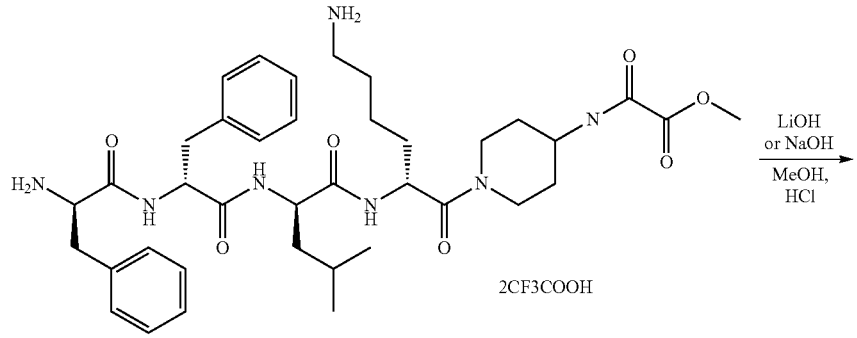

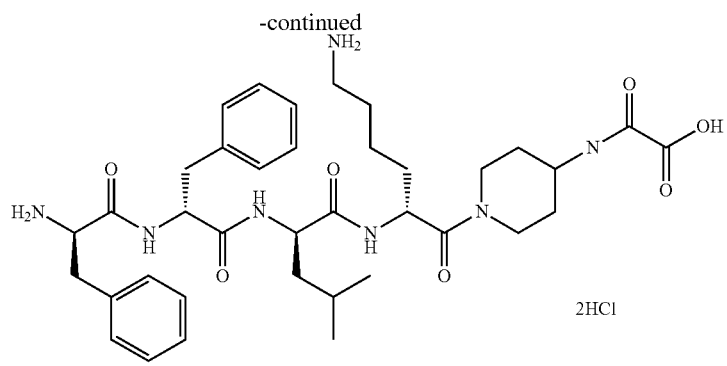

13-30

The compound (13-29) (150 mg, 0.158 mmol, 1.0 eq) was placed into a reaction flask under nitrogen, followed by adding methanol (3 mL). To the resulting solution was added a solution of NaOH (0.75 mL, 1.0 M, 0.75 mmol), 4.8 eq.) dropwise. The reaction mixture was stirred at room temperature for 2 hours until HPLC analysis indicated the reaction was completed. Then, HCl solution (1.0 M) was added dropwise until pH=4~5 was achieved. The solution was then purified on reverse-phase HPLC, the collection fraction was lyophillized and it provided a white solid product (13-30), 50 mg, yield=40.6%. LC-MS m/z=708.4 [M+H]$^+$.

Example 40: Synthesis of Compound 13-31

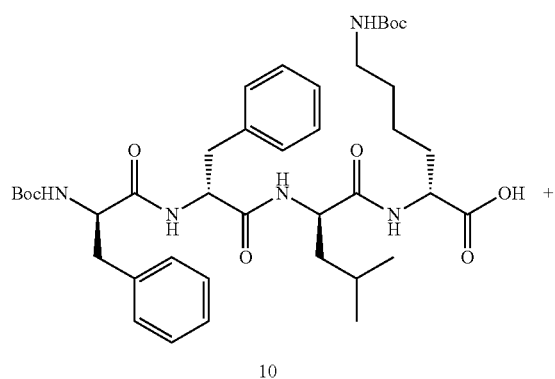

10

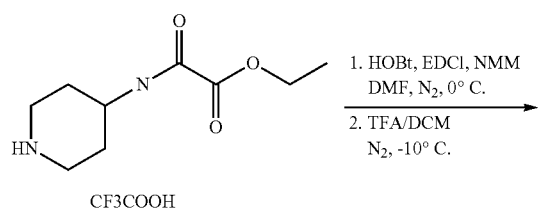

CF3COOH

1. HOBt, EDCl, NMM DMF, N$_2$, 0° C.
2. TFA/DCM N$_2$, -10° C.

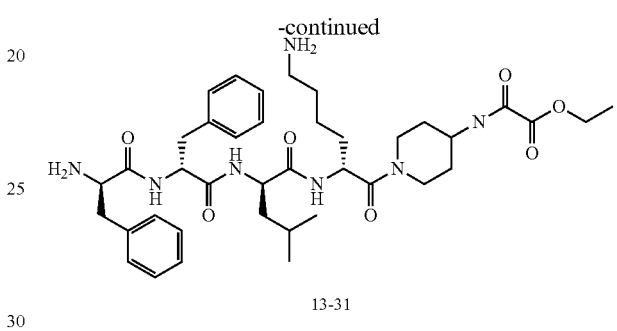

13-31

Into a reaction flask under nitrogen was added compound (10) (500 mg, 0.663 mmol, 1.0 eq) and DMF (10.6 mL) under nitrogen. The resulting reaction mixture was cooled to 0° C. in ice bath. To the cooled reaction mixture was added HOBt. H$_2$O (152.34 mg, 0.995 mmol, 1.5 eq) and EDCl (190.7 mg, 0.995 mmol, 1.5 eq). After stirring for 30 minutes in ice bath, ethyl 2-oxo-2-(4-piperidylamino)acetate; 2,2,2-trifluoroacetic acid (281.3 mg, 0.895 mmol, 1.35 eq) and N-methylmorpholine (NMM) (216 mg, 2.14 mmol, 3.2 eq) were added. The reaction mixture was stirred at 0° C. for 8 hours, HPLC analysis indicated the reaction was completed. The reaction solution was added dropwise into water (30 mL) with stirring. After addition was completed, stirring was stopped and a precipitate formed. The reaction mixture stood for one hour. The precipitate was collected by filtration, washed with water (25 mL×3) and then dried under vacuum (30° C.). The isolated solid intermediate was a white solid, 0.51 g, LCMS: m/z=936.5[M+H]$^+$.

The intermediate obtained above (400 mg, 0.427 mmol, 1.0 eq) was placed into a reaction flask under nitrogen; to the flask was added dichloromethane (8 mL); the resulting solution was cooled to -10° C. for 10 minutes; then to the cooled reaction was added a mixture of TFA (7 mL) and dichloromethane (14 mL). The resulting solution was stirred at -10° C. for 2 hours; HPLC analysis indicated the reaction was completed. The volatiles were removed on rotavapor. To the residue was added dichloromethane (15 mL). The resulting solution was evaporated on rotavapor to a residue again. The dichloromethane dissolution/evaporation was repeated three times. Then, the residue was dissolved in methanol (15 mL) and the resulting solution was evaporated to dryness on rotavapor; repeating the methanol dissolving and evaporating twice, then the residue was dissolved in water and then lyophilized to a white solid product (13-31), 348 mg, 84.5% yield; LCMS: MS m/z=736.4[M+H]$^+$.

Example 41: Synthesis of Compound 13-32

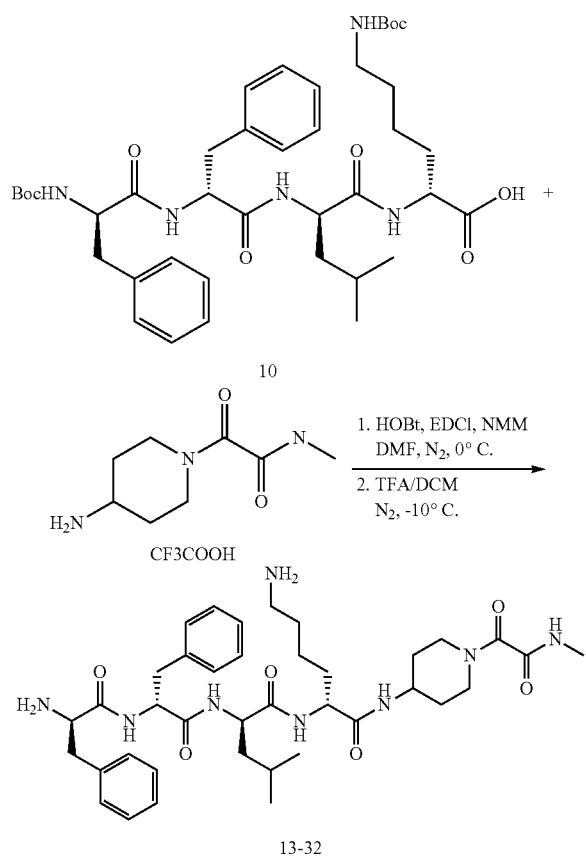

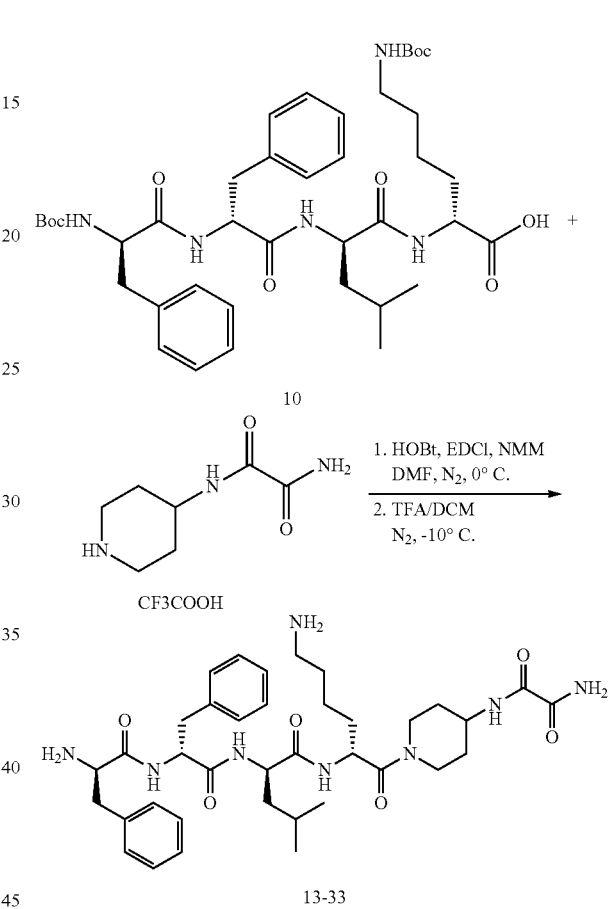

Into a reaction flask under nitrogen was added compound (10) (200 mg, 0.265 mmol, 1.0 eq) and DMF (4.2 mL) under nitrogen. The resulting reaction mixture was cooled to 0° C. in ice bath. To the cooled reaction mixture was added HOBt.H$_2$O (60.94 mg, 0.398 mmol, 1.5 eq) and EDCI (76.28 mg, 0.398 mmol, 1.5 eq). After stirring for 30 minutes in ice bath, 2-(4-amino-1-piperidyl)-N-methyl-2-oxo-acetamide; 2,2,2-trifluoroacetic acid (124.0 mg, 0.414 mmol, 1.56 eq) and N-methylmorpholine (NMM) (90 mg, 0.89 mmol, 3.4 eq) were added. The reaction mixture was stirred at 0° C. for 4 hours, HPLC analysis indicated the reaction was completed. The reaction solution was added dropwise into water (12 mL) with stirring. After addition was completed, stirring was stopped and a precipitate formed. The reaction mixture stood for one hour. The precipitate was collected by filtration, washed with water (15 mL×4) and then dried under vacuum (30° C.). The isolated solid intermediate was a white solid, 0.195 g, LCMS: m/z=921.5[M+H]$^+$.

The intermediate obtained above (120 mg, 0.130 mmol, 1.0 eq) was placed into a reaction flask under nitrogen; to the flask was added dichloromethane (2.4 mL); the resulting solution was cooled to −10° C. for 10 minutes; then to the cooled reaction was added a mixture of TFA (2.4 mL) and dichloromethane (4.8 mL). The resulting solution was stirred at −10° C. for 2 hours; HPLC analysis indicated the reaction was completed. The volatiles were removed on rotavapor. To the residue was added dichloromethane (10 mL). The resulting solution was evaporated on rotavapor to a residue again. The dichloromethane dissolution/evaporation was repeated three times. Then, the residue was dissolved in methanol (10 mL) and the resulting solution was evaporated to dryness on rotavapor; repeating the methanol dissolving and evaporating twice, then the residue was dissolved in water and then lyophilized to a white solid product (13-32), 112 mg, 90.6% yield; LCMS: MS m/z=721.4[M+H]$^+$.

Example 42: Synthesis of Compound 13-33

Into a reaction flask under nitrogen was added compound (10) (200 mg, 0.265 mmol, 1.0 eq) and DMF (4.2 mL) under nitrogen. The resulting reaction mixture was cooled to 0° C. in ice bath. To the cooled reaction mixture was added HOBt.H$_2$O (60.94 mg, 0.398 mmol, 1.5 eq) and EDCI (76.28 mg, 0.398 mmol, 1.5 eq). After stirring for 30 minutes in ice bath, N'-(4-piperidyl)oxamide; 2,2,2-trifluoroacetic acid (140.0 mg, 0.491 mmol, 1.85 eq) and N-methylmorpholine (NMM) (100 mg, 0.988 mmol, 3.7 eq) were added. The reaction mixture was stirred at 0° C. for 3 hours, HPLC analysis indicated the reaction was completed. The reaction solution was added dropwise into water (12 mL) with stirring. After addition was completed, stirring was stopped and a precipitate formed. The reaction mixture stood for one hour. The precipitate was collected by filtration, washed with water (15 mL×4) and then dried under vacuum (30° C.). The isolated solid intermediate was a white solid, 0.175 g, LCMS: m/z=907.5[M+H]$^+$.

The intermediate obtained above (120 mg, 0.132 mmol, 1.0 eq) was placed into a reaction flask under nitrogen; to the flask was added dichloromethane (2.4 mL); the resulting solution was cooled to −10° C. for 10 minutes; then to the cooled reaction was added a mixture of TFA (2.4 mL) and dichloromethane (4.8 mL). The resulting solution was stirred at −10° C. for 2 hours; HPLC analysis indicated the reaction was completed. The volatiles were removed on rotavapor. To the residue was added dichloromethane (10 mL). The resulting solution was evaporated on rotavapor to a residue again. The dichloromethane dissolution/evaporation was repeated three times. Then, the residue was dissolved in methanol (10 mL) and the resulting solution was evaporated to dryness on rotavapor; repeating the methanol dissolving and evaporating twice, then the residue was dissolved in water and then lyophilized to a white solid product (13-33), 109 mg, 88.1% yield; LCMS: MS m/z=707.4[M+H]$^+$.

Example 43: Synthesis of Compound 13-34

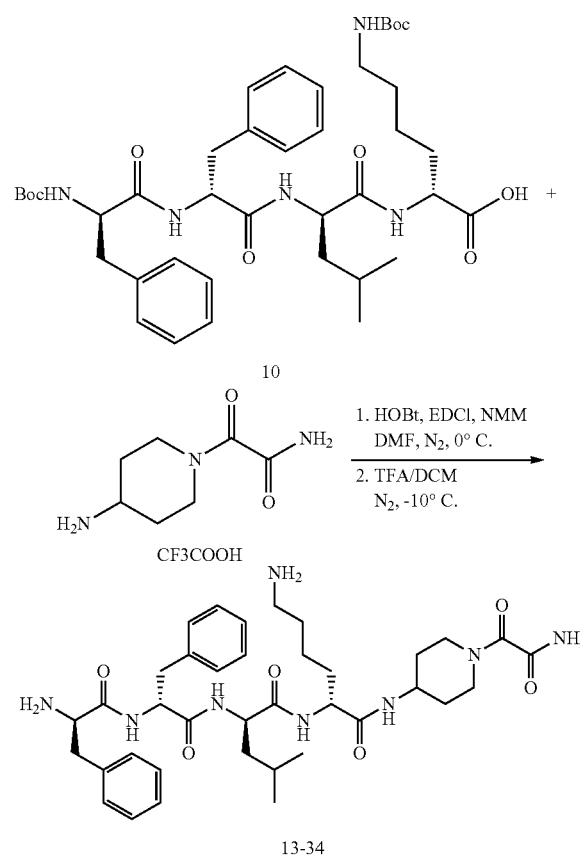

Into a reaction flask under nitrogen was added compound (10) (200 mg, 0.265 mmol, 1.0 eq) and DMF (4.2 mL) under nitrogen. The resulting reaction mixture was cooled to 0° C. in ice bath. To the cooled reaction mixture was added HOBt. H$_2$O (60.94 mg, 0.398 mmol, 1.5 eq) and EDCI (76.28 mg, 0.398 mmol, 1.5 eq). After stirring for 30 minutes in ice bath, 2-(4-amino-1-piperidyl)-2-oxo-acetamide; 2,2,2-trifluoroacetic acid (120.0 mg, 0.421 mmol, 1.59 eq) and N-methylmorpholine (NMM) (100 mg, 0.988 mmol, 3.7 eq) were added. The reaction mixture was stirred at 0° C. for 10 hours, HPLC analysis indicated the reaction was completed. The reaction solution was added dropwise into water (12 mL) with stirring. After addition was completed, stirring was stopped and precipitates formed. The reaction mixture stood for one hour. The precipitates were collected by filtration, washed with water (15 mL×4) and then dried under vacuum (30° C.). The isolated solid intermediate was a white solid, 0.183 g, LCMS: m/z=907.5[M+H]$^+$.

The intermediate obtained above (120 mg, 0.132 mmol, 1.0 eq) was placed into a reaction flask under nitrogen; to the flask was added dichloromethane (2.4 mL); the resulting solution was cooled to −10° C. for 10 minutes; then to the cooled reaction was added a mixture of TFA (2.4 mL) and dichloromethane (4.8 mL). The resulting solution was stirred at −10° C. for 2 hours; HPLC analysis indicated the reaction was completed. The volatiles were removed on rotavapor. To the residue was added dichloromethane (10 mL). The resulting solution was evaporated on rotavapor to a residue again. The dichloromethane dissolution/evaporation was repeated three times. Then, the residue was dissolved in methanol (10 mL) and the resulting solution was evaporated to dryness on rotavapor; repeating the methanol dissolving and evaporating twice, then the residue was dissolved in water and then lyophilized to a white solid product (13-34), 89 mg, 72.0% yield; LCMS: MS m/z=707.4[M+H]$^+$.

Example 44: Synthesis of Compound 13-35

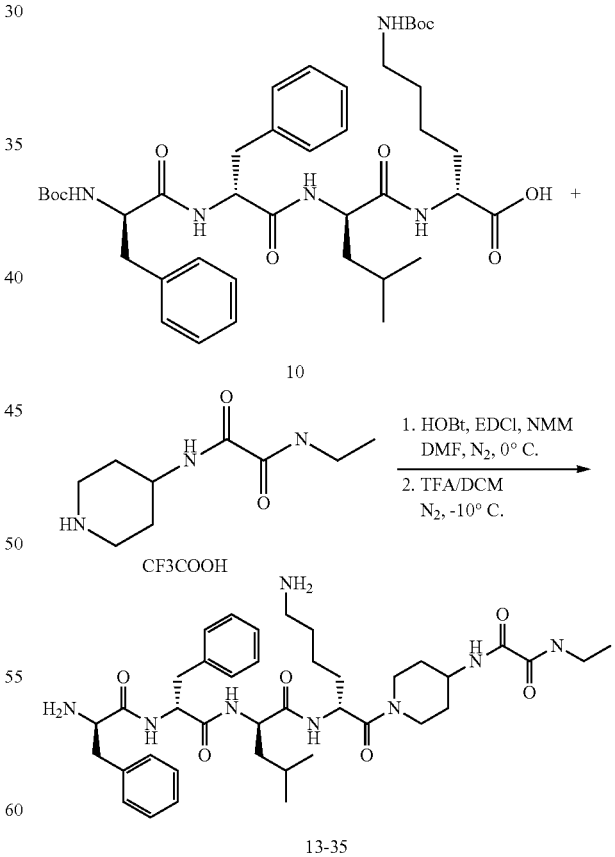

Into a reaction flask under nitrogen was added compound (10) (200 mg, 0.265 mmol, 1.0 eq) and DMF (4.2 mL) under nitrogen. The resulting reaction mixture was cooled to 0° C. in ice bath. To the cooled reaction mixture was added HOBt.

H₂O (60.94 mg, 0.398 mmol, 1.5 eq) and EDCI (76.28 mg, 0.398 mmol, 1.5 eq). After stirring for 30 minutes in ice bath, N-ethyl-N'-(4-piperidyl)oxamide; 2,2,2-trifluoroacetic acid (123.7 mg, 0.398 mmol, 1.50 eq) and N-methylmorpholine (NMM) (126 mg, 1.245 mmol, 4.6 eq) were added. The reaction mixture was stirred at 0° C. for 4 hours, HPLC analysis indicated the reaction was completed. The reaction solution was added dropwise into water (12 mL) with stirring. After addition was completed, stirring was stopped and a precipitate formed. The reaction mixture stood for one hour. The precipitate was collected by filtration, washed with water (15 mL×4) and then dried under vacuum (30° C.). The isolated solid intermediate was a white solid, 0.150 g, LCMS: m/z=935.6[M+H]⁺.

The intermediate obtained above (100 mg, 0.107 mmol, 1.0 eq) was placed into a reaction flask under nitrogen; to the flask was added dichloromethane (2.0 mL); the resulting solution was cooled to −10° C. for 10 minutes; then to the cooled reaction was added a mixture of TFA (2.0 mL) and dichloromethane (4.0 mL). The resulting solution was stirred at −10° C. for 2 hours; HPLC analysis indicated the reaction was completed. The volatiles were removed on rotavapor. To the residue was added dichloromethane (10 mL). The resulting solution was evaporated on rotavapor to a residue again. The dichloromethane dissolution/evaporation was repeated three times. Then, the residue was dissolved in methanol (10 mL) and the resulting solution was evaporated to dryness on rotavapor; repeating the methanol dissolving and evaporating twice, then the residue was dissolved in water and then lyophilized to a white solid product (13-35), 50 mg, 48.6% yield; LCMS: MS m/z=735.5[M+H]⁺.

Example 45: Synthesis of Compound 13-36

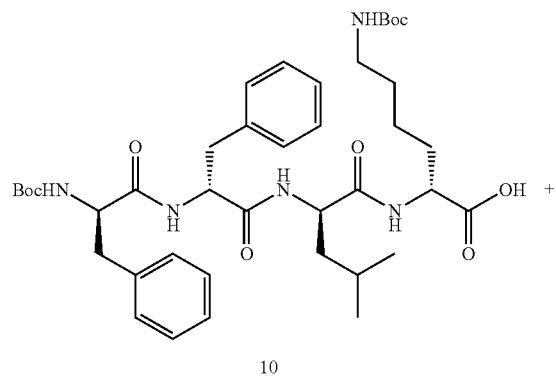

10

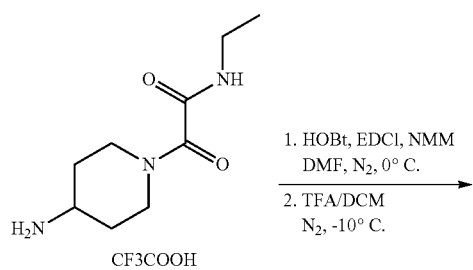

CF3COOH

1. HOBt, EDCl, NMM
   DMF, N₂, 0° C.
2. TFA/DCM
   N₂, -10° C.

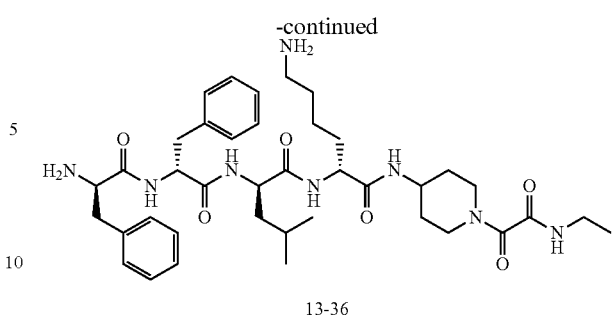

13-36

Into a reaction flask under nitrogen was added compound (10) (200 mg, 0.265 mmol, 1.0 eq) and DMF (4.2 mL) under nitrogen. The resulting reaction mixture was cooled to 0° C. in ice bath. To the cooled reaction mixture was added HOBt. H₂O (60.94 mg, 0.398 mmol, 1.5 eq) and EDCI (76.28 mg, 0.398 mmol, 1.5 eq). After stirring for 30 minutes in ice bath, 2-(4-amino-1-piperidyl)-N-ethyl-2-oxo-acetamide; 2,2,2-trifluoroacetic acid (123.7 mg, 0.398 mmol, 1.50 eq) and N-methylmorpholine (NMM) (126 mg, 1.245 mmol, 4.6 eq) were added. The reaction mixture was stirred at 0° C. for 4 hours, HPLC analysis indicated the reaction was completed. The reaction solution was added dropwise into water (12 mL) with stirring. After addition was completed, stirring was stopped and a precipitate formed. The reaction mixture stood for one hour. The precipitate was collected by filtration, washed with water (15 mL×4) and then dried under vacuum (30° C.). The isolated solid intermediate was a white solid, 100 mg, LCMS: m/z=935.6[M+H]⁺.

The intermediate obtained above (35 mg, 0.036 mmol, 1.0 eq) was placed into a reaction flask under nitrogen; to the flask was added dichloromethane (0.7 mL); the resulting solution was cooled to −10° C. for 10 minutes; then to the cooled reaction was added a mixture of TFA (0.7 mL) and dichloromethane (1.4 mL). The resulting solution was stirred at −10° C. for 2 hours; HPLC analysis indicated the reaction was completed. The volatiles were removed on rotavapor. To the residue was added dichloromethane (7 mL). The resulting solution was evaporated on rotavapor to a residue again. The dichloromethane dissolution/evaporation was repeated three times. Then, the residue was dissolved in methanol (7 mL) and the resulting solution was evaporated to dryness on rotavapor; repeating the methanol dissolving and evaporating twice, then the residue was dissolved in water and then lyophilized to a white solid product (13-36), 29 mg; LCMS: MS m/z=735.5[M+H]⁺.

Example 46: Synthesis of Compound 13-37

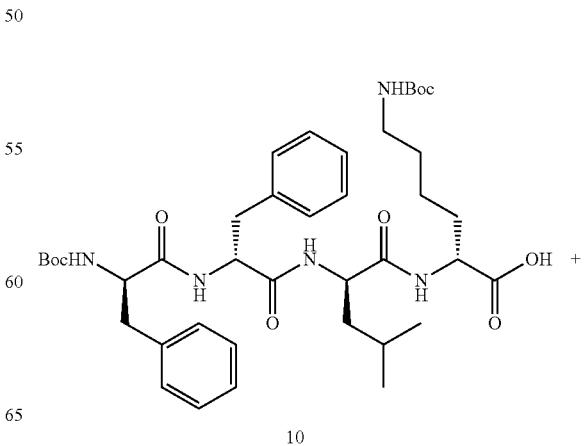

10

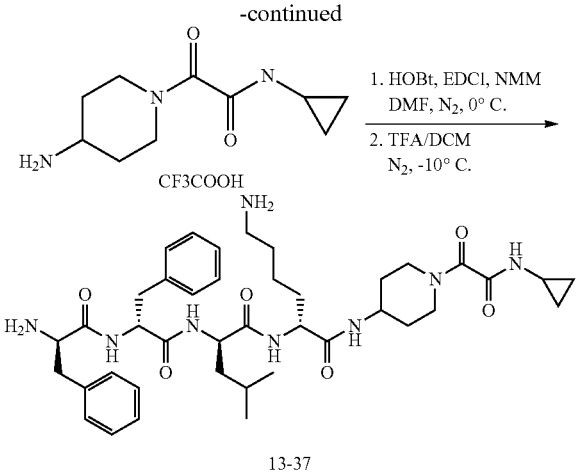

Into a reaction flask under nitrogen was added compound (10) (200 mg, 0.265 mmol, 1.0 eq) and DMF (4.2 mL) under nitrogen. The resulting reaction mixture was cooled to 0° C. in ice bath. To the cooled reaction mixture was added HOBt.H₂O (60.94 mg, 0.398 mmol, 1.5 eq) and EDCI (76.28 mg, 0.398 mmol, 1.5 eq). After stirring for 30 minutes in ice bath, 2-(4-amino-1-piperidyl)-N-cyclopropyl-2-oxo-acetamide; 2,2,2-trifluoroacetic acid (129.4 mg, 0.398 mmol, 1.50 eq) and N-methylmorpholine (NMM) (100 mg, 0.988 mmol, 3.7 eq) were added. The reaction mixture was stirred at 0° C. for 4 hours, HPLC analysis indicated the reaction was completed. The reaction solution was added dropwise into water (12 mL) with stirring. After addition was completed, stirring was stopped and a precipitate formed. The reaction mixture stood for one hour. The precipitate was collected by filtration, washed with water (15 mL×4) and then dried under vacuum (30° C.). The isolated solid intermediate was a white solid, 0.110 g, LCMS: m/z=947.6[M+H]⁺.

The intermediate obtained above (100 mg, 0.106 mmol, 1.0 eq) was placed into a reaction flask under nitrogen; to the flask was added dichloromethane (2 mL); the resulting solution was cooled to −10° C. for 10 minutes; then to the cooled reaction was added a mixture of TFA (2 mL) and dichloromethane (4 mL). The resulting solution was stirred at −10° C. for 3 hours; HPLC analysis indicated the reaction was completed. The volatiles were removed on rotavapor. To the residue was added dichloromethane (10 mL). The resulting solution was evaporated on rotavapor to a residue again. The dichloromethane dissolution/evaporation was repeated three times. Then, the residue was dissolved in methanol (10 mL) and the resulting solution was evaporated to dryness on rotavapor; repeating the methanol dissolving and evaporating twice, then the residue was dissolved in water and then lyophilized to a white solid product (13-37), 50 mg; LCMS: MS m/z=747.5[M+H]⁺.

Example 47: Synthesis of Compound 13-38

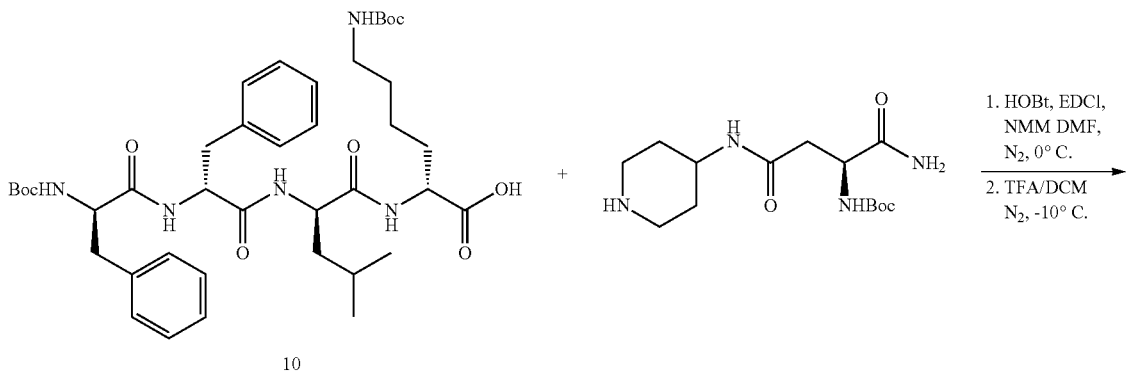

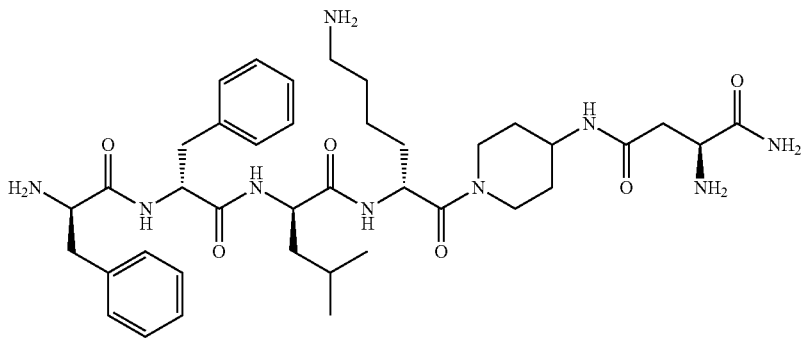

Into a reaction flask under nitrogen was added compound (10) (200 mg, 0.265 mmol, 1.0 eq) and DMF (4.2 mL) under nitrogen. The resulting reaction mixture was cooled to 0° C. in ice bath. To the cooled reaction mixture was added HOBt. H₂O (60.94 mg, 0.398 mmol, 1.5 eq) and EDCI (76.28 mg, ing twice, then to the residue was added ether (10 mL) to form white suspension; the mixture was evaporated on rotavapor and it provided a white solid product (13-38), 50 mg; LCMS: MS m/z=750.5[M+H]⁺.

Example 48: Synthesis of Compound 13-39

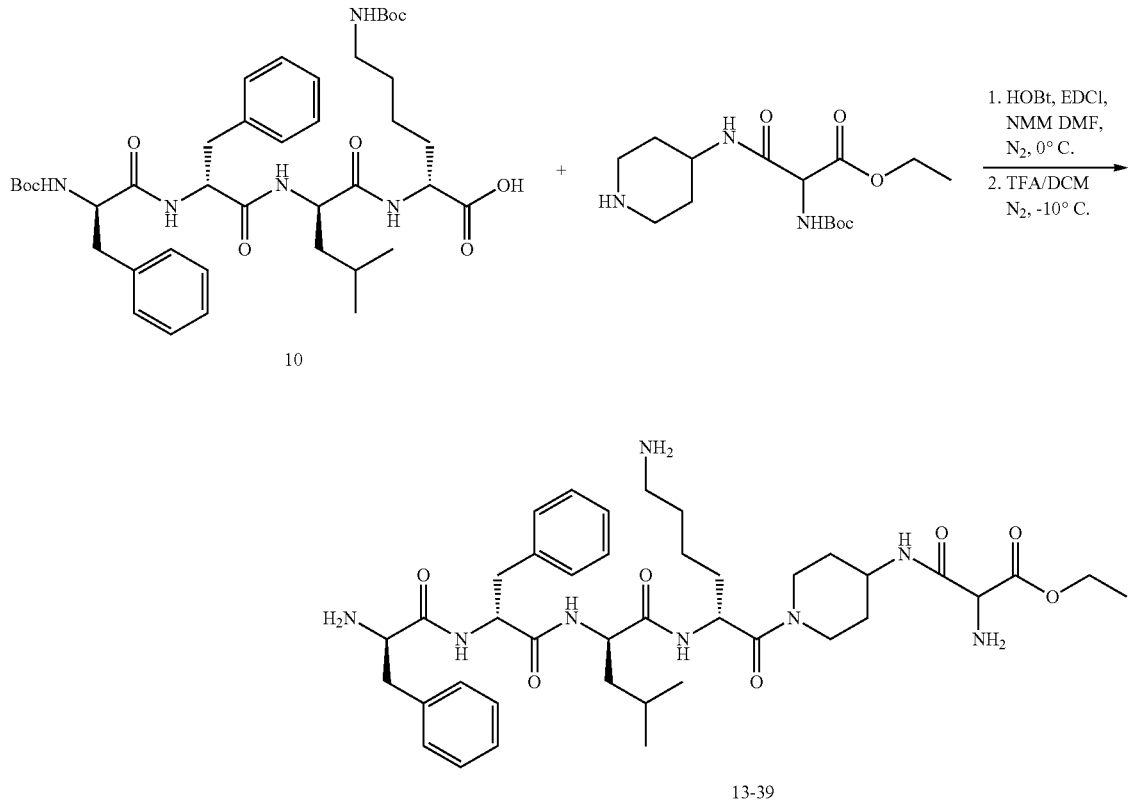

0.398 mmol, 1.5 eq). After stirring for 30 minutes in ice bath, tert-butyl N-[(1S)-1-carbamoyl-3-oxo-3-(4-piperidylamino)propyl]carbamate (125.5 mg, 0.399 mmol, 1.50 eq) and N-methylmorpholine (NMM) (100 mg, 0.988 mmol, 3.7 eq) were added. The reaction mixture was stirred at 0° C. for 2 hours, HPLC analysis indicated the reaction was completed. The reaction solution was added dropwise into water (12 mL) with stirring. After addition was completed, stirring was stopped and a precipitate formed. The reaction mixture stood for one hour. The precipitate was collected by filtration, washed with water (15 mL×4) and then dried under vacuum (30° C.). The isolated solid intermediate was a white solid, 0.217 g, LCMS: m/z=1050.6[M+H]⁺.

The intermediate obtained above (100 mg, 0.095 mmol, 1.0 eq) was placed into a reaction flask under nitrogen; to the flask was added dichloromethane (2 mL); the resulting solution was cooled to −10° C. for 10 minutes; then to the cooled reaction was added a mixture of TFA (2 mL) and dichloromethane (4 mL). The resulting solution was stirred at −10° C. for 3 hours; HPLC analysis indicated the reaction was completed. The volatiles were removed on rotavapor. To the residue was added dichloromethane (10 mL). The resulting solution was evaporated on rotavapor to a residue again. The dichloromethane dissolution/evaporation was repeated three times. Then, the residue was dissolved in methanol (10 mL) and the resulting solution was evaporated to dryness on rotavapor; repeating the methanol dissolving and evaporat- Into a reaction flask under nitrogen was added compound (10) (500 mg, 0.663 mmol, 1.0 eq) and DMF (10.6 mL) under nitrogen. The resulting reaction mixture was cooled to 0° C. in ice bath. To the cooled reaction mixture was added HOBt. H₂O (152.34 mg, 0.995 mmol, 1.5 eq) and EDCI (190.7 mg, 0.995 mmol, 1.5 eq). After stirring for 30 minutes in ice bath, ethyl 2-(tert-butoxycarbonylamino)-3-oxo-3-(4-piperidylamino)propanoate (330.0 mg, 1.002 mmol, 1.50 eq) and N-methylmorpholine (NMM) (234 mg, 2.32 mmol, 3.5 eq) were added. The reaction mixture was stirred at 0° C. for 2 hours, HPLC analysis indicated the reaction was completed. The reaction solution was added dropwise into water (30 mL) with stirring. After addition was completed, stirring was stopped and a precipitate formed. The reaction mixture stood for one hour. The precipitate was collected by filtration, washed with water (25 mL×3) and then dried under vacuum (30° C.). The isolated solid intermediate was a white solid, 0.537 g, LCMS: m/z=1065.6[M+H]⁺.

The intermediate obtained above (400 mg, 0.375 mmol, 1.0 eq) was placed into a reaction flask under nitrogen; to the flask was added dichloromethane (8 mL); the resulting solution was cooled to −10° C. for 10 minutes; then to the cooled reaction was added a mixture of TFA (7 mL) and dichloromethane (14 mL). The resulting solution was stirred at −10° C. for 3 hours; HPLC analysis indicated the reaction was completed. The volatiles were removed on rotavapor. To the residue was added dichloromethane (15 mL). The resulting solution was evaporated on rotavapor to a residue again. The dichloromethane dissolution/evaporation was repeated three times. Then, the residue was dissolved in methanol (15 mL) and the resulting solution was evaporated to dryness on rotavapor; repeating the methanol dissolving and evaporating twice, then to the residue was added ether (10 mL) to form white suspension; the mixture was evaporated on rotavapor and it provided a white solid product (13-39), 232 mg; LCMS: MS m/z=765.5[M+H]$^+$.

Example 49: Synthesis of Compound 13-40

The compound (13-39) (100 mg, 0.090 mmol, 1.0 eq) was placed into a reaction flask under nitrogen, followed by adding methanol (2 mL). To the resulting solution was added a solution of NaOH (0.5 mL, 1.0 M, 0.5 mmol, 5.6 eq.) dropwise. The reaction mixture was stirred at room temperature for 4 hours until HPLC analysis indicated the reaction was completed. Then, a HCl solution (1.0 M) was added dropwise until pH=4~5 was achieved. The solution was then purified on reverse-phase HPLC, the collection fraction was lyophillized and it provided a white solid product (13-40), 35 mg, LC-MS m/z=737.4 [M+H]$^+$.

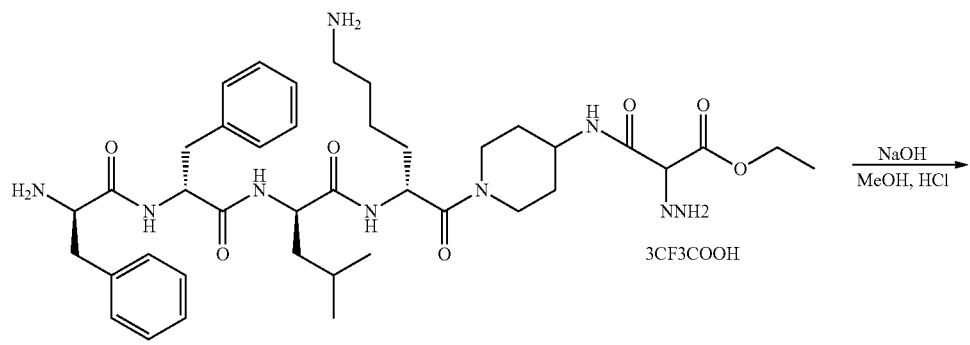

13-39

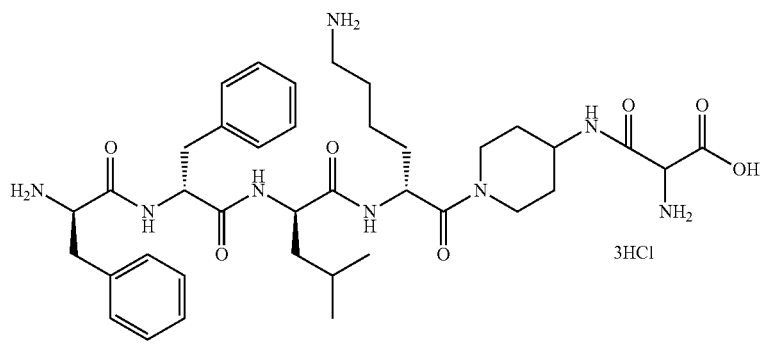

13-40

Example 50: Synthesis of Compound 13-41

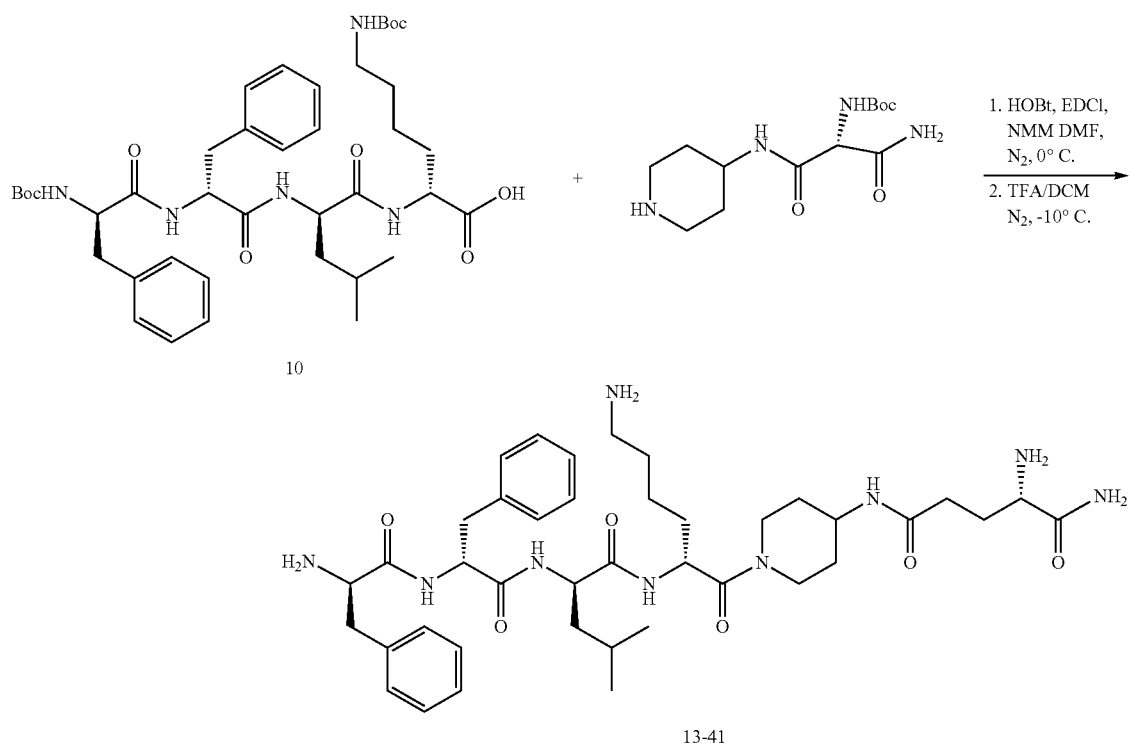

Into a reaction flask under nitrogen was added compound (10) (200 mg, 0.265 mmol, 1.0 eq) and DMF (4.2 mL) under nitrogen. The resulting reaction mixture was cooled to 0° C. in ice bath. To the cooled reaction mixture was added HOBt.H₂O (60.94 mg, 0.398 mmol, 1.5 eq) and EDCI (76.28 mg, 0.398 mmol, 1.5 eq). After stirring for 30 minutes in ice bath, tert-butyl N-[(1S)-1-carbamoyl-4-oxo-4-(4-piperidylamino)butyl]carbamate (131.0 mg, 0.398 mmol, 1.50 eq) and N-methylmorpholine (NMM) (100 mg, 0.988 mmol, 3.7 eq) were added. The reaction mixture was stirred at 0° C. for 2 hours, HPLC analysis indicated the reaction was completed. The reaction solution was added dropwise into water (12 mL) with stirring. After addition was completed, stirring was stopped and a precipitate formed. The reaction mixture stood for one hour. The precipitate was collected by filtration, washed with water (15 mL×4) and then dried under vacuum (30° C.). The isolated solid intermediate was a white solid, 0.190 g, LCMS: m/z=1064.6 [M+H]⁺.

The intermediate obtained above (100 mg, 0.094 mmol, 1.0 eq) was placed into a reaction flask under nitrogen; to the flask was added dichloromethane (2 mL); the resulting solution was cooled to −10° C. for 10 minutes; then to the cooled reaction was added a mixture of TFA (2 mL) and dichloromethane (4 mL). The resulting solution was stirred at −10° C. for 3 hours; HPLC analysis indicated the reaction was completed. The volatiles were removed on rotavapor. To the residue was added dichloromethane (10 mL). The resulting solution was evaporated on rotavapor to a residue again. The dichloromethane dissolution/evaporation was repeated three times. Then, the residue was dissolved in methanol (10 mL) and the resulting solution was evaporated to dryness on rotavapor; repeating the methanol dissolving and evaporating twice, then to the residue was added ether (10 mL) to form white suspension; the mixture was evaporated on rotavapor and it provided a white solid product (13-41), 69 mg; LCMS: MS m/z=764.5[M+H]⁺.

Example 51: Synthesis of Compound 13-42

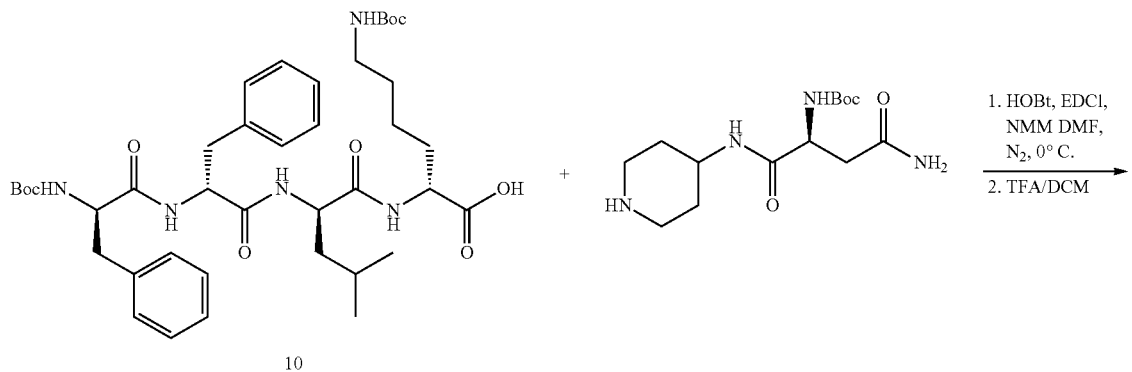

-continued

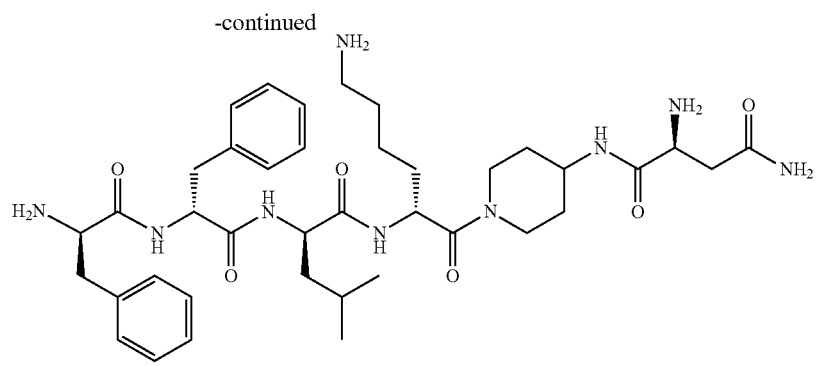

13-42

Into a reaction flask under nitrogen was added compound (10) (200 mg, 0.265 mmol, 1.0 eq) and DMF (4.2 mL) under nitrogen. The resulting reaction mixture was cooled to 0° C. in ice bath. To the cooled reaction mixture was added HOBt.H$_2$O (60.94 mg, 0.398 mmol, 1.5 eq) and EDCI (76.28 mg, 0.398 mmol, 1.5 eq). After stirring for 30 minutes in ice bath, tert-butyl N-[(1S)-3-amino-3-oxo-1-(4-piperidylcarbamoyl) propyl]carbamate (125.0 mg, 0.398 mmol, 1.50 eq) and N-methylmorpholine (NMM) (100 mg, 0.988 mmol, 3.7 eq) were added. The reaction mixture was stirred at 0° C. for 10 hours, HPLC analysis indicated the reaction was completed. The reaction solution was added dropwise into water (12 mL) with stirring. After addition was completed, stirring was stopped and a precipitate formed. The reaction mixture stood for one hour. The precipitate was collected by filtration, washed with water (15 mL×4) and then dried under vacuum (30° C.). The isolated solid intermediate was a white solid, 0.215 g, LCMS: m/z=1050.6 [M+H]$^+$.

The intermediate obtained above (150 mg, 0.143 mmol, 1.0 eq) was placed into a reaction flask under nitrogen; to the flask was added dichloromethane (3 mL); the resulting solution was cooled to −10° C. for 10 minutes; then to the cooled reaction was added a mixture of TFA (3 mL) and dichloromethane (6 mL). The resulting solution was stirred at −10° C. for 4 hours; HPLC analysis indicated the reaction was completed. The volatiles were removed on rotavapor. To the residue was added dichloromethane (15 mL). The resulting solution was evaporated on rotavapor to a residue again. The dichloromethane dissolution/evaporation was repeated three times. Then, the residue was dissolved in methanol (15 mL) and the resulting solution was evaporated to dryness on rotavapor; repeating the methanol dissolving and evaporating twice, then to the residue was added ether (15 mL) to form white suspension; the mixture was evaporated on rotavapor and it provided a white solid product (13-42), 144 mg; LCMS: MS m/z=750.5[M+H]$^+$.

Example 52: Synthesis of Compound 13-43

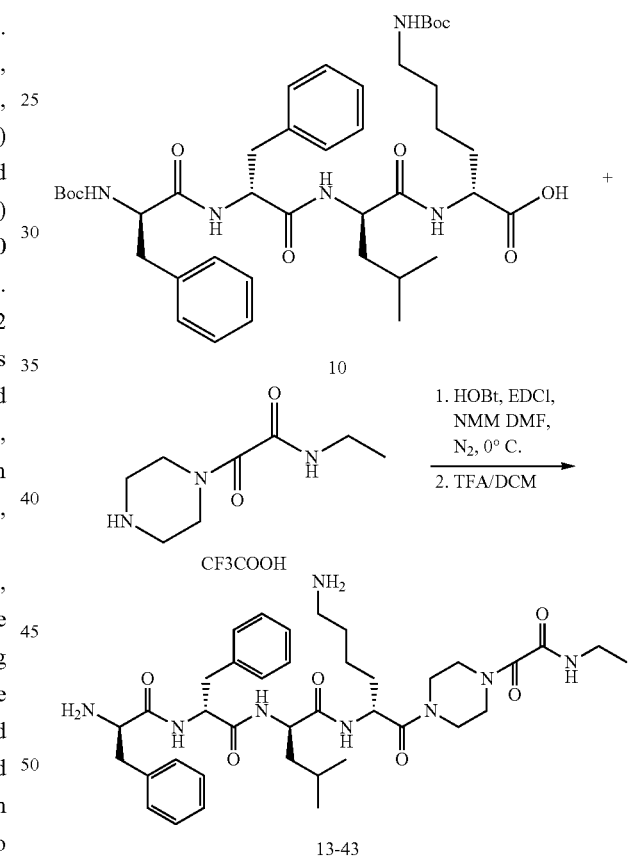

Into a reaction flask under nitrogen was added compound (10) (200 mg, 0.265 mmol, 1.0 eq) and DMF (4.2 mL) under nitrogen. The resulting reaction mixture was cooled to 0° C. in ice bath. To the cooled reaction mixture was added HOBt.H$_2$O (60.94 mg, 0.398 mmol, 1.5 eq) and EDCI (76.28 mg, 0.398 mmol, 1.5 eq). After stirring for 30 minutes in ice bath, N-ethyl-2-oxo-2-piperazin-1-yl-acetamide; 2,2,2-trifluoroacetic acid (119.1 mg, 0.398 mmol, 1.50 eq) and N-methylmorpholine (NMM) (72 mg, 0.663 mmol, 2.5 eq) were added. The reaction mixture was stirred at 0° C. for 10 hours, HPLC analysis indicated the reaction was completed. The reaction solution was added dropwise into water (12 mL)

with stirring. After addition was completed, stirring was stopped and a precipitate formed. The reaction mixture stood for one hour. The precipitate was collected by filtration, washed with water (15 mL×4) and then dried under vacuum (30° C.). The isolated solid intermediate was a white solid, 0.197 g, LCMS: m/z=921.5 [M+H]⁺.

The intermediate obtained above (100 mg, 0.109 mmol, 1.0 eq) was placed into a reaction flask under nitrogen; to the flask was added dichloromethane (2 mL); the resulting solution was cooled to −10° C. for 10 minutes; then to the cooled reaction was added a mixture of TFA (2 mL) and dichloromethane (4 mL). The resulting solution was stirred at −10° C. for 4 hours; HPLC analysis indicated the reaction was completed. The volatiles were removed on rotavapor. To the residue was added dichloromethane (10 mL). The resulting solution was evaporated on rotavapor to a residue again. The dichloromethane dissolution/evaporation was repeated three times. Then, the residue was dissolved in methanol (10 mL) and the resulting solution was evaporated to dryness on rotavapor; repeating the methanol dissolving and evaporating twice, then to the residue was added ether (10 mL) to form white suspension; the mixture was evaporated on rotavapor and it provided a white solid product (13-43), 75 mg; LCMS: MS m/z=721.4[M+H]⁺.

Example 53: Synthesis of Compound 13-44

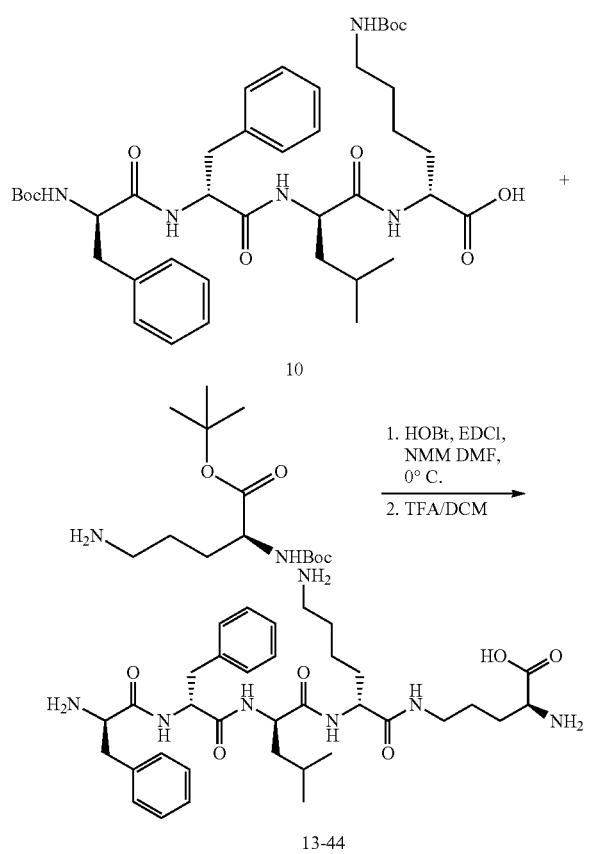

13-44

Into a reaction flask under nitrogen was added compound (10) (200 mg, 0.260 mmol, 1.0 eq) and DMF (4.2 mL) under nitrogen. The resulting reaction mixture was cooled to 0° C. in ice bath. To the cooled reaction mixture was added HOBt.

H₂O (40 mg, 0.312 mmol, 1.2 eq) and EDCI (60 mg, 0.312 mmol, 1.2 eq). After stirring for 30 minutes in ice bath, tert-butyl (2S)-5-amino-2-(tert-butoxycarbonylamino)pentanoate (90 mg, 0.312 mmol, 1.20 eq) and N-methylmorpholine (NMM) (32 mg, 0.312 mmol, 1.2 eq) were added. The reaction mixture was stirred at 0° C. for 2 hours, HPLC analysis indicated the reaction was completed. The reaction solution was added dropwise into water (12 mL) with stirring. After addition was completed, stirring was stopped and a precipitate formed. The reaction mixture stood for one hour. The precipitate was collected by filtration, washed with water (15 mL×4) and then dried under vacuum (30° C.). The isolated solid intermediate was a white solid, 0.231 g, LCMS: m/z=1024.63 [M+H]⁺.

The intermediate obtained above (100 mg, 0.10 mmol, 1.0 eq) was placed into a reaction flask under nitrogen; to the flask was added dichloromethane (2 mL); the resulting solution was cooled to −10° C. for 10 minutes; then to the cooled reaction was added a mixture of TFA (2 mL) and dichloromethane (4 mL). The resulting solution was stirred at −10° C. for 4 hours; HPLC analysis indicated the reaction was completed. The volatiles were removed on rotavapor. To the residue was added dichloromethane (10 mL). The resulting solution was evaporated on rotavapor to a residue again. The dichloromethane dissolution/evaporation was repeated three times. Then, the residue was dissolved in methanol (10 mL) and the resulting solution was evaporated to dryness on rotavapor; repeating the methanol dissolving and evaporating twice, then to the residue was added ether (10 mL) to form white suspension; the mixture was evaporated on rotavapor and it provided a white solid product (13-44), 73 mg; LCMS: MS m/z=668.4[M+H]⁺.

Example 54: Synthesis of Compound 13-45

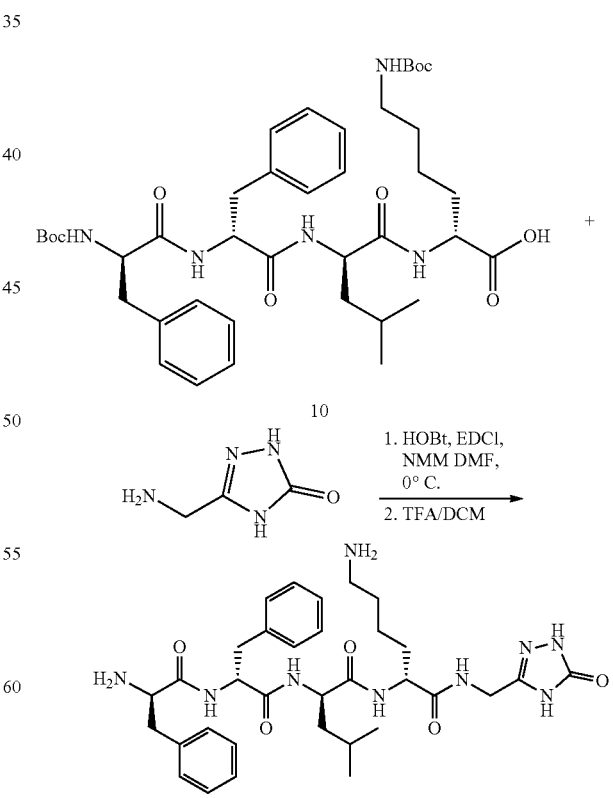

13-45

Into a reaction flask under nitrogen was added compound (10) (1.15 g, 1.53 mmol, 1.0 eq) and DMF (24 mL) under nitrogen. The resulting reaction mixture was cooled to 0° C. in ice bath. To the cooled reaction mixture was added HOBt.H₂O (280 mg, 1.84 mmol, 1.2 eq) and EDCI (350 mg, 1.84 mmol, 1.2 eq). After stirring for 30 minutes in ice bath, 3-(aminomethyl)-1,4-dihydro-1,2,4-triazol-5-one (210 mg, 1.84 mmol, 1.20 eq) and N-methylmorpholine (NMM) (180 mg, 1.84 mmol, 1.2 eq) were added. The reaction mixture was stirred at 0° C. for 2 hours, HPLC analysis indicated the reaction was completed. The reaction solution was added dropwise into water (69 mL) with stirring. After addition was completed, stirring was stopped and a precipitate formed. The reaction mixture stood for one hour. The precipitate was collected by filtration, washed with water (85 mL×4) and then dried under vacuum (30° C.). The isolated solid intermediate was a white solid, 1.12 g, LCMS: m/z=850.5 [M+H]⁺.

The intermediate obtained above (750 mg, 0.89 mmol, 1.0 eq) was placed into a reaction flask under nitrogen; to the flask was added dichloromethane (15 mL); the resulting solution was cooled to −10° C. for 10 minutes; then to the cooled reaction was added a mixture of TFA (15 mL) and dichloromethane (30 mL). The resulting solution was stirred at −10° C. for 4 hours; HPLC analysis indicated the reaction was completed. The volatiles were removed on rotavapor. To the residue was added dichloromethane (75 mL). The resulting solution was evaporated on rotavapor to a residue again. The dichloromethane dissolution/evaporation was repeated three times. Then, the residue was dissolved in methanol (75 mL) and the resulting solution was evaporated to dryness on rotavapor; repeating the methanol dissolving and evaporating twice, then to the residue was added ether (75 mL) to form white suspension; the mixture was evaporated on rotavapor and it provided a white solid product (13-45), 505 mg; LCMS: MS m/z=650.4[M+H]⁺.

Example 55: Synthesis of Compound 13-46

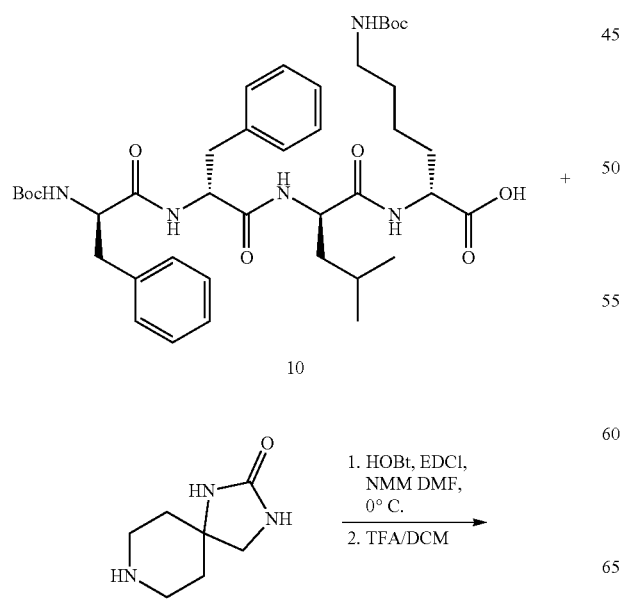

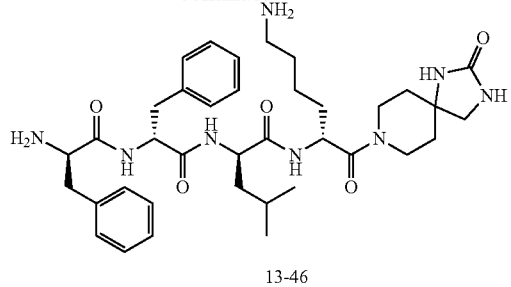

13-46

Into a reaction flask under nitrogen was added compound (10) (0.27 g, 0.358 mmol, 1.0 eq) and DMF (6 mL) under nitrogen. The resulting reaction mixture was cooled to 0° C. in ice bath. To the cooled reaction mixture was added HOBt.H₂O (66 mg, 0.43 mmol, 1.2 eq) and EDCI (82 mg, 0.43 mmol, 1.2 eq). After stirring for 30 minutes in ice bath, 1,3,8-triazaspiro[4.5]decan-2-one (66 mg, 0.43 mmol, 1.20 eq) and N-methylmorpholine (NMM) (43 mg, 0.43 mmol, 1.2 eq) were added. The reaction mixture was stirred at 0° C. for 2 hours, HPLC analysis indicated the reaction was completed. The reaction solution was added dropwise into water (16.2 mL) with stirring. After addition was completed, stirring was stopped and a precipitate formed. The reaction mixture stood for one hour. The precipitate was collected by filtration, washed with water (20 mL×4) and then dried under vacuum (30° C.). The isolated solid intermediate was a white solid, 0.271 g, LCMS: m/z=891.5 [M+H]⁺.

The intermediate obtained above (130 mg, 0.15 mmol, 1.0 eq) was placed into a reaction flask under nitrogen; to the flask was added dichloromethane (2.6 mL); the resulting solution was cooled to −10° C. for 10 minutes; then to the cooled reaction was added a mixture of TFA (2.6 mL) and dichloromethane (5.2 mL). The resulting solution was stirred at −10° C. for 4 hours; HPLC analysis indicated the reaction was completed. The volatiles were removed on rotavapor. To the residue was added dichloromethane (13 mL). The resulting solution was evaporated on rotavapor to a residue again. The dichloromethane dissolution/evaporation was repeated three times. Then, the residue was dissolved in methanol (13 mL) and the resulting solution was evaporated to dryness on rotavapor; repeating the methanol dissolving and evaporating twice, then to the residue was added ether (13 mL) to form white suspension; the mixture was evaporated on rotavapor and it provided a white solid product (13-46), 160 mg; LCMS: MS m/z=650.4 [M+H]⁺.

Example 56: Synthesis of Compound 13-47

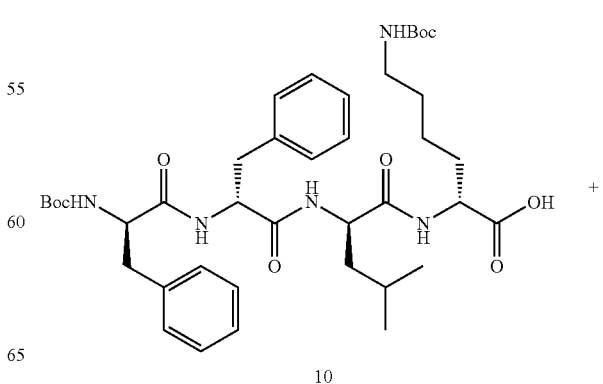

10

-continued

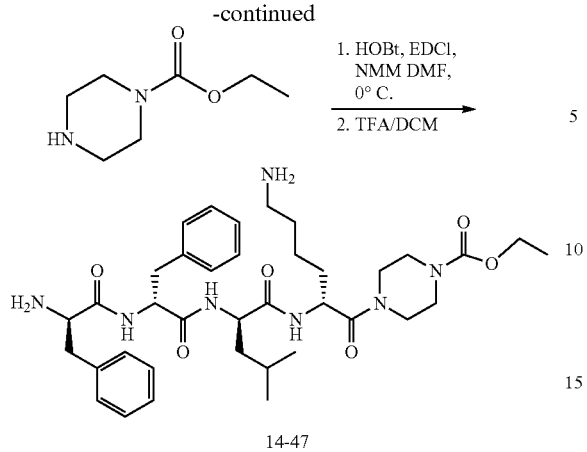

14-47

Example 57: Synthesis of Compound 13-48

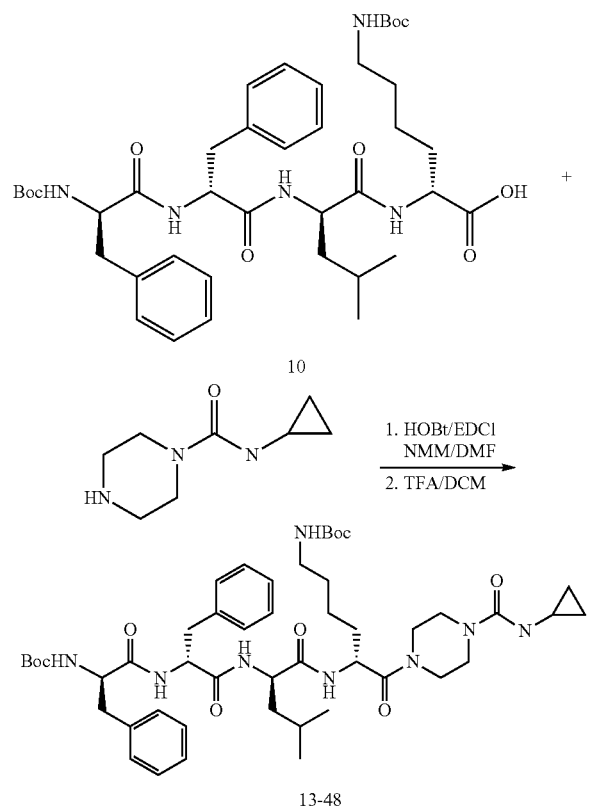

13-48

Into a reaction flask under nitrogen was added compound (10) (1.14 g, 1.51 mmol, 1.0 eq) and DMF (25 mL) under nitrogen. The resulting reaction mixture was cooled to 0° C. in ice bath. To the cooled reaction mixture was added HOBt. $H_2O$ (0.28 mg, 1.81 mmol, 1.2 eq) and EDCI (350 mg, 1.81 mmol, 1.2 eq). After stirring for 30 minutes in ice bath, ethyl piperazine-1-carboxylate (290 mg, 1.81 mmol, 1.20 eq) and N-methylmorpholine (NMM) (180 mg, 1.81 mmol, 1.2 eq) were added. The reaction mixture was stirred at 0° C. for 2 hours, HPLC analysis indicated the reaction was completed. The reaction solution was added dropwise into water (68 mL) with stirring. After addition was completed, stirring was stopped and a precipitate formed. The reaction mixture stood for one hour. The precipitate was collected by filtration, washed with water (85 mL×4) and then dried under vacuum (30° C.). The isolated solid intermediate was a white solid, 1.15 g, LCMS: m/z=894.5 [M+H]$^+$.

The intermediate obtained above (120 mg, 0.131 mmol, 1.0 eq) was placed into a reaction flask under nitrogen; to the flask was added dichloromethane (2.4 mL); the resulting solution was cooled to −10° C. for 10 minutes; then to the cooled reaction was added a mixture of TFA (2.4 mL) and dichloromethane (4.8 mL). The resulting solution was stirred at −10° C. for 4 hours; HPLC analysis indicated the reaction was completed. The volatiles were removed on rotavapor. To the residue was added dichloromethane (12 mL). The resulting solution was evaporated on rotavapor to a residue again. The dichloromethane dissolution/evaporation was repeated three times. Then, the residue was dissolved in methanol (12 mL) and the resulting solution was evaporated to dryness on rotavapor; repeating the methanol dissolving and evaporating twice, then to the residue was added ether (12 mL) to form white suspension; the mixture was evaporated on rotavapor and it provided a white solid product (13-47), 100 mg; LCMS: MS m/z=694.4[M+H]$^+$.

Into a reaction flask under nitrogen was added compound (10) (1.14 g, 1.51 mmol, 1.0 eq) and DMF (25 mL) under nitrogen. The resulting reaction mixture was cooled to 0° C. in ice bath. To the cooled reaction mixture was added HOBt. $H_2O$ (170 mg, 1.13 mmol, 1.2 eq) and EDCI (220 mg, 1.13 mmol, 1.2 eq). After stirring for 30 minutes in ice bath, N-cyclopropylpiperazine-1-carboxamide (190 mg, 1.13 mmol, 1.20 eq) and N-methylmorpholine (NMM) (110 mg, 1.13 mmol, 1.2 eq) were added. The reaction mixture was stirred at 0° C. for 2 hours, HPLC analysis indicated the reaction was completed. The reaction solution was added dropwise into water (69 mL) with stirring. After addition was completed, stirring was stopped and a precipitate formed. The reaction mixture stood for one hour. The precipitate was collected by filtration, washed with water (85 mL×4) and then dried under vacuum (30° C.). The isolated solid intermediate was a white solid, 0.735 g, LCMS: m/z=905.5 [M+H]$^+$.

The intermediate obtained above (510 mg, 0.56 mmol, 1.0 eq) was placed into a reaction flask under nitrogen; to the flask was added dichloromethane (10.2 mL); the resulting solution was cooled to −10° C. for 10 minutes; then to the cooled reaction was added a mixture of TFA (2.6 mL) and dichloromethane (5.2 mL). The resulting solution was stirred at −10° C. for 4 hours; HPLC analysis indicated the reaction was completed. The volatiles were removed on rotavapor. To the residue was added dichloromethane (13 mL). The resulting solution was evaporated on rotavapor to a residue again. The dichloromethane dissolution/evaporation was repeated three times. Then, the residue was dissolved in methanol (13 mL) and the resulting solution was evaporated to dryness on rotavapor; repeating the methanol dissolving and evaporating twice, then to the residue was added ether (13 mL) to form white suspension; the mixture was evaporated on rotavapor and it provided a white solid product (13-48), 441 mg; LCMS: MS m/z=705.4[M+H]$^+$.

Example 58: Synthesis of Compound 13-49

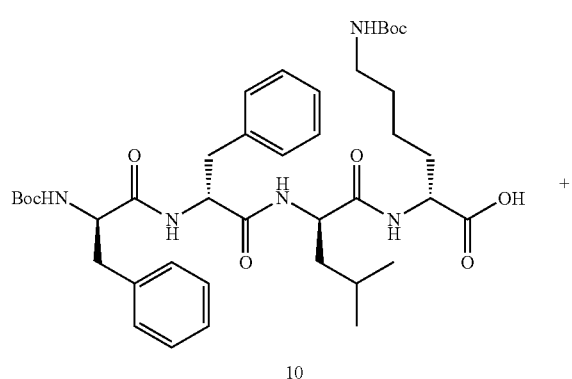

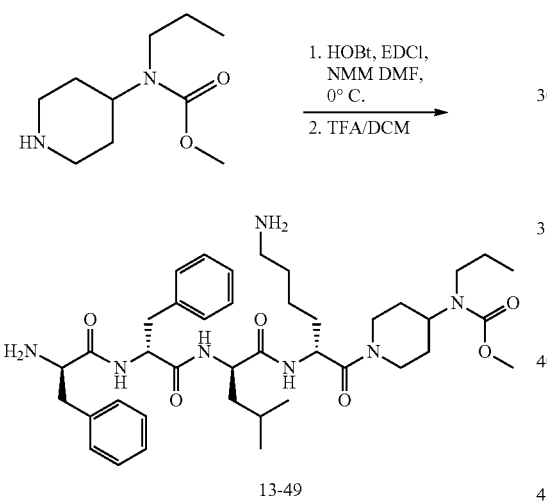

13-49

Into a reaction flask under nitrogen was added compound (10) (0.3 g, 0.4 mmol, 1.0 eq) and DMF (6.3 mL) under nitrogen. The resulting reaction mixture was cooled to 0° C. in ice bath. To the cooled reaction mixture was added HOBt. H$_2$O (74 mg, 0.48 mmol, 1.2 eq) and EDCI (92 mg, 0.48 mmol, 1.2 eq). After stirring for 30 minutes in ice bath, methyl N-(4-piperidyl)-N-propyl-carbamate (96 mg, 0.48 mmol, 1.20 eq) and N-methylmorpholine (NMM) (48 mg, 0.48 mmol, 1.2 eq) were added. The reaction mixture was stirred at 0° C. for 2 hours, HPLC analysis indicated the reaction was completed. The reaction solution was added dropwise into water (18 mL) with stirring. After addition was completed, stirring was stopped and a precipitate formed. The reaction mixture stood for one hour. The precipitate was collected by filtration, washed with water (22 mL×4) and then dried under vacuum (30° C.). The isolated solid intermediate was a white solid, 0.328 g, LCMS: m/z=921.5 [M+H]$^+$.

The intermediate obtained above (180 mg, 0.19 mmol, 1.0 eq) was placed into a reaction flask under nitrogen; to the flask was added dichloromethane (3.6 mL); the resulting solution was cooled to −10° C. for 10 minutes; then to the cooled reaction was added a mixture of TFA (3.6 mL) and dichloromethane (7.2 mL). The resulting solution was stirred at −10° C. for 4 hours; HPLC analysis indicated the reaction was completed. The volatiles were removed on rotavapor. To the residue was added dichloromethane (18 mL). The resulting solution was evaporated on rotavapor to a residue again. The dichloromethane dissolution/evaporation was repeated three times. Then, the residue was dissolved in methanol (18 mL) and the resulting solution was evaporated to dryness on rotavapor; repeating the methanol dissolving and evaporating twice, then to the residue was added ether (18 mL) to form white suspension; the mixture was evaporated on rotavapor and it provided a white solid product (13-49), 149 mg; LCMS: MS m/z=705.4[M+H]$^+$.

Example 59: Synthesis of Compound 13-50

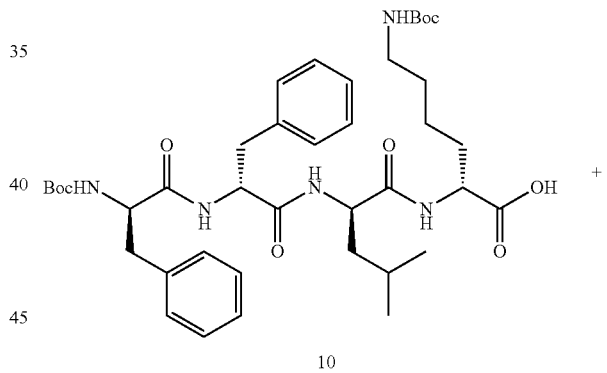

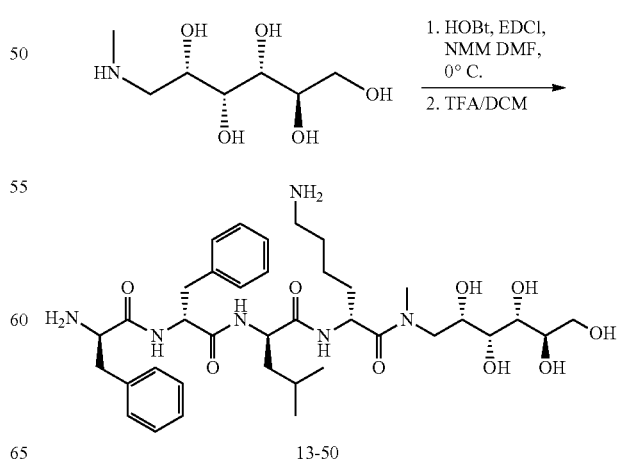

13-50

Into a reaction flask under nitrogen was added compound (10) (0.38 g, 0.51 mmol, 1.0 eq) and DMF (8.5 mL) under nitrogen. The resulting reaction mixture was cooled to 0° C. in ice bath. To the cooled reaction mixture was added HOBt. H₂O (74 mg, 0.61 mmol, 1.2 eq) and EDCI (120 mg, 0.61 mmol, 1.2 eq). After stirring for 30 minutes in ice bath, (2R,3R,4R,5S)-6-(methylamino)hexane-1,2,3,4,5-pentol (120 mg, 0.61 mmol, 1.20 eq) and N-methylmorpholine (NMM) (61 mg, 0.61 mmol, 1.2 eq) were added. The reaction mixture was stirred at 0° C. for 2 hours, HPLC analysis indicated the reaction was completed. The reaction solution was added dropwise into water (23 mL) with stirring. After addition was completed, stirring was stopped and a precipitate formed. The reaction mixture stood for one hour. The precipitate was collected by filtration, washed with water (24 mL×4) and then dried under vacuum (30° C.). The isolated solid intermediate was a white solid, 0.423 g, LCMS: m/z=931.5 [M+H]⁺.

The intermediate obtained above (98 mg, 0.105 mmol, 1.0 eq) was placed into a reaction flask under nitrogen; to the flask was added dichloromethane (3.6 mL); the resulting solution was cooled to −10° C. for 10 minutes; then to the cooled reaction was added a mixture of TFA (3.6 mL) and dichloromethane (7.2 mL). The resulting solution was stirred at −10° C. for 4 hours; HPLC analysis indicated the reaction was completed. The volatiles were removed on rotavapor. To the residue was added dichloromethane (18 mL). The resulting solution was evaporated on rotavapor to a residue again. The dichloromethane dissolution/evaporation was repeated three times. Then, the residue was dissolved in methanol (18 mL) and the resulting solution was evaporated to dryness on rotavapor; repeating the methanol dissolving and evaporating twice, then to the residue was added ether (18 mL) to form white suspension; the mixture was evaporated on rotavapor and it provided a white solid product (13-50), 88 mg; LCMS: MS m/z=731.4[M+H]⁺.

Example 60: Synthesis of Compound 13-51

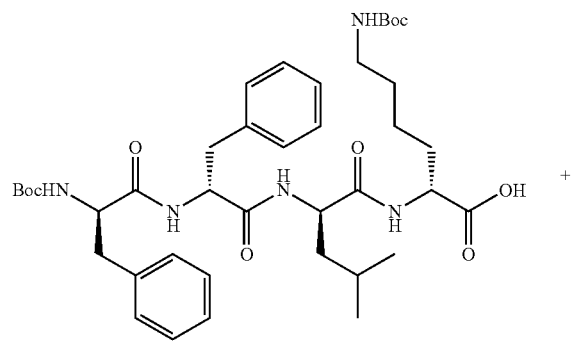

10

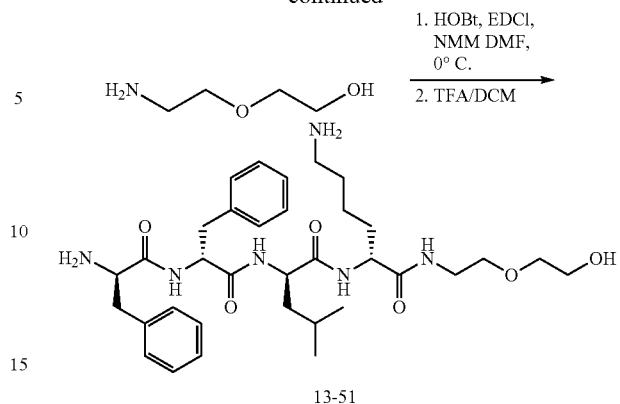

13-51

Into a reaction flask under nitrogen was added compound (10) (0.95 g, 1.06 mmol, 1.0 eq) and DMF (21 mL) under nitrogen. The resulting reaction mixture was cooled to 0° C. in ice bath. To the cooled reaction mixture was added HOBt. H₂O (190 mg, 1.27 mmol, 1.2 eq) and EDCI (240 mg, 1.27 mmol, 1.2 eq). After stirring for 30 minutes in ice bath, 2-(2-aminoethoxy)ethanol (130 mg, 1.27 mmol, 1.20 eq) and N-methylmorpholine (NMM) (130 mg, 1.27 mmol, 1.2 eq) were added. The reaction mixture was stirred at 0° C. for 2 hours, HPLC analysis indicated the reaction was completed. The reaction solution was added dropwise into water (57 mL) with stirring. After addition was completed, stirring was stopped and a precipitate formed. The reaction mixture stood for one hour. The precipitate was collected by filtration, washed with water (71 mL×4) and then dried under vacuum (30° C.). The isolated solid intermediate was a white solid, 0.762 g, LCMS: m/z=841.5 [M+H]⁺.

The intermediate obtained above (130 mg, 0.16 mmol, 1.0 eq) was placed into a reaction flask under nitrogen; to the flask was added dichloromethane (3.6 mL); the resulting solution was cooled to −10° C. for 10 minutes; then to the cooled reaction was added a mixture of TFA (3.6 mL) and dichloromethane (7.2 mL). The resulting solution was stirred at −10° C. for 4 hours; HPLC analysis indicated the reaction was completed. The volatiles were removed on rotavapor. To the residue was added dichloromethane (18 mL). The resulting solution was evaporated on rotavapor to a residue again. The dichloromethane dissolution/evaporation was repeated three times. Then, the residue was dissolved in methanol (18 mL) and the resulting solution was evaporated to dryness on rotavapor; repeating the methanol dissolving and evaporating twice, then to the residue was added ether (18 mL) to form white suspension; the mixture was evaporated on rotavapor and it provided a white solid product (13-51), 89 mg; LCMS: MS m/z=641.4[M+H]⁺.

Example 61: Synthesis of Compound 13-52

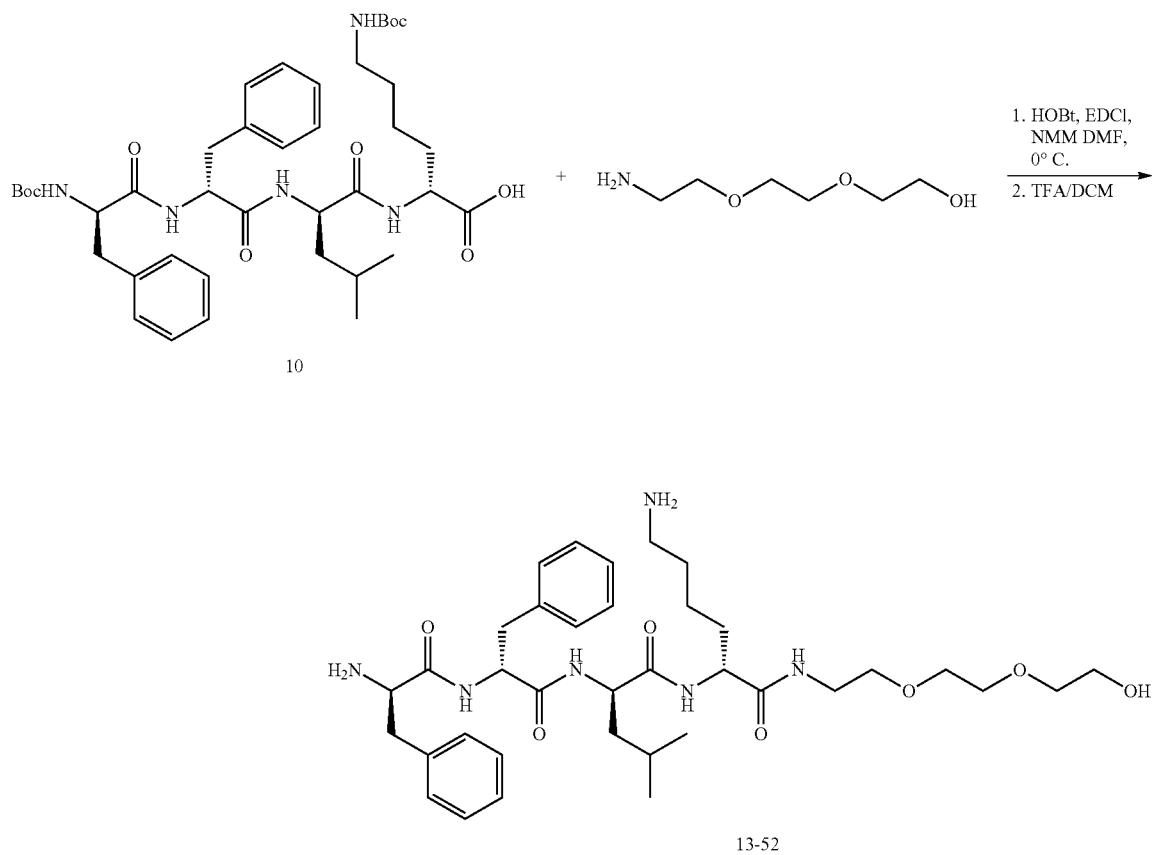

Into a reaction flask under nitrogen was added compound (10) (0.58 g, 0.77 mmol, 1.0 eq) and DMF (13 mL) under nitrogen. The resulting reaction mixture was cooled to 0° C. in ice bath. To the cooled reaction mixture was added HOBt. H$_2$O (140 mg, 0.924 mmol, 1.2 eq) and EDCI (180 mg, 0.924 mmol, 1.2 eq). After stirring for 30 minutes in ice bath, 2-(2-(2-aminoethoxy)ethoxy)ethanol (140 mg, 0.924 mmol, 1.20 eq) and N-methylmorpholine (NMM) (93 mg, 0.924 mmol, 1.2 eq) were added. The reaction mixture was stirred at 0° C. for 2 hours, HPLC analysis indicated the reaction was completed. The reaction solution was added dropwise into water (35 mL) with stirring. After addition was completed, stirring was stopped and a precipitate formed. The reaction mixture stood for one hour. The precipitate was collected by filtration, washed with water (46 mL×4) and then dried under vacuum (30° C.). The isolated solid intermediate was a white solid, 0.597 g, LCMS: m/z=885.5 [M+H]$^+$.

The intermediate obtained above (150 mg, 0.17 mmol, 1.0 eq) was placed into a reaction flask under nitrogen; to the flask was added dichloromethane (3.0 mL); the resulting solution was cooled to −10° C. for 10 minutes; then to the cooled reaction was added a mixture of TFA (3.0 mL) and dichloromethane (6.0 mL). The resulting solution was stirred at −10° C. for 4 hours; HPLC analysis indicated the reaction was completed. The volatiles were removed on rotavapor. To the residue was added dichloromethane (15 mL). The resulting solution was evaporated on rotavapor to a residue again. The dichloromethane dissolution/evaporation was repeated three times. Then, the residue was dissolved in methanol (15 mL) and the resulting solution was evaporated to dryness on rotavapor; repeating the methanol dissolving and evaporating twice, then to the residue was added ether (15 mL) to form white suspension; the mixture was evaporated on rotavapor and it provided a white solid product (13-52), 100 mg; LCMS: MS m/z=685.4 [M+H]$^+$.

Example 62: Synthesis of Compound 13-53

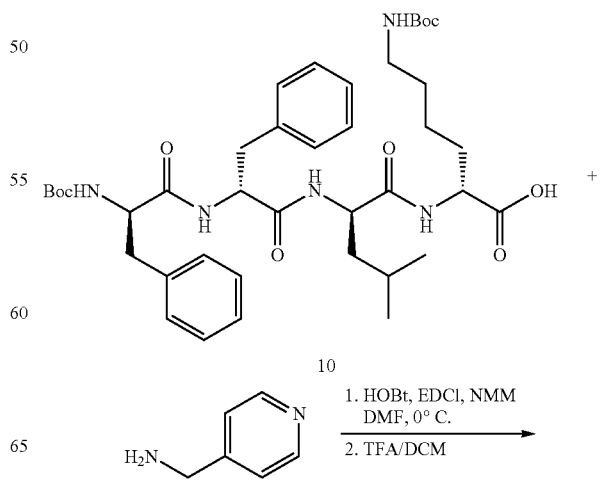

-continued

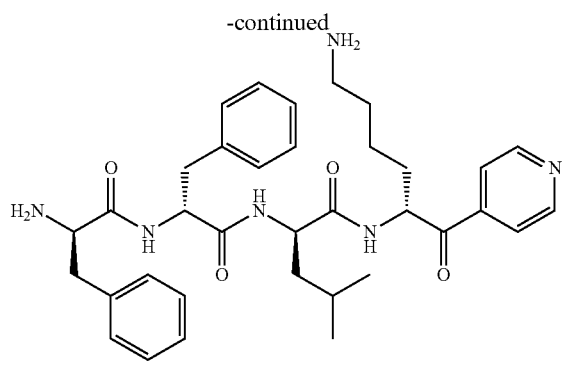

13-53

Into a reaction flask under nitrogen was added compound (10) (0.54 g, 0.71 mmol, 1.0 eq) and DMF (11.7 mL) under nitrogen. The resulting reaction mixture was cooled to 0° C. in ice bath. To the cooled reaction mixture was added HOBt.H$_2$O (130 mg, 0.852 mmol, 1.2 eq) and EDCI (160 mg, 0.852 mmol, 1.2 eq). After stirring for 30 minutes in ice bath, pyridin-4-ylmethanamine (92 mg, 0.852 mmol, 1.20 eq) and N-methylmorpholine (NMM) (86 mg, 0.852 mmol, 1.2 eq) were added. The reaction mixture was stirred at 0° C. for 2 hours, HPLC analysis indicated the reaction was completed. The reaction solution was added dropwise into water (32 mL) with stirring. After addition was completed, stirring was stopped and a precipitate formed. The reaction mixture stood for one hour. The precipitate was collected by filtration, washed with water (41 mL×4) and then dried under vacuum (30° C.). The isolated solid intermediate was a white solid, 0.537 g, LCMS: m/z=844.5 [M+H]$^+$.

The intermediate obtained above (410 mg, 0.48 mmol, 1.0 eq) was placed into a reaction flask under nitrogen; to the flask was added dichloromethane (3.0 mL); the resulting solution was cooled to −10° C. for 10 minutes; then to the cooled reaction was added a mixture of TFA (3.0 mL) and dichloromethane (6.0 mL). The resulting solution was stirred at −10° C. for 4 hours; HPLC analysis indicated the reaction was completed. The volatiles were removed on rotavapor. To the residue was added dichloromethane (15 mL). The resulting solution was evaporated on rotavapor to a residue again. The dichloromethane dissolution/evaporation was repeated three times. Then, the residue was dissolved in methanol (15 mL) and the resulting solution was evaporated to dryness on rotavapor; repeating the methanol dissolving and evaporating twice, then to the residue was added ether (15 mL) to form white suspension; the mixture was evaporated on rotavapor and it provided a white solid product (13-53), 368 mg; LCMS: MS m/z=644.4 [M+H]$^+$.

Example 63: Synthesis of Compound 13-54

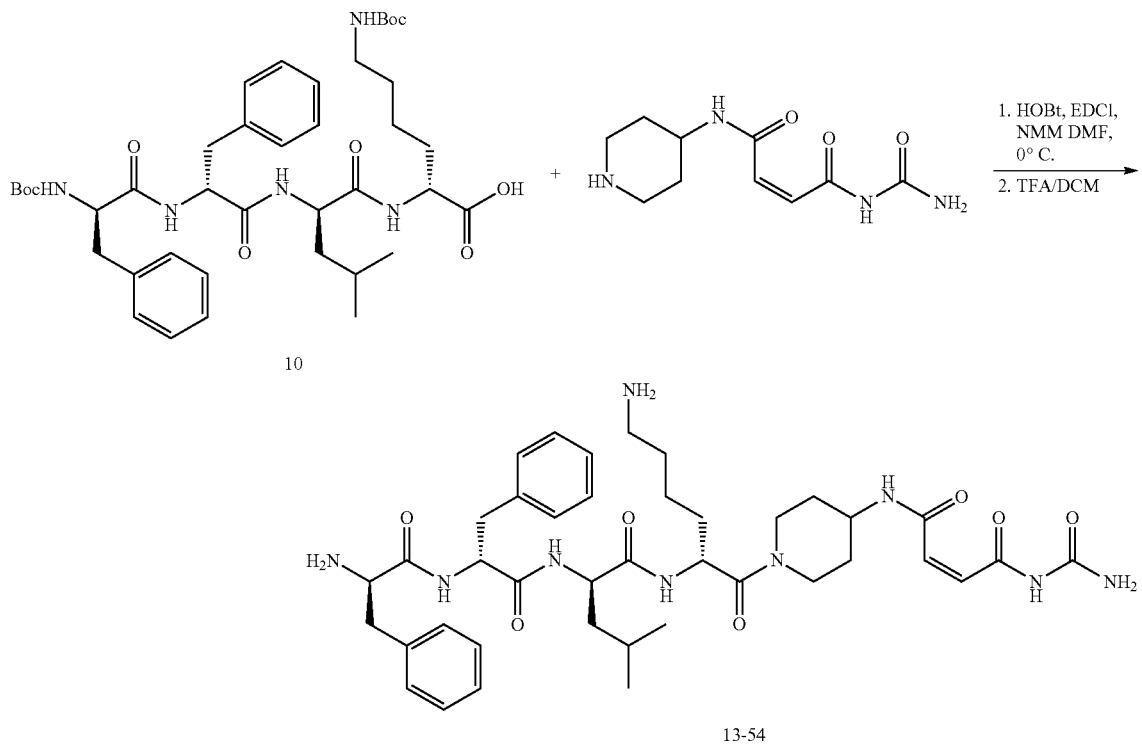

Into a reaction flask under nitrogen was added compound (10) (0.44 g, 0.58 mmol, 1.0 eq) and DMF (9.5 mL) under nitrogen. The resulting reaction mixture was cooled to 0° C. in ice bath. To the cooled reaction mixture was added HOBt.H$_2$O (110 mg, 0.70 mmol, 1.2 eq) and EDCI (130 mg, 0.70 mmol, 1.2 eq). After stirring for 30 minutes in ice bath, (Z)—N'-carbamoyl-N-(4-piperidyl)but-2-enediamide (170 mg, 0.70 mmol, 1.20 eq) and N-methylmorpholine (NMM) (71 mg, 0.70 mmol, 1.2 eq) were added. The reaction mixture was stirred at 0° C. for 2 hours, HPLC analysis indicated the reaction was completed. The reaction solution was added dropwise into water (26 mL) with stirring. After addition was completed, stirring was stopped and a precipitate formed. The reaction mixture stood for one hour. The precipitate was collected by filtration, washed with water (34 mL×4) and then dried under vacuum (30° C.). The isolated solid intermediate was a white solid, 0.50 g, LCMS: m/z=976.5 [M+H]+.

The intermediate obtained above (310 mg, 0.32 mmol, 1.0 eq) was placed into a reaction flask under nitrogen; to the flask was added dichloromethane (6.2 mL); the resulting solution was cooled to −10° C. for 10 minutes; then to the cooled reaction was added a mixture of TFA (6.2 mL) and dichloromethane (12.4 mL). The resulting solution was stirred at −10° C. for 4 hours; HPLC analysis indicated the reaction was completed. The volatiles were removed on rotavapor. To the residue was added dichloromethane (31 mL). The resulting solution was evaporated on rotavapor to a residue again. The dichloromethane dissolution/evaporation was repeated three times. Then, the residue was dissolved in methanol (31 mL) and the resulting solution was evaporated to dryness on rotavapor; repeating the methanol dissolving and evaporating twice, then to the residue was added ether (31 mL) to form white suspension; the mixture was evaporated on rotavapor and it provided a white solid product (13-54), 278 mg; LCMS: MS m/z=776.4[M+H]+.

1.20 eq) and N-methylmorpholine (NMM) (47 mg, 0.463 mmol, 1.2 eq) were added. The reaction mixture was stirred at 0° C. for 2 hours, HPLC analysis indicated the reaction was completed. The reaction solution was added dropwise into water (17 mL) with stirring. After addition was completed, stirring was stopped and a precipitate formed. The reaction mixture stood for one hour. The precipitate was collected by filtration, washed with water (22 mL×4) and then dried under vacuum (30° C.). The isolated solid intermediate was a white solid, 0.314 g, LCMS: m/z=936.6 [M+H]+.

The intermediate obtained above (19 mg, 0.02 mmol, 1.0 eq) was placed into a reaction flask under nitrogen; to the flask was added dichloromethane (0.4 mL); the resulting solution was cooled to −10° C. for 10 minutes; then to the cooled reaction was added a mixture of TFA (0.4 mL) and dichloromethane (0.8 mL). The resulting solution was stirred at −10° C. for 4 hours; HPLC analysis indicated the reaction was completed. The volatiles were removed on rotavapor. To the residue was added dichloromethane (1.9 mL). The resulting solution was evaporated on rotavapor to a residue again. The dichloromethane dissolution/evapora-

Example 64: Synthesis of Compound 13-55

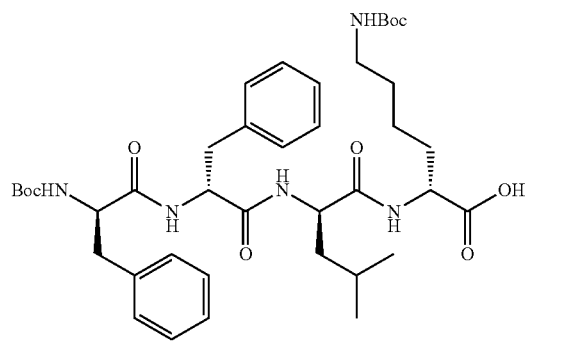

10

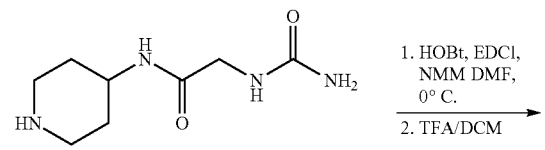

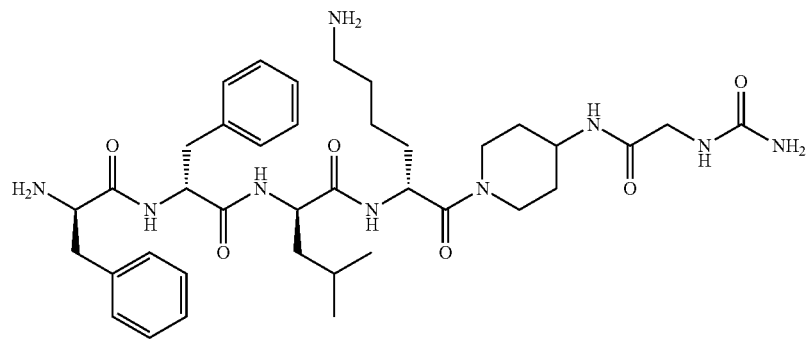

13-55

Into a reaction flask under nitrogen was added compound (10) (0.29 g, 0.386 mmol, 1.0 eq) and DMF (6.3 mL) under nitrogen. The resulting reaction mixture was cooled to 0° C. in ice bath. To the cooled reaction mixture was added HOBt. H2O (71 mg, 0.463 mmol, 1.2 eq) and EDCI (89 mg, 0.463 mmol, 1.2 eq). After stirring for 30 minutes in ice bath, N-(4-piperidyl)-2-ureido-acetamide (93 mg, 0.463 mmol, tion was repeated three times. Then, the residue was dissolved in methanol (1.9 mL) and the resulting solution was evaporated to dryness on rotavapor; repeating the methanol dissolving and evaporating twice, then to the residue was added ether (1.9 mL) to form white suspension; the mixture was evaporated on rotavapor and it provided a white solid product (13-55), 17 mg; LCMS: MS m/z=736.4 [M+H]+.

Example 65: Synthesis of Compound 13-56

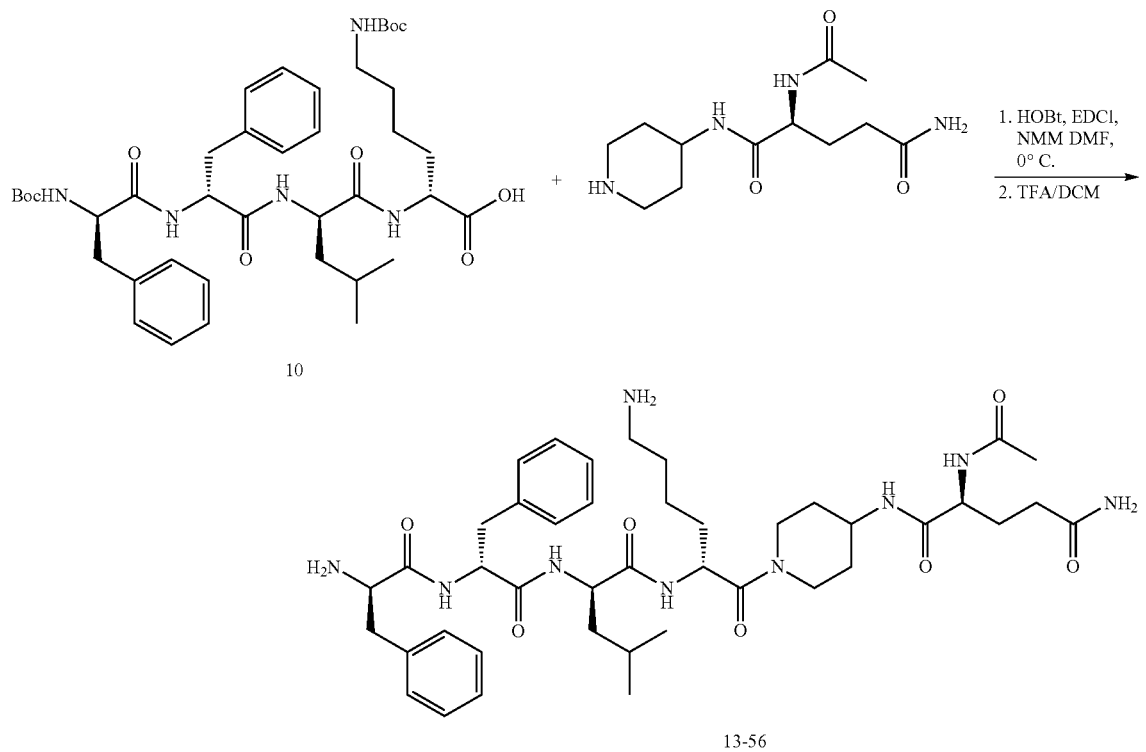

Into a reaction flask under nitrogen was added compound (10) (0.22 g, 0.288 mmol, 1.0 eq) and DMF (4.2 mL) under nitrogen. The resulting reaction mixture was cooled to 0° C. in ice bath. To the cooled reaction mixture was added HOBt.H$_2$O (53 mg, 0.345 mmol, 1.2 eq) and EDCI (66 mg, 0.345 mmol, 1.2 eq). After stirring for 30 minutes in ice bath, (2S)-2-acetamido-N-(4-piperidyl)pentanediamide (93 mg, 0.345 mmol, 1.20 eq) and N-methylmorpholine (NMM) (35 mg, 0.345 mmol, 1.2 eq) were added. The reaction mixture was stirred at 0° C. for 2 hours, HPLC analysis indicated the reaction was completed. The reaction solution was added dropwise into water (12 mL) with stirring. After addition was completed, stirring was stopped and a precipitate formed. The reaction mixture stood for one hour. The precipitate was collected by filtration, washed with water (17 mL×4) and then dried under vacuum (30° C.). The isolated solid intermediate was a white solid, 0.257 g, LCMS: m/z=1006.6 [M+H]$^+$.

The intermediate obtained above (110 mg, 0.105 mmol, 1.0 eq) was placed into a reaction flask under nitrogen; to the flask was added dichloromethane (2.2 mL); the resulting solution was cooled to −10° C. for 10 minutes; then to the cooled reaction was added a mixture of TFA (2.2 mL) and dichloromethane (4.4 mL). The resulting solution was stirred at −10° C. for 4 hours; HPLC analysis indicated the reaction was completed. The volatiles were removed on rotavapor. To the residue was added dichloromethane (11 mL). The resulting solution was evaporated on rotavapor to a residue again. The dichloromethane dissolution/evaporation was repeated three times. Then, the residue was dissolved in methanol (11 mL) and the resulting solution was evaporated to dryness on rotavapor; repeating the methanol dissolving and evaporating twice, then to the residue was added ether (11 mL) to form white suspension; the mixture was evaporated on rotavapor and it provided a white solid product (13-56), 94 mg; LCMS: MS m/z=806.5[M+H]$^+$.

Example 66: Synthesis of Compound 13-57

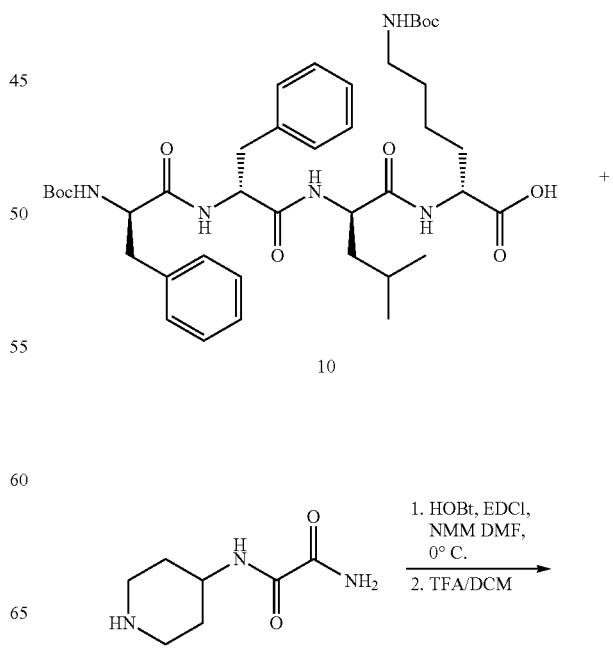

-continued

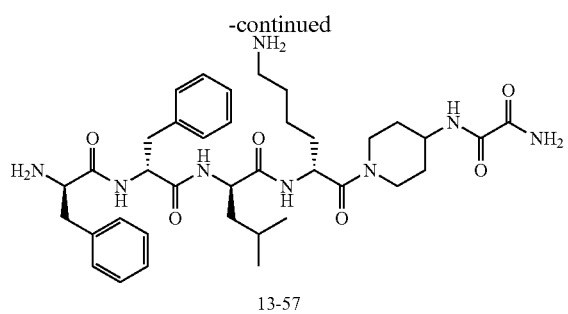

13-57

Into a reaction flask under nitrogen was added compound (10) (0.23 g, 0.303 mmol, 1.0 eq) and DMF (5.3 mL) under nitrogen. The resulting reaction mixture was cooled to 0° C. in ice bath. To the cooled reaction mixture was added HOBt. $H_2O$ (56 mg, 0.364 mmol, 1.2 eq) and EDCI (70 mg, 0.364 mmol, 1.2 eq). After stirring for 30 minutes in ice bath, N'-(4-piperidyl)oxamide (62 mg, 0.364 mmol, 1.20 eq) and N-methylmorpholine (NMM) (37 mg, 0.364 mmol, 1.2 eq) were added. The reaction mixture was stirred at 0° C. for 2 hours, HPLC analysis indicated the reaction was completed. The reaction solution was added dropwise into water (15 mL) with stirring. After addition was completed, stirring was stopped and a precipitate formed. The reaction mixture stood for one hour. The precipitate was collected by filtration, washed with water (17 mL×4) and then dried under vacuum (30° C.). The isolated solid intermediate was a white solid, 0.239 g, LCMS: m/z=907.5 [M+H]$^+$.

The intermediate obtained above (67 mg, 0.074 mmol, 1.0 eq) was placed into a reaction flask under nitrogen; to the flask was added dichloromethane (1.4 mL); the resulting solution was cooled to −10° C. for 10 minutes; then to the cooled reaction was added a mixture of TFA (1.4 mL) and dichloromethane (2.8 mL). The resulting solution was stirred at −10° C. for 4 hours; HPLC analysis indicated the reaction was completed. The volatiles were removed on rotavapor. To the residue was added dichloromethane (6.7 mL). The resulting solution was evaporated on rotavapor to a residue again. The dichloromethane dissolution/evaporation was repeated three times. Then, the residue was dissolved in methanol (6.7 mL) and the resulting solution was evaporated to dryness on rotavapor; repeating the methanol dissolving and evaporating twice, then to the residue was added ether (6.7 mL) to form white suspension; the mixture was evaporated on rotavapor and it provided a white solid product (13-57), 60 mg; LCMS: MS m/z=707.4[M+H]$^+$.

Example 67: Synthesis of Compound 13-58

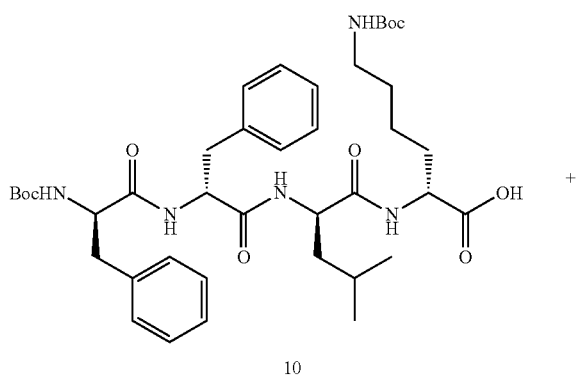

10

-continued

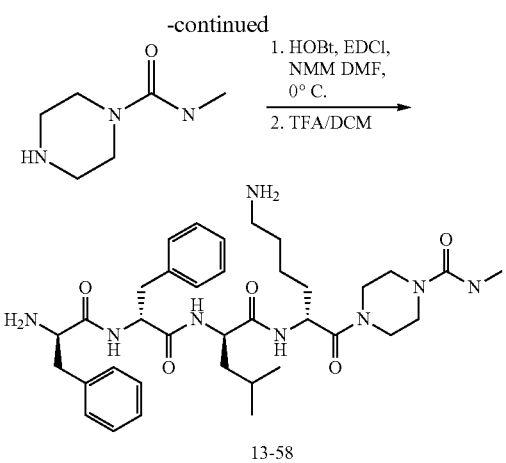

13-58

Into a reaction flask under nitrogen was added compound (10) (0.20 g, 0.260 mmol, 1.0 eq) and DMF (4.2 mL) under nitrogen. The resulting reaction mixture was cooled to 0° C. in ice bath. To the cooled reaction mixture was added HOBt. $H_2O$ (48 mg, 0.312 mmol, 1.2 eq) and EDCI (60 mg, 0.312 mmol, 1.2 eq). After stirring for 30 minutes in ice bath, N-methylpiperazine-1-carboxamide (45 mg, 0.312 mmol, 1.20 eq) and N-methylmorpholine (NMM) (32 mg, 0.312 mmol, 1.2 eq) were added. The reaction mixture was stirred at 0° C. for 2 hours, HPLC analysis indicated the reaction was completed. The reaction solution was added dropwise into water (12 mL) with stirring. After addition was completed, stirring was stopped and a precipitate formed. The reaction mixture stood for one hour. The precipitate was collected by filtration, washed with water (15 mL×4) and then dried under vacuum (30° C.). The isolated solid intermediate was a white solid, 0.201 g, LCMS: m/z=879.5 [M+H]$^+$.

The intermediate obtained above (140 mg, 0.158 mmol, 1.0 eq) was placed into a reaction flask under nitrogen; to the flask was added dichloromethane (2.8 mL); the resulting solution was cooled to −10° C. for 10 minutes; then to the cooled reaction was added a mixture of TFA (2.8 mL) and dichloromethane (5.6 mL). The resulting solution was stirred at −10° C. for 4 hours; HPLC analysis indicated the reaction was completed. The volatiles were removed on rotavapor. To the residue was added dichloromethane (14 mL). The resulting solution was evaporated on rotavapor to a residue again. The dichloromethane dissolution/evaporation was repeated three times. Then, the residue was dissolved in methanol (14 mL) and the resulting solution was evaporated to dryness on rotavapor; repeating the methanol dissolving and evaporating twice, then to the residue was added ether (14 mL) to form white suspension; the mixture was evaporated on rotavapor and it provided a white solid product (13-58), 123 mg; LCMS: MS m/z=679.4 [M+H]$^+$.

Example 68: Synthesis of Compound 13-59

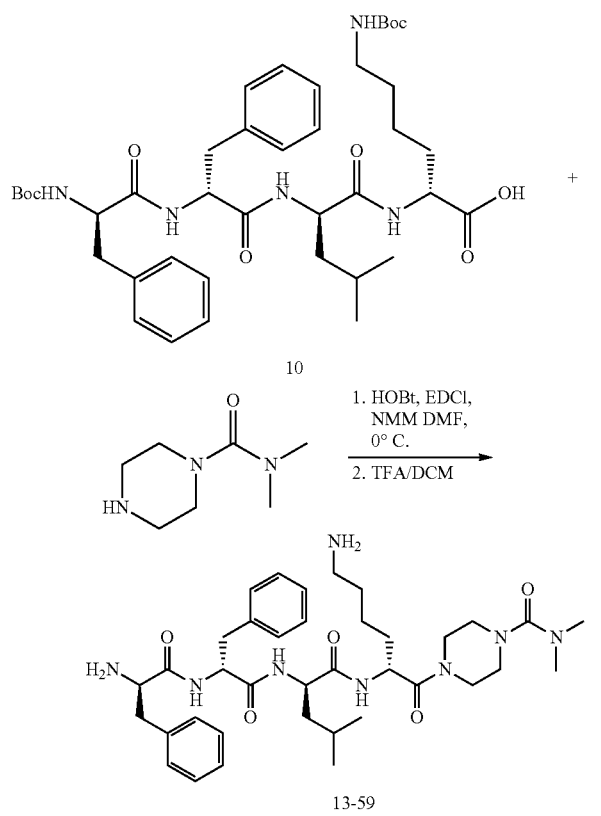

Into a reaction flask under nitrogen was added compound (10) (0.22 g, 0.290 mmol, 1.0 eq) and DMF (4.2 mL) under nitrogen. The resulting reaction mixture was cooled to 0° C. in ice bath. To the cooled reaction mixture was added HOBt. H$_2$O (53 mg, 0.348 mmol, 1.2 eq) and EDCI (67 mg, 0.348 mmol, 1.2 eq). After stirring for 30 minutes in ice bath, N,N-dimethylpiperazine-1-carboxamide (55 mg, 0.348 mmol, 1.20 eq) and N-methylmorpholine (NMM) (35 mg, 0.348 mmol, 1.2 eq) were added. The reaction mixture was stirred at 0° C. for 2 hours, HPLC analysis indicated the reaction was completed. The reaction solution was added dropwise into water (12 mL) with stirring. After addition was completed, stirring was stopped and a precipitate formed. The reaction mixture stood for one hour. The precipitate was collected by filtration, washed with water (25 mL×4) and then dried under vacuum (30° C.). The isolated solid intermediate was a white solid, 0.217 g, LCMS: m/z=893.5 [M+H]$^+$.

The intermediate obtained above (70 mg, 0.078 mmol, 1.0 eq) was placed into a reaction flask under nitrogen; to the flask was added dichloromethane (1.4 mL); the resulting solution was cooled to −10° C. for 10 minutes; then to the cooled reaction was added a mixture of TFA (1.4 mL) and dichloromethane (2.8 mL). The resulting solution was stirred at −10° C. for 4 hours; HPLC analysis indicated the reaction was completed. The volatiles were removed on rotavapor. To the residue was added dichloromethane (7 mL). The resulting solution was evaporated on rotavapor to a residue again. The dichloromethane dissolution/evaporation was repeated three times. Then, the residue was dissolved in methanol (7 mL) and the resulting solution was evaporated to dryness on rotavapor; repeating the methanol dissolving and evaporating twice, then to the residue was added ether (7.0 mL) to form white suspension; the mixture was evaporated on rotavapor and it provided a white solid product (13-59), 62.5 mg; LCMS: MS m/z=693.4 [M+H]$^+$.

Example 69: Synthesis of Compound 13-60

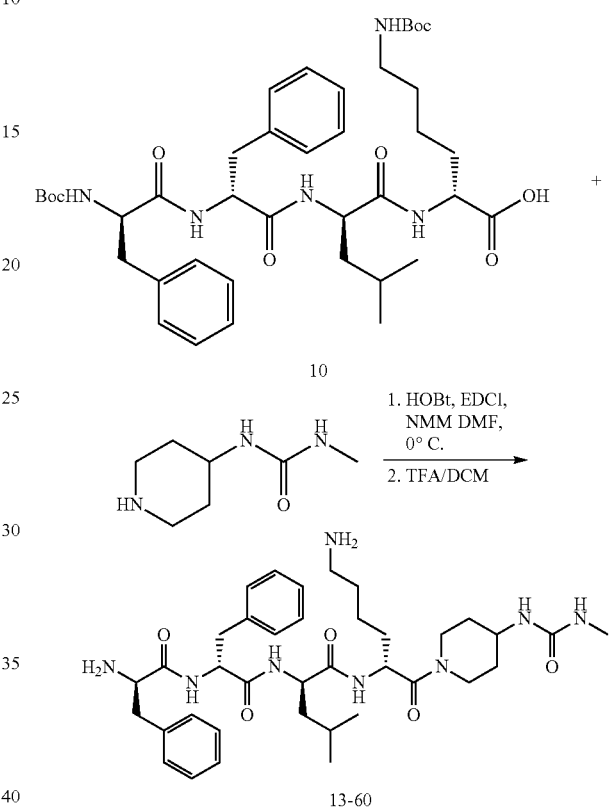

Into a reaction flask under nitrogen was added compound (10) (0.32 g, 0.42 mmol, 1.0 eq) and DMF (6.3 mL) under nitrogen. The resulting reaction mixture was cooled to 0° C. in ice bath. To the cooled reaction mixture was added HOBt. H$_2$O (77 mg, 0.50 mmol, 1.2 eq) and EDCI (96 mg, 0.50 mmol, 1.2 eq). After stirring for 30 minutes in ice bath, 1-methyl-3-(4-piperidyl)urea (78 mg, 0.50 mmol, 1.20 eq) and N-methylmorpholine (NMM) (51 mg, 0.50 mmol, 1.2 eq) were added. The reaction mixture was stirred at 0° C. for 2 hours, HPLC analysis indicated the reaction was completed. The reaction solution was added dropwise into water (19 mL) with stirring. After addition was completed, stirring was stopped and a precipitate formed. The reaction mixture stood for one hour. The precipitate was collected by filtration, washed with water (24 mL×4) and then dried under vacuum (30° C.). The isolated solid intermediate was a white solid, 0.327 g, LCMS: m/z=893.5 [M+H]$^+$.

The intermediate obtained above (250 mg, 0.276 mmol, 1.0 eq) was placed into a reaction flask under nitrogen; to the flask was added dichloromethane (5 mL); the resulting solution was cooled to −10° C. for 10 minutes; then to the cooled reaction was added a mixture of TFA (5 mL) and dichloromethane (10 mL). The resulting solution was stirred at −10° C. for 4 hours; HPLC analysis indicated the reaction was completed. The volatiles were removed on rotavapor. To the residue was added dichloromethane (25 mL). The resulting solution was evaporated on rotavapor to a residue again. The dichloromethane dissolution/evaporation was repeated three times. Then, the residue was dissolved in methanol (25 mL) and the resulting solution was evaporated to dryness on rotavapor; repeating the methanol dissolving and evaporating twice, then to the residue was added ether (25 mL) to form white suspension; the mixture was evaporated on rotavapor and it provided a white solid product (13-60), 219 mg; LCMS: MS m/z=693.4[M+H]+.

Example 70: Synthesis of Compound 13-61

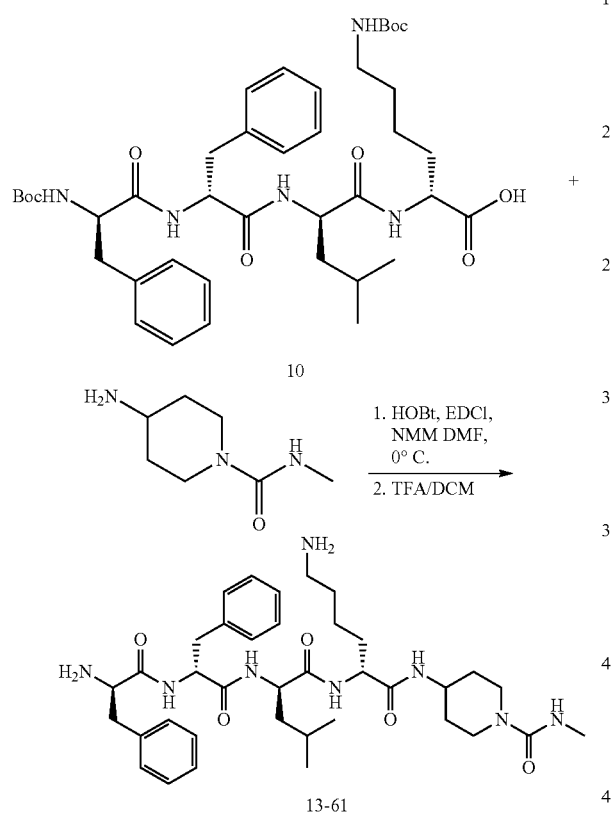

Into a reaction flask under nitrogen was added compound (10) (0.36 g, 0.48 mmol, 1.0 eq) and DMF (7.4 mL) under nitrogen. The resulting reaction mixture was cooled to 0° C. in ice bath. To the cooled reaction mixture was added HOBt. H$_2$O (89 mg, 0.58 mmol, 1.2 eq) and EDCI (110 mg, 0.58 mmol, 1.2 eq). After stirring for 30 minutes in ice bath, 4-amino-N-methyl-piperidine-1-carboxamide (91 mg, 0.58 mmol, 1.20 eq) and N-methylmorpholine (NMM) (59 mg, 0.58 mmol, 1.2 eq) were added. The reaction mixture was stirred at 0° C. for 2 hours, HPLC analysis indicated the reaction was completed. The reaction solution was added dropwise into water (22 mL) with stirring. After addition was completed, stirring was stopped and a precipitate formed. The reaction mixture stood for one hour. The precipitate was collected by filtration, washed with water (25 mL×4) and then dried under vacuum (30° C.). The isolated solid intermediate was a white solid, 0.379 g, LCMS: m/z=893.5 [M+H]+.

The intermediate obtained above (180 mg, 0.203 mmol, 1.0 eq) was placed into a reaction flask under nitrogen; to the flask was added dichloromethane (3.6 mL); the resulting solution was cooled to −10° C. for 10 minutes; then to the cooled reaction was added a mixture of TFA (3.6 mL) and dichloromethane (7.2 mL). The resulting solution was stirred at −10° C. for 4 hours; HPLC analysis indicated the reaction was completed. The volatiles were removed on rotavapor. To the residue was added dichloromethane (18 mL). The resulting solution was evaporated on rotavapor to a residue again. The dichloromethane dissolution/evaporation was repeated three times. Then, the residue was dissolved in methanol (18 mL) and the resulting solution was evaporated to dryness on rotavapor; repeating the methanol dissolving and evaporating twice, then to the residue was added ether (18 mL) to form white suspension; the mixture was evaporated on rotavapor and it provided a white solid product (13-61), 167 mg; LCMS: MS m/z=693.4 [M+H]+.

Example 71: Synthesis of Compound 13-62

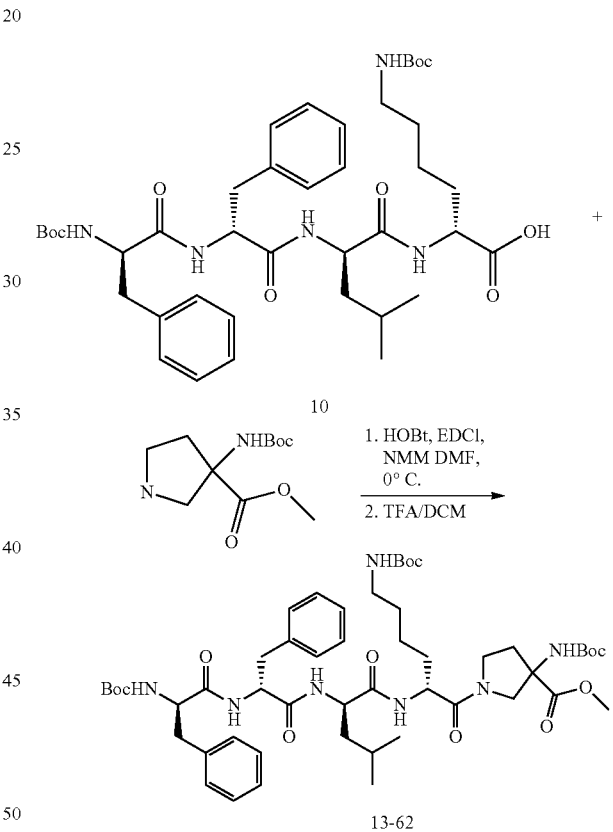

Into a reaction flask under nitrogen was added compound (10) (0.754 g, 1.0 mmol, 1.0 eq) and DMF (15.8 mL) under nitrogen. The resulting reaction mixture was cooled to 0° C. in ice bath. To the cooled reaction mixture was added HOBt. H$_2$O (184 mg, 1.2 mmol, 1.2 eq) and EDCI (230 mg, 1.2 mmol, 1.2 eq). After stirring for 30 minutes in ice bath, methyl 3-(tert-butoxycarbonylamino)pyrrolidine-3-carboxylate (262 mg, 1.2 mmol, 1.20 eq) and N-methylmorpholine (NMM) (121 mg, 1.2 mmol, 1.2 eq) were added. The reaction mixture was stirred at 0° C. for 2 hours, then at room temperature until HPLC analysis indicated the reaction was completed. The reaction solution was added dropwise into water (45 mL) with stirring. After addition was completed, stirring was stopped and a precipitate formed. The reaction mixture stood for one hour. The precipitate was collected by filtration, washed with water (55 mL×4) and then dried under vacuum (30° C.). The isolated solid intermediate was a white solid, 0.946 g, LCMS: m/z=981.2 [M+H]⁺.

The intermediate obtained above (980 mg, 1.0 mmol, 1.0 eq) was placed into a reaction flask under nitrogen; to the flask was added dichloromethane (48 mL); the resulting solution was cooled to −10° C. for 10 minutes; then to the cooled reaction was added a mixture of TFA (12 mL) and dichloromethane (24 mL). The resulting solution was stirred at −10° C. for 2 hours; HPLC analysis indicated the reaction was completed. The volatiles were removed on rotavapor. To the residue was added in methanol (12 mL) and the resulting solution was evaporated to dryness on rotavapor; the residue was dissolved in water; the resulting mixture was lyophilized to a white solid product (13-62), 953 mg; LCMS: MS m/z=680.8[M+H]⁺.

Example 72: Synthesis of Compound 13-63

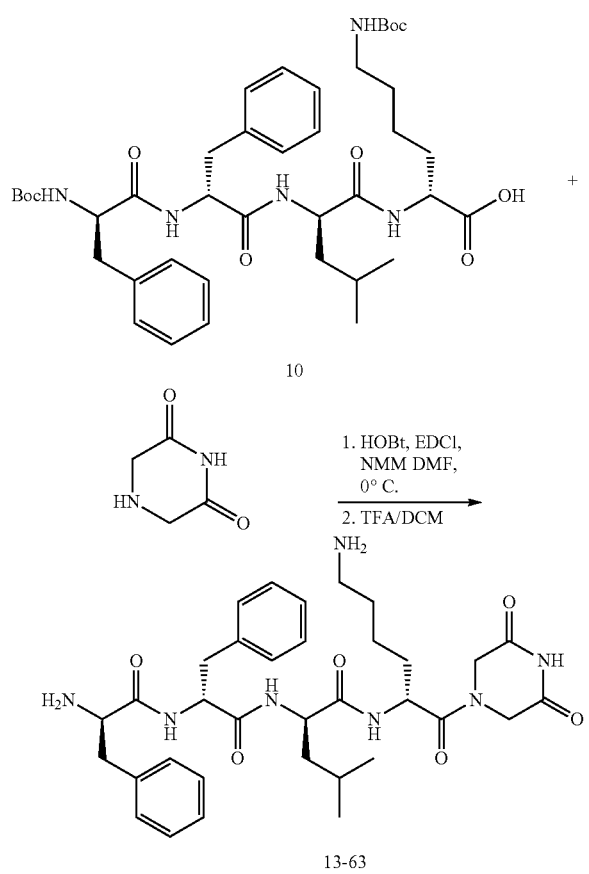

Into a reaction flask under nitrogen was added compound (10) (0.754 g, 1.0 mmol, 1.0 eq) and DMF (15.8 mL) under nitrogen. The resulting reaction mixture was cooled to 0° C. in ice bath. To the cooled reaction mixture was added HOBt. H₂O (184 mg, 1.2 mmol, 1.2 eq) and EDCI (230 mg, 1.2 mmol, 1.2 eq). After stirring for 30 minutes in ice bath, methyl 3-(tert-butoxycarbonylamino)pyrrolidine-3-carboxylate (137 mg, 1.2 mmol, 1.20 eq) and N-methylmorpholine (NMM) (121 mg, 1.2 mmol, 1.2 eq) were added. The reaction mixture was stirred at 0° C. for 2 hours, then at room temperature until HPLC analysis indicated the reaction was completed. The reaction solution was added dropwise into water (45 mL) with stirring. After addition was completed, stirring was stopped and a precipitate formed. The reaction mixture stood for one hour. The precipitate was collected by filtration, washed with water (55 mL×4) and then dried under vacuum (30° C.). The isolated solid intermediate was a white solid, 0.837 g, LCMS: m/z=851.3 [M+H]⁺.

The intermediate obtained above (460 mg, 0.46 mmol, 1.0 eq) was placed into a reaction flask under nitrogen; to the flask was added dichloromethane (1.4 mL); the resulting solution was cooled to −10° C. for 10 minutes; then to the cooled reaction was added a mixture of TFA (1.4 mL) and dichloromethane (2.8 mL). The resulting solution was stirred at −10° C. for 4 hours; HPLC analysis indicated the reaction was completed. The volatiles were removed on rotavapor. The volatiles were removed on rotavapor. To the residue was added dichloromethane (7 mL). The resulting solution was evaporated on rotavapor to a residue again. The dichloromethane dissolution/evaporation was repeated three times. Then, the residue was dissolved in methanol (7 mL) and the resulting solution was evaporated to dryness on rotavapor; repeating the methanol dissolving and evaporating twice, then to the residue was added ether (7 mL) to form white suspension; the mixture was evaporated on rotavapor and it provided a white solid product 13-63), 265 mg; LCMS: MS m/z=650.4 [M+H]⁺.

Example 73: Synthesis of Compound 13-64

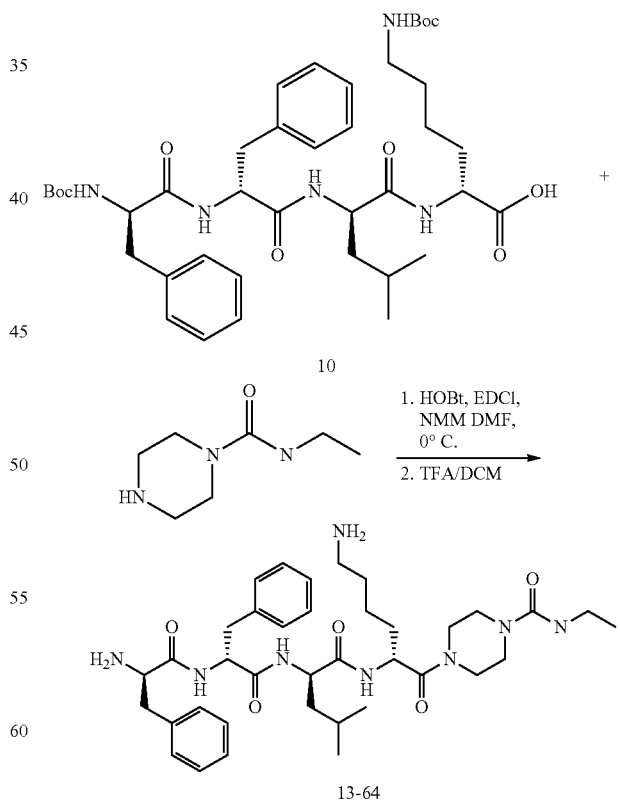

Into a reaction flask under nitrogen was added compound (10) (0.754 g, 1.0 mmol, 1.0 eq) and DMF (15.8 mL) under nitrogen. The resulting reaction mixture was cooled to 0° C.

in ice bath. To the cooled reaction mixture was added HOBt. H₂O (184 mg, 1.2 mmol, 1.2 eq) and EDCI (230 mg, 1.2 mmol, 1.2 eq). After stirring for 30 minutes in ice bath, N-ethylpiperazine-1-carboxamide (262 mg, 1.2 mmol, 1.20 eq) and N-methylmorpholine (NMM) (121 mg, 1.2 mmol, 1.2 eq) were added. The reaction mixture was stirred at 0° C. for 2 hours, then at room temperature until HPLC analysis indicated the reaction was completed. The reaction solution was added dropwise into water (45 mL) with stirring. After addition was completed, stirring was stopped and a precipitate formed. The reaction mixture stood for one hour. The precipitate was collected by filtration, washed with water (55 mL×4) and then dried under vacuum (30° C.); it provided a white solid, 0.881 g, LCMS: m/z=894.1 [M+H]⁺.

The intermediate obtained above (470 mg, 0.53 mmol, 1.0 eq) was placed into a reaction flask under nitrogen; to the flask was added dichloromethane (9.4 mL); the resulting solution was cooled to −10° C. for 10 minutes; then to the cooled reaction was added a mixture of TFA (9.4 mL) and dichloromethane (18.8 mL). The resulting solution was stirred at −10° C. for 4 hours; HPLC analysis indicated the reaction was completed. The volatiles were removed on rotavapor. The volatiles were removed on rotavapor. To the residue was added dichloromethane (47 mL). The resulting solution was evaporated on rotavapor to a residue again. The dichloromethane dissolution/evaporation was repeated three times. Then, the residue was dissolved in methanol (47 mL) and the resulting solution was evaporated to dryness on rotavapor; repeating the methanol dissolving and evaporating twice, then to the residue was added ether (47 mL) to form white suspension; the mixture was evaporated on rotavapor and it provided a white solid product (13-64), 413 mg; LCMS: MS m/z=693.4 [M+H]⁺.

Example 74: Synthesis of Compound 13-65

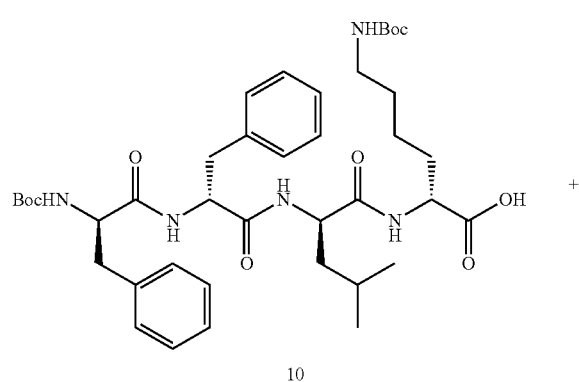

10

1. HOBt, EDCI, NMM DMF, 0° C.
2. TFA/DCM

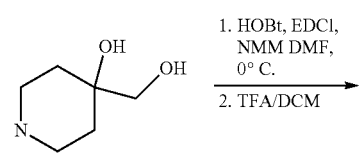

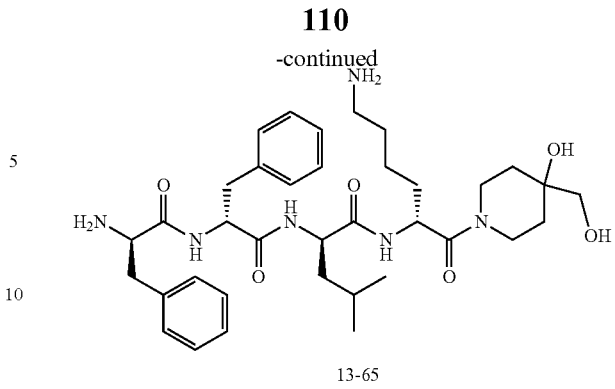

13-65

Into a reaction flask under nitrogen was added compound (10) (0.754 g, 1.0 mmol, 1.0 eq) and DMF (15.8 mL) under nitrogen. The resulting reaction mixture was cooled to 0° C. in ice bath. To the cooled reaction mixture was added HOBt. H₂O (184 mg, 1.2 mmol, 1.2 eq) and EDCI (230 mg, 1.2 mmol, 1.2 eq). After stirring for 30 minutes in ice bath, (157 mg, 1.2 mmol, 1.20 eq) and N-methylmorpholine (NMM) (121 mg, 1.2 mmol, 1.2 eq) were added. The reaction mixture was stirred at 0° C. for 2 hours, then at room temperature until HPLC analysis indicated the reaction was completed. The reaction solution was added dropwise into water (45 mL) with stirring. After addition was completed, stirring was stopped and a precipitate formed. The reaction mixture stood for one hour. The precipitate was collected by filtration, washed with water (55 mL×4) and then dried under vacuum (30° C.). The isolated solid intermediate was a white solid, 0.854 g, LCMS: m/z=868.2 [M+H]⁺.

The intermediate obtained above (100 mg, 1.0 mmol, 1.0 eq) was placed into a reaction flask under nitrogen; to the flask was added dichloromethane (2 mL); the resulting solution was cooled to −10° C. for 10 minutes; then to the cooled reaction was added a mixture of TFA (2 mL) and dichloromethane (4 mL). The resulting solution was stirred at −10° C. for 2 hours; HPLC analysis indicated the reaction was completed. The volatiles were removed on rotavapor. To the residue was added dichloromethane (10 mL). The resulting solution was evaporated on rotavapor to a residue again. The dichloromethane dissolution/evaporation was repeated three times. Then, the residue was dissolved in methanol (10 mL) and the resulting solution was evaporated to dryness on rotavapor; repeating the methanol dissolving and evaporating twice, then to the residue was added ether (10 mL) to form white suspension the resulting mixture was lyophilized to a white solid product (13-65), 64 mg; LCMS: MS m/z=667.4[M+H]⁺.

111

IV. Demonstrated Below are the Preparations for the Peptide Mimics for Medical Products: Compound 22, 23, 28, 29

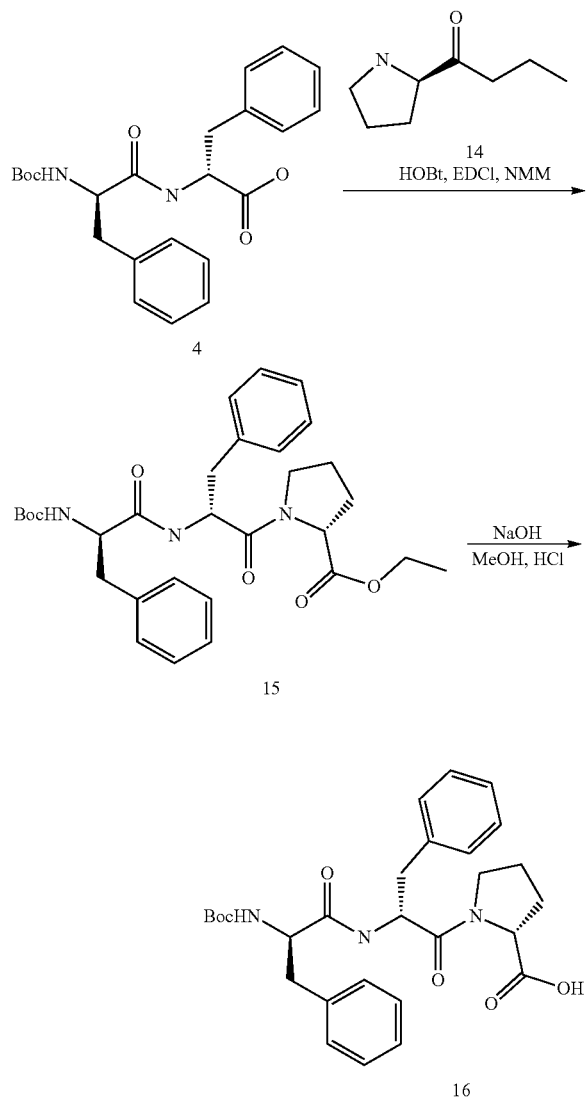

Reaction Scheme 3

112

Example 75: Synthesis of Compound 15

Into a reaction flask under nitrogen was added compound (4) (10 g, 24.2 mmol, 1.0 eq) and DMF (212 mL) under nitrogen. The resulting reaction mixture was cooled to 0° C. in ice bath. To the cooled reaction mixture was added HOBt. $H_2O$ (3.69 g, 26.7 mmol, 1.2 eq) and EDCI (4.79 g, 26.7 mmol, 1.2 eq). After stirring for 30 minutes in ice bath, ethyl proline hydrochloride (14) (4.79 g, 26.7 mmol, 1.1 eq) and N-methylmorpholine (NMM) (5.15 g, 50.9 mmol, 1.2 eq) were added. The reaction mixture was stirred at 0° C. for 1 hours, then at room temperature until HPLC analysis indicated the reaction was completed. The reaction solution was added dropwise into water (600 mL) with stirring. After addition was completed, stirring was stopped and a precipitate formed. The reaction mixture stood for one hour. The precipitate was collected by filtration, washed with water (400 mL×3) and then dried under vacuum (30° C.). The isolated solid intermediate (15) was a white solid, 12.41 g, LCMS: m/z=538.7 [M+H]$^+$.

Example 76: Synthesis of Compound 16

The compound (15) (10 g, 18.6 mmol, 1.0 eq) was placed into a reaction flask under nitrogen, followed by adding methanol (200 mL). To the resulting solution was added a solution of NaOH (50 mL, 1.0 M, 50 mmol, 2.7 eq.) dropwise. The reaction mixture was stirred at room temperature for 2 hours until HPLC analysis indicated the reaction was completed. Then, a HCl solution (1.0 M) was added dropwise until pH=2~2.5 was achieved. To mixture was added water (400 mL); the precipitate was collected by filtration and washed with water (270 mL×3). The wet cake was dried in vacuum (30° C.) and it provided a white solid (16), 9.23 g. LC-MS m/z=510.6 [M+H]$^+$.

Example 77: Synthesis of Compound 19

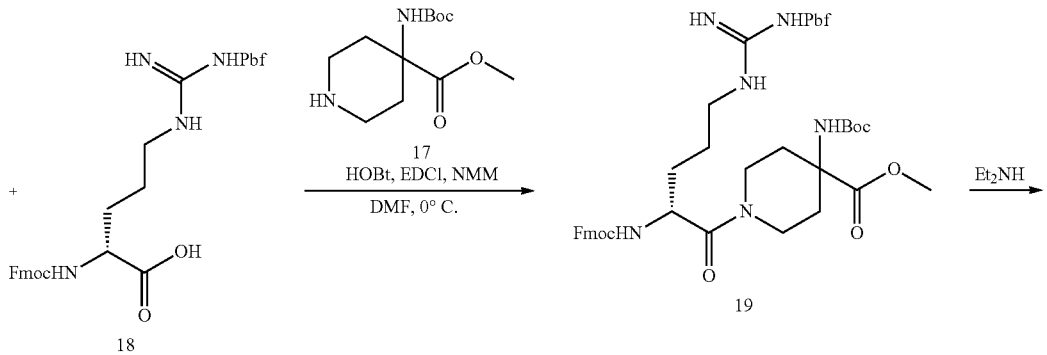

Reaction Scheme 4

-continued
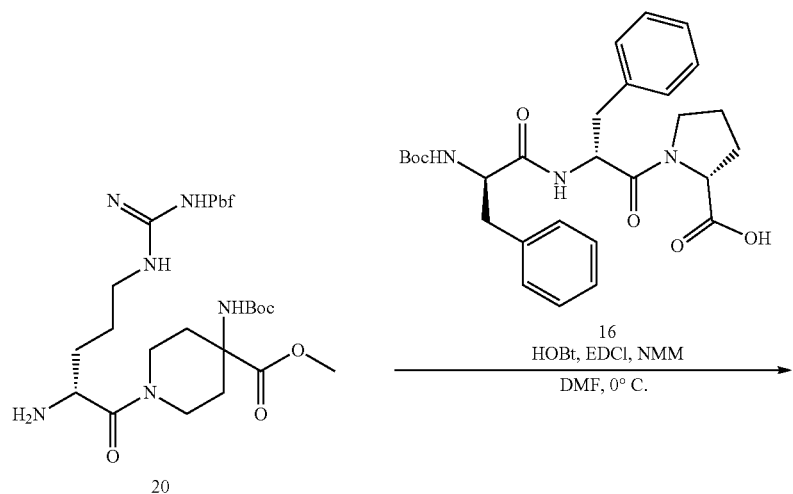
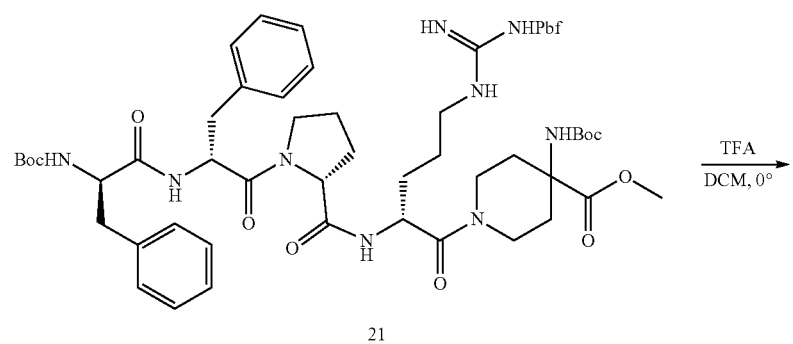
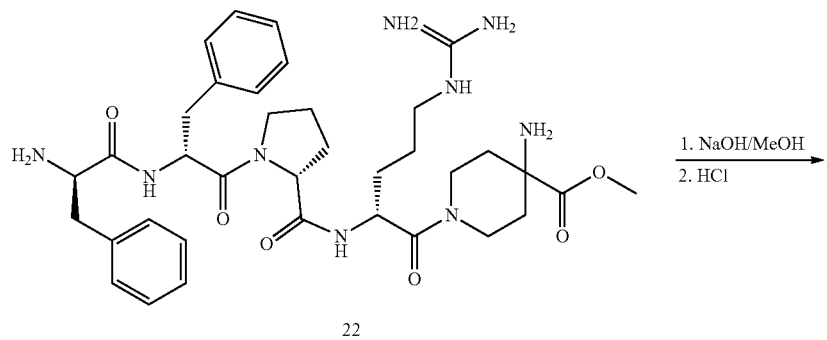
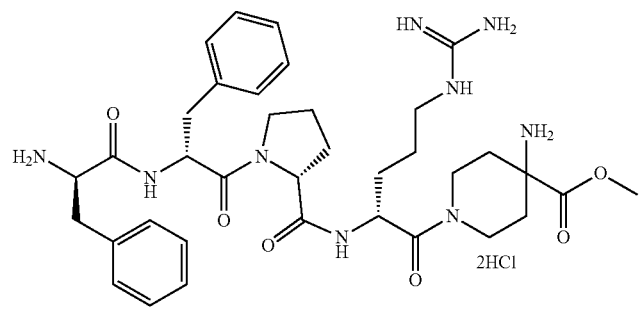

Into a reaction flask under nitrogen was added N-Fmoc-N-Pbf-D-arginine (18) (5 g, 19.4 mmol, 1.0 eq) and DMF (106 mL) under nitrogen. The resulting reaction mixture was cooled to 0° C. in ice bath. To the cooled reaction mixture was added HOBt. H$_2$O (2.88 g, 22.3 mmol, 1.1 eq) and EDCI (4.08 g, 21.3 mmol, 1.1 eq). After stirring for 30 minutes in ice bath, methyl 4-N—Boc-Peridine-4-formate (17) (5.50 g, 21.3 mmol, 1.1 eq) and N-methylmorpholine (NMM) (4.11 g, 40.6 mmol, 1.1 eq) were added. The reaction mixture was stirred at 0° C. for 1 hours, then at room temperature until HPLC analysis indicated the reaction was completed. The reaction solution was added dropwise into water (300 mL) with stirring. After addition was completed, stirring was stopped and a precipitate formed. The reaction mixture stood for one hour. The precipitate was collected by filtration, washed with water (200 mL×3) and then dried under vacuum (30° C.). The isolated solid compound (19) was a white solid, 15.11 g, LCMS: m/z=890.1 [M+H]$^+$.

Example 78: Synthesis of Compound 20

To a reaction flask was added compound (19) (12 g, 13.50 mmol, 1.0 eq), followed by added diethylamine (120 mL). The mixture was cooled to 0° C. in ice bath. The reaction was monitored until HPLC analysis indicated the reaction was completed. The volatiles were removed on rotavapor; to the residue was added ether (60 mL) under stirring, precipitates were formed. The precipitates were collected by filtration and washed with ether (60 mL). The collected solid was dried in vacuum, it proved a white solid (20), 8.52 g. LC-MS m/z=688.1 [M+H]$^+$ Example 79: Synthesis of Compound 21

Into a reaction flask under nitrogen was added compound (16) (5 g, 9.81 mmol, 1.0 eq) and DMF (106 mL) under nitrogen. The resulting reaction mixture was cooled to 0° C. in ice bath. To the cooled reaction mixture was added HOBt. H$_2$O (1.46 g, 10.79 mmol, 1.1 eq) and EDCI (2.07 g, 10.79 mmol, 1.1 eq). After stirring for 30 minutes in ice bath, compound (20) (7.19 g, 10.79 mmol, 1.1 eq) and N-methylmorpholine (NMM) (2.08 g, 20.6 mmol, 1.1 eq) were added. The reaction mixture was stirred at 0° C. for 1 hours and then stirred at room temperature until HPLC analysis indicated the reaction was completed. The reaction solution was added dropwise into water (300 mL) with stirring. After addition was completed, stirring was stopped and a precipitate formed. The reaction mixture stood for one hour. The precipitate was collected by filtration, washed with water (200 mL×3) and then dried under vacuum (30° C.). The isolated solid compound (21) was a white solid, 10.34 g, LCMS: m/z=1159.3 [M+H]$^+$.

Example 80: Synthesis of Peptide Product 22

The intermediate obtained above (21) (5.0 g, 4.23 mmol, 1.0 eq) was placed into a reaction flask under nitrogen; to the flask was added dichloromethane (10 mL); the resulting solution was cooled to −10° C. for 10 minutes; then to the cooled reaction was added dropwise a mixture of TFA (10 mL) and dichloromethane (20 mL). The resulting solution was stirred at 0° C. for 1 hours until HPLC analysis indicated the reaction was completed. The volatiles were removed on rotavapor. To the residue was added in dichloromethane (10 mL), the resulting solution was concentrated on rotapor; the dichloromethane disolvation/concentration was repeated three time; then to the residue was added methanol (10 mL) and the resulting solution was evaporated to dryness on rotavapor; the methanol disolvation/concentration was repeated three times; the residue was purified on reverse phase HPLC to provided a white solid compound (22), 3.89 g, LCMS: MS m/z=706.4 [M+H]$^+$.

Example 81: Synthesis of Compound 23

The compound (22) (1 g, 0.954 mmol, 1.0 eq) was placed into a reaction flask under nitrogen, followed by adding methanol (20 mL). To the resulting solution was added a solution of NaOH (5 mL, 1.0 M, 5 mmol, 5.2 eq.) dropwise. The reaction mixture was stirred at room temperature for 2 hours until HPLC analysis indicated the reaction was completed. Then, a HCl solution (1.0 M) was added dropwise until pH=2~2.5 was achieved. The reaction mixture was further purified on reverse phase HPLC and provide a white compound (23), 559 mg; LC-MS m/z=765.8 [M+H]$^+$.

VI. Demonstrate Synthesis of Compound 28, 29

Reaction Scheme 5

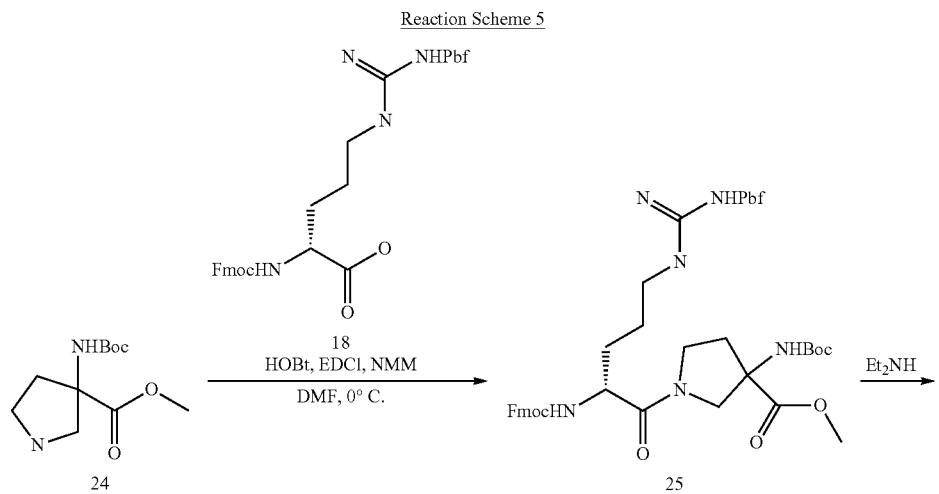

-continued
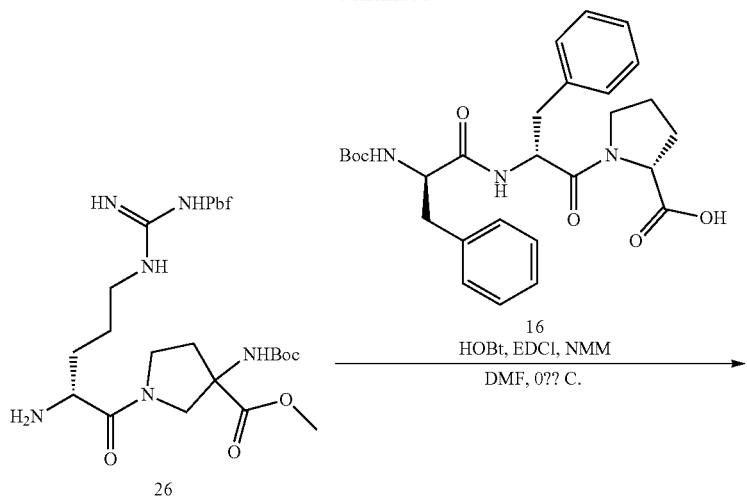
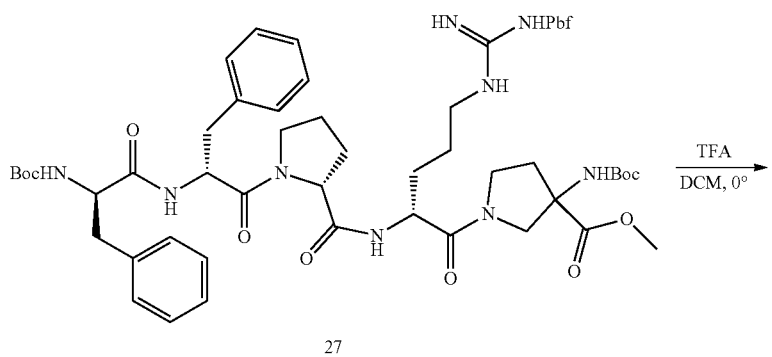
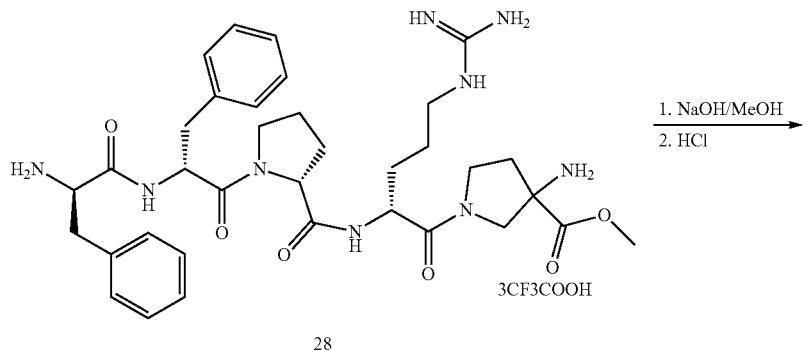
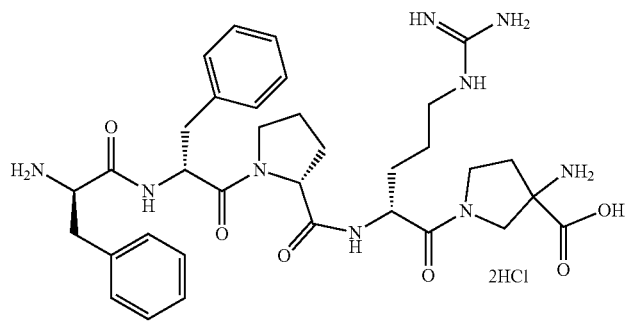

Example 82: Synthesis of Compound 25

Into a reaction flask under nitrogen was added) N-Fmoc-N-Pbf-D-arginine (18) (5 g, 20.4 mmol, 1.0 eq) and DMF (106 mL) under nitrogen. The resulting reaction mixture was cooled to 0° C. in ice bath. To the cooled reaction mixture was added HOBt. H$_2$O (3.04 g, 22.5 mmol, 1.1 eq) and EDCI (4.32 g, 22.5 mmol, 1.1 eq). After stirring for 30 minutes in ice bath, Methyl 3-N—Boc-pyrrole-3-formate (24) (14.61 g, 22.5 mmol, 1.1 eq) and N-methylmorpholine (NMM) (4.35 g, 43.0 mmol, 2.1 eq) were added. The reaction mixture was stirred at 0° C. for 1 hours, then at room temperature until HPLC analysis indicated the reaction was completed. The reaction solution was added dropwise into water (300 mL) with stirring. After addition was completed, stirring was stopped and a precipitate formed. The reaction mixture stood for one hour. The precipitate was collected by filtration, washed with water (200 mL×3) and then dried under vacuum (30° C.). The isolated solid compound (25) was a white solid, 15.89 g, LCMS: m/z=876.4 [M+H]$^+$.

Example 83: Synthesis of Compound 26

To a reaction flask was added compound (25) (12 g, 13.50 mmol, 1.0 eq), followed by added diethylamine (120 mL). The mixture was cooled to 0° C. in ice bath. The reaction was monitored until HPLC analysis indicated the reaction was completed. The volatiles were removed on rotavapor; to the residue was added ether (60 mL) under stirring, precipitates were formed. The precipitates were collected by filtration and washed with ether (60 mL). The collected solid was dried in vacuum, it proved a white solid (26), 8.14 g. LC-MS m/z=653.3 [M+H]$^+$

Example 84: Synthesis of Compound 27

Into a reaction flask under nitrogen was added compound (16) (5 g, 9.81 mmol, 1.0 eq) and DMF (106 mL) under nitrogen. The resulting reaction mixture was cooled to 0° C. in ice bath. To the cooled reaction mixture was added HOBt. H$_2$O (1.46 g, 10.79 mmol, 1.1 eq) and EDCI (2.07 g, 10.79 mmol, 1.1 eq). After stirring for 30 minutes in ice bath, compound (26) (6.40 g, 10.79 mmol, 1.1 eq) and N-methylmorpholine (NMM) (2.08 g, 20.6 mmol, 2.1 eq) were added. The reaction mixture was stirred at 0° C. for 1 hours, HPLC analysis indicated the reaction was completed. The reaction solution was added dropwise into water (300 mL) with stirring. After addition was completed, stirring was stopped and a precipitate formed. The reaction mixture stood for one hour. The precipitate was collected by filtration, washed with water (200 mL×3) and then dried under vacuum (30° C.). The isolated solid compound (27) was a white solid, 10.11 g, LCMS: m/z=1145.3 [M+H]$^+$.

Example 85: Synthesis of Compound 28

The intermediate obtained above (27) (5.0 g, 4.37 mmol, 1.0 eq) was placed into a reaction flask under nitrogen; to the flask was added dichloromethane (10 mL); the resulting solution was cooled to 0° C. for 10 minutes; then to the cooled reaction was added dropwise a mixture of TFA (10 mL) and dichloromethane (20 mL). The resulting solution was stirred at 0° C. for 1 hours until HPLC analysis indicated the reaction was completed. The volatiles were removed on rotavapor. To the residue was added in dichloromethane (10 mL), the resulting solution was concentrated on rotapor; the dichloromethane desolvation/concentration was repeated three time; then to the residue was added methanol (10 mL) and the resulting solution was evaporated to dryness on rotavapor; the methanol desolvation/concentration was repeated three times; the residue was purified on reverse phase HPLC and the collected fractions were lyophillized to provided a white solid compound (28), 4.20 g, LCMS: MS m/z=692.4 [M+H]$^+$.

Example 86: Synthesis of Compound 29

The compound (28) (1 g, 0.967 mmol, 1.0 eq) was placed into a reaction flask under nitrogen, followed by adding methanol (20 mL). To the resulting solution was added a solution of NaOH (5 mL, 1.0 M, 5 mmol, 5.2 eq.) dropwise. The reaction mixture was stirred at room temperature for 2 hours until HPLC analysis indicated the reaction was completed. Then, a HCl solution (1.0 M) was added dropwise until pH=2~2.5 was achieved. The mixture was then purified on reverse phase HPLC; the collected fractions were lyophilized into the white solid compound (29), 613 mg; LC-MS m/z=678.4 [M+H]$^+$.

V. Demonstrated Below are the Preparations for the Peptide Mimics for Medical Products: Compounds 35, 40, 45, 50, 55, 60

Reaction Scheme 6

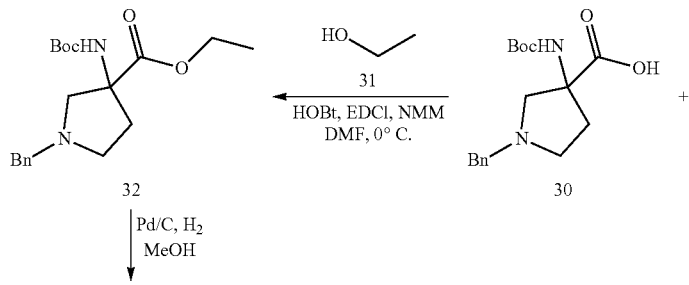

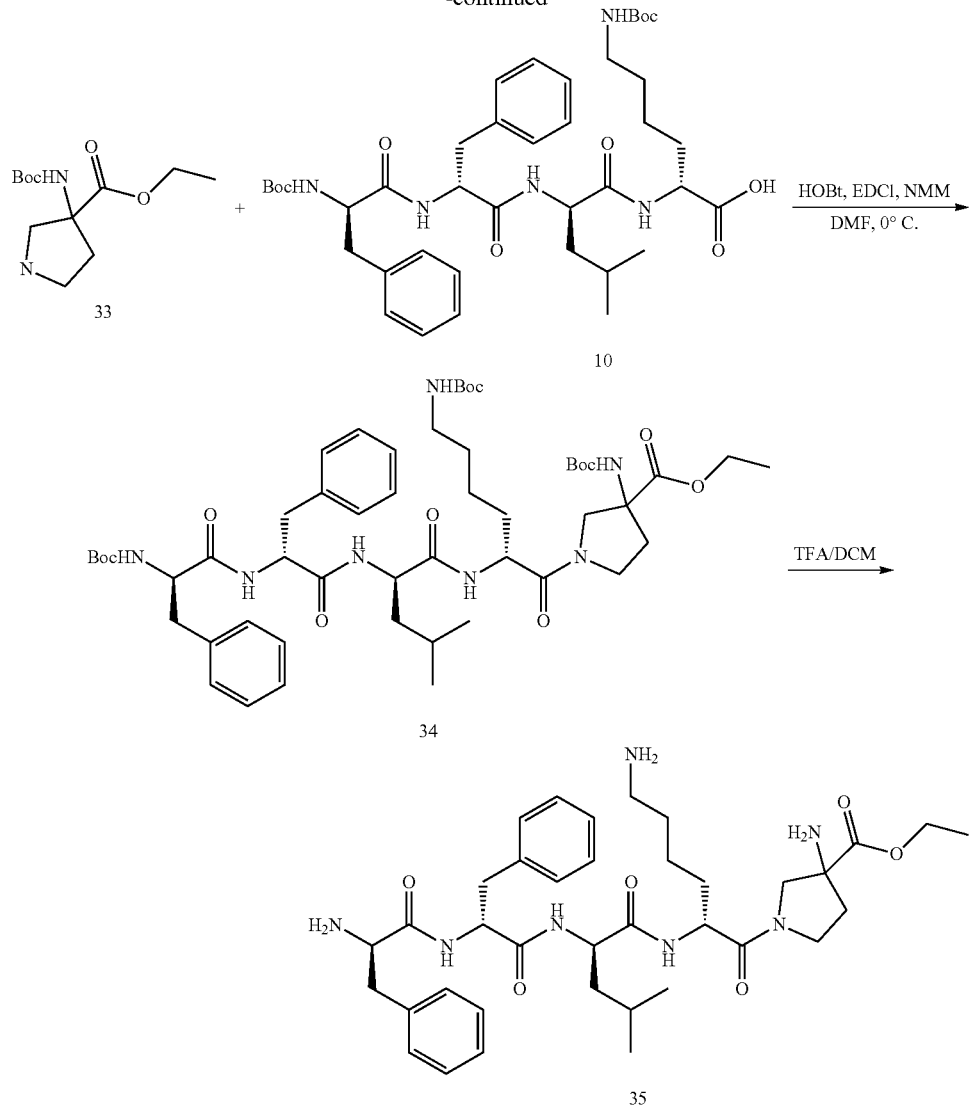

Example 87: Synthesis of Compound 32

Into a reaction flask under nitrogen was added compound 1-benzyl-3-(tert-butoxycarbonylamino)pyrrolidine-3-carboxylic acid (30) (5 g, 15.6 mmol, 1.0 eq) and DMF (106 mL) under nitrogen. The resulting reaction mixture was cooled to 0° C. in ice bath. To the cooled reaction mixture was added HOBt. $H_2O$ (2.32 g, 17.2 mmol, 1.1 eq) and EDCI (3.29 g, 17.2 mmol, 1.1 eq). After stirring for 30 minutes in ice bath, ethanol (31) (790.9 mg, 17.2 mmol, 1.1 eq) and N-methylmorpholine (NMM) (3.31 g, 32.8 mmol, 2.1 eq) were added. The reaction mixture was stirred at 0° C. for 1 hours, HPLC analysis indicated the reaction was completed. The reaction solution was added dropwise into water (300 mL) with stirring. After addition was completed, stirring was stopped and a precipitate formed. The reaction mixture stood for one hour. The precipitate was collected by filtration, washed with water (200 mL×3) and then dried under vacuum (30° C.). The isolated solid compound (32) was a white solid, 5.11 g, LCMS: m/z=349.4 [M+H]$^+$.

Example 88: Synthesis of Compound 33

To the reaction flask was added ethyl 1-benzyl-3-(tert-butoxycarbonylamino)pyrrolidine-3-carboxylate (32)(5.0 g, 14.5 mmol) and methanol (12.6 mL). The reaction atmosphere was replaced with nitrogen, then to the reaction was added Pd/C 5 g). Then the reaction atmosphere was replaced with hydrogen; the reaction was stirred at room temperature until the reaction was done. The reaction was filtered and the residue was washed with methanol (12.6 mL). The filtrate was concentrated on rotavapor and it provided a yellow oil (33), 3.55 g. LCMS: m/z=259.3 [M+H]$^+$.

Example 89: Synthesis of Compound 34

Into a reaction flask under nitrogen was added compound (10) (5 g, 6.63 mmol, 1 eq) and DMF (106 mL) under nitrogen. The resulting reaction mixture was cooled to 0° C. in ice bath. To the cooled reaction mixture was added HOBt. $H_2O$ (1.12 g, 7.29 mmol, 1.1 eq) and EDCI (1.40 g, 7.29 mmol, 1.1 eq). After stirring for 30 minutes in ice bath, compound (33) (1.88 g, 7.29 mmol, 1.1 eq) and N-methylmorpholine (NMM) (1.41 g, 13.9 mmol, 2.1 eq) were added. The reaction mixture was stirred at 0° C. for 1 hours, HPLC analysis indicated the reaction was completed. The reaction solution was added dropwise into water (300 mL) with stirring. After addition was completed, stirring was stopped and a precipitate formed. The reaction mixture stood for one hour. The precipitate was collected by filtration, washed with water (200 mL×3) and then dried under vacuum (30° C.). The isolated solid compound (34) was a white solid, 5.45 g, LCMS: m/z=995.4 [M+H]$^+$.

Example 90: Synthesis of Compound 35

The intermediate (34) (1.0 g, 1.01 mmol, 1.0 eq) was placed into a reaction flask under nitrogen; to the flask was added dichloromethane (10 mL); the resulting solution was cooled to 0° C. for 10 minutes; then to the cooled reaction was added dropwise a mixture of TFA (10 mL) and dichloromethane (20 mL). The resulting solution was stirred at 0° C. for 1 hours until HPLC analysis indicated the reaction was completed. The volatiles were removed on rotavapor. To the residue was added in dichloromethane (10 mL), the resulting solution was concentrated on rotapor; the dichloromethane disolvation/concentration was repeated three time; then to the residue was added methanol (10 mL) and the resulting solution was evaporated to dryness on rotavapor; the methanol disolvation/concentration was repeated three times; the residue was purified on reverse phase HPLC and the collected fractions were lyophillized to provided a white solid compound (35), 852 mg, LCMS: MS m/z=694.4 [M+H]$^+$.

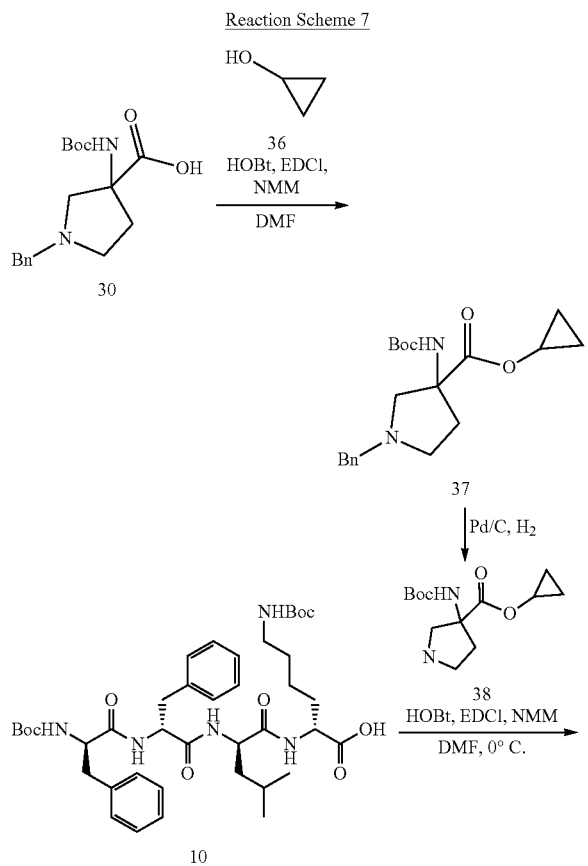

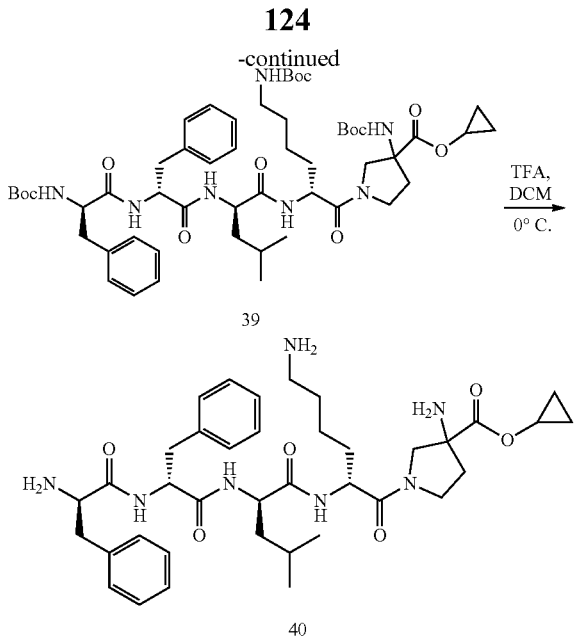

Example 91: Synthesis of Compound 37

Into a reaction flask under nitrogen was added 1-benzyl-3-(tert-butoxycarbonylamino) pyrrolidine-3-carboxylic acid (30) (5 g, 15.6 mmol, 1 eq) and DMF (106 mL) under nitrogen. The resulting reaction mixture was cooled to 0° C. in ice bath. To the cooled reaction mixture was added HOBt.H$_2$O (2.32 g, 17.2 mmol, 1.1 eq) and EDCI (3.29 g, 17.2 mmol, 1.1 eq). After stirring for 30 minutes in ice bath, cyclopropanol (36) (998.9 mg, 17.2 mmol, 1.1 eq) and N-methylmorpholine (NMM) (3.31 g, 32.8 mmol, 2.1 eq) were added. The reaction mixture was stirred at 0° C. for 1 hours, then at room temperature until HPLC analysis indicated the reaction was completed. The reaction solution was added dropwise into water (300 mL) with stirring. After addition was completed, stirring was stopped and a precipitate formed. The reaction mixture stood for one hour. The precipitate was collected by filtration, washed with water (200 mL×3) and then dried under vacuum (30° C.). The isolated solid compound (37) was a white solid, 5.15 g, LCMS: m/z=361.4 [M+H]$^+$.

Example 92: Synthesis of Compound 38

To the reaction flask was added ethyl 1-benzyl-3-(tert-butoxycarbonylamino)pyrrolidine-3-carboxylate (37) (5.0 g, 13.8 mmol, 1.0 eq) and methanol (12.6 mL). The reaction atmosphere was replaced with nitrogen, then to the reaction was added Pd/C (5 g). Then the reaction atmosphere was replaced with hydrogen; the reaction was stirred at room temperature until the reaction was done. The reaction was filtered and the residue was washed with methanol (12.6 mL). The filtrate was concentrated on rotavapor and it provided a yellow oil (38), 3.01 g. LCMS: m/z=271.3 [M+H]$^+$.

Example 93: Synthesis of Synthesis of Compound 39

Into a reaction flask under nitrogen was added compound (10) (5 g, 6.63 mmol, 1 eq) and DMF (106 mL) under nitrogen. The resulting reaction mixture was cooled to 0° C.

in ice bath. To the cooled reaction mixture was added HOBt. H₂O (1.12 g, 7.29 mmol, 1.1 eq) and EDCI (1.40 g, 7.29 mmol, 1.1 eq). After stirring for 30 minutes in ice bath, compound (38) (1.97 g, 7.29 mmol, 1.1 eq) and N-methylmorpholine (NMM) (1.41 g, 13.9 mmol, 2.1 eq) were added. The reaction mixture was stirred at 0° C. for 1 hours, then at room temperature until HPLC analysis indicated the reaction was completed. The reaction solution was added dropwise into water (300 mL) with stirring. After addition was completed, stirring was stopped and a precipitate formed. The reaction mixture stood for one hour. The precipitate was collected by filtration, washed with water (200 mL×3) and then dried under vacuum (30° C.). The isolated solid compound (39) was a white solid, 4.90 g, LCMS: m/z=1007.1 [M+H]⁺.

Example 94: Synthesis of Compound 40

The intermediate (39) (1.0 g, 0.99 mmol, 1.0 eq) was placed into a reaction flask under nitrogen; to the flask was added dichloromethane (10 mL); the resulting solution was cooled to 0° C. for 10 minutes; then to the cooled reaction was added dropwise a mixture of TFA (10 mL) and dichloromethane (20 mL). The resulting solution was stirred at 0° C. for 1 hours until HPLC analysis indicated the reaction was completed. The volatiles were removed on rotavapor. To the residue was added in dichloromethane (10 mL), the resulting solution was concentrated on rotapor; the dichloromethane disolvation/concentration was repeated three time; then to the residue was added methanol (10 mL) and the resulting solution was evaporated to dryness on rotavapor; the methanol disolvation/concentration was repeated three times; the residue was purified on reverse phase HPLC and the collected fractions were lyophillized to provided a white solid compound (40), 890 mg, LCMS: MS m/z=706.4 [M+H]⁺.

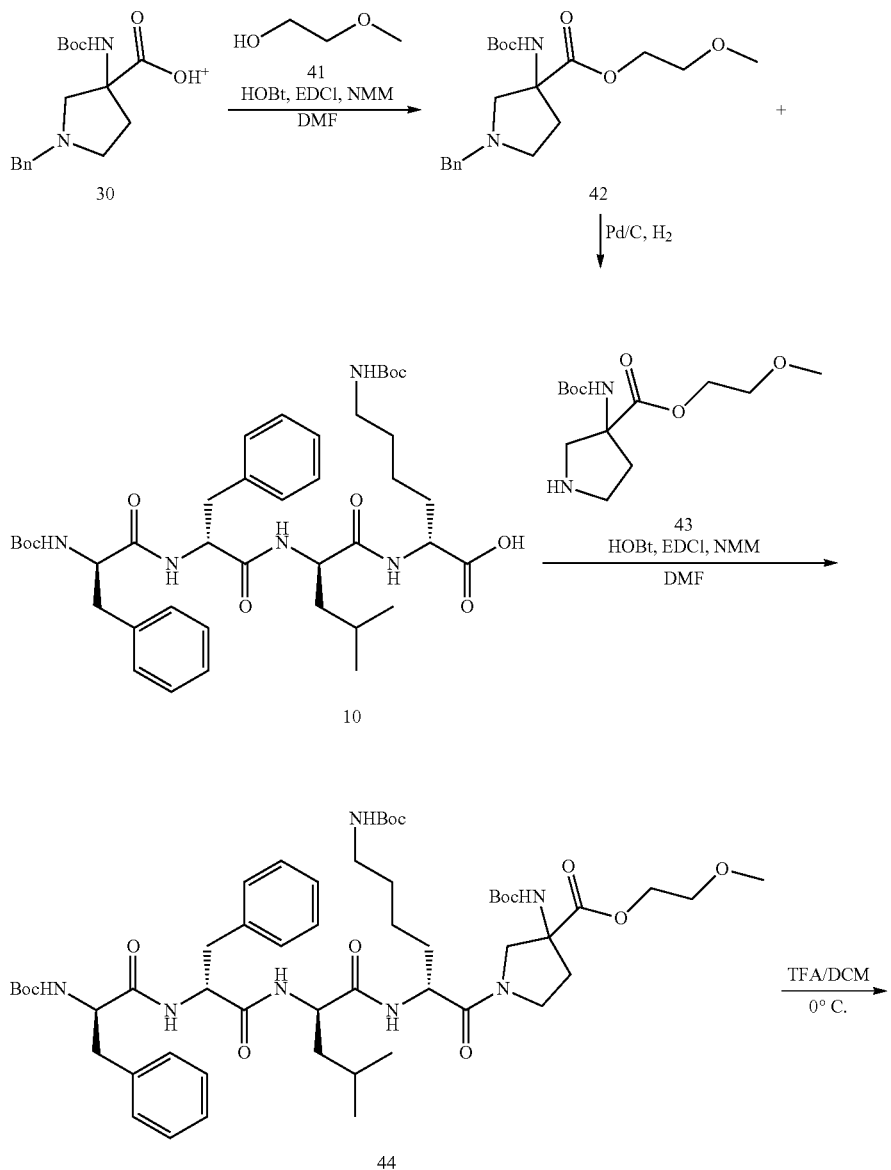

Reaction Scheme 8

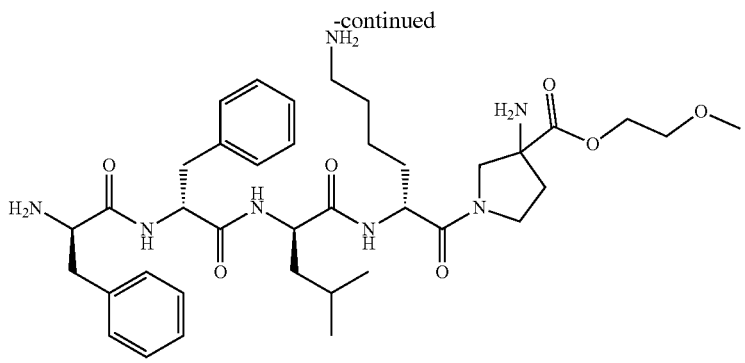

45

Example 95: Synthesis of Compound 42

Into a reaction flask under nitrogen was added 1-benzyl-3-(tert-butoxycarbonylamino) pyrrolidine-3-carboxylic acid (30) (5 g, 15.6 mmol, 1 eq) and DMF (106 mL) under nitrogen. The resulting reaction mixture was cooled to 0° C. in ice bath. To the cooled reaction mixture was added HOBt. $H_2O$ (2.32 g, 17.2 mmol, 1.1 eq) and EDCI (3.29 g, 17.2 mmol, 1.1 eq). After stirring for 30 minutes in ice bath, 2-methoxyethanol (41) (1.31 g, 17.2 mmol, 1.1 eq) and N-methylmorpholine (NMM) (3.31 g, 32.8 mmol, 2.1 eq) were added. The reaction mixture was stirred at 0° C. for 1 hours, then at room temperature until HPLC analysis indicated the reaction was completed. The reaction solution was added dropwise into water (300 mL) with stirring. After addition was completed, stirring was stopped and a precipitate formed. The reaction mixture stood for one hour. The precipitate was collected by filtration, washed with water (200 mL×3) and then dried under vacuum (30° C.). The isolated solid compound (42) was a white solid, 5.65 g, LCMS: m/z=379.4 [M+H]+.

Example 96: Synthesis of Compound 43

To the reaction flask was added compound (42) (5.0, 13.2 mmol, 1.0 eq) and methanol (12.6 mL). The reaction atmosphere was replaced with nitrogen, then to the reaction was added Pd/C (5 g). Then, the reaction atmosphere was replaced with hydrogen; the reaction was stirred at room temperature until the reaction was done. The reaction was filtered and the residue was washed with methanol (12.6 mL). The filtrate was concentrated on rotavapor and it provided a yellow oil (43), 3.56 g. LCMS: m/z=289.3 [M+H]+.

Example 97: Synthesis of Compound 44

Into a reaction flask under nitrogen was added compound (10) (5 g, 6.63 mmol, 1 eq) and DMF (106 mL) under nitrogen. The resulting reaction mixture was cooled to 0° C. in ice bath. To the cooled reaction mixture was added HOBt. $H_2O$ (1.12 g, 7.29 mmol, 1.1 eq) and EDCI (1.40 g, 7.29 mmol, 1.1 eq). After stirring for 30 minutes in ice bath, compound (43) (2.1 g, 7.29 mmol, 1.1 eq) and N-methylmorpholine (NMM) (1.41 g, 13.9 mmol, 2.1 eq) were added. The reaction mixture was stirred at 0° C. for 1 hours, then at room temperature until HPLC analysis indicated the reaction was completed. The reaction solution was added dropwise into water (300 mL) with stirring. After addition was completed, stirring was stopped and a precipitate formed. The reaction mixture stood for one hour. The precipitate was collected by filtration, washed with water (200 mL×3) and then dried under vacuum (30° C.). The isolated solid compound (44) was a white solid, 5.11 g, LCMS: m/z=1024.6 [M+H]+.

Example 98: Synthesis of Compound 45

The intermediate (44) (1.0 g, 0.99 mmol, 1.0 eq) was placed into a reaction flask under nitrogen; to the flask was added dichloromethane (10 mL); the resulting solution was cooled to 0° C. for 10 minutes; then to the cooled reaction was added dropwise a mixture of TFA (10 mL) and dichloromethane (20 mL). The resulting solution was stirred at 0° C. for 1 hours until HPLC analysis indicated the reaction was completed. The volatiles were removed on rotavapor. To the residue was added in dichloromethane (10 mL), the resulting solution was concentrated on rotapor; the dichloromethane disolvation/concentration was repeated three time; then to the residue was added methanol (10 mL) and the resulting solution was evaporated to dryness on rotavapor; the methanol disolvation/concentration was repeated three times; the residue was purified on reverse phase HPLC and the collected fractions were lyophillized to provided a white solid compound (45), 931 mg, LCMS: MS m/z=724.4 [M+H]+.

Reaction Scheme 9

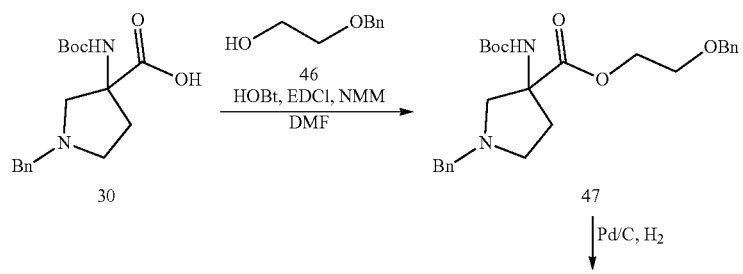

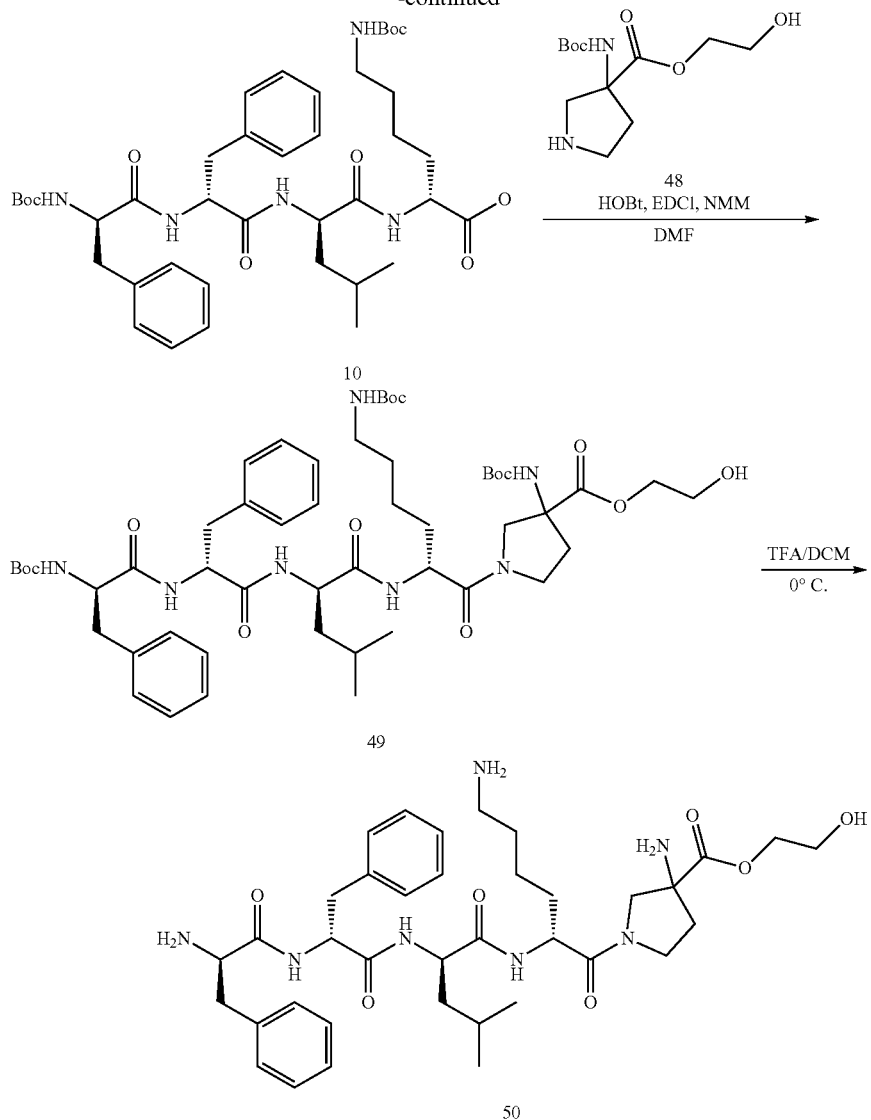

Example 99: Synthesis of Compound 47

Into a reaction flask under nitrogen was added 1-benzyl-3-(tert-butoxycarbonylamino) pyrrolidine-3-carboxylic acid (30) (5 g, 15.6 mmol, 1 eq) and DMF (106 mL) under nitrogen. The resulting reaction mixture was cooled to 0° C. in ice bath. To the cooled reaction mixture was added HOBt. $H_2O$ (2.32 g, 17.2 mmol, 1.1 eq) and EDCI (3.29 g, 17.2 mmol, 1.1 eq). After stirring for 30 minutes in ice bath, 2-benzyloxyethanol (46) (2.62 g, 17.2 mmol, 1.1 eq) and N-methylmorpholine (NMM) (3.31 g, 32.8 mmol, 2.1 eq) were added. The reaction mixture was stirred at 0° C. for 1 hours, then at room temperature until HPLC analysis indicated the reaction was completed. The reaction solution was added dropwise into water (300 mL) with stirring. After addition was completed, stirring was stopped and a precipitate formed. The reaction mixture stood for one hour. The precipitate was collected by filtration, washed with water (200 mL×3) and then dried under vacuum (30° C.). The isolated solid compound (47) was a white solid, 6.22 g, LCMS: m/z=455.7 $[M+H]^+$.

Example 100: Synthesis of Compound 48

To the reaction flask was added compound (47) (5.0 g, 11.0 mmol, 1.0 eq) and methanol (12.6 mL). The reaction atmosphere was replaced with nitrogen, then to the reaction was added Pd/C (5 g). Then the reaction atmosphere was replaced with hydrogen; the reaction was stirred at room temperature until the reaction was done. The reaction was filtered and the residue was washed with methanol (12.6 mL). The filtrate was concentrated on rotavapor and it provided a yellow oil (48), 2.50 g. LCMS: m/z=275.2 $[M+H]^+$.

Example 101: Synthesis of Compound 49

Into a reaction flask under nitrogen was added compound (10) (5 g, 6.63 mmol, 1 eq) and DMF (106 mL) under nitrogen. The resulting reaction mixture was cooled to 0° C. in ice bath. To the cooled reaction mixture was added HOBt. $H_2O$ (1.12 g, 7.29 mmol, 1.1 eq) and EDCI (1.40 g, 7.29 mmol, 1.1 eq). After stirring for 30 minutes in ice bath, compound (48) (2.0 g, 7.29 mmol, 1.1 eq) and N-methylmorpholine (NMM) (1.41 g, 13.9 mmol, 2.1 eq) were added. The reaction mixture was stirred at 0° C. for 1 hours, then at room temperature until HPLC analysis indicated the reaction was completed. The reaction solution was added dropwise into water (300 mL) with stirring. After addition was completed, stirring was stopped and a precipitate formed. The reaction mixture stood for one hour. The precipitate was collected by filtration, washed with water (200 mL×3) and then dried under vacuum (30° C.). The isolated solid compound (49) was a white solid, 6.0 g, LCMS: m/z=1011.2 [M+H]$^+$.

Example 102: Synthesis of Compound 50

The intermediate (49) (1.0 g, 0.99 mmol, 1.0 eq) was placed into a reaction flask under nitrogen; to the flask was added dichloromethane (10 mL); the resulting solution was cooled to 0° C. for 10 minutes; then to the cooled reaction was added dropwise a mixture of TFA (10 mL) and dichloromethane (20 mL). The resulting solution was stirred at 0° C. for 1 hours until HPLC analysis indicated the reaction was completed. The volatiles were removed on rotavapor. To the residue was added in dichloromethane (10 mL), the resulting solution was concentrated on rotapor; the dichloromethane disolvation/concentration was repeated three time; then to the residue was added methanol (10 mL) and the resulting solution was evaporated to dryness on rotavapor; the methanol disolvation/concentration was repeated three times; the residue was purified on reverse phase HPLC and the collected fractions were lyophillized to provided a white solid compound (50), 879 mg, LCMS: MS m/z=710.4 [M+H]$^+$.

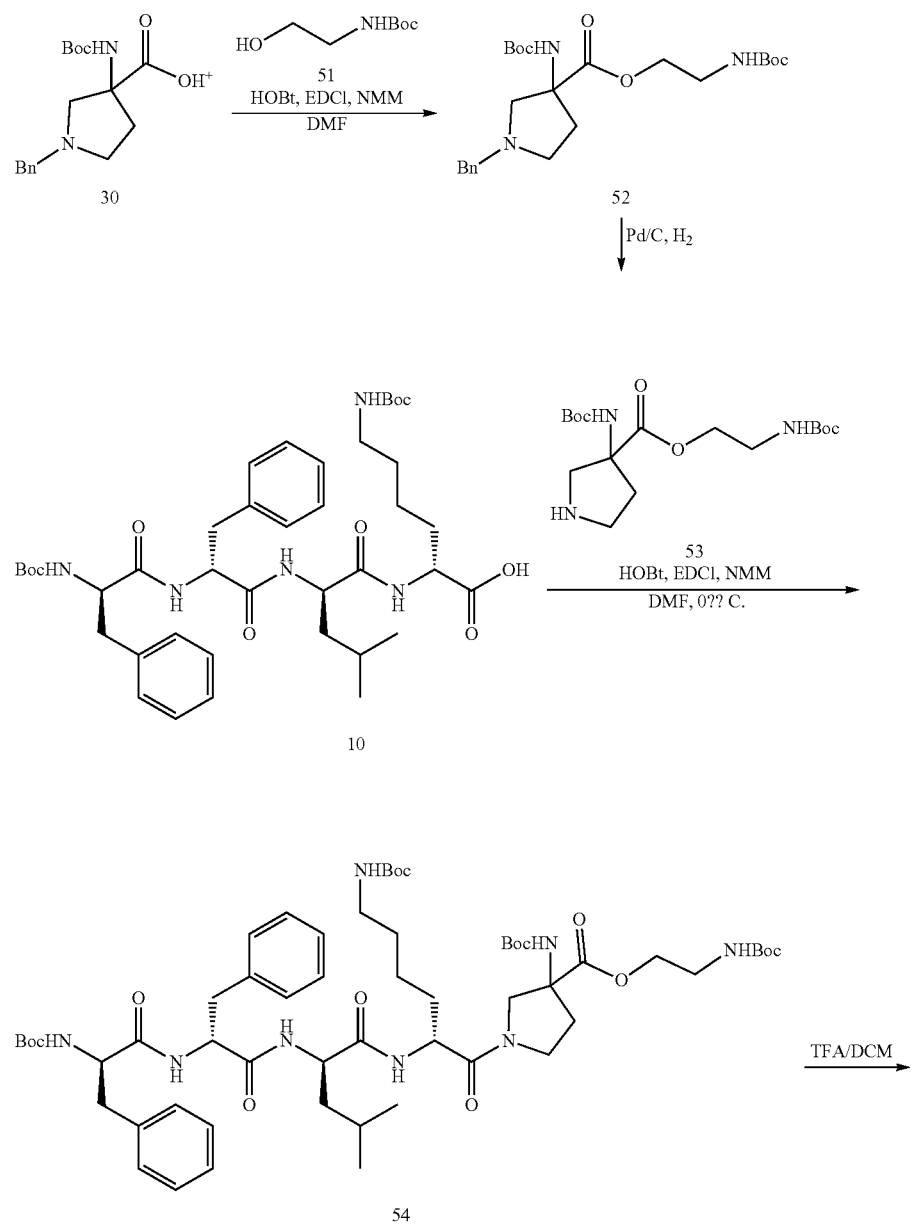

Reaction Scheme 10

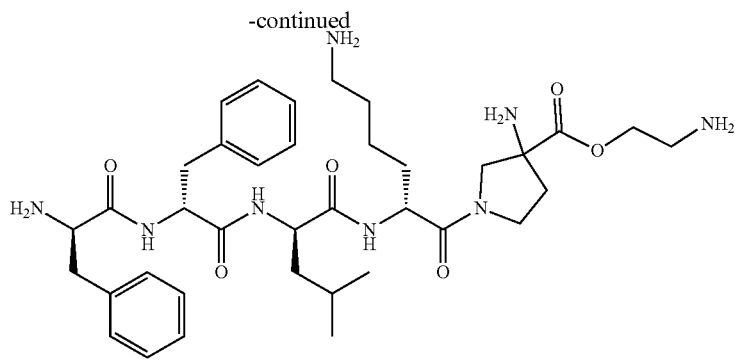

Example 103: Synthesis of Compound 52

Into a reaction flask under nitrogen was added 1-benzyl-3-(tert-butoxycarbonylamino) pyrrolidine-3-carboxylic acid (30) (5 g, 15.6 mmol, 1 eq) and DMF (106 mL) under nitrogen. The resulting reaction mixture was cooled to 0° C. in ice bath. To the cooled reaction mixture was added HOBt.H$_2$O (2.32 g, 17.2 mmol, 1.1 eq) and EDCI (3.29 g, 17.2 mmol, 1.1 eq). After stirring for 30 minutes in ice bath, tert-butyl N-(2-hydroxyethyl)carbamate (51) (2.77 g, 17.2 mmol, 1.1 eq) and N-methylmorpholine (NMM) (3.31 g, 32.8 mmol, 2.1 eq) were added. The reaction mixture was stirred at 0° C. for 1 hours, HPLC analysis indicated the reaction was completed. The reaction solution was added dropwise into water (300 mL) with stirring. After addition was completed, stirring was stopped and a precipitate formed. The reaction mixture stood for one hour. The precipitate was collected by filtration, washed with water (200 mL×3) and then dried under vacuum (30° C.). The isolated solid compound (52) was a white solid, 6.07 g, LCMS: m/z=464.3 [M+H]$^+$.

Example 104: Synthesis of Compound 53

To the reaction flask was added compound (52) (5.0 g, 10.8 mmol, 1.0 eq) and methanol (12.6 mL). The reaction atmosphere was replaced with nitrogen, then to the reaction was added Pd/C (5 g). Then the reaction atmosphere was replaced with hydrogen; the reaction was stirred at room temperature until the reaction was done. The reaction was filtered and the residue was washed with methanol (12.6 mL). The filtrate was concentrated on rotavapor and it provided a yellow oil (53), 3.50 g. LCMS: m/z=374.2 [M+H]$^+$.

Example 105: Synthesis of Compound 54

Into a reaction flask under nitrogen was added compound (10) (5 g, 6.63 mmol, 1 eq) and DMF (106 mL) under nitrogen. The resulting reaction mixture was cooled to 0° C. in ice bath. To the cooled reaction mixture was added HOBt.H$_2$O (1.12 g, 7.29 mmol, 1.1 eq) and EDCI (1.40 g, 7.29 mmol, 1.1 eq). After stirring for 30 minutes in ice bath, compound (53) (2.72 g, 7.29 mmol, 1.1 eq) and N-methylmorpholine (NMM) (1.41 g, 13.9 mmol, 2.1 eq) were added. The reaction mixture was stirred at 0° C. for 1 hours, HPLC analysis indicated the reaction was completed. The reaction solution was added dropwise into water (300 mL) with stirring. After addition was completed, stirring was stopped and a precipitate formed. The reaction mixture stood for one hour. The precipitate was collected by filtration, washed with water (200 mL×3) and then dried under vacuum (30° C.). The isolated solid compound (54) was a white solid, 6.09 g, LCMS: m/z=1110.05 [M+H]$^+$.

Example 106: Synthesis of Compound 55

The intermediate (54) (1.0 g, 0.90 mmol, 1.0 eq) was placed into a reaction flask under nitrogen; to the flask was added dichloromethane (10 mL); the resulting solution was cooled to 0° C. for 10 minutes; then to the cooled reaction was added dropwise a mixture of TFA (10 mL) and dichloromethane (20 mL). The resulting solution was stirred at 0° C. for 1 hours until HPLC analysis indicated the reaction was completed. The volatiles were removed on rotavapor. To the residue was added in dichloromethane (10 mL), the resulting solution was concentrated on rotapor; the dichloromethane disolvation/concentration was repeated three time; then to the residue was added methanol (10 mL) and the resulting solution was evaporated to dryness on rotavapor; the methanol disolvation/concentration was repeated three times; the residue was purified on reverse phase HPLC and the collected fractions were lyophillized to provided a white solid compound (55), 900 mg, LCMS: MS m/z=709.4 [M+H]$^+$.

Reaction Scheme 11

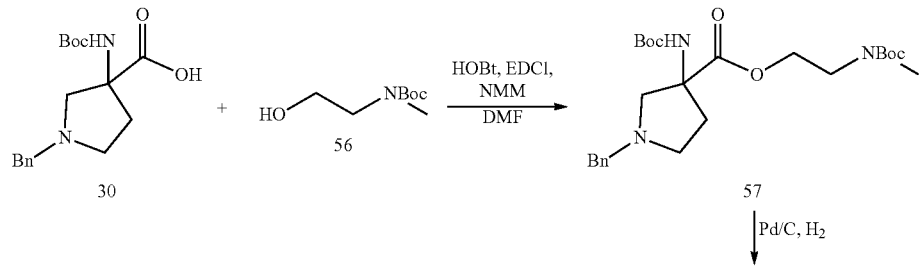

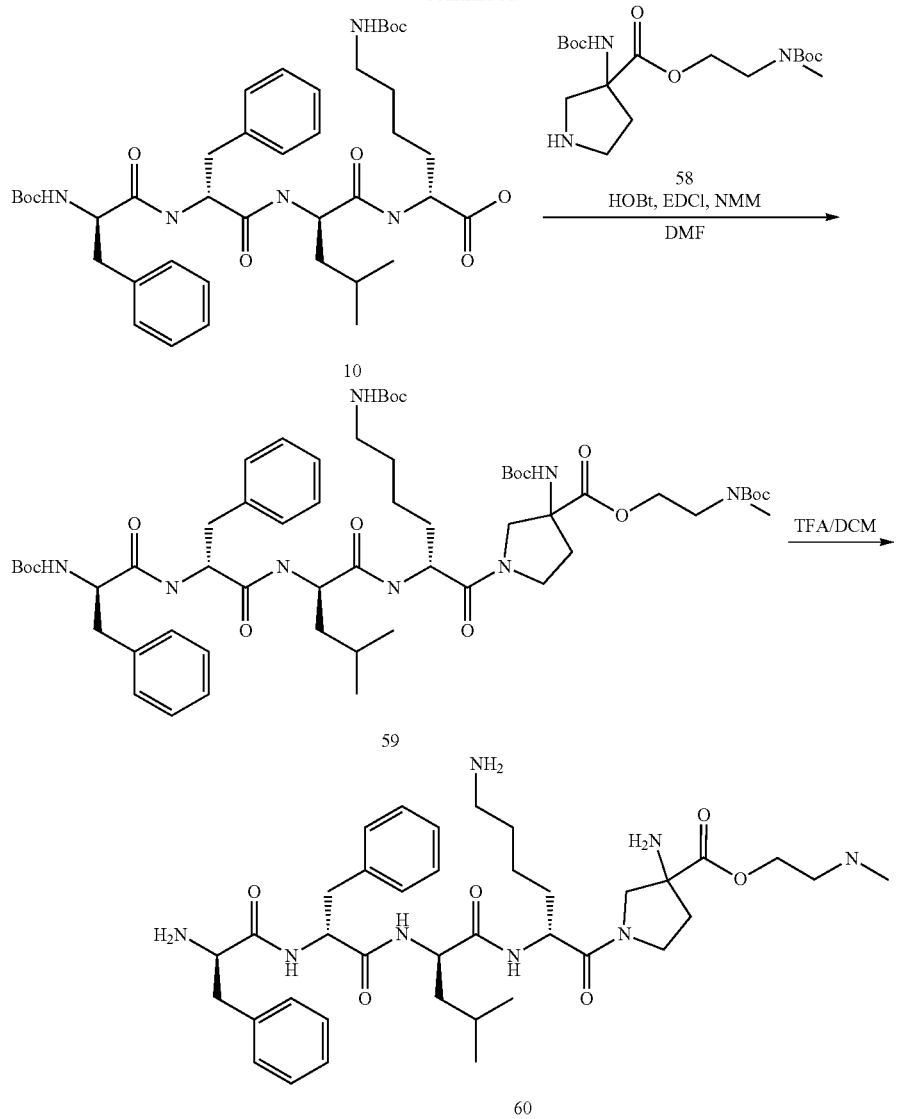

Example 107: Synthesis of Compound 56

Into a reaction flask under nitrogen was added 1-benzyl-3-(tert-butoxycarbonylamino) pyrrolidine-3-carboxylic acid (30) (5 g, 15.6 mmol, 1 eq) and DMF (106 mL) under nitrogen. The resulting reaction mixture was cooled to 0° C. in ice bath. To the cooled reaction mixture was added HOBt. $H_2O$ (2.32 g, 17.2 mmol, 1.1 eq) and EDCI (3.29 g, 17.2 mmol, 1.1 eq). After stirring for 30 minutes in ice bath, tert-butyl N-(2-hydroxyethyl)carbamate (56) (3.01 g, 17.2 mmol, 1.1 eq) and N-methylmorpholine (NMM) (3.31 g, 32.8 mmol, 2.1 eq) were added. The reaction mixture was stirred at 0° C. for 1 hours, then at room temperature until HPLC analysis indicated the reaction was completed. The reaction solution was added dropwise into water (300 mL) with stirring. After addition was completed, stirring was stopped and a precipitate formed. The reaction mixture stood for one hour. The precipitate was collected by filtration, washed with water (200 mL×3) and then dried under vacuum (30° C.). The isolated solid compound (57) was a white solid, 6.59 g, LCMS: m/z=478.3 [M+H]$^+$.

Example 108: Synthesis of Compound 58

To the reaction flask was added compound (57) (5.0 g, 10.5 mmol, 1.0 eq) and methanol (12.6 mL). The reaction atmosphere was replaced with nitrogen, then to the reaction was added Pd/C (5 g). Then the reaction atmosphere was replaced with hydrogen; the reaction was stirred at room temperature until the reaction was done. The reaction was filtered and the residue was washed with methanol (12.6 mL). The filtrate was concentrated on rotavapor and it provided a yellow oil (58), 3.59 g. LCMS: m/z=388.3 [M+H]$^+$.

Example 109: Synthesis of Compound 59

Into a reaction flask under nitrogen was added compound (10) (5 g, 6.63 mmol, 1 eq) and DMF (106 mL) under nitrogen. The resulting reaction mixture was cooled to 0° C. in ice bath. To the cooled reaction mixture was added HOBt. $H_2O$ (1.12 g, 7.29 mmol, 1.1 eq) and EDCI (1.40 g, 7.29 mmol, 1.1 eq). After stirring for 30 minutes in ice bath, compound (58) (2.82 g, 7.29 mmol, 1.1 eq) and N-methylmorpholine (NMM) (1.41 g, 13.9 mmol, 2.1 eq) were added. The reaction mixture was stirred at 0° C. for 1 hours, HPLC analysis indicated the reaction was completed. The reaction solution was added dropwise into water (300 mL) with stirring. After addition was completed, stirring was stopped and a precipitate formed. The reaction mixture stood for one hour. The precipitate was collected by filtration, washed with water (200 mL×3) and then dried under vacuum (30° C.). The isolated solid compound (59) was a white solid, 6.33 g, LCMS: m/z=1123.7 [M+H]+.

Example 110: Synthesis of Compound 60

The intermediate (59) (1.0 g, 0.89 mmol, 1.0 eq) was placed into a reaction flask under nitrogen; to the flask was added dichloromethane (10 mL); the resulting solution was cooled to 0° C. for 10 minutes; then to the cooled reaction was added dropwise a mixture of TFA (10 mL) and dichloromethane (20 mL). The resulting solution was stirred at 0° C. for 1 hours until HPLC analysis indicated the reaction was completed. The volatiles were removed on rotavapor. To the residue was added in dichloromethane (10 mL), the resulting solution was concentrated on rotapor; the dichloromethane disolvation/concentration was repeated three time; then to the residue was added methanol (10 mL) and the resulting solution was evaporated to dryness on rotavapor; the methanol disolvation/concentration was repeated three times; the residue was purified on reverse phase HPLC and the collected fractions were lyophillized to provided a white solid compound (60), 864 mg, LCMS: MS m/z=723.5 [M+H]+.

VI. Demonstrated Below are the Preparations for the Peptide Mimics for Medical Products: Compound 64

Reaction Scheme 12

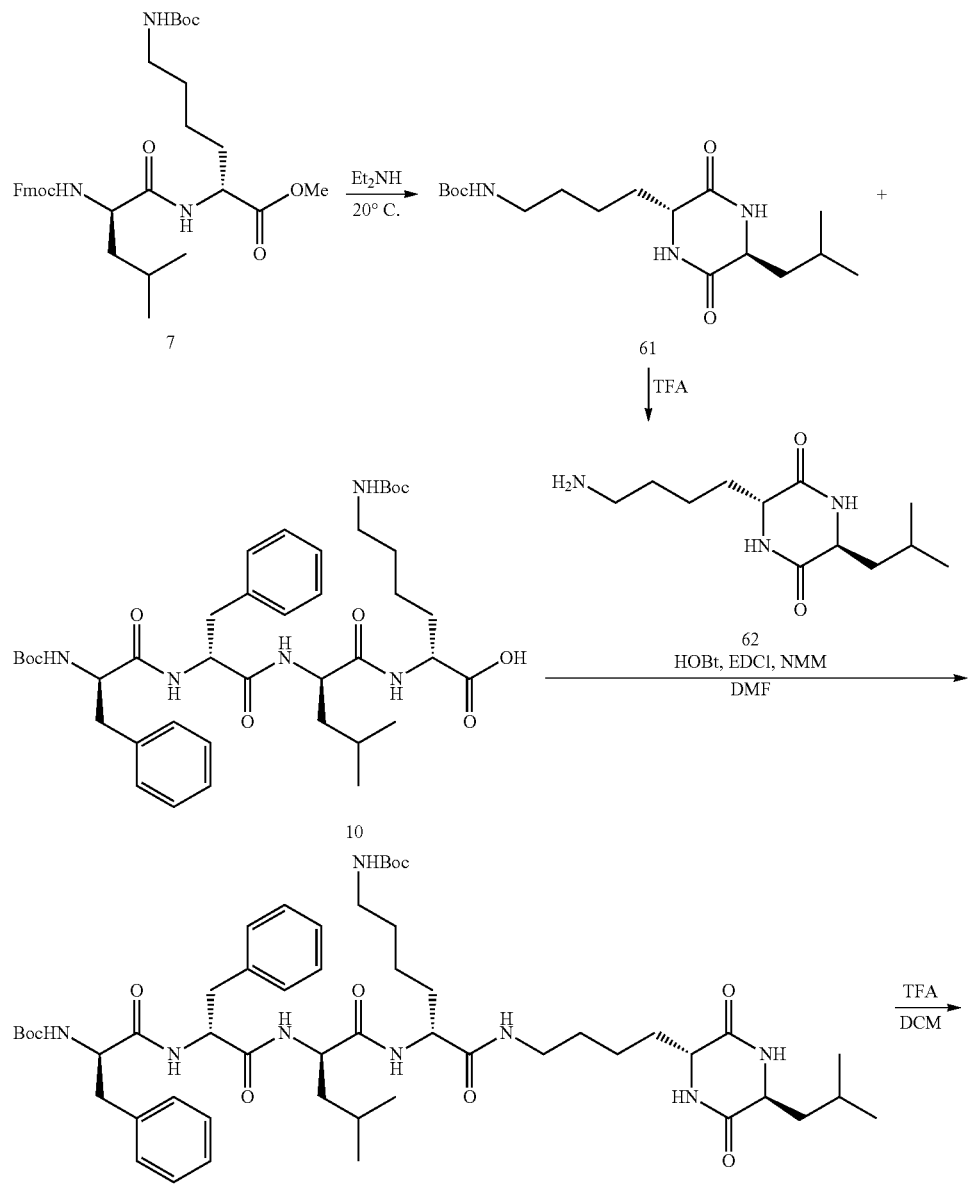

-continued

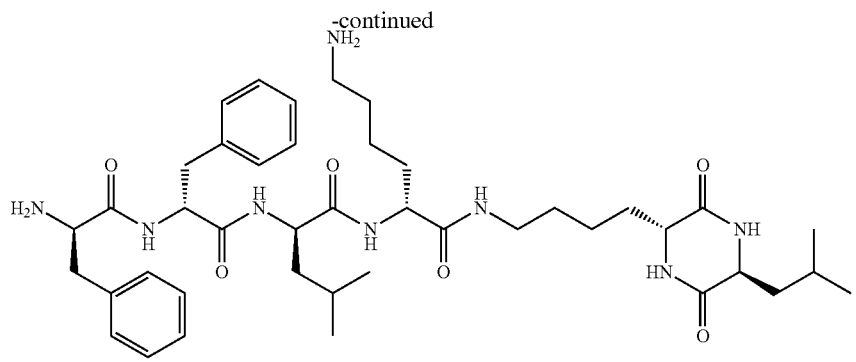

64

Example 111: Synthesis of Compound 61

To a reaction flask was added compound (7) (596 mg, 1.0 mmol, 1.0 eq), followed by added diethylamine (6 mL). The mixture was stirred at room temperature. The reaction was monitored until HPLC analysis indicated the reaction was completed. The volatiles were removed on rotavapor; to the residue was added ether (8.3 mL) under stirring, precipitates were formed. The precipitates were collected by filtration. The collected solid was dried in vacuum, it proved a white solid (61), 0.172 g. LC-MS m/z=342.3 [M+H]$^+$

Example 112: Synthesis of Compound 62

The intermediate (61) (5.0 g, 14.6 mmol, 1.0 eq) was placed into a reaction flask under nitrogen; to the flask was added dichloromethane (50 mL); the resulting solution was cooled to 0° C. for 10 minutes; then to the cooled reaction was added dropwise a mixture of TFA (50 mL) and dichloromethane (100 mL). The resulting solution was stirred at 0° C. for 1 hours until HPLC analysis indicated the reaction was completed. The volatiles were removed on rotavapor. To the residue was added in dichloromethane (50 mL), the resulting solution was concentrated on rotapor; the dichloromethane disolvation/concentration was repeated three time; then to the residue was added methanol (50 mL) and the resulting solution was evaporated to dryness on rotavapor; the methanol disolvation/concentration was repeated three times; the residue was purified on silica gel column and the collected fractions were evaporated to a white solid compound (62), 4.11 g, LCMS: MS m/z=356.4 [M+H]$^+$.

Example 113: Synthesis of Compound 63

Into a reaction flask under nitrogen was added compound (10) (5 g, 6.63 mmol, 1 eq) and DMF (106 mL) under nitrogen. The resulting reaction mixture was cooled to 0° C. in ice bath. To the cooled reaction mixture was added HOBt.

H$_2$O (1.12 g, 7.29 mmol, 1.1 eq) and EDCI (1.40 g, 7.29 mmol, 1.1 eq). After stirring for 30 minutes in ice bath, compound (62) (2.59 g, 7.29 mmol, 1.1 eq) and N-methylmorpholine (NMM) (1.41 g, 13.9 mmol, 2.1 eq) were added. The reaction mixture was stirred at 0° C. for 1 hours, HPLC analysis indicated the reaction was completed. The reaction solution was added dropwise into water (300 mL) with stirring. After addition was completed, stirring was stopped and a precipitate formed. The reaction mixture stood for one hour. The precipitate was collected by filtration, washed with water (200 mL×3) and then dried under vacuum (30° C.). The isolated solid compound (63) was a white solid, 5.98 g, LCMS: m/z=978.8 [M+H]$^+$.

Example 114: Synthesis of Compound 64

The intermediate (63) (1.0 g, 1.02 mmol, 1.0 eq) was placed into a reaction flask under nitrogen; to the flask was added dichloromethane (10 mL); the resulting solution was cooled to 0° C. for 10 minutes; then to the cooled reaction was added dropwise a mixture of TFA (10 mL) and dichloromethane (20 mL). The resulting solution was stirred at 0° C. for 1 hours until HPLC analysis indicated the reaction was completed. The volatiles were removed on rotavapor. To the residue was added in dichloromethane (10 mL), the resulting solution was concentrated on rotapor; the dichloromethane disolvation/concentration was repeated three time; then to the residue was added methanol (10 mL) and the resulting solution was evaporated to dryness on rotavapor; the methanol disolvation/concentration was repeated three times; the residue was purified on reverse phase HPLC and the collected fractions were lyophillized to provided a white solid compound (64), 904 mg, LCMS: MS m/z=778.2 [M+H]$^+$.

VII. Demonstrated Below are the Preparations for the Peptide Mimics for Medical Products 66, 67
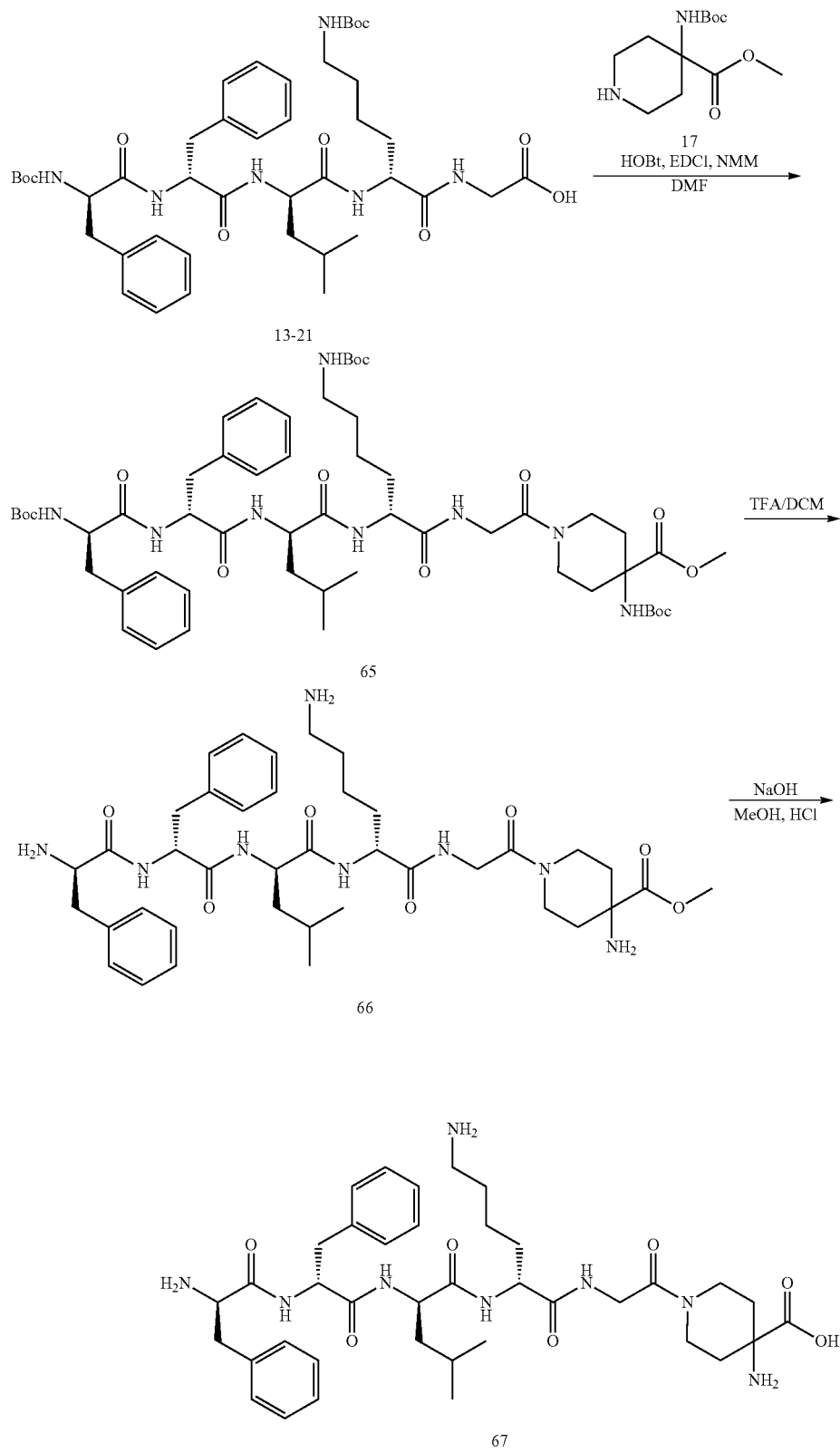

Example 115: Synthesis of Compound 65

Into a reaction flask under nitrogen was added compound (13-21) (368 g, 0.45 mmol, 1 eq) and DMF (9 mL) under nitrogen. The resulting reaction mixture was cooled to 0° C. in ice bath. To the cooled reaction mixture was added HOBt.H$_2$O (83 mg, 0.5 mmol, 1.1 eq) and EDCI (104 mg, 0.54 mmol, 1.1 eq). After stirring for 30 minutes in ice bath, methyl 4-(tert-butoxycarbonylamino)piperidine-4-carboxylate (17) (140 mg, 0.5 mmol, 1.2 eq) and N-methylmorpholine (NMM) (55 mg, 0.5 mmol, 1.2 eq) were added. The reaction mixture was stirred at 0° C. for 1 hours, then stirred at room temperature until HPLC analysis indicated the reaction was completed. To the reaction was added dichloromethane (8 mL); the resulting solution was added into 5% KHSO4·H2O (18 mL) with stirring. After stirring for 15 minutes, the solid was separated by filtration; the organic filtrate was washed with 5% KHSO4·H2O (3×7 mL), 5% NaHCO3 (7 mL×3), and brine (7 ml×3), then dried over anhydrous sodium sulfate. The drying reagent was filtered and the filtrate was concentrated in vacuum, it provided a solid (65), 0.375 g, LCMS: m/z=1052.3 [M+H]$^+$.

Example 116: Synthesis of Compound 66

The intermediate (65) (0.315 g, 0.3 mmol, 1.0 eq) was placed into a reaction flask under nitrogen; to the flask was added dichloromethane (5 mL); the resulting solution was cooled to 0° C. for 10 minutes; then to the cooled reaction was added dropwise a mixture of TFA (0.2 mL). The resulting solution was stirred at 0° C. for 30 minutes, then at room temperature until HPLC analysis indicated the reaction was completed. The volatiles were removed on rotavapor. To the residue was added ether (4.2 mL) under vigorously stirring; plenty of precipitates formed; after standing for 30 minutes, the solid was collected by filtration; the solid was further dried in vacuum; it provided a white solid compound (66), 233 mg, LCMS: MS m/z=751.4 [M+H]$^+$.

Example 117: Synthesis of Compound 67

The compound (66) (0.15 g, 0.20 mmol, 1.0 eq) was placed into a reaction flask under nitrogen, followed by adding methanol (3.6 mL). To the resulting solution was added a solution of NaOH (0.22 mL, 1.0 M, 0.22 mmol, 1.1 eq.) dropwise. The reaction mixture was stirred at room temperature for one hours until HPLC analysis indicated the reaction was completed. Then, a HCl solution (1.0 M) was added dropwise until pH=2~3 was achieved. The reaction mixture was concentrated; the aqueous phase was extracted with dichloromethane (17 mL×3); the combined organic extracts were dried over anhydrous sodium sulfate; concentrating the dried organic extracts provided a white compound (67), 100 mg; LC-MS m/z=737.4[M+H]$^+$.

VIII. Demonstrated Below are the Preparations for the Peptide Mimics for Medical Products 70, 71

Reaction Scheme 14

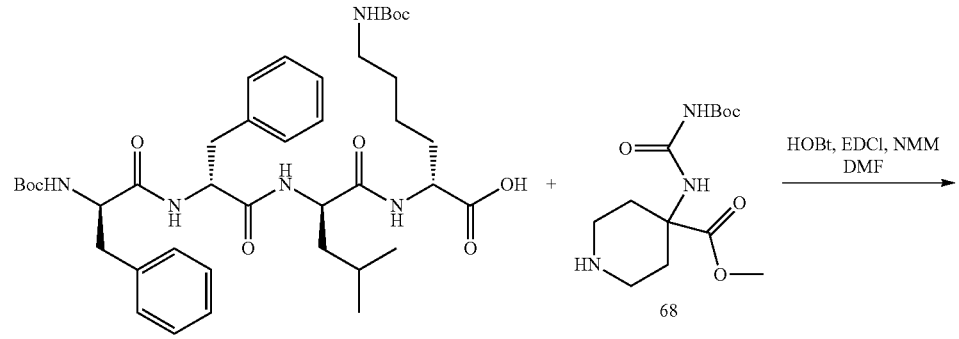

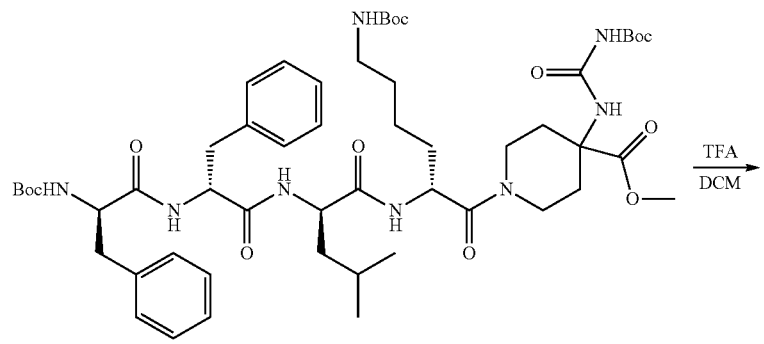

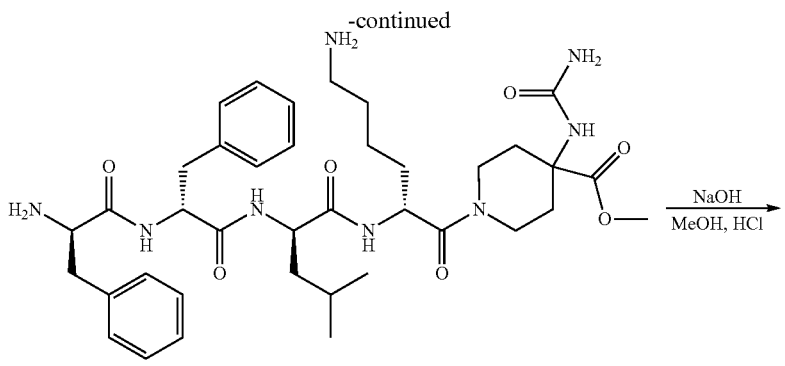

70

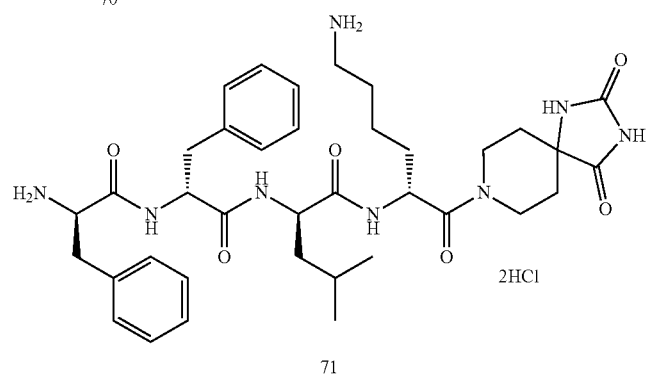

71

Example 118: Synthesis of Compound 69

Into a reaction flask under nitrogen was added compound (10) (754 mg, 1.0 mmol, 1 eq) and DMF (16.2 mL) under nitrogen. The resulting reaction mixture was cooled to 0° C. in ice bath. To the cooled reaction mixture was added HOBt. $H_2O$ (184 mg, 1.2 mmol, 1.2 eq) and EDCI (230 mg, 1.2 mmol, 1.2 eq). After stirring for 30 minutes in ice bath, methyl 4-(3-(tert-butoxycarbonyl)ureido)piperidine-4-carboxylate (68) (363 mg, 1.2 mmol, 1.2 eq) and N-methylmorpholine (NMM) (121 mg, 1.2 mmol, 1.2 eq) were added. The reaction mixture was stirred at 0° C. for 1 hours, then stirred at room temperature until HPLC analysis indicated the reaction was completed. The reaction was added dropwise to water (45 mL) under stirring; precipitates were formed; the mixture stood for one hour; the solid was collected by filtration and washed with water (45 mL×4). The solid was dried in vacuum (30° C.) and it provided a white solid (69), 0.938 g, LCMS: m/z=737.9 [M+H]$^+$.

Example 119: Synthesis of Compound 70

The intermediate (69) (1.04 g, 1.0 mmol, 1.0 eq) was placed into a reaction flask under nitrogen; to the flask was added dichloromethane (48 mL); the resulting solution was cooled to 0° C. for 10 minutes; then to the cooled reaction was added dropwise a mixture of TFA (12 mL) and dichloromethane (12 mL). The resulting solution was stirred at 0° C. for 4 hours, then 2 hours at room temperature until HPLC analysis indicated the reaction was completed. The volatiles were removed on rotavapor. To the residue was added methanol (12 mL) and the resulting solution was evaporated to dryness on rotavapor; to the residue was added water; the resulting solution was lyophilized to a white solid compound (70), 953 mg, LCMS: MS m/z=680.8 [M+H]$^+$.

Example 120: Synthesis of Compound 71

The compound (70) (0.2 g, 0.191 mmol, 1.0 eq) was placed into a reaction flask under nitrogen, followed by adding methanol (4 mL). To the resulting solution was added a solution of NaOH (1.0 mL, 1.0 M, 1 mmol, 5 eq.) dropwise. The reaction mixture was stirred at room temperature for one hours until HPLC analysis indicated the reaction was completed. Then, HCl solution (1.0 M) was added dropwise until pH=4-5 was achieved. The reaction mixture was further purified on reverse phase HPLC; the collected fractions were lyophilized to a white compound (71), 52 mg; LC-MS m/z=705.2 [M+H]$^+$.

IX. Demonstrated Below are the Preparations for the Peptide Mimics for Medical Products 79, 80, 82, 83

Reaction Scheme 15

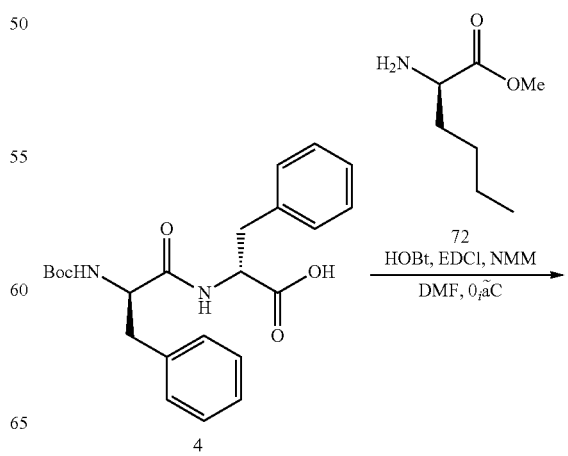

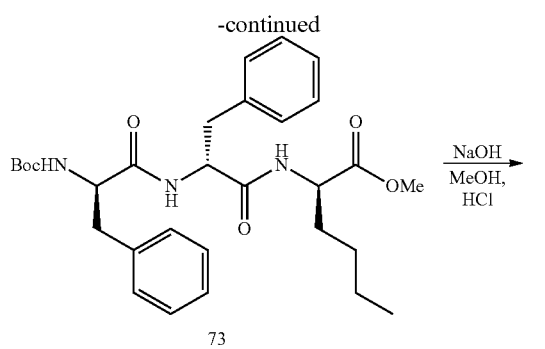

73

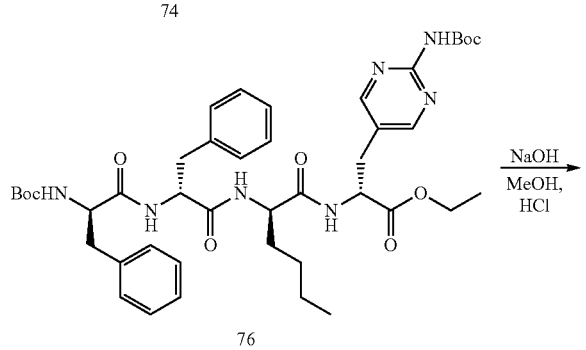

74

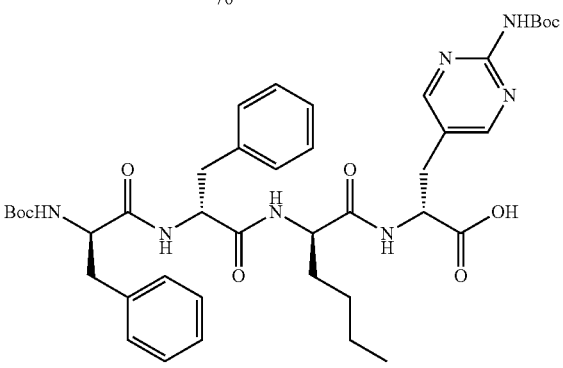

76

BocHN—[structure]—OH

77

Example 121: Synthesis of Compound 73

Into a reaction flask under nitrogen was added compound (4) (3.0 g, 7.3 mmol, 1 eq) and DMF (65 mL) under nitrogen. The resulting reaction mixture was cooled to 0° C. in ice bath. To the cooled reaction mixture was added HOBt. H₂O (1.35 g, 8.8 mmol, 1.1 eq) and EDCI (1.69 g, 8.8 mmol, 1.2 eq). After stirring for 30 minutes in ice bath, methyl (R)-2-aminohexanoate hydrochloride (72) (1.6 g, 8.8 mmol, 1.2 eq) and N-methylmorpholine (NMM) (1.8 g, 19.6 mmol, 2.4 eq) were added. The reaction mixture was stirred at 0° C. for 1 hours, then stirred at room temperature until HPLC analysis indicated the reaction was completed. To the reaction was added dichloromethane (60 mL); the resulting solution was added into 5% KHSO4·H2O (60 mL) with stirring; plenty of solids were formed; the solid was separated by filtration; the organic filtrate was washed with 5% KHSO4·H2O (3×60 mL), 5% NaHCO3 (60 mL×3), and brine (60 ml×3), then dried over anhydrous sodium sulfate. The drying reagent was filtered and the filtrate was concentrated in vacuum, it provided a solid (73), 2.64 g, LCMS: m/z=540.6 [M+H]⁺.

Example 122: Synthesis of Compound 74

The compound (73) (2.0 g, 3.7 mmol, 1.0 eq) was placed into a reaction flask under nitrogen, followed by adding methanol (50 mL). To the resulting solution was added a solution of NaOH (4.1 mL, 1.0 M, 4.1 mmol, 1.1 eq.) dropwise. The reaction mixture was stirred at 0° C. for one hours, then at room temperature until HPLC analysis indicated the reaction was completed. Then, HCl solution (1.0 M) was added dropwise until pH=4~5 was achieved. The reaction solution was concentrated; the aqueous phase was extracted with dichloromethane (17 mL×3); the combined organic extracts were dried over anhydrous sodium sulfate; concentrating the dried organic extracts provided a white solid (74), 1.68 g; LC-MS m/z=526.7[M+H]⁺.

Example 123: Synthesis of Compound 76

Into a reaction flask under nitrogen was added compound (74) (1.0 g, 1.9 mmol, 1 eq) and DMF (20 mL) under nitrogen. The resulting reaction mixture was cooled to 0° C. in ice bath. To the cooled reaction mixture was added HOBt. H₂O (0.242 g, 1.6 mmol, 1.2 eq) and EDCI (0.307 g, 1.6 mmol, 1.2 eq). After stirring for 30 minutes in ice bath, ethyl (R)-2-amino-3-(2-((tert-butoxycarbonyl)amino)pyrimidin-5-yl)propanoate (75) (0.162 g, 1.6 mmol, 1.2 eq) and N-methylmorpholine (NMM) (0.232 mg, 2.3 mmol, 1.2 eq) were added. The reaction mixture was stirred at 0° C. for 1 hours, then stirred at room temperature until HPLC analysis indicated the reaction was completed. To the reaction was added dichloromethane (60 mL); the resulting solution was added into 5% KHSO4·H2O (60 mL) with stirring. After addition was completed, the solid was separated by filtration; the organic filtrate was washed with 5% KHSO4·H2O (20 mL×3), 5% NaHCO3 (20 mL×3), and brine (20 ml×3), then dried over anhydrous sodium sulfate. The drying reagent was filtered and the filtrate was concentrated in vacuum, it provided a solid (76), 0.79 g, LCMS: m/z=818.99 [M+H]⁺.

Example 124: Synthesis of Compound 77

The compound (76) (0.5 g, 0.6 mmol, 1.0 eq) was placed into a reaction flask under nitrogen, followed by adding methanol (12.7 mL). To the resulting solution was added a solution of NaOH (0.66 mL, 1.0 M, 0.66 mmol, 1.1 eq.) dropwise. The reaction mixture was stirred at 0° C. for one hours until HPLC analysis indicated the reaction was completed. Then, a HCl solution (1.0 M) was added dropwise until pH=4~5 was achieved. The resulting solution was concentrated; the aqueous phase was extracted with dichloromethane (17 mL×3); the combined organic extracts were dried over anhydrous sodium sulfate; concentration of the dried organic extracts provided a white solid (77), 0.35 g; LC-MS m/z=800.9[M+H]⁺.

Example 125: Synthesis of Compound 78

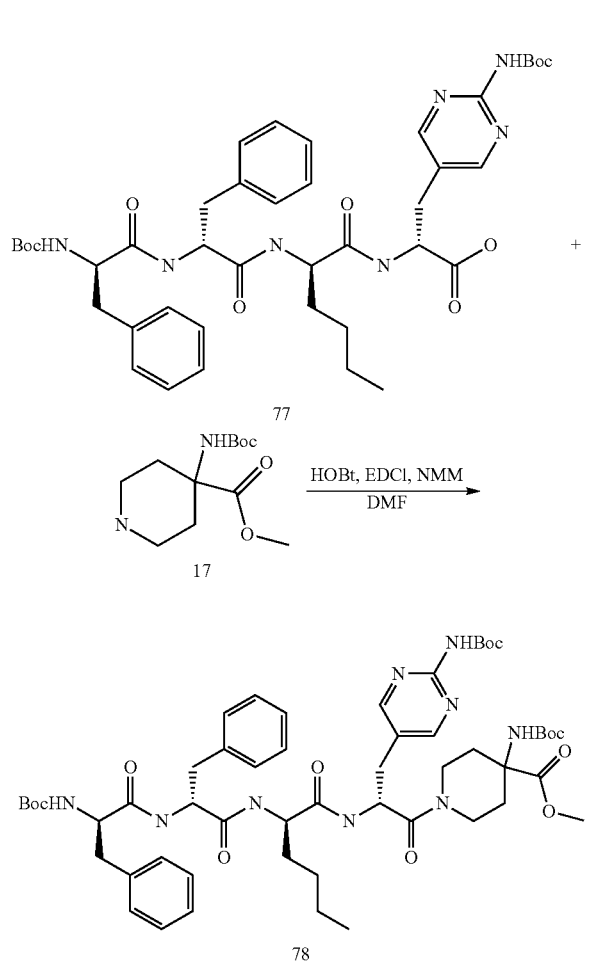

Into a reaction flask under nitrogen was added compound (77) (300 mg, 0.4 mmol, 1 eq) and DMF (6.5 mL) under nitrogen. The resulting reaction mixture was cooled to 0° C. in ice bath. To the cooled reaction mixture was added HOBt. $H_2O$ (71 mg, 0.46 mmol, 1.2 eq) and EDCI (88 mg, 0.46 mmol, 1.2 eq). After stirring for 30 minutes in ice bath, methyl 4-((tert-butoxycarbonyl)amino)piperidine-4-carboxylate (17) (98 mg, 0.38 mmol, 1.2 eq) and N-methylmorpholine (NMM) (47 mg, 0.46 mmol, 1.2 eq) were added. The reaction mixture was stirred at 0° C. for 1 hours, then stirred at room temperature until HPLC analysis indicated the reaction was completed. To the reaction was added dichloromethane (6 mL); the resulting solution was added into 5% KHSO4·H2O (6 mL) with stirring. After addition was completed, the solid was separated by filtration; the organic filtrate was washed with 5% KHSO4·H2O (6 mL×3), 5% NaHCO3 (6 mL×3), and brine (6 ml×3), then dried over anhydrous sodium sulfate. The drying reagent was filtered and the filtrate was concentrated in vacuum, it provided a solid (78), 0.249 g, LCMS: m/z=1031.23 [M+H]⁺.

Example 126: Synthesis of Compound 79

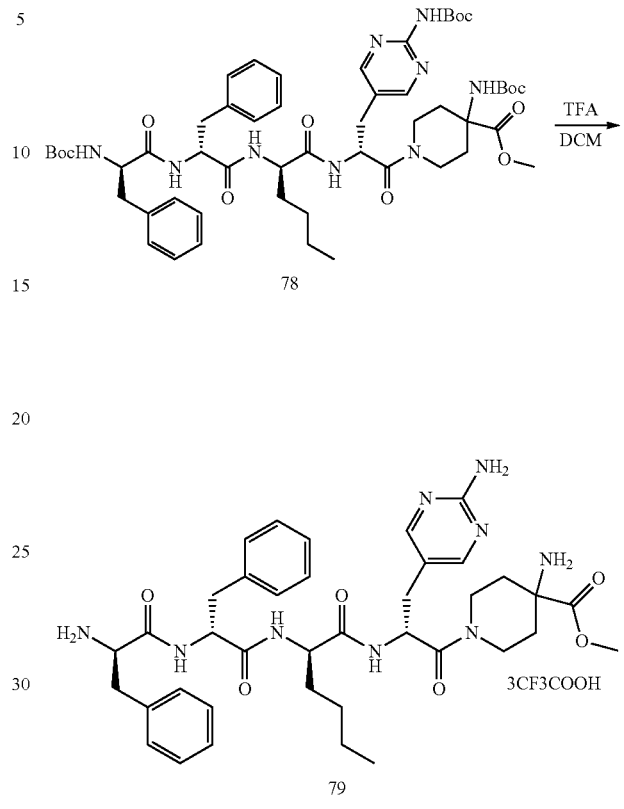

The intermediate (78) (0.2 g, 1.0 mmol, 1.0 eq) was placed into a reaction flask under nitrogen; to the flask was added dichloromethane (4 mL); the resulting solution was cooled to 0° C. for 10 minutes; then to the cooled reaction was added dropwise a mixture of TFA (0.2 mL). The resulting solution was stirred at 0° C. for 30 minutes, then at room temperature until HPLC analysis indicated the reaction was completed. The volatiles were removed on rotavapor. To the residue was added ether (2 mL) with vigorously stirring; the resulting suspension standed for 30 minutes; the solid was collected by filtration and dried in vacuum (30° C.); it provided a white solid compound (79), 137 mg, LCMS: MS m/z=730.9 [M+H]⁺.

Example 127: Synthesis of Compound 80

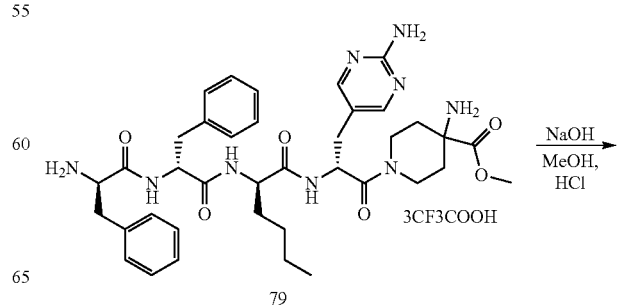

151

-continued

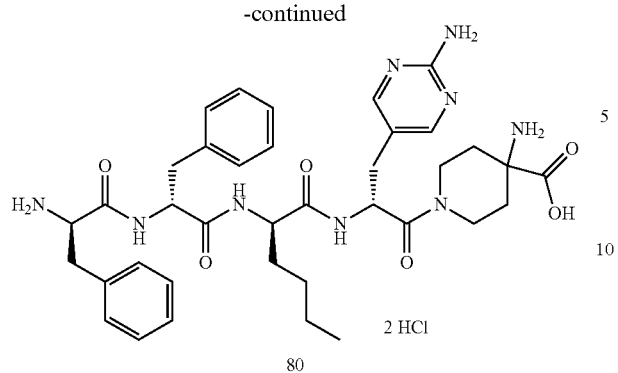

80

The compound (79) (80 mg, 0.08 mmol, 1.0 eq) was placed into a reaction flask under nitrogen, followed by adding methanol (2 mL). To the resulting solution was added a solution of NaOH (0.088 mL, 1.0 M, 0.088 mmol, 1.1 eq.) dropwise. The reaction mixture was stirred at 0° C. for one hours until HPLC analysis indicated the reaction was completed. Then, HCl solution (1.0 M) was added dropwise until pH=4~5 was achieved. The resulting solution was separated on reverse phase HPLC; the collected fractions were lyophilized to a white solid (80), 10 mg; LC-MS m/z=716.4 [M+H]+.

Example 128: Synthesis of Compound 81

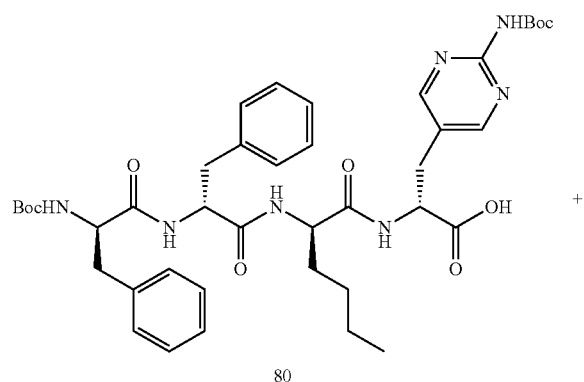

80

152

-continued

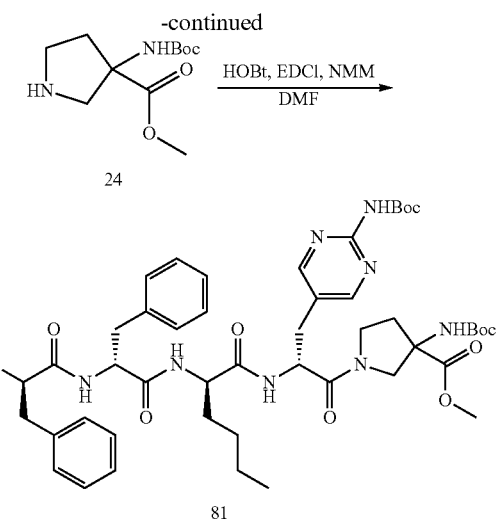

Into a reaction flask under nitrogen was added compound (80) (300 mg, 0.4 mmol, 1 eq) and DMF (6.3 mL) under nitrogen. The resulting reaction mixture was cooled to 0° C. in ice bath. To the cooled reaction mixture was added HOBt.H₂O (71 mg, 0.46 mmol, 1.2 eq) and EDCI (88 mg, 0.46 mmol, 1.2 eq). After stirring for 30 minutes in ice bath, methyl 3-((tert-butoxycarbonyl)amino)pyrrolidine-3-carboxylate (24) (93 mg, 0.38 mmol, 1.2 eq) and N-methylmorpholine (NMM) (47 mg, 0.46 mmol, 1.2 eq) were added. The reaction mixture was stirred at 0° C. for 1 hours, then stirred at room temperature until HPLC analysis indicated the reaction was completed. To the reaction was added dichloromethane (6 mL); to the solution was added into 5% KHSO4·H2O (6 mL) with stirring; plenty of solids were formed, the solid was separated by filtration; the organic filtrate was washed with 5% KHSO4·H2O (6 mL×3), 5% NaHCO₃ (6 mL×3), and brine (6 ml×3), then dried over anhydrous sodium sulfate. The drying reagent was filtered and the filtrate was concentrated in vacuum, it provided a solid (81), 0.234 g, LCMS: m/z=1017.2 [M+H]+.

Example 129: Synthesis of Compound 82

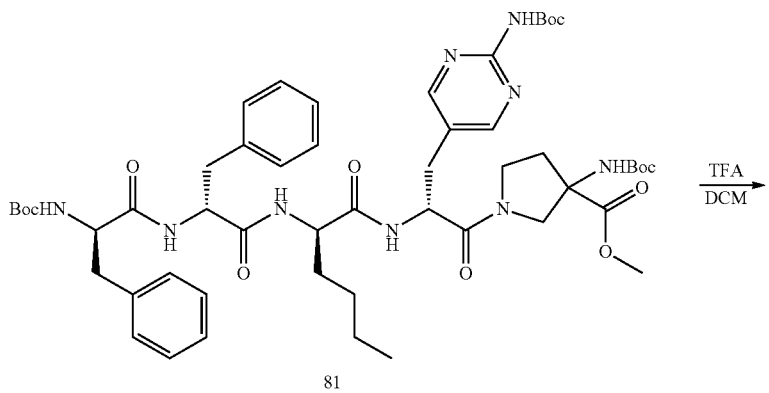

81

-continued

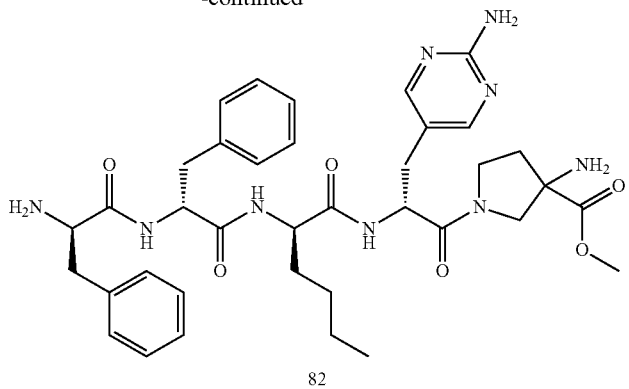

82

The intermediate (81) (0.2 g, 1.0 mmol, 1.0 eq) was placed into a reaction flask under nitrogen; to the flask was added dichloromethane (4 mL); the resulting solution was cooled to 0° C. for 10 minutes; then to the cooled reaction was added dropwise a mixture of TFA (0.2 mL). The resulting solution was stirred at 0° C. for 30 minutes, then at room temperature until HPLC analysis indicated the reaction was completed. The volatiles were removed on rotavapor. To the residue was added ether (2 mL) with vigorously stirring; the resulting suspension standed for 30 minutes; the solid was collected by filtration and dried in vacuum (30° C.); it provided a white solid compound (82), 67 mg, LCMS: MS m/z=817.0 [M+H]⁺.

Example 130: Synthesis of Compound 83

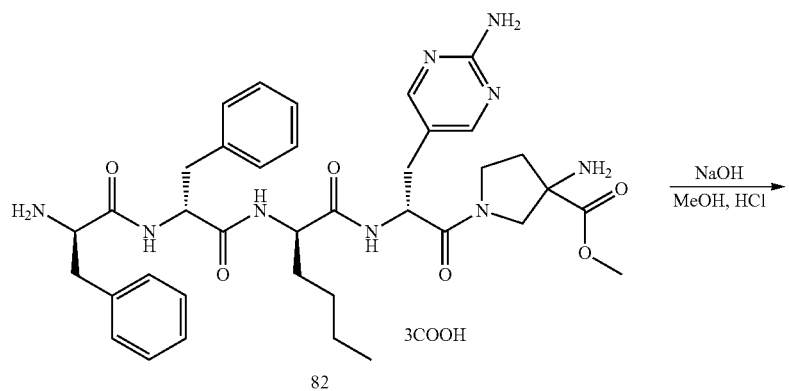

82

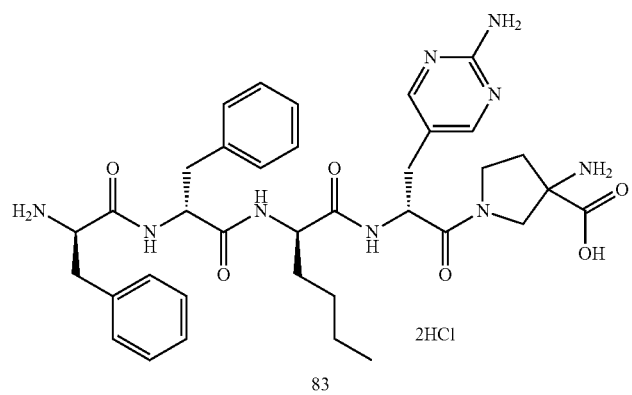

83

The compound (82) (50 mg, 0.06 mmol, 1.0 eq) was placed into a reaction flask under nitrogen, followed by adding methanol (1.3 mL). To the resulting solution was added a solution of NaOH (0.077 mL, 1.0 M, 0.077 mmol, 1.1 eq.) dropwise. The reaction mixture was stirred at 0° C. for one hours until HPLC analysis indicated the reaction was completed. Then, a HCl solution (1.0 M) was added dropwise until pH=4~5 was achieved. The resulting solution was then separated on reverse phase HPLC; the collected fractions were lyophilized to a white solid (83), 10 mg; LC-MS m/z=803.0[M+H]+.

VIIII. Demonstrated Below are the Preparations for the Peptide Mimics for Medical Products 89, 90, 92, 93

Reaction Scheme 16

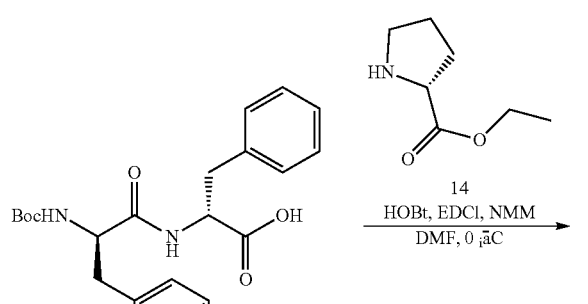

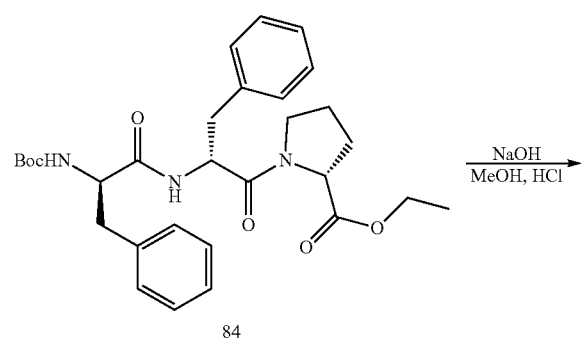

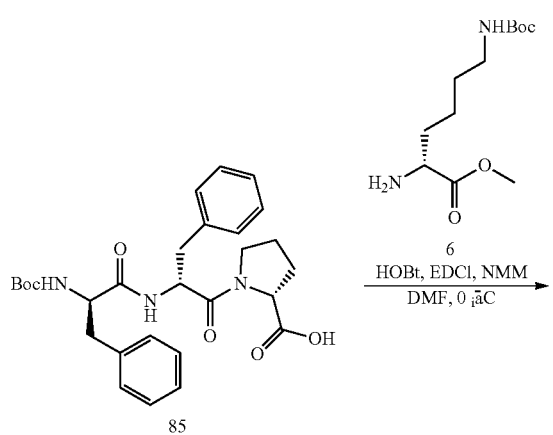

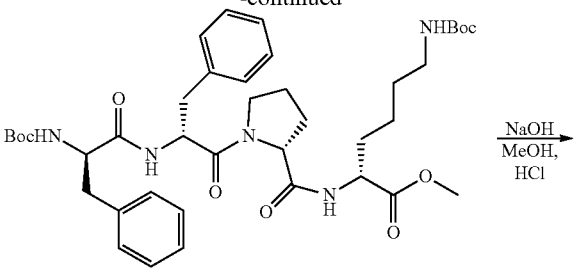

Example 131: Synthesis of Compound 84

Into a reaction flask under nitrogen was added compound (4) (5.0 g, 12.1 mmol, 1 eq) and DMF (106 mL) under nitrogen. The resulting reaction mixture was cooled to 0° C. in ice bath. To the cooled reaction mixture was added HOBt. H2O (2.22 g, 14.5 mmol, 1.2 eq) and EDCI (2.78 g, 14.5 mmol, 1.2 eq). After stirring for 30 minutes in ice bath, ethyl D-prolinate (14) (2.07 g, 14.5 mmol, 1.2 eq) and N-methylmorpholine (NMM) (1.46 g, 14.5 mmol, 1.2 eq) were added. The reaction mixture was stirred at 0° C. for 1 hours, then stirred at room temperature until HPLC analysis indicated the reaction was completed. To the reaction was added dichloromethane (106 mL); the resulting solution was added into 5% KHSO4·H2O (106 mL) with stirring; plenty of solids were formed; the solid was separated by filtration; the organic filtrate was washed with 5% KHSO4·H2O (3×60 mL), 5% NaHCO3 (60 mL×3), and brine (60 ml×3), then dried over anhydrous sodium sulfate. The drying reagent was filtered and the filtrate was concentrated in vacuum, it provided a solid (84), 6.01 g, LCMS: m/z=538.7 [M+H]+.

Example 132: Synthesis of Compound 85

The compound (84) (2.0 g, 3.7 mmol, 1.0 eq) was placed into a reaction flask under nitrogen, followed by adding methanol (40 mL). To the resulting solution was added a solution of NaOH (4.1 mL, 1.0 M, 4.1 mmol, 1.1 eq.) dropwise. The reaction mixture was stirred at 0° C. for one hours until HPLC analysis indicated the reaction was completed. Then, HCl solution (1.0 M) was added dropwise until pH=4-5 was achieved. The resulting solution was concentrated; the aqueous phase was extracted with dichloromethane (17 mL×3); the organic extracts were dried over anhydrous sodium sulfate; the dried organic extracts were concentrated on rotavapor; it provided a white solid (85), 1.52 g; LC-MS m/z=510.6[M+H]+.

Example 133: Synthesis of Compound 86

Into a reaction flask under nitrogen was added compound (85) (2.0 g, 3.9 mmol, 1 eq) and DMF (42.5 mL) under nitrogen. The resulting reaction mixture was cooled to 0° C. in ice bath. To the cooled reaction mixture was added HOBt.H$_2$O (0.72 g, 4.7 mmol, 1.2 eq) and EDCI (0.90 g, 4.7 mmol, 1.2 eq). After stirring for 30 minutes in ice bath, methyl N$^6$-(tert-butoxycarbonyl)-D-lysinate (6) (1.22 g g, 4.7 mmol, 1.2 eq) and N-methylmorpholine (NMM) (0.48 g, 4.7 mmol, 1.2 eq) were added. The reaction mixture was stirred at 0° C. for 1 hours, then stirred at room temperature until HPLC analysis indicated the reaction was completed. To the reaction was added dichloromethane (40 mL); the resulting solution was added into 5% KHSO4·H$_2$O (40 mL) with stirring. After addition was completed, the solid was separated by filtration; the organic filtrate was washed with 5% KHSO4·H$_2$O (3×40 mL), 5% NaHCO$_3$ (40 mL×3), and brine (40 ml×3), then dried over anhydrous sodium sulfate. The drying reagent was filtered and the filtrate was concentrated in vacuum, it provided a solid (86), 1.4 g, LCMS: m/z=752.9 [M+H]$^+$.

Example 134: Synthesis of Compound 87

The compound (86) (1.0 g, 1.3 mmol, 1.0 eq) was placed into a reaction flask under nitrogen, followed by adding methanol (25.2 mL). To the resulting solution was added a solution of NaOH (1.4 mL, 1.0 M, 1.4 mmol, 1.1 eq.) dropwise. The reaction mixture was stirred at 0° C. for one hours until HPLC analysis indicated the reaction was completed. Then, HCl solution (1.0 M) was added dropwise until pH=4~5 was achieved. The resulting solution was concentrated on rotavapor; the aqueous phase was extracted with dichloromethane (17 mL×3); the organic extracts were derived over anhydrous sodium sulfate; concentrated the dried organic extracts provided a white solid (87), 0.8 g; LC-MS m/z=738.9 [M+H]$^+$.

Synthesis of Peptide Analogues

Example 135: Synthesis of Compound 88

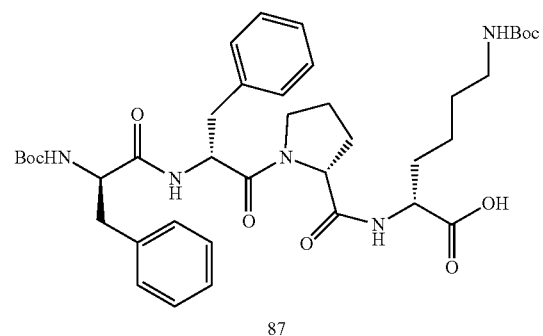

87

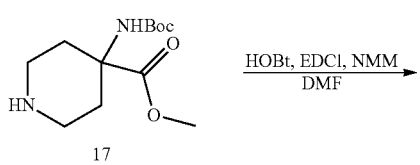

17

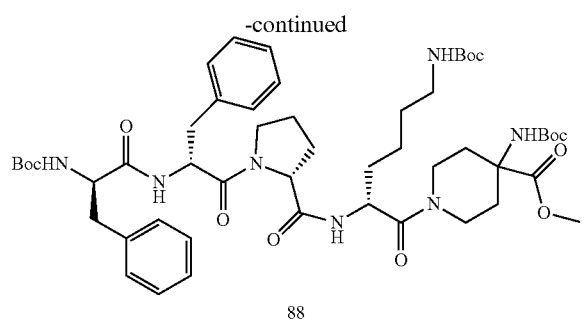

88

Into a reaction flask under nitrogen was added compound (87) (0.738 g, 1.0 mmol, 1 eq) and DMF (16.1 mL) under nitrogen. The resulting reaction mixture was cooled to 0° C. in ice bath. To the cooled reaction mixture was added HOBt.H$_2$O (184 mg, 1.2 mmol, 1.2 eq) and EDCI (0.23 g, 1.2 mmol, 1.2 eq). After stirring for 30 minutes in ice bath, methyl 4-((tert-butoxycarbonyl)amino)piperidine-4-carboxylate (17) (0.310 g, 1.2 mmol, 1.2 eq) and N-methylmorpholine (NMM) (0.121 g, 1.2 mmol, 1.2 eq) were added. The reaction mixture was stirred at 0° C. for 1 hours, then stirred at room temperature until HPLC analysis indicated the reaction was completed. The reaction was added dropwise into water (45 mL) under stirring; precipitates were formed; the mixture stood for one hour; the solid was collection by filtration and washed with water (55 mL×4). The solid was dried in vacuum (30° C.), it provided a white solid (88), 0.6 g, LCMS: m/z=979.2 [M+H]$^+$.

Example 136: Synthesis of Compound 89

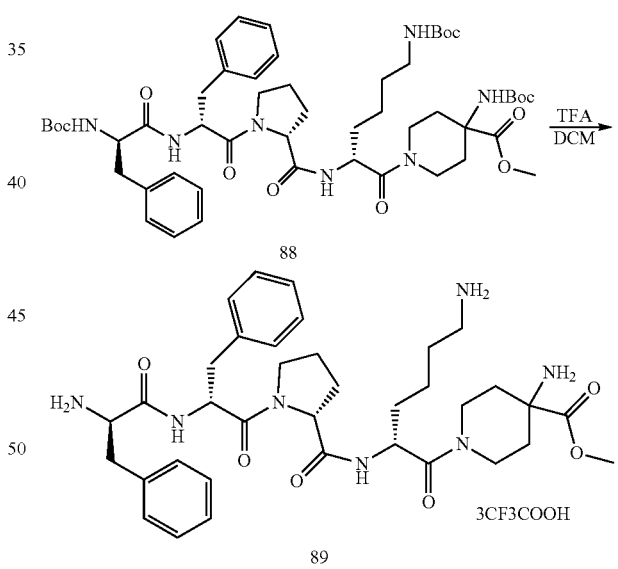

The intermediate (88) (0.2 g, 0.2 mmol, 1.0 eq) was placed into a reaction flask under nitrogen; to the flask was added dichloromethane (4 mL); the resulting solution was cooled to 0° C. for 10 minutes; then to the cooled reaction was added dropwise a mixture of TFA (0.2 mL). The resulting solution was stirred at 0° C. for 30 minutes, then at room temperature until HPLC analysis indicated the reaction was completed. The volatiles were removed on rotavapor. To the residue was added ether (2 mL) with vigorously stirring; the resulting suspension standed for 30 minutes; the solid was collected by filtration and dried in vacuum (30° C.); it provided a white solid compound (89), 30 mg, LCMS: MS m/z=678.9 [M+H]$^+$.

Example 137: Synthesis of Compound 90

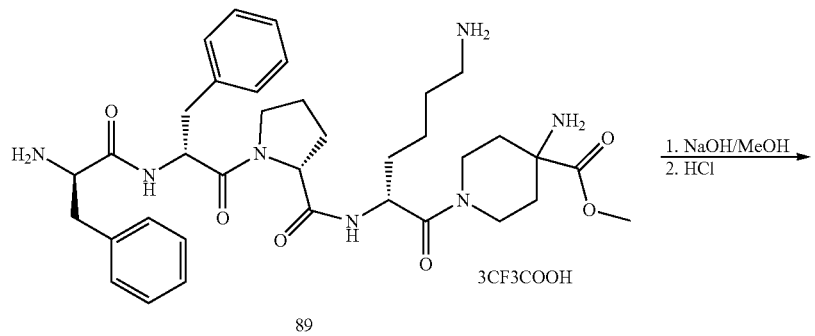

89

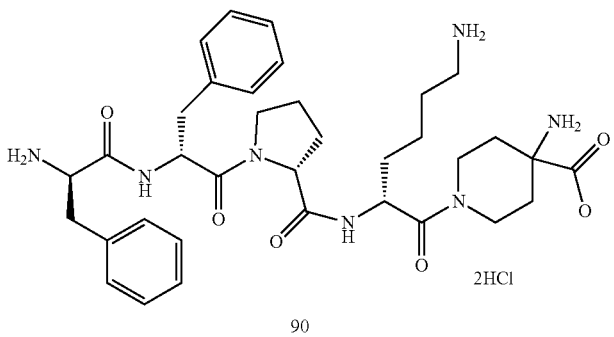

90

The compound (89) (110 mg, 0.1 mmol, 1.0 eq) was placed into a reaction flask under nitrogen, followed by adding methanol (2.5 mL). To the resulting solution was added a solution of NaOH (0.11 mL, 1.0 M, 0.11 mmol, 1.1 eq.) dropwise. The reaction mixture was stirred at 0° C. for one hours until HPLC analysis indicated the reaction was completed. Then, a HCl solution (1.0 M) was added dropwise until pH=4~5 was achieved. The resulting solution was then lyophilized to a white solid (90), 50 mg; LC-MS m/z=664.8 [M+H]$^+$.

Example 138: Synthesis of Compound 91

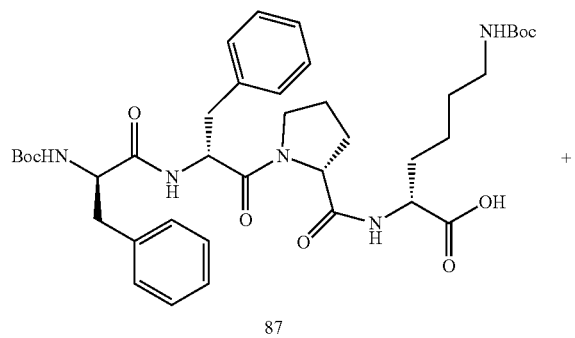

87

+

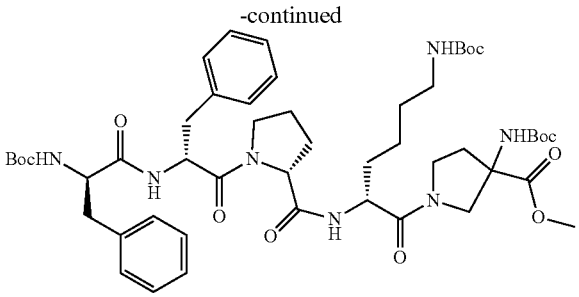

24

-continued

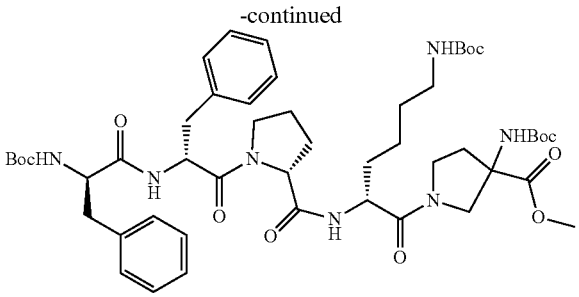

91

Into a reaction flask under nitrogen was added compound (87) (0.738 g, 1.0 mmol, 1 eq) and DMF (16.1 mL) under nitrogen. The resulting reaction mixture was cooled to 0° C. in ice bath. To the cooled reaction mixture was added HOBt. H$_2$O (184 mg, 1.2 mmol, 1.2 eq) and EDCI (0.23 g, 1.2 mmol, 1.2 eq). After stirring for 30 minutes in ice bath, methyl 3-((tert-butoxycarbonyl)amino)pyrrolidine-3-carboxylate (24)(0.293 g, 1.2 mmol, 1.2 eq) and N-methylmorpholine (NMM) (0.121 g, 1.2 mmol, 1.2 eq) were added. The reaction mixture was stirred at 0° C. for 1 hours, then stirred at room temperature until HPLC analysis indicated the reaction was completed. The reaction was added dropwise into water (45 mL) under stirring; precipitates were formed; the mixture stood for one hour; the solid was collection by filtration and washed with water (55 mL×4). The solid was dried in vacuum (30° C.), it provided a white solid (91), 0.6 g, LCMS: m/z=964.2 [M+H]$^+$.

Example 139: Synthesis of Compound 92

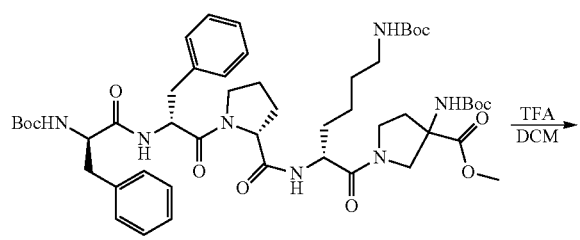

91

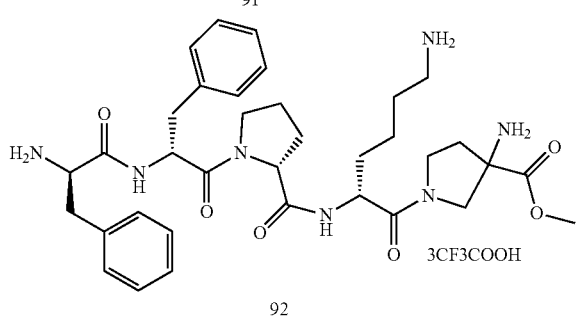

92

The intermediate (91) (0.193 g, 0.2 mmol, 1.0 eq) was placed into a reaction flask under nitrogen; to the flask was added dichloromethane (4 mL); the resulting solution was cooled to 0° C. for 10 minutes; then to the cooled reaction was added dropwise a mixture of TFA (0.2 mL). The resulting solution was stirred at 0° C. for 4 hours, then at room temperature until HPLC analysis indicated the reaction was completed. The volatiles were removed on rotavapor. To the residue was added ether (2 mL) with vigorously stirring; the resulting suspension standed for 30 minutes; the solid was collected by filtration and dried in vacuum (30° C.); it provided a white solid compound (92), 150 mg, LCMS: MS m/z=664.8 [M+H]$^+$.

Example 140: Synthesis of Compound 93

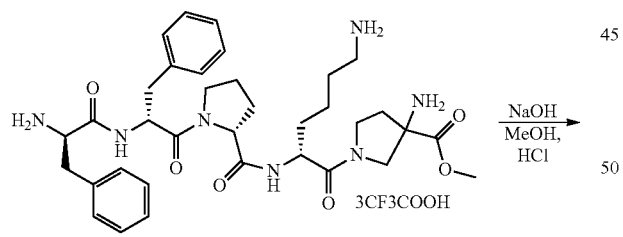

92

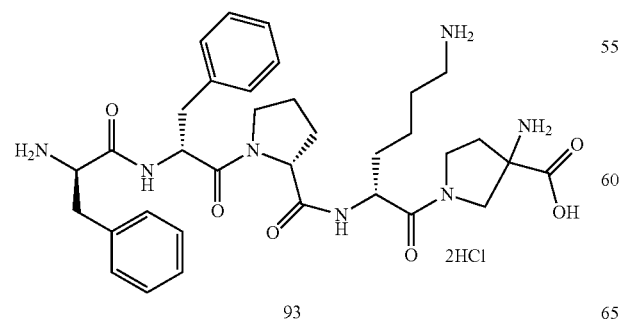

93

The compound (92) (100 mg, 0.1 mmol, 1.0 eq) was placed into a reaction flask under nitrogen, followed by adding methanol (2.5 mL). To the resulting solution was added a solution of NaOH (0.11 mL, 1.0 M, 0.11 mmol, 1.1 eq.) dropwise. The reaction mixture was stirred at 0° C. for one hours until HPLC analysis indicated the reaction was completed. Then, a HCl solution (1.0 M) was added dropwise until pH=4~5 was achieved. The resulting solution was then purified on reverse phase HPLC; the collected fractions were lyophilized to a white solid (93), 50 mg; LC-MS m/z=650.4 [M+H]$^+$.

X. Demonstrated Below are the Preparations for the Peptide Mimics for Medical Products 100, 101, 103, 104, 112, 118, 119, 126, 127, 133, 134

Reaction Scheme 17

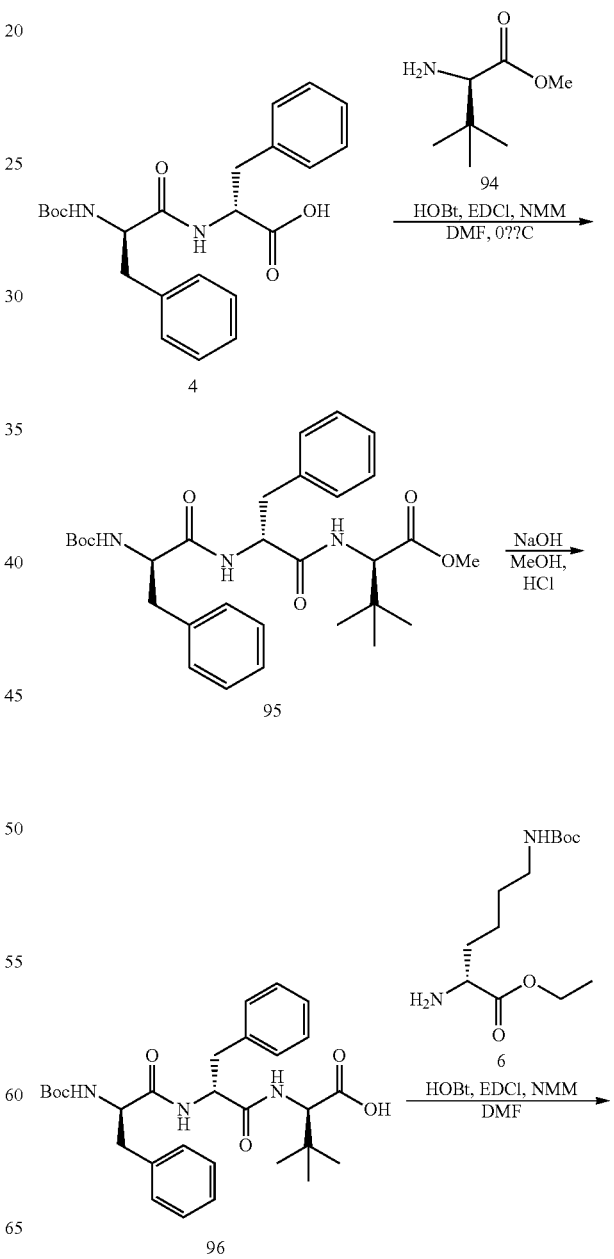

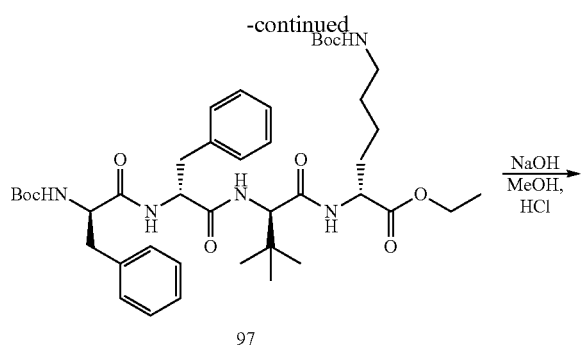

Example 141: Synthesis of Compound 95

Into a reaction flask under nitrogen was added compound (4) (5.0 g, 12.1 mmol, 1 eq) and DMF (106 mL) under nitrogen. The resulting reaction mixture was cooled to 0° C. in ice bath. To the cooled reaction mixture was added HOBt.H$_2$O (2.22 g, 14.5 mmol, 1.2 eq) and EDCI (2.78 g, 14.5 mmol, 1.2 eq). After stirring for 30 minutes in ice bath, compound (94) (1.17 g, 14.5 mmol, 1.2 eq) and N-methylmorpholine (NMM) (1.46 g, 14.5 mmol, 1.2 eq) were added. The reaction mixture was stirred at 0° C. for 1 hours, then stirred at room temperature until HPLC analysis indicated the reaction was completed. To the reaction was added dichloromethane (106 mL); the resulting solution was added into 5% KHSO4·H2O (106 mL) with stirring. After addition was completed, the solid was separated by filtration; the organic filtrate was washed with 5% KHSO4·H$_2$O (3×60 mL), 5% NaHCO$_3$ (60 mL×3), and brine (60 ml×3), then dried over anhydrous sodium sulfate. The drying reagent was filtered and the filtrate was concentrated in vacuum, it provided a solid (95), 6.01 g, LCMS: m/z=540.3 [M+H]$^+$.

Example 142: Synthesis of Compound 96

The compound (95) (1.00 g, 1.86 mmol, 1.0 eq) was placed into a reaction flask under nitrogen, followed by adding methanol (25.3 mL). To the resulting solution was added a solution of NaOH (2.04 mL, 1.0 M, 2.04 mmol, 1.1 eq.) dropwise. The reaction mixture was stirred at 0° C. for one hours until HPLC analysis indicated the reaction was completed. Then, a HCl solution (1.0 M) was added dropwise until pH=4~5 was achieved. The resulting solution was then lyophilized to a white solid (96), 0.80; LC-MS m/z=525.7 [M+H]$^+$.

Example 143: Synthesis of Compound 97

Into a reaction flask under nitrogen was added compound (96) (2.6 g, 5.0 mmol, 1 eq) and DMF (56 mL) under nitrogen. The resulting reaction mixture was cooled to 0° C. in ice bath. To the cooled reaction mixture was added HOBt.H$_2$O (0.918 g, 6.0 mmol, 1.2 eq) and EDCI (1.15 g, 6.0 mmol, 1.2 eq). After stirring for 30 minutes in ice bath, methyl N6-(tert-butoxycarbonyl)-D-lysinate (6) (1.56 g, 6.0 mmol, 1.2 eq) and N-methylmorpholine (NMM) (0.606 g, 6.0 mmol, 1.2 eq) were added. The reaction mixture was stirred at 0° C. for 1 hours, then stirred at room temperature until HPLC analysis indicated the reaction was completed. The reaction was added dropwise into water (156 mL) under stirring; plenty of precipitate formed; the solid was collected and washed with water (55 mL×4). The solid was then dried in vacuum (30° C.); it provided a white solid (97), 2.5 g; LCMS: m/z=769.0 [M+H]$^+$.

Example 144: Synthesis of Compound 98

The compound (97) (0.768 g, 1.0 mmol, 1.0 eq) was placed into a reaction flask under nitrogen, followed by adding methanol (16.1 mL). To the resulting solution was added a solution of NaOH (1.1 mL, 1.0 M, 1.1 mmol, 1.1 eq.) dropwise. The reaction mixture was stirred at 0° C. for one hours until HPLC analysis indicated the reaction was completed. Then, a HCl solution (1.0 M) was added dropwise until pH=4~5 was achieved. The resulting solution was concentrated and the aqueous phase was extracted with dichloromethane (17 mL×3). The combined organic extracts were dried over anhydrous sodium sulfate and concentrated on rotavapor to provide a white solid (98), 0.5 g; LC-MS m/z=754.8 [M+H]$^+$.

Synthesis of Peptide Analogues

Example 145: Synthesis of Compound 99

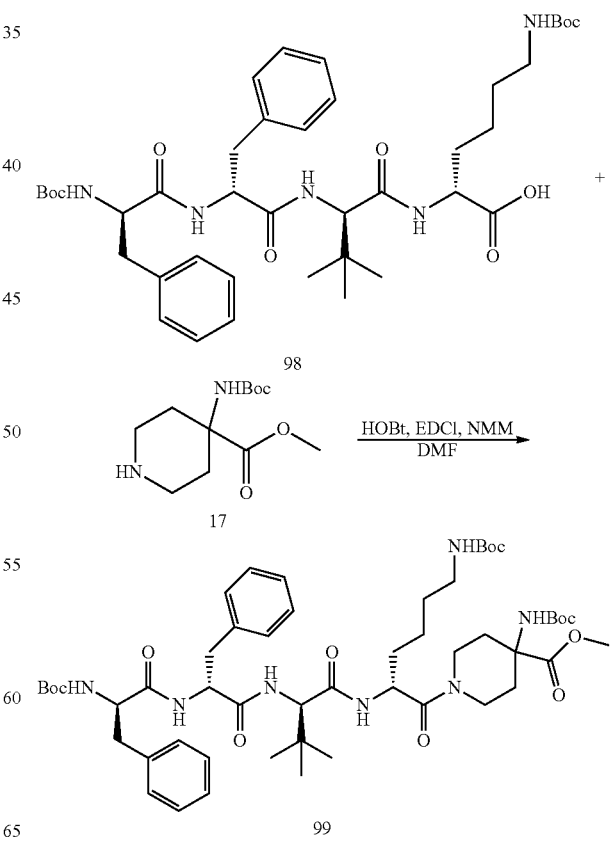

Into a reaction flask under nitrogen was added compound (98) (0.745 g, 1.0 mmol, 1 eq) and DMF (16.1 mL) under nitrogen. The resulting reaction mixture was cooled to 0° C. in ice bath. To the cooled reaction mixture was added HOBt. $H_2O$ (0.184 g, 1.2 mmol, 1.2 eq) and EDCI (0.23 g, 1.2 mmol, 1.2 eq). After stirring for 30 minutes in ice bath, methyl 4-((tert-butoxycarbonyl)amino)piperidine-4-carboxylate (17) (0.31 g, 1.2 mmol, 1.2 eq) and N-methylmorpholine (NMM) (0.121 g, 1.2 mmol, 1.2 eq) were added. The reaction mixture was stirred at 0° C. for 1 hours, then stirred at room temperature until HPLC analysis indicated the reaction was completed. The reaction was added dropwise into water (45 mL) under stirring; plenty of precipitate formed; the solid was collected after standing 30 minutes and washed with water (55 mL×4). The solid was then dried in vacuum (30° C.); it provided a white solid (99), 0.5 g; LCMS: m/z=995.2 $[M+H]^+$.

Example 146: Synthesis of Compound 100

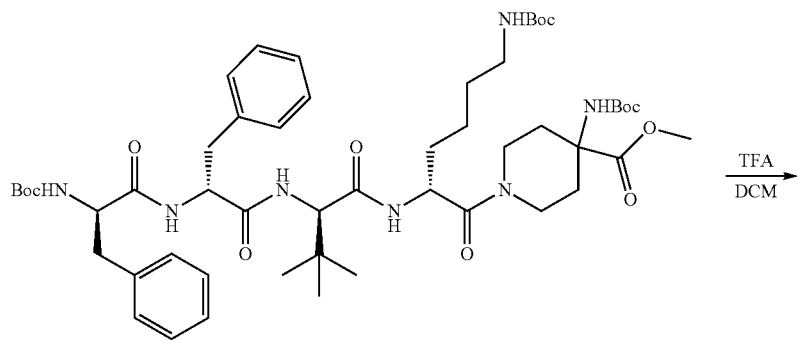

99

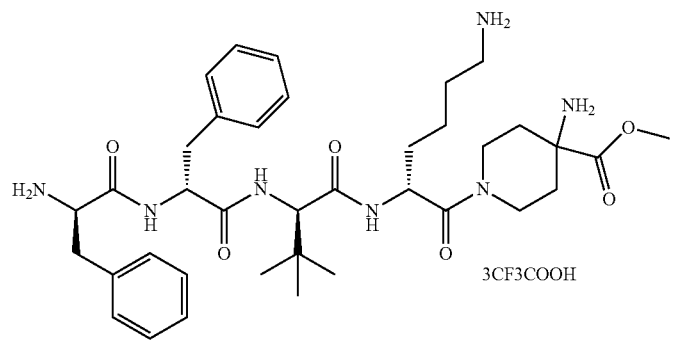

100

The compound (99) (0.199 g, 0.2 mmol, 1.0 eq) was placed into a reaction flask under nitrogen; to the flask was added dichloromethane (4 mL); the resulting solution was cooled to 0° C. for 10 minutes; then to the cooled reaction was added dropwise a mixture of TFA (0.2 mL). The resulting solution was stirred at 0° C. for 30 minutes, then 2 hours at room temperature until HPLC analysis indicated the reaction was completed. The volatiles were removed on rotavapor. To the residue was added ether (2 mL) with vigorously stirring; the resulting suspension standed for 30 minutes; the solid was collected by filtration and dried in vacuum (30° C.); it provided a white solid compound (100), 150 mg, LCMS: MS m/z=694.8 [M+H]⁺.

Example 147: Synthesis of Compound 101

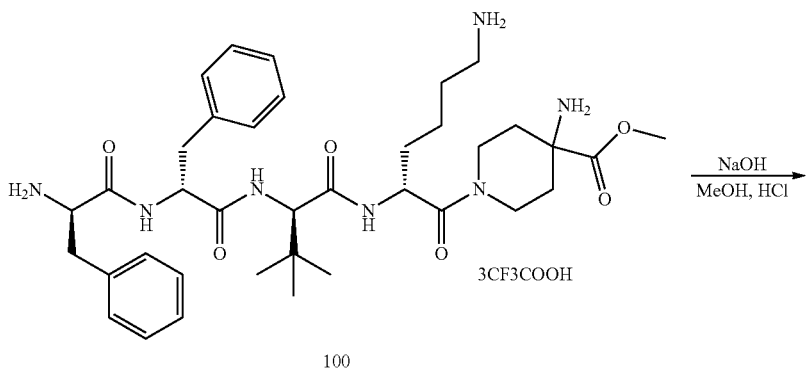

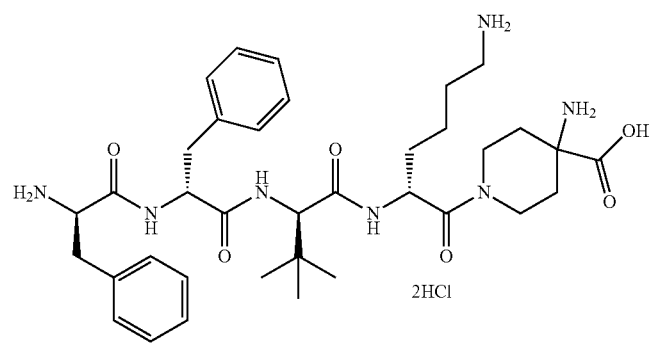

The compound (100) (0.104 g, 0.1 mmol, 1.0 eq) was placed into a reaction flask under nitrogen, followed by adding methanol (2 mL). To the resulting solution was added a solution of NaOH (0.11 mL, 1.0 M, 0.11 mmol, 1.1 eq.) dropwise. The reaction mixture was stirred at 0° C. for one hours until HPLC analysis indicated the reaction was completed. Then, a HCl solution (1.0 M) was added dropwise until pH=4~5 was achieved. The resulting solution was then lyophilized to a white solid (101), 50 mg; LC-MS m/z=680.9 $[M+H]^+$.

Example 148: Synthesis of Compound 102

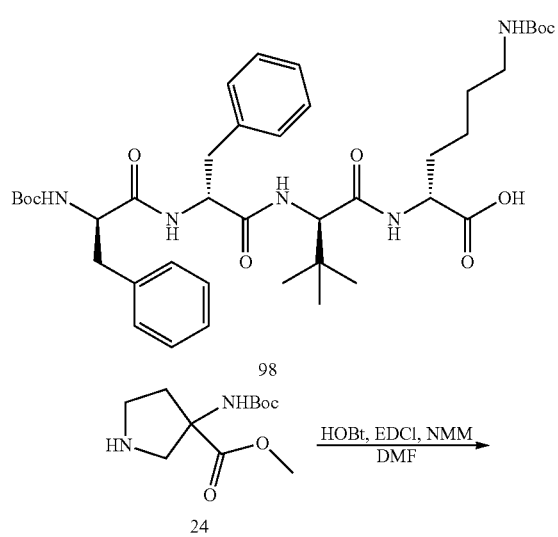

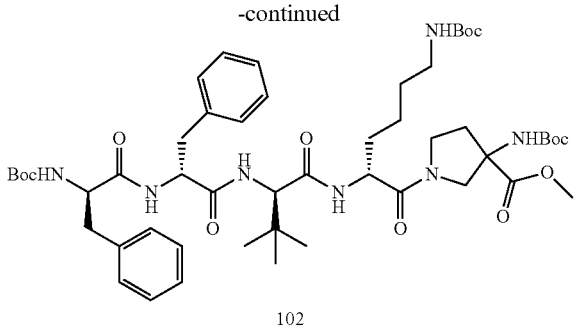

Into a reaction flask under nitrogen was added compound (98) (0.745 g, 1.0 mmol, 1 eq) and DMF (16 mL) under nitrogen. The resulting reaction mixture was cooled to 0° C. in ice bath. To the cooled reaction mixture was added HOBt.H$_2$O (0.184 g, 1.2 mmol, 1.2 eq) and EDCI (0.23 g, 1.2 mmol, 1.2 eq). After stirring for 30 minutes in ice bath, methyl 3-((tert-butoxycarbonyl)amino)pyrrolidine-3-carboxylate (24) (0.29 g, 1.2 mmol, 1.2 eq) and N-methylmorpholine (NMM) (0.121 g, 1.2 mmol, 1.2 eq) were added. The reaction mixture was stirred at 0° C. for 1 hours, then stirred at room temperature until HPLC analysis indicated the reaction was completed. The reaction was added dropwise into water (45 mL) under stirring; plenty of precipitate formed; the solid was collected and washed with water (56 mL×4). The solid was then dried in vacuum (30° C.); it provided a white solid (102), 0.5 g; LCMS: m/z=981.2 $[M+H]^+$.

Example 149: Synthesis of Compound 103

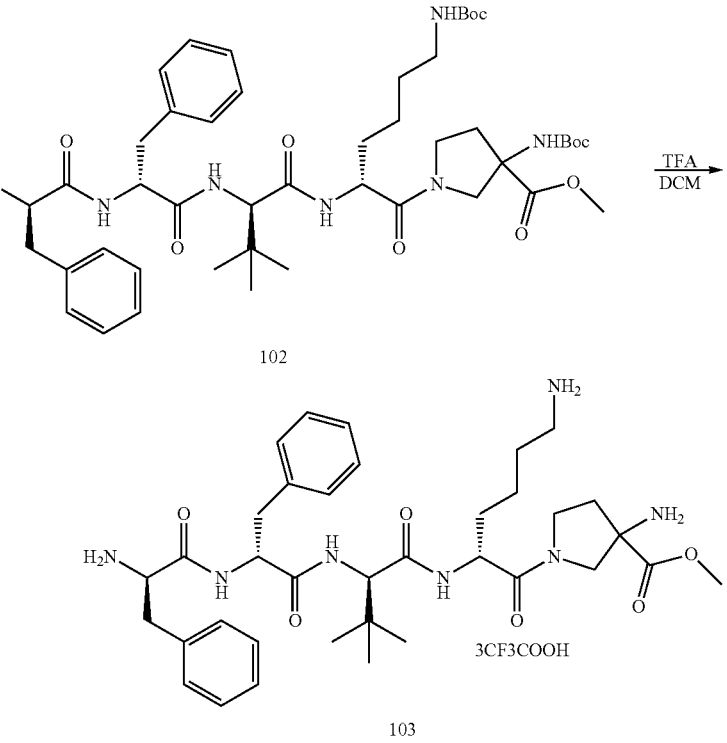

The compound (102) (0.196 g, 0.2 mmol, 1.0 eq) was placed into a reaction flask under nitrogen; to the flask was added dichloromethane (4 mL); the resulting solution was cooled to 0° C. for 10 minutes; then to the cooled reaction was added dropwise TFA (0.2 mL). The resulting solution was stirred at 0° C. for 30 minutes, then 2 hours at room temperature until HPLC analysis indicated the reaction was completed. The volatiles were removed on rotavapor. To the residue was added ether (2 mL) with vigorously stirring; the resulting suspension standed for 30 minutes; the solid was collected by filtration and dried in vacuum (30° C.); it provided a white solid compound (103), 150 mg, LCMS: MS m/z=680.8 [M+H]$^+$.

Example 150: Synthesis of Compound 104

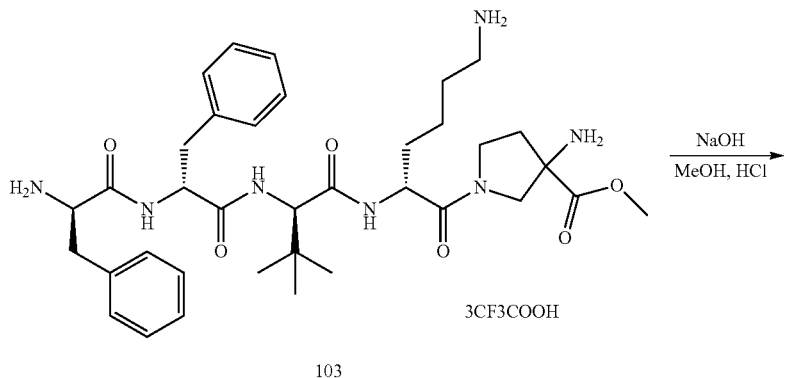

103

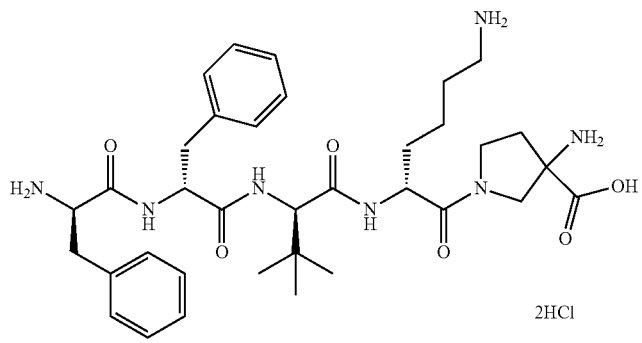

104

The compound (103) (0.102 g, 0.1 mmol, 1.0 eq) was placed into a reaction flask under nitrogen, followed by adding methanol (2.5 mL). To the resulting solution was added a solution of NaOH (0.11 mL, 1.0 M, 0.11 mmol, 1.1 eq.) dropwise. The reaction mixture was stirred at 0° C. for one hours until HPLC analysis indicated the reaction was completed. Then, a HCl solution (1.0 M) was added dropwise until pH=4~5 was achieved. The resulting solution was then purified on reverse HPLC; the collected fractions were lyophilized to a white solid (104), 50 mg; LC-MS m/z=666.8 [M+H]⁺.

X1. Demonstrated below are the Preparations for the Peptide Mimics for Medical Products 112, 118, 119, 126, 127, 133, 134

Example 151: Synthesis of Compound 106

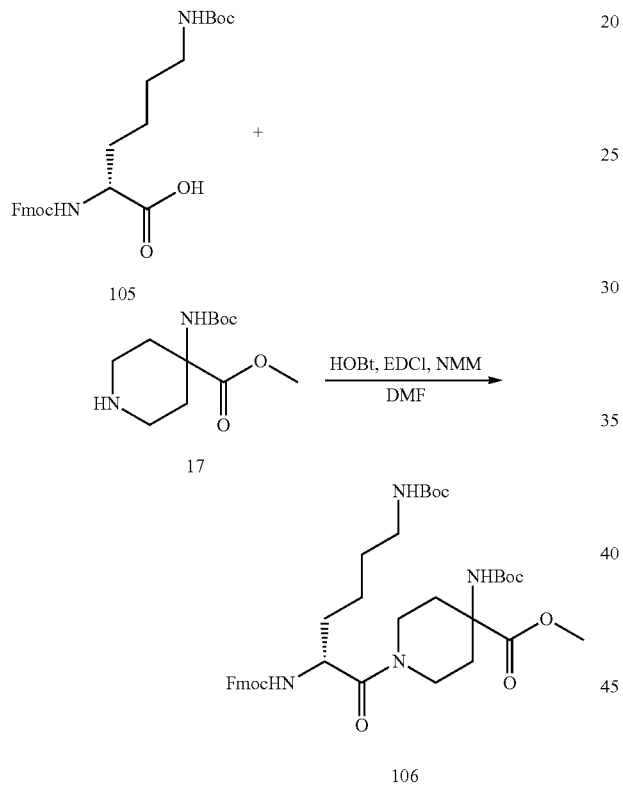

Into a reaction flask under nitrogen was added Fmoc-D-Lys(Boc)-OH (105) (469 mg, 1.0 mmol, 1 eq) and DMF (9.5 mL) under nitrogen. The resulting reaction mixture was cooled to 0° C. in ice bath. To the cooled reaction mixture was added HOBt. H₂O (0.184 g, 1.2 mmol, 1.2 eq) and EDCI (0.23 g, 1.2 mmol, 1.2 eq). After stirring for 30 minutes in ice bath, methyl 4-((tert-butoxycarbonyl)amino) piperidine-4-carboxylate (17) (0.31 g, 1.2 mmol, 1.2 eq) and N-methylmorpholine (NMM) (0.121 g, 1.2 mmol, 1.2 eq) were added. The reaction mixture was stirred at 0° C. for 1 hours, then stirred at room temperature until HPLC analysis indicated the reaction was completed. The reaction was added dropwise into water (28 mL) under stirring; plenty of precipitate formed; the solid was collected and washed with water (35 mL×4). The solid was then dried in vacuum (30° C.); it provided a white solid (106), 0.682 g; LCMS: m/z=709.2 [M+H]⁺.

Example 152: Synthesis of Compound 107

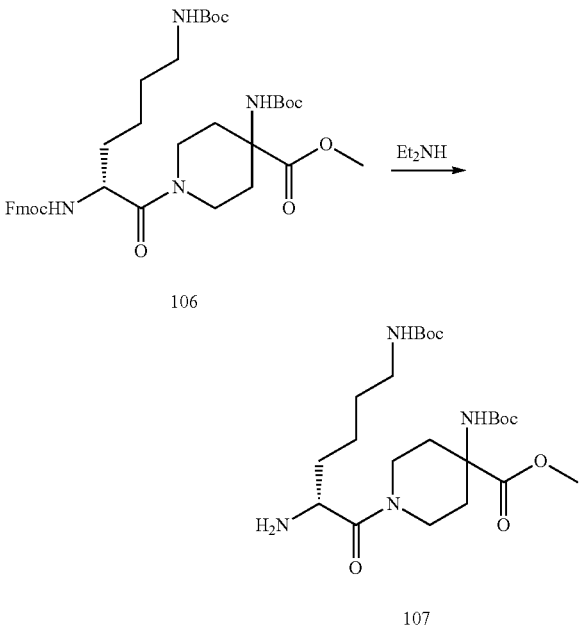

To a reaction flask was added compound (106) (709 mg, 1.0 mmol, 1.0 eq), followed by added diethylamine (5.3 mL). The mixture was stirred at room temperature. The reaction was monitored until HPLC analysis indicated the reaction was completed. The volatiles were removed on rotavapor; to the residue was added ether (7 mL) under stirring, precipitates were formed. The precipitates were collected by filtration. The collected solid was dried in vacuum, it proved a white solid (107), 0.372 g. LC-MS m/z=487.9 [M+H]⁺

Example 153: Synthesis of Compound 108

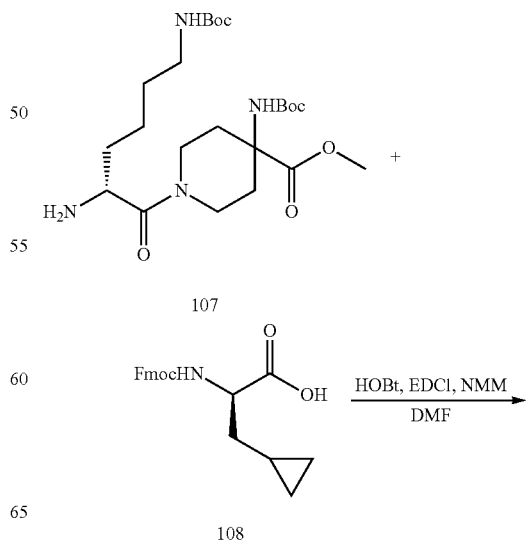

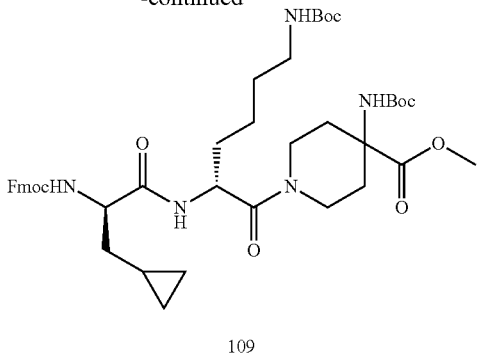

109

Into a reaction flask under nitrogen was added (2R)-3-cyclopropyl-2-(9H-fluoren-9-ylmethoxycarbonylamino)propanoic acid (108) (351 mg, 1.0 mmol, 1 eq) and DMF (7.4 mL) under nitrogen. The resulting reaction mixture was cooled to 0° C. in ice bath. To the cooled reaction mixture was added HOBt. H₂O (0.184 g, 1.2 mmol, 1.2 eq) and EDCI (0.23 g, 1.2 mmol, 1.2 eq). After stirring for 30 minutes in ice bath, compound (107) (0.584 g, 1.2 mmol, 1.2 eq) and N-methylmorpholine (NMM) (0.121 g, 1.2 mmol, 1.2 eq) were added. The reaction mixture was stirred at 0° C. for 1 hours, then stirred at room temperature until HPLC analysis indicated the reaction was completed. The reaction was added dropwise into water (21 mL) under stirring; plenty of precipitate formed; the solid was collected and washed with water (21 mL×3). The solid was then dried in vacuum (30° C.); it provided a white solid (109), 0.768 g; LCMS: m/z=821.6 [M+H]⁺.

Example 154: Synthesis of Compound 110

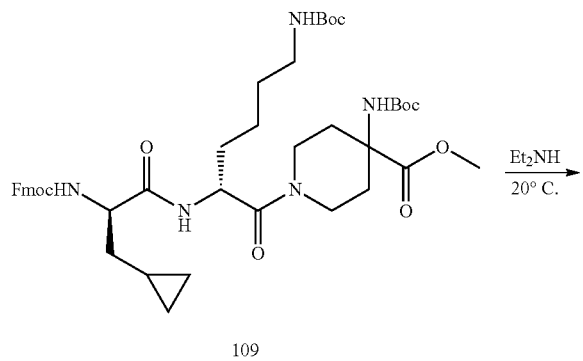

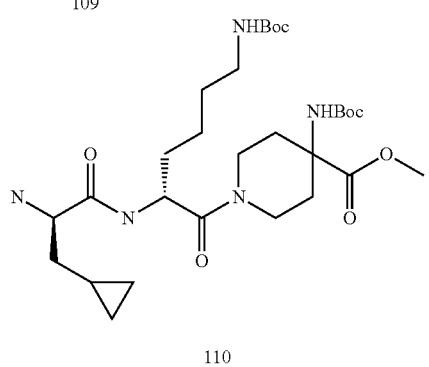

110

To a reaction flask was added compound (109) (709 mg, 1.0 mmol, 1.0 eq), followed by added diethylamine (5.4 mL). The mixture was stirred at room temperature. The reaction was monitored until HPLC analysis indicated the reaction was completed. The volatiles were removed on rotavapor; to the residue was added ether (7 mL) under stirring, precipitates were formed. The precipitates were collected after 30 minutes standing by filtration. The collected solid was dried in vacuum, it proved a white solid (110), 0.325 g. LC-MS m/z=598.3 [M+H]⁺

Example 155: Synthesis of Compound 111

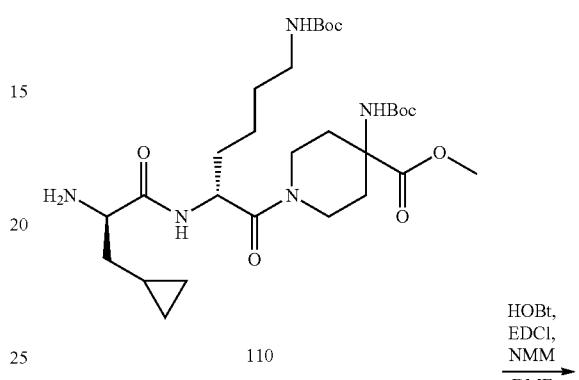

110

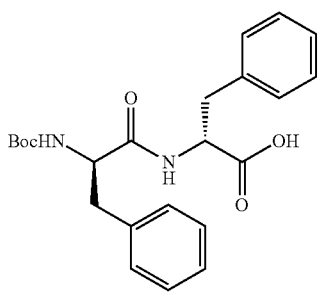

4

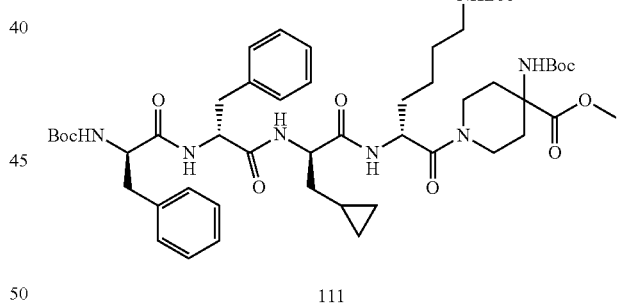

111

Into a reaction flask under nitrogen was added compound (4) (0.412 g, 1.0 mmol, 1 eq) and DMF (8.4 mL) under nitrogen. The resulting reaction mixture was cooled to 0° C. in ice bath. To the cooled reaction mixture was added HOBt. H₂O (0.184 g, 1.2 mmol, 1.2 eq) and EDCI (0.23 g, 1.2 mmol, 1.2 eq). After stirring for 30 minutes in ice bath, compound (110) (0.717 g, 1.2 mmol, 1.2 eq) and N-methylmorpholine (NMM) (0.121 g, 1.2 mmol, 1.2 eq) were added. The reaction mixture was stirred at 0° C. for 1 hours, then stirred at room temperature until HPLC analysis indicated the reaction was completed. The reaction was added dropwise into water (42 mL) under stirring; plenty of precipitate formed; the solid was collected and washed with water (30 mL×4). The solid was then dried in vacuum (30° C.); it provided a white solid (111), 0.376 g; LCMS: m/z=993.7 [M+H]⁺.

Example 156: Synthesis of Compound 112

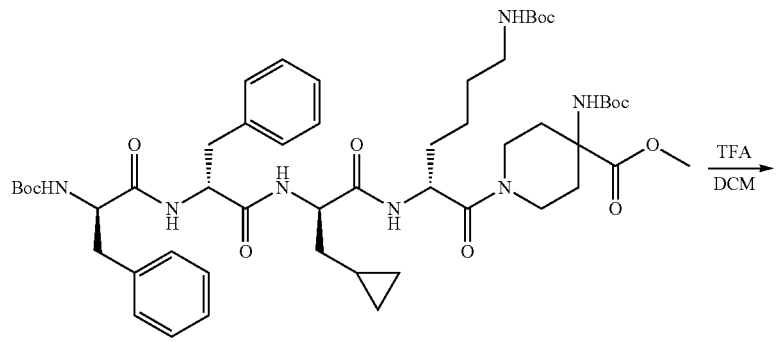

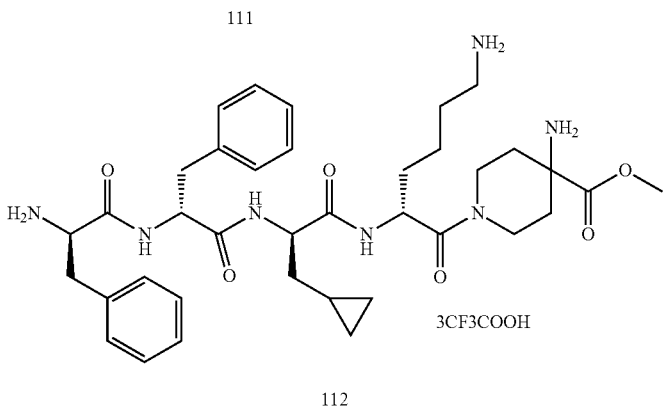

The compound (111) (0.992 g, 1.0 mmol, 1.0 eq) was placed into a reaction flask under nitrogen; to the flask was added dichloromethane (40 mL); the resulting solution was cooled to 0° C. for 10 minutes; then to the cooled reaction was added dropwise a mixture of TFA (5 mL) and dichloromethane (9 mL). The resulting solution was stirred at 0° C. for 4 hours, then 2 hours at room temperature until HPLC analysis indicated the reaction was completed. The volatiles were removed on rotavapor. To the residue was added methanol (9 mL), the resulting solution was evaporated on rotavapor; to the residue was added water/The resulting solution was lyophilized into a white solid (112), 0.978 g; LCMS: MS m/z=692.9 [M+H]⁺.

Example 157: Synthesis of Compound 113

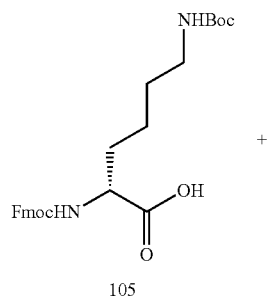

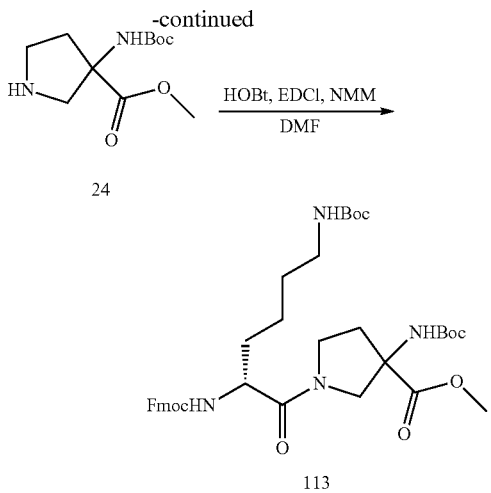

Into a reaction flask under nitrogen was added Fmoc-D-Lys(Boc)-OH (105) (0.469 g, 1.0 mmol, 1 eq) and DMF (9.6 mL) under nitrogen. The resulting reaction mixture was cooled to 0° C. in ice bath. To the cooled reaction mixture was added HOBt. H₂O (0.184 g, 1.2 mmol, 1.2 eq) and EDCI (0.23 g, 1.2 mmol, 1.2 eq). After stirring for 30 minutes in ice bath, methyl 3-((tert-butoxycarbonyl) amino) pyrrolidine-3-carboxylate (24) (0.293 g, 1.2 mmol, 1.2 eq) and N-methylmorpholine (NMM) (0.121 g, 1.2 mmol, 1.2 eq) were added. The reaction mixture was stirred at 0° C. for 1 hours, then stirred at room temperature until HPLC analysis indicated the reaction was completed. The reaction was added dropwise into water (28 mL) under stirring;

plenty of precipitate formed; the mixture stood for one hour; then the solid was collected and washed with water (35 mL×4). The solid was then dried in vacuum (30° C.); it provided a white solid (113), 0.654 g; LCMS: m/z=695.8 [M+H]⁺.

Example 158: Synthesis of Compound 114

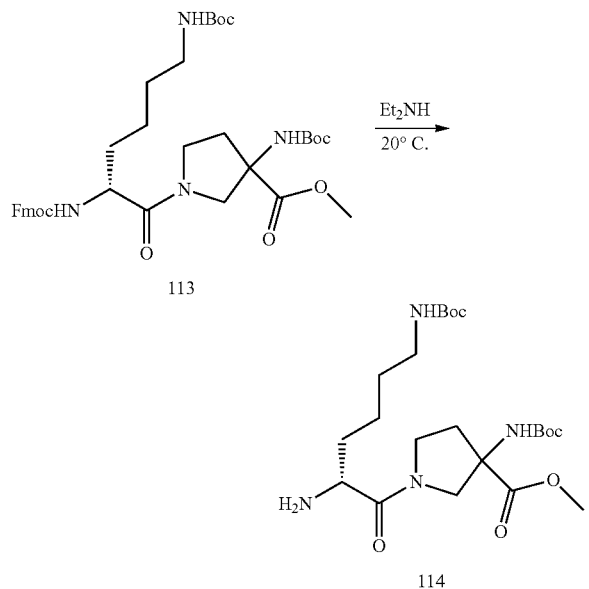

To a reaction flask was added compound (113) (695 mg, 1.0 mmol, 1.0 eq), followed by added diethylamine (5.2 mL). The mixture was stirred at room temperature. The reaction was monitored until HPLC analysis indicated the reaction was completed. The volatiles were removed on rotavapor; to the residue was added ether (7.0 mL) under stirring, precipitates were formed. The precipitates were collected by filtration. The collected solid was dried in vacuum, it proved a white solid (114), 0.342 g. LC-MS m/z=473.1 [M+H]⁺

Example 159: Synthesis of Compound 115

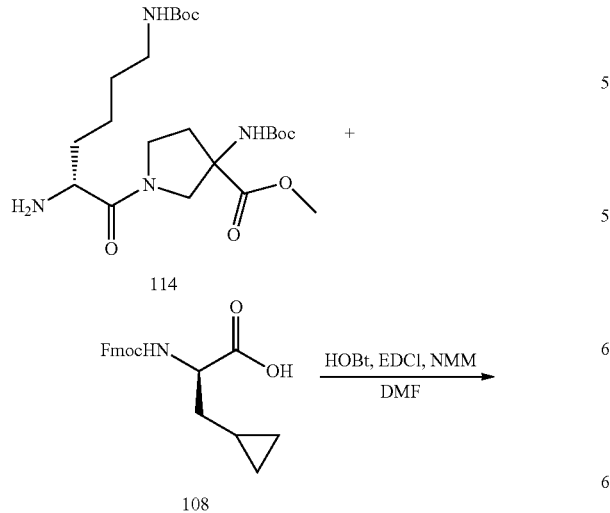

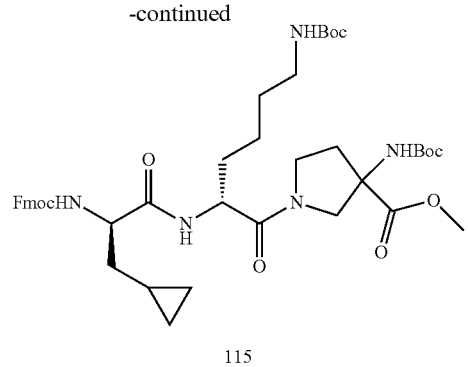

Into a reaction flask under nitrogen was added (2R)-3-cyclopropyl-2-(9H-fluoren-9-ylmethoxycarbonylamino) propanoic acid (108)(0.351 g, 1.0 mmol, 1 eq) and DMF (7.4 mL) under nitrogen. The resulting reaction mixture was cooled to 0° C. in ice bath. To the cooled reaction mixture was added HOBt. H₂O (0.184 g, 1.2 mmol, 1.2 eq) and EDCI (0.23 g, 1.2 mmol, 1.2 eq). After stirring for 30 minutes in ice bath, compound (114) (0.567 g, 1.2 mmol, 1.2 eq) and N-methylmorpholine (NMM) (0.121 g, 1.2 mmol, 1.2 eq) were added. The reaction mixture was stirred at 0° C. for 1 hours, then stirred at room temperature until HPLC analysis indicated the reaction was completed. The reaction was added dropwise into water (21 mL) under stirring; plenty of precipitate formed; the mixture stood for one hour; then the solid was collected and washed with water (35 mL×3). The solid was then dried in vacuum (30° C.); it provided a white solid (115), 0.729 g; LCMS: m/z=806.3 [M+H]⁺.

Example 160: Synthesis of Compound 116

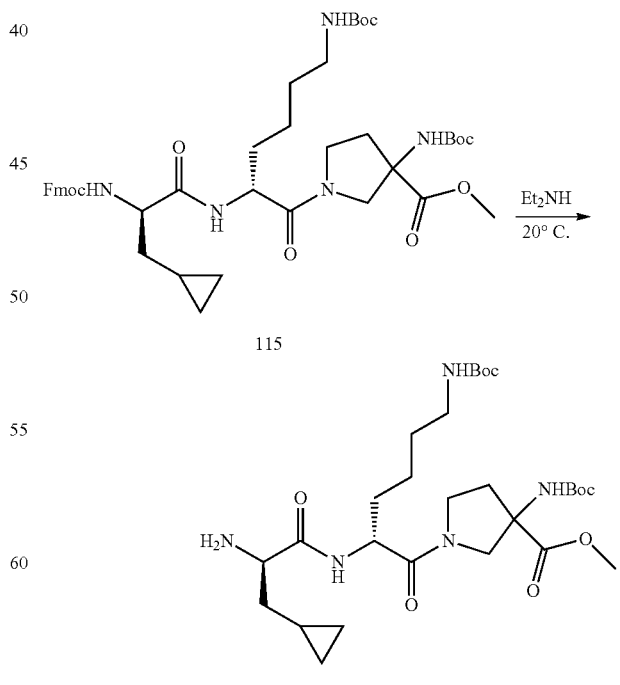

To a reaction flask was added compound (115) (806 mg, 1.0 mmol, 1.0 eq), followed by added diethylamine (5.4 mL). The mixture was stirred at room temperature. The reaction was monitored until HPLC analysis indicated the reaction was completed. The volatiles were removed on rotavapor; to the residue was added ether (8 mL) under stirring, precipitates were formed. The precipitates were collected by filtration. The collected solid was dried in vacuum, it proved a white solid (116), 0.315 g. LC-MS m/z=584.9 [M+H]$^+$ Example 161: Synthesis of Compound 117

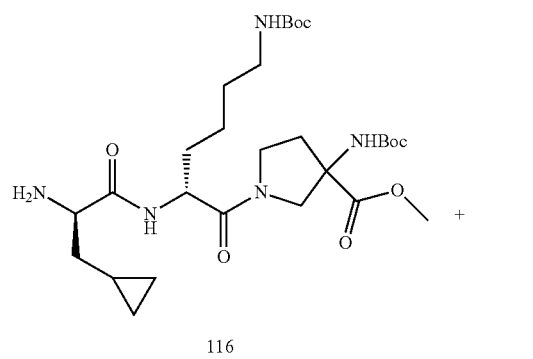

116

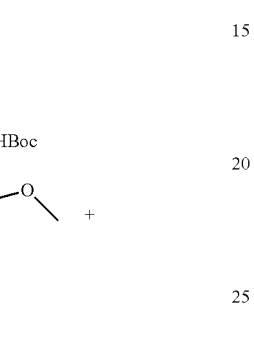

4

-continued

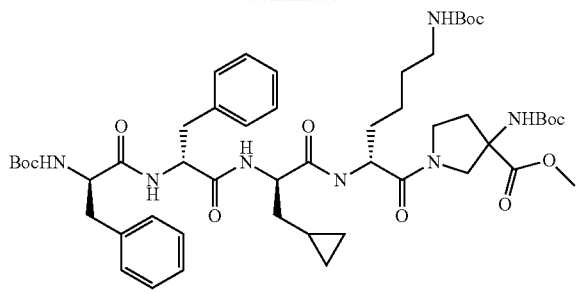

117

Into a reaction flask under nitrogen was added compound (4) (0.412 g, 1.0 mmol, 1 eq) and DMF (8.4 mL) under nitrogen. The resulting reaction mixture was cooled to 0° C. in ice bath. To the cooled reaction mixture was added HOBt. H$_2$O (0.184 g, 1.2 mmol, 1.2 eq) and EDCI (0.23 g, 1.2 mmol, 1.2 eq). After stirring for 30 minutes in ice bath, compound (116) (0.717 g, 1.2 mmol, 1.2 eq) and N-methylmorpholine (NMM) (0.121 g, 1.2 mmol, 1.2 eq) were added. The reaction mixture was stirred at 0° C. for 1 hours, then stirred at room temperature until HPLC analysis indicated the reaction was completed. The reaction was added dropwise into water (24 mL) under stirring; plenty of precipitate formed; the mixture stood for one hour; then the solid was collected and washed with water (30 mL×4). The solid was then dried in vacuum (30° C.); it provided a white solid (117), 0.936 g; LCMS: m/z=979.1 [M+H]$^+$.

Example 162: Synthesis of Compound 118

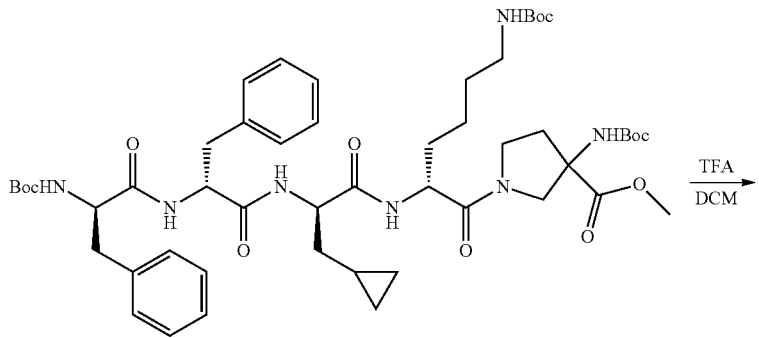

117

-continued

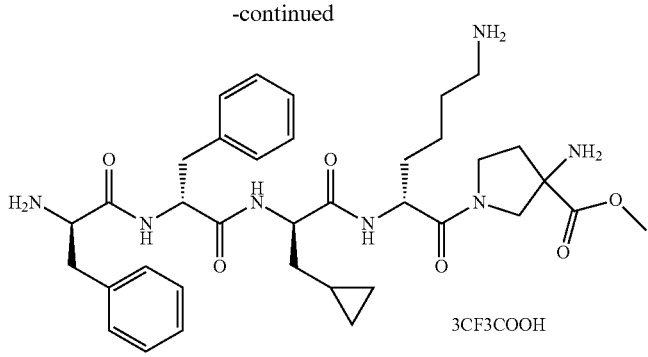

118

The compound (117) (0.978 g, 1.0 mmol, 1.0 eq) was placed into a reaction flask under nitrogen; to the flask was added dichloromethane (40 mL); the resulting solution was cooled to 0° C. for 10 minutes; then to the cooled reaction was added dropwise a mixture of TFA (5 mL) and dichloromethane (10 mL). The resulting solution was stirred at 0° C. for 4 hours, then 2 hours at room temperature until HPLC analysis indicated the reaction was completed. The volatiles were removed on rotavapor. To the residue was added methanol (10 mL), the resulting solution was evaporated on rotavapor; to the residue was added water, the resulting solution was lyophilized into a white solid (118), 0.986 g; LCMS: MS m/z=678.4 [M+H]$^+$.

Example 163: Synthesis of Compound 119

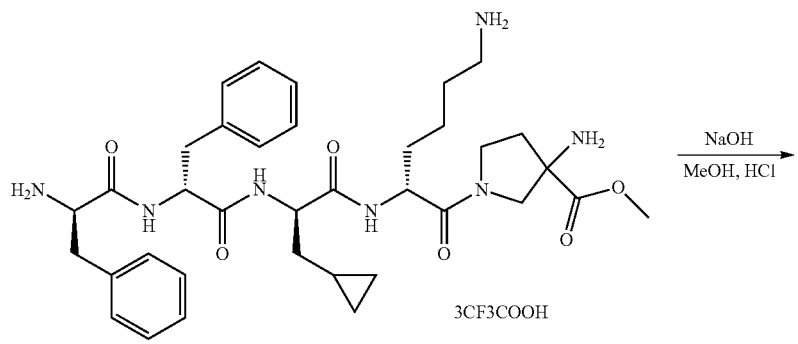

118

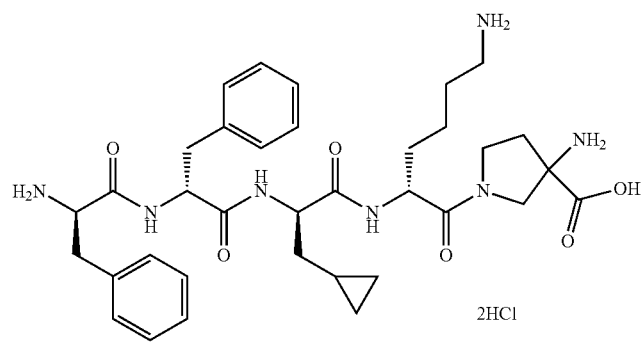

119

The compound (118) (0.20 g, 0.193 mmol, 1.0 eq) was placed into a reaction flask under nitrogen, followed by adding methanol (4 mL). To the resulting solution was added a solution of NaOH (1.0 mL, 1.0 M, 1.0 mmol, 5.2 eq.) dropwise. The reaction mixture was stirred at 0° C. for one hours until HPLC analysis indicated the reaction was completed. Then, a HCl solution (1.0 M) was added dropwise until pH=4~5 was achieved. The resulting solution was then lyophilized to a white solid (119), 56.0 mg; LC-MS m/z=664.4 [M+H]$^+$.

Example 164: Synthesis of Compound 121

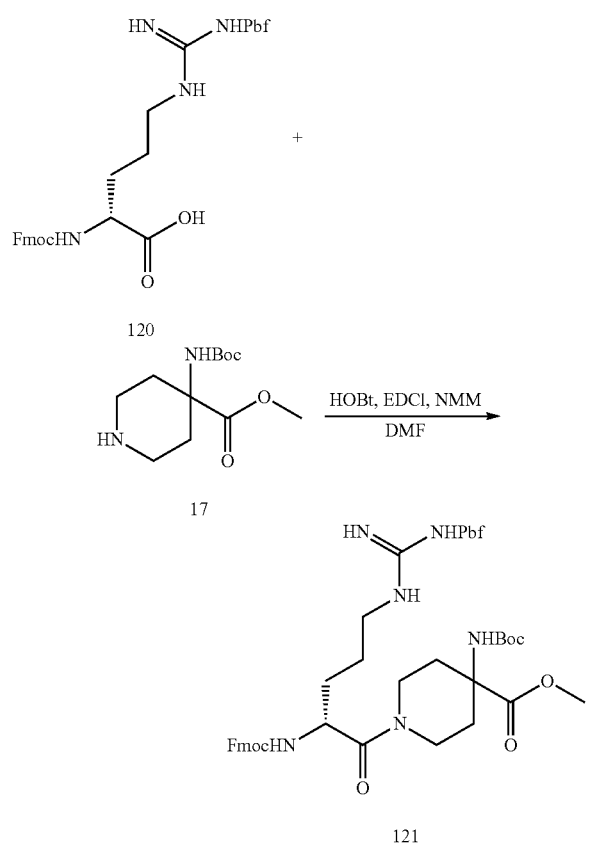

Into a reaction flask under nitrogen was added Fmoc-D-Arg(Pbf)-OH (120)(0.649 g, 1.0 mmol, 1 eq) and DMF (14 mL) under nitrogen. The resulting reaction mixture was cooled to 0° C. in ice bath. To the cooled reaction mixture was added HOBt. H$_2$O (0.184 g, 1.2 mmol, 1.2 eq) and EDCI (0.23 g, 1.2 mmol, 1.2 eq). After stirring for 30 minutes in ice bath, methyl 4-((tert-butoxycarbonyl)amino)piperidine-4-carboxylate (17) (0.31 g, 1.2 mmol, 1.2 eq) and N-methylmorpholine (NMM) (0.121 g, 1.2 mmol, 1.2 eq) were added. The reaction mixture was stirred at 0° C. for 1 hours, then stirred at room temperature until HPLC analysis indicated the reaction was completed. The reaction was added dropwise into water (39 mL) under stirring; plenty of precipitate formed; the mixture stood for one hour; then the solid was collected and washed with water (48 mL×4). The solid was then dried in vacuum (30° C.); it provided a white solid (121), 0.876 g; LCMS: m/z=890.1 [M+H]$^+$.

Example 165: Synthesis of Peptide Analogue 122

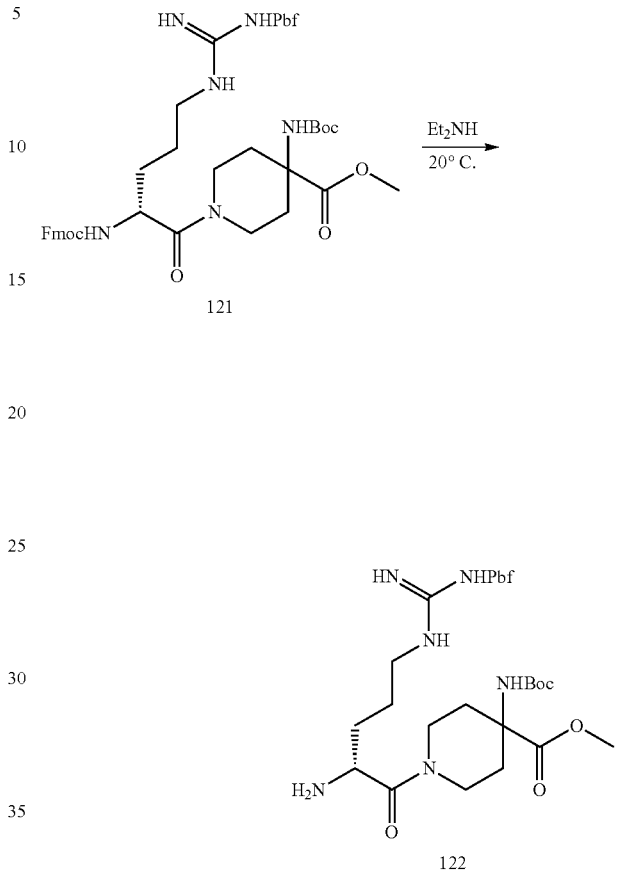

To a reaction flask was added compound (121) (889 mg, 1.0 mmol, 1.0 eq), followed by added diethylamine (6 mL). The mixture was stirred at room temperature. The reaction was monitored until HPLC analysis indicated the reaction was completed. The volatiles were removed on rotavapor; to the residue was added ether (9 mL) under stirring, plenty of precipitates were formed. The precipitates were collected by filtration. The collected solid was dried in vacuum, it proved a white solid (122), 0.275 g. LC-MS m/z=667.8 [M+H]$^+$ Example 166: Synthesis of Compound 123

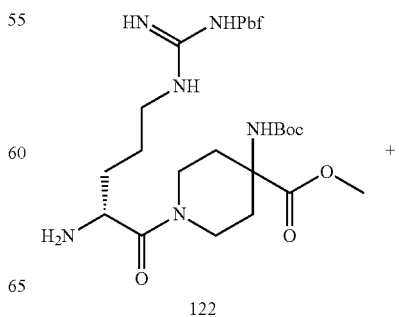

187

-continued

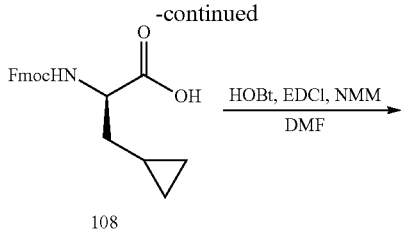

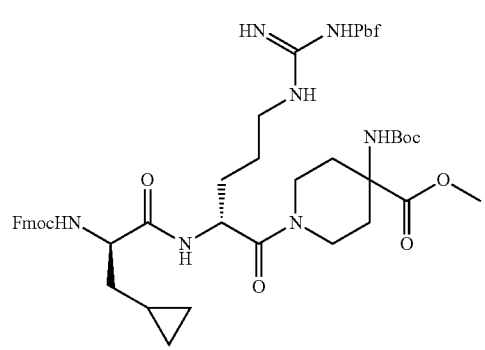

Into a reaction flask under nitrogen was added (2R)-3-cyclopropyl-2-(9H-fluoren-9-ylmethoxycarbonylamino) propanoic acid (108) (0.351 g, 1.0 mmol, 1 eq) and DMF (7.4 mL) under nitrogen. The resulting reaction mixture was cooled to 0° C. in ice bath. To the cooled reaction mixture was added HOBt. H$_2$O (0.184 g, 1.2 mmol, 1.2 eq) and EDCI (0.23 g, 1.2 mmol, 1.2 eq). After stirring for 30 minutes in ice bath, compound (122) (0.80 g, 1.2 mmol, 1.2 eq) and N-methylmorpholine (NMM) (0.121 g, 1.2 mmol, 1.2 eq) were added. The reaction mixture was stirred at 0° C. for 1 hours, then stirred at room temperature until HPLC analysis indicated the reaction was completed. The reaction was added dropwise into water (21 mL) under stirring; plenty of precipitate formed; the mixture stood for one hour; then the solid was collected and washed with water (35 mL×3). The solid was then dried in vacuum (30° C.); it provided a white solid (123), 0.729 g; LCMS: m/z=1001.1 [M+H]$^+$.

188

Example 167: Synthesis of Compound 124

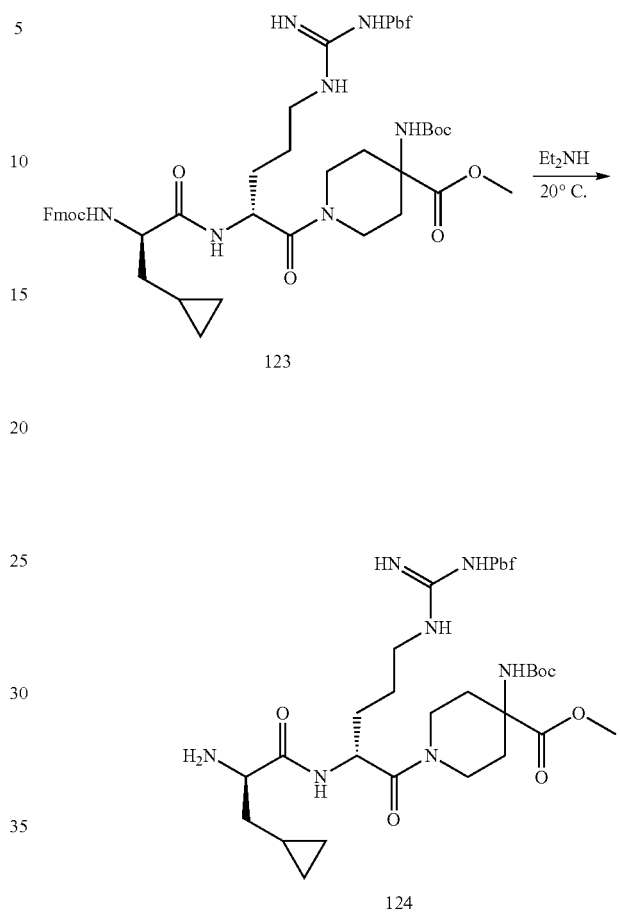

To a reaction flask was added compound (123) (1000 mg, 1.0 mmol, 1.0 eq), followed by added diethylamine (0.84 mL). The mixture was stirred at room temperature. The reaction was monitored until HPLC analysis indicated the reaction was completed. The volatiles were removed on rotavapor; to the residue was added ether (1.0 mL) under stirring, precipitates were formed. The precipitates were collected by filtration. The collected solid was dried in vacuum, it proved a white solid (124), 0.302 g. LC-MS m/z=778.7 [M+H]$^+$ Example 168: Synthesis of Compound 125

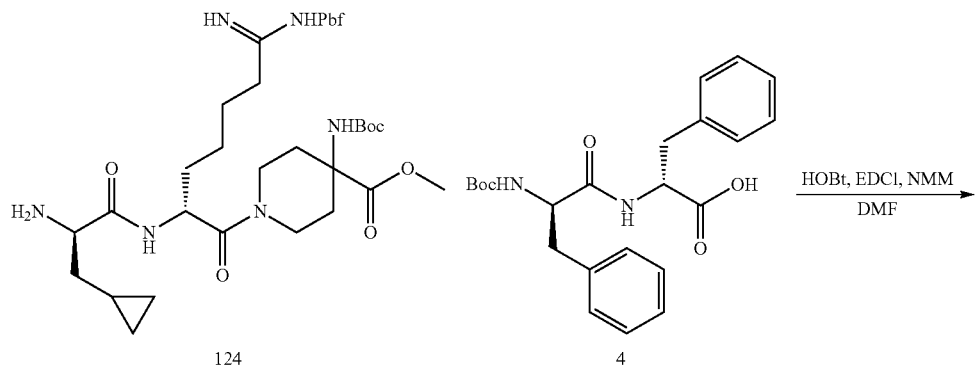

-continued

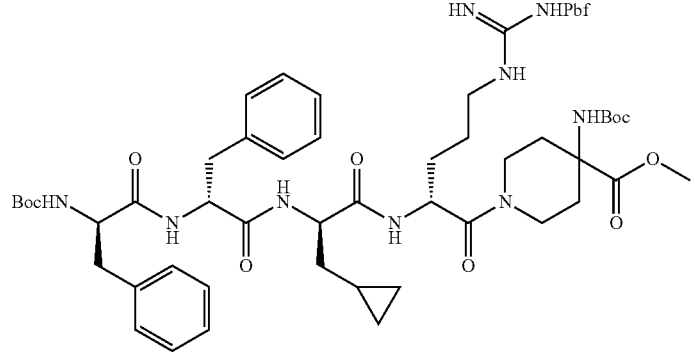
125

Into a reaction flask under nitrogen was added Compound (4) (0.412 g, 1.0 mmol, 1 eq) and DMF (8.5 mL) under nitrogen. The resulting reaction mixture was cooled to 0° C. in ice bath. To the cooled reaction mixture was added HOBt. H₂O (0.184 g, 1.2 mmol, 1.2 eq) and EDCI (0.23 g, 1.2 mmol, 1.2 eq). After stirring for 30 minutes in ice bath, compound (124) (0.932 g, 1.2 mmol, 1.2 eq) and N-methylmorpholine (NMM) (0.121 g, 1.2 mmol, 1.2 eq) were added. The reaction mixture was stirred at 0° C. for 1 hours, then stirred at room temperature until HPLC analysis indicated the reaction was completed. The reaction was added dropwise into water (24 mL) under stirring; plenty of precipitate formed; the mixture stood for one hour; then the solid was collected and washed with water (30 mL×4). The solid was then dried in vacuum (30° C.); it provided a white solid (125), 1.081 g; LCMS: m/z=1173.3 [M+H]⁺.

Example 169: Synthesis of Compound 126

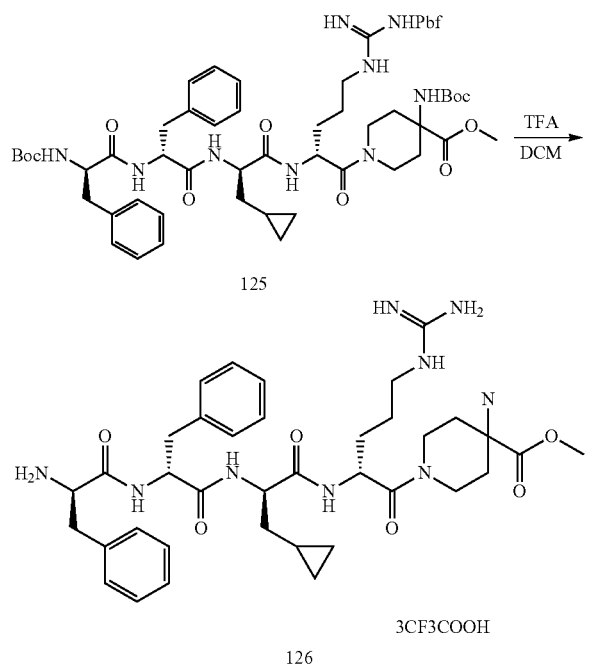

The compound (125) (0.978 g, 1.0 mmol, 1.0 eq) was placed into a reaction flask under nitrogen; to the flask was added dichloromethane (48 mL); the resulting solution was cooled to 0° C. for 10 minutes; then to the cooled reaction was added dropwise a mixture of TFA (12 mL) and dichloromethane (12 mL). The resulting solution was stirred at 0° C. for 4 hours, then 2 hours at room temperature until HPLC analysis indicated the reaction was completed. The volatiles were removed on rotavapor. To the residue was added methanol (12 mL), the resulting solution was evaporated on rotavapor; to the residue was added water/The resulting solution was lyophilized into a white solid (126), 0.982 g; LCMS: MS m/z=720.5 [M+H]⁺.

Example 170: Synthesis of Compound 127

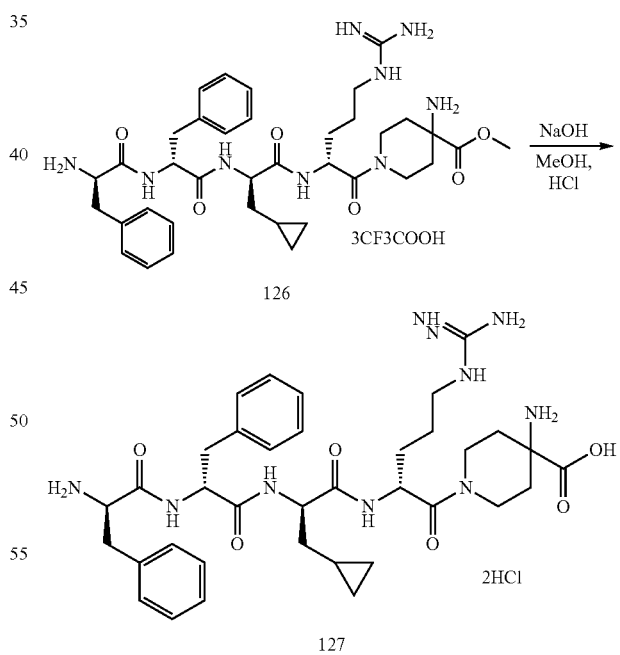

The compound (126) (0.20 g, 0.188 mmol, 1.0 eq) was placed into a reaction flask under nitrogen, followed by adding methanol (4 mL). To the resulting solution was added a solution of NaOH (1.0 mL, 1.0 M, 1.0 mmol, 5.3 eq.) dropwise.

The reaction mixture was stirred at room temperature for two hours until HPLC analysis indicated the reaction was completed. Then, HCl solution (1.0 M) was added dropwise until pH=4~5 was achieved. The resulting solution was then lyophilized to a white solid (127), 62.0 mg; LC-MS m/z=706.2 [M+H]⁺.

Example 171: Synthesis of Compound 128

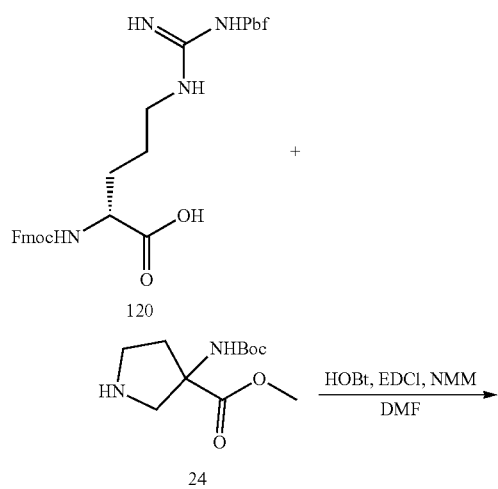

Into a reaction flask under nitrogen was added Fmoc-D-Arg(Pbf)-OH (120)(0.649 g, 1.0 mmol, 1 eq) and DMF (14 mL) under nitrogen. The resulting reaction mixture was cooled to 0° C. in ice bath. To the cooled reaction mixture was added HOBt. H₂O (0.184 g, 1.2 mmol, 1.2 eq) and EDCI (0.23 g, 1.2 mmol, 1.2 eq). After stirring for 30 minutes in ice bath, methyl 3-(Boc-NH)pyrolidine-3-carboxylate (24) (0.31 g, 1.2 mmol, 1.2 eq) and N-methylmorpholine (NMM) (0.121 g, 1.2 mmol, 1.2 eq) were added. The reaction mixture was stirred at 0° C. for 1 hours, then stirred at room temperature until HPLC analysis indicated the reaction was completed. The reaction was added dropwise into water (39 mL) under stirring; plenty of precipitate formed; the mixture stood for one hour; then the solid was collected and washed with water (65 mL×3). The solid was then dried in vacuum (30° C.); it provided a white solid (128), 0.831 g; LCMS: m/z=875.4 [M+H]⁺.

Example 172: Synthesis of Compound 129

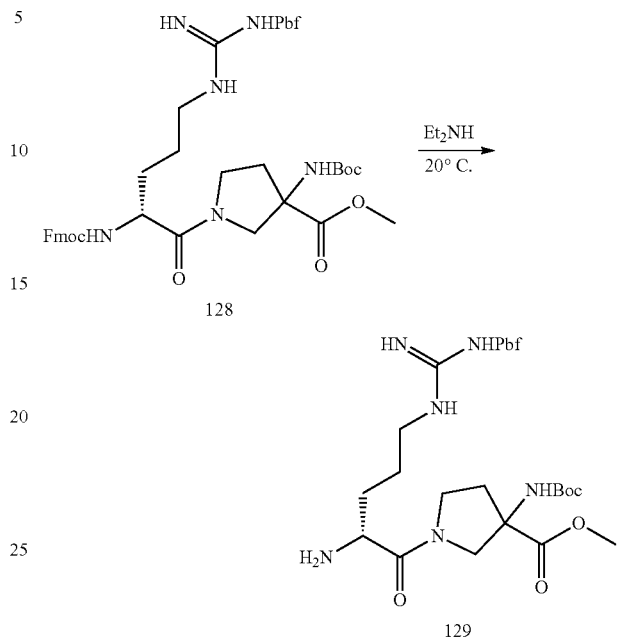

To a reaction flask was added compound (128) (875 mg, 1.0 mmol, 1.0 eq), followed by added diethylamine (6 mL). The mixture was stirred at room temperature. The reaction was monitored until HPLC analysis indicated the reaction was completed. The volatiles were removed on rotavapor; to the residue was added ether (9 mL) under stirring, precipitates were formed. The precipitates were collected after standing 30 minutes by filtration. The collected solid was dried in vacuum, it proved a white solid (129), 0.296 g. LC-MS m/z=653.9 [M+H]⁺

Example 173: Compound 130

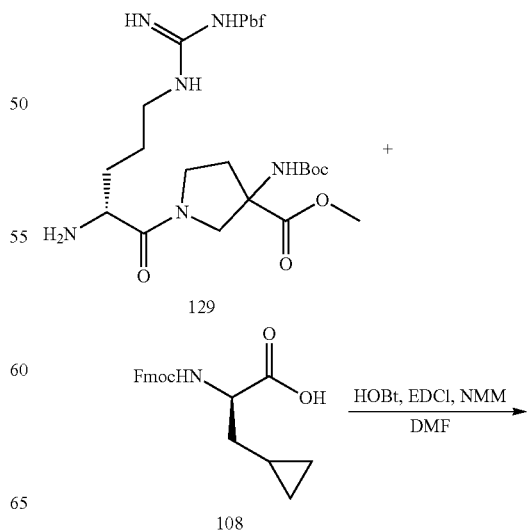

-continued

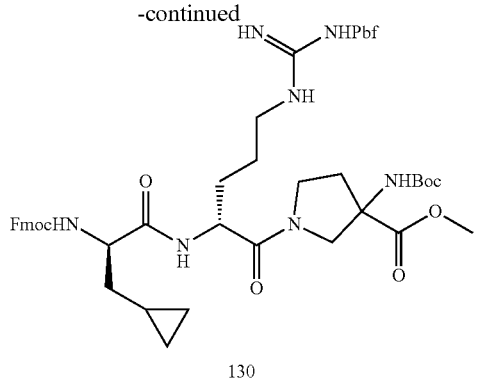

130

Into a reaction flask under nitrogen was added (2R)-3-cyclopropyl-2-(9H-fluoren-9-ylmethoxycarbonylamino) propanoic acid (108) ((0.351 g, 1.0 mmol, 1 eq) and DMF (7.4 mL) under nitrogen. The resulting reaction mixture was cooled to 0° C. in ice bath. To the cooled reaction mixture was added HOBt. H$_2$O (0.184 g, 1.2 mmol, 1.2 eq) and EDCI (0.23 g, 1.2 mmol, 1.2 eq). After stirring for 30 minutes in ice bath, compound (129) (0.80 g, 1.2 mmol, 1.2 eq) and N-methylmorpholine (NMM) (0.121 g, 1.2 mmol, 1.2 eq) were added. The reaction mixture was stirred at 0° C. for 1 hours, then stirred at room temperature until HPLC analysis indicated the reaction was completed. The reaction was added dropwise into water (21 mL) under stirring; plenty of precipitate formed; the mixture stood for one hour; then the solid was collected and washed with water (35 mL×3). The solid was then dried in vacuum (30° C.); it provided a white solid (130), 0.953 g; LCMS: m/z=987.1 [M+H]$^+$.

Example 174: Synthesis of Compound 131

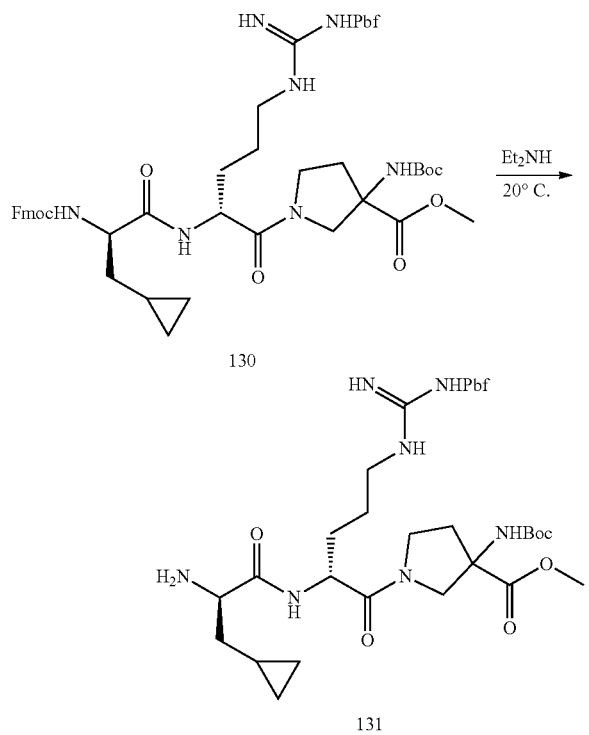

To a reaction flask was added compound (130) (100 mg, 1.0 mmol, 1.0 eq), followed by added diethylamine (0.85 mL). The mixture was stirred at room temperature. The reaction was monitored until HPLC analysis indicated the reaction was completed. The volatiles were removed on rotavapor; to the residue was added ether (1.0 mL) under stirring, precipitates were formed. The precipitates were collected after 30 minutes by filtration. The collected solid was dried in vacuum, it provided a white solid (131), 0.301 g. LC-MS m/z=764.9 [M+H]$^+$ Example 175: Synthesis of Compound 132

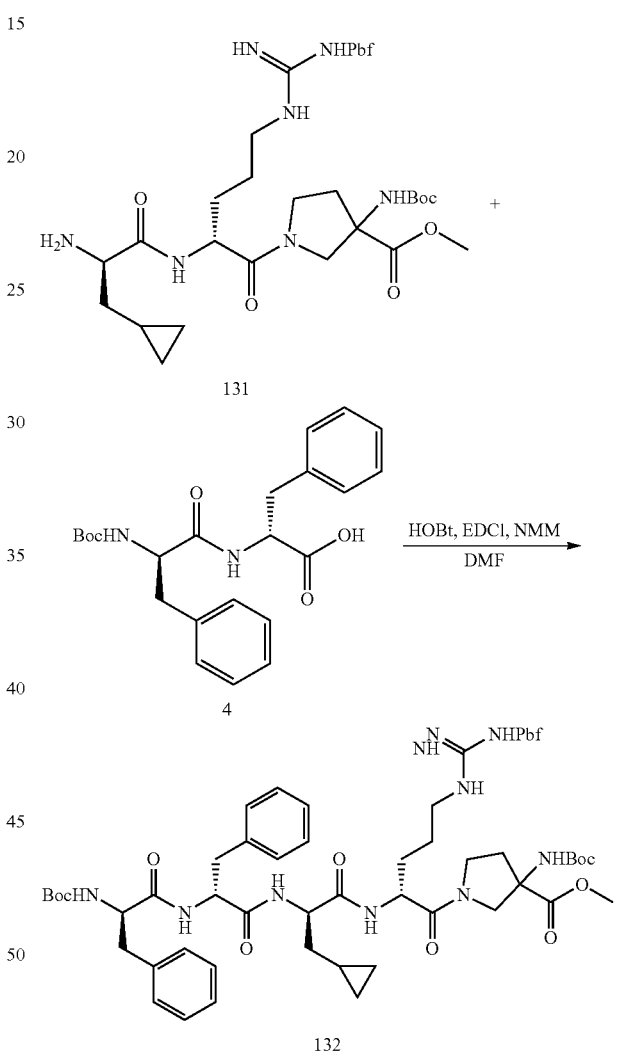

Into a reaction flask under nitrogen was added compound (4) ((0.412 g, 1.0 mmol, 1 eq) and DMF (4.2 mL) under nitrogen. The resulting reaction mixture was cooled to 0° C. in ice bath. To the cooled reaction mixture was added HOBt. H$_2$O (0.184 g, 1.2 mmol, 1.2 eq) and EDCI (0.23 g, 1.2 mmol, 1.2 eq). After stirring for 30 minutes in ice bath, compound (131) (0.932 g, 1.2 mmol, 1.2 eq) and N-methylmorpholine (NMM) (0.121 g, 1.2 mmol, 1.2 eq) were added. The reaction mixture was stirred at 0° C. for 1 hours, then stirred at room temperature until HPLC analysis indicated the reaction was completed. The reaction was added dropwise into water (12 mL) under stirring; plenty of precipitate formed; the mixture stood for one hour; then the solid was collected and washed with water (20 mL×3). The solid was then dried in vacuum (30° C.); it provided a white solid (132), 1.11 g; LCMS: m/z=1159.2 [M+H]⁺.

Example 176: Synthesis of Compound 133

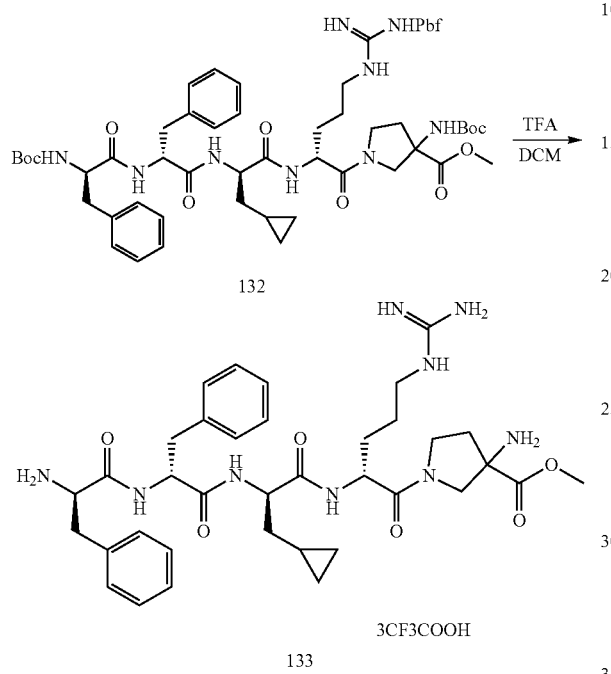

The compound (132) (1.158 g, 1.0 mmol, 1.0 eq) was placed into a reaction flask under nitrogen; to the flask was added dichloromethane (48 mL); the resulting solution was cooled to 0° C. for 10 minutes; then to the cooled reaction was added dropwise a mixture of TFA (12 mL) and dichloromethane (12 mL). The resulting solution was stirred at 0° C. for 4 hours, then 2 hours at room temperature until HPLC analysis indicated the reaction was completed. The volatiles were removed on rotavapor. To the residue was added methanol (12 mL), the resulting solution was evaporated on rotavapor; to the residue was added water/The resulting solution was lyophilized into a white solid (133), 0.977 g; LCMS: MS m/z=706.8 [M+H]⁺.

Example 177: Synthesis of Compound Duct 134

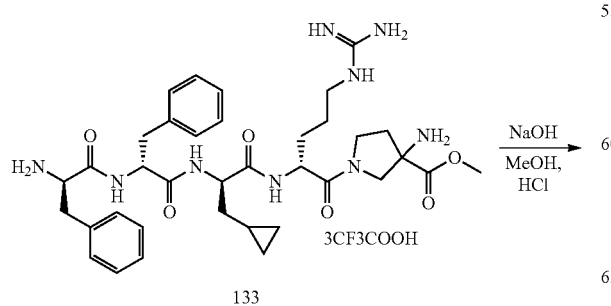

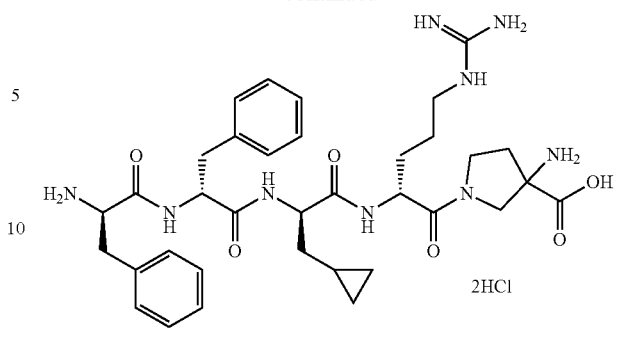

The compound (133) (0.20 g, 0.191 mmol, 1.0 eq) was placed into a reaction flask under nitrogen, followed by adding methanol (4 mL). To the resulting solution was added a solution of NaOH (1.0 mL, 1.0 M, 1.0 mmol, 5.2 eq.) dropwise. The reaction mixture was stirred at room temperature for two hours until HPLC analysis indicated the reaction was completed. Then, a HCl solution (1.0 M) was added dropwise until pH=4~5 was achieved. The resulting solution was then lyophilized to a white solid (134), 73 mg; LC-MS m/z=692.4 [M+H]⁺.

XII. Demonstrated Below are the Preparations for the Peptide Mimics for Medical Products 144, 146, 147

Reaction Scheme 18

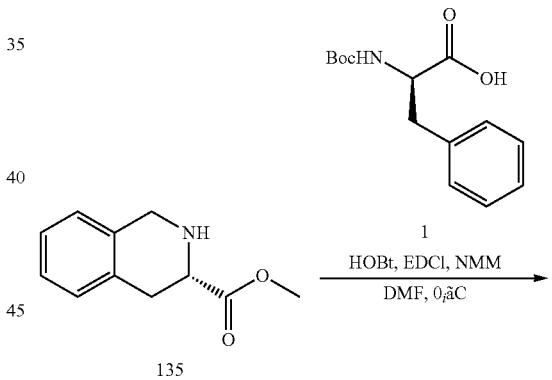

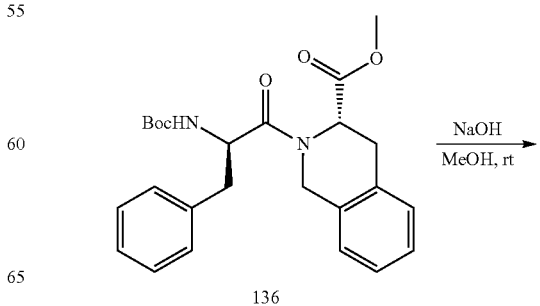

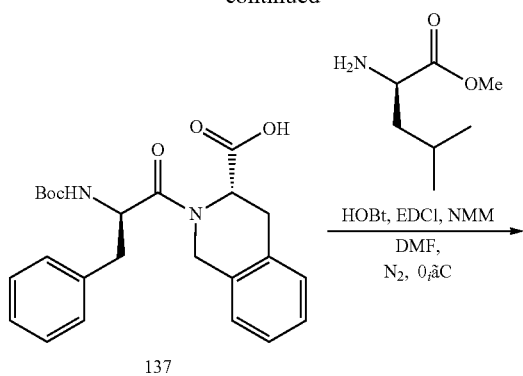

137

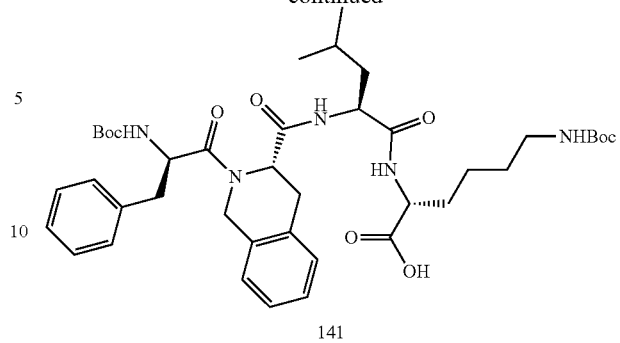

141

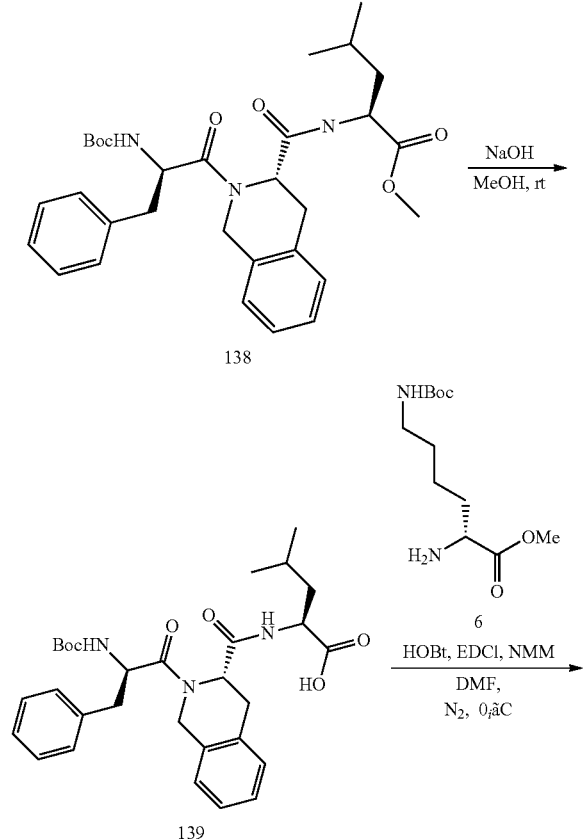

138

139

140

Example 178: Synthesis of Compound 136

Into a reaction flask under nitrogen was added (R)-2-((tert-butoxycarbonyl)amino)-3-phenylpropanoic acid (1) (4.24 g, 16.0 mmol, 1 eq) and DMF (90 mL) under nitrogen. The resulting reaction mixture was cooled to 0° C. in ice bath. To the cooled reaction mixture was added HOBt. $H_2O$ (2.69 g, 17.6 mmol, 1.1 eq) and EDCI (3.37 g, 17.6 mmol, 1.1 eq). After stirring for 30 minutes in ice bath, methyl rac-(3S)-1,2,3,4-tetrahydroisoquinoline-3-carboxylate; hydrochloride (135) (4.0 g, 17.6 mmol, 1.1 eq) and N-methylmorpholine (NMM) (3.71 g, 36.7 mmol, 2.3 eq) were added. The reaction mixture was stirred at 0° C. for 2 hours, then stirred at room temperature until HPLC analysis indicated the reaction was completed. The reaction was added dropwise into water (254 mL) under stirring; plenty of precipitate formed; the mixture stood for one hour; then the solid was collected and washed with water (434 mL×3). The solid was then dried in vacuum (30° C.); it provided a white solid (136), 6.0 g; LCMS: m/z=439.2 [M+H]$^+$.

Example 179: Synthesis of Compound 137

The compound (136) (5.0 g, 11.4 mmol, 1.0 eq) was placed into a reaction flask under nitrogen, followed by adding methanol (100 mL). To the resulting solution was added a solution of NaOH (25 mL, 1.0 M, 25 mmol, 2.2 eq.) dropwise. The reaction mixture was stirred at room temperature for 18 hours until HPLC analysis indicated the reaction was completed. Then, a HCl solution (1.0 M) was added dropwise until pH=2~2.5 was achieved. To the reaction was added dropwise water (200 mL). The resulting mixture stood for one hour; then the solid was collected by filtration and washed with water (60 mL×3). The solid was dried in vacuum (30° C.); it provided a white solid (137), 4.2 g. LC-MS m/z=425.2 [M+H]$^+$.

Example 180: Synthesis of Peptide Analogue 138

Into a reaction flask under nitrogen was added compound (137) (3.5 g g, 8.24 mmol, 1 eq) and DMF (73 mL) under nitrogen. The resulting reaction mixture was cooled to 0° C. in ice bath. To the cooled reaction mixture was added HOBt. $H_2O$ (1.39 g, 9.08 mmol, 1.1 eq) and EDCI (1.74 g, 9.08 mmol, 1.1 eq). After stirring for 30 minutes in ice bath, Methyl (R)-leucine ester hydrochloride (5) (1.65 g, 9.08 mmol, 1.1 eq) and N-methylmorpholine (NMM) (1.92 g, 19.0 mmol, 2.3 eq) were added. The reaction mixture was stirred at 0° C. for 1 hours, then stirred at room temperature until HPLC analysis indicated the reaction was completed.

The reaction was added dropwise into water (210 mL) under stirring; plenty of precipitate formed; the mixture stood for one hour; then the solid was collected and washed with water (350 mL×3). The solid was then dried in vacuum (30° C.); it provided a white solid (138), 3.96 g; LCMS: m/z=552.3 [M+H]⁺.

Example 181 Synthesis of Compound 139

The compound (138) (3.96 g, 7.18 mmol, 1.0 eq) was placed into a reaction flask under nitrogen, followed by adding methanol (79 mL). To the resulting solution was added a solution of NaOH (20 mL, 1.0 M, 20 mmol, 2.79 eq.) dropwise. The reaction mixture was stirred at room temperature for 7 hours until HPLC analysis indicated the reaction was completed. Then, a HCl solution (1.0 M) was added dropwise until pH=2~2.5 was achieved. To the reaction was added dropwise water (60 mL) under stirring. Then the mixture stood overnight; the solid was collected by filtration and washed with water (30 mL×3). The solid was then dried in vacuum (30° C.); it provided a white solid (139), 3.37 g. LC-MS m/z=538.3 [M+H]⁺.

Example 182: Synthesis of Compound 140

Into a reaction flask under nitrogen was added compound (139) (3.37 g, 6.27 mmol, 1 eq) and DMF (72 mL) under nitrogen. The resulting reaction mixture was cooled to 0° C. in ice bath. To the cooled reaction mixture was added HOBt.H₂O (1.14 g, 7.51 mmol, 1.2 eq) and EDCI (1.44 g, 7.51 mmol, 1.1 eq). After stirring for 30 minutes in ice bath, D-H-Lys(Boc)-OMe·HCl (6) (2.23 g, 7.51 mmol, 1.2 eq) and N-methylmorpholine (NMM) (1.52 g, 15.0 mmol, 2.4 eq) were added. The reaction mixture was stirred at 0° C. for 1 hours, then stirred at room temperature until HPLC analysis indicated the reaction was completed. The reaction was added dropwise into water (200 mL) under stirring; plenty of precipitate formed; the mixture stood for one hour; then the solid was collected and washed with water (330 mL×3). The solid was then dried in vacuum (30° C.); it provided a white solid (140), 4.41 g; LCMS: m/z=781.0 [M+H]⁺.

Example 183: Synthesis of Compound 141

The compound (140) (4.41 g, 7.18 mmol, 1.0 eq) was placed into a reaction flask under nitrogen, followed by adding methanol (88 mL). To the resulting solution was added a solution of NaOH (22 mL, 1.0 M, 22 mmol, 3.01 eq.) dropwise. The reaction mixture was stirred at room temperature for 7 hours until HPLC analysis indicated the reaction was completed. Then, a HCl solution (1.0 M) was added dropwise until pH=~4 was achieved. To the reaction was added dropwise water (300 mL) under stirring. Then the mixture stood overnight; the solid was collected by filtration and washed with water (200 mL×3). The solid was then dried in vacuum (30° C.); it provided a white solid (141), 3.54 g. LC-MS m/z=766.4 [M+H]⁺.

Synthesis of Peptide Analogue

Example 184: Synthesis of Compound 142

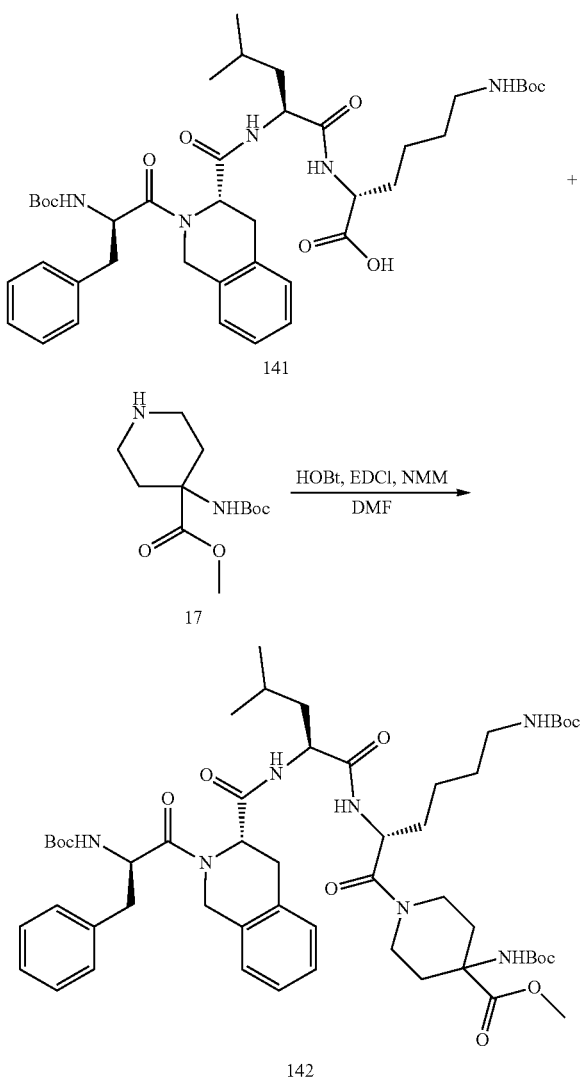

Into a reaction flask under nitrogen was added compound (141) (0.5 g, 0.65 mmol, 1 eq) and DMF (10.6 mL) under nitrogen. The resulting reaction mixture was cooled to 0° C. in ice bath. To the cooled reaction mixture was added HOBt.H₂O (0.12 g, 0.79 mmol, 1.2 eq) and EDCI (0.15 g, 0.79 mmol, 1.2 eq). After stirring for 30 minutes in ice bath, Methyl 4-(Boc-NH)piperidine-4-carboxylate (17) (0.2 g, 0.79 mmol, 1.2 eq) and N-methylmorpholine (NMM) (0.18 g, 1.58 mmol, 2.4 eq) were added. The reaction mixture was stirred at 0° C. for 1 hours, then stirred at room temperature until HPLC analysis indicated the reaction was completed. The reaction was added dropwise into water (30 mL) under stirring; plenty of precipitate formed; the mixture stood for one hour; then the solid was collected and washed with water (50 mL×3). The solid was then dried in vacuum (30° C.); it provided a white solid (142), 0.58 g; LCMS: m/z=1006.6 [M+H]⁺.

Example 185: Synthesis of Compound 143

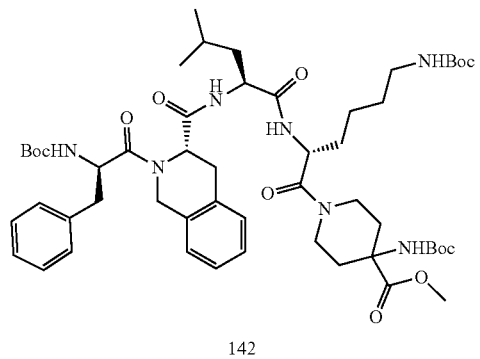

142

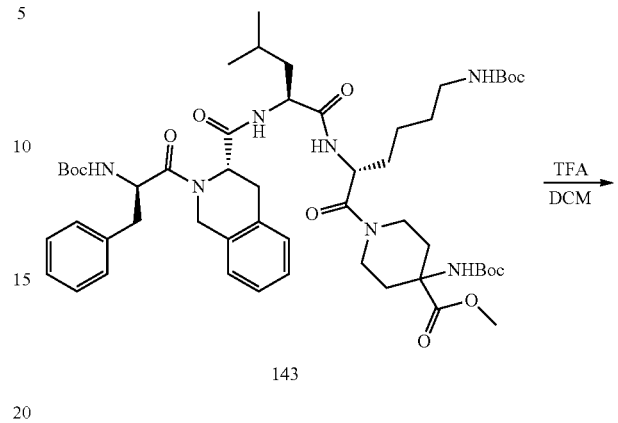

143

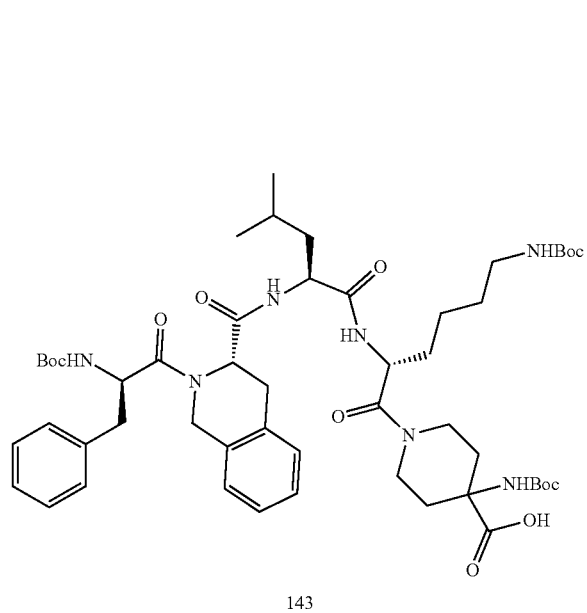

143

The compound (142) (0.58 g, 0.58 mmol, 1.0 eq) was placed into a reaction flask under nitrogen, followed by adding methanol (11 mL). To the resulting solution was added a solution of NaOH (2.5 mL, 1.0 M, 2.5 mmol, 4.31 eq.) dropwise. The reaction mixture was stirred at room temperature for 47 hours until HPLC analysis indicated the reaction was completed. Then, HCl solution (1.0 M) was added dropwise until pH=2~2.5 was achieved. To the reaction was added dropwise water (22 mL) under stirring. Then the mixture stood overnight; the solid was collected by filtration and washed with water (7 mL×3). The solid was then dried in vacuum (30° C.); it provided a white solid (143), 0.27 g. LC-MS m/z=993.2 [M+H]$^+$.

Example 186: Synthesis of Compound 144

144

The compound (143) (0.20 g, 0.202 mmol, 1.0 eq) was placed into a reaction flask under nitrogen; to the flask was added dichloromethane (4 mL); the resulting solution was cooled to 0° C. for 10 minutes; then to the cooled reaction was added dropwise a mixture of TFA (4 mL) and dichloromethane (8 mL). The resulting solution was stirred at 0° C. for 4 hours, then 2 hours at room temperature until HPLC analysis indicated the reaction was completed. The volatiles were removed on rotavapor. To the residue was added dichloromethane (10 mL); the resulting solution was evaporated on rotavapor; the dissolving/evaporating with dichloromethane was repeat three times; to the residue was added methanol (10 mL), the resulting solution was evaporated on rotavapor; the dissolving/evaporation with methanol was repeated twice; to the residue was added ether (10 mL) under vigorously stirring; plenty of white precipitates formed; the volatile were removed on rotavapor; the solid was further dried in vacuum (30° C.); it provided a white solid (144), 135.5 mg; LCMS: MS m/z=692.4 [M+H]$^+$.

Example 187: Synthesis of Compound 145

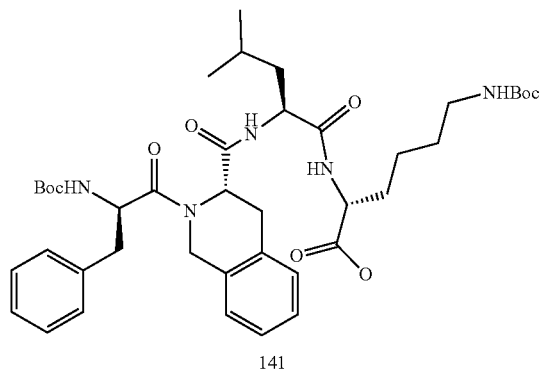

141

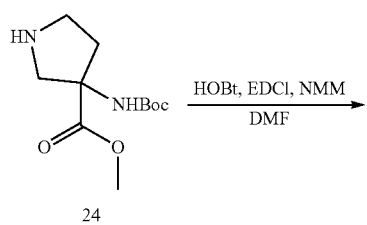

24

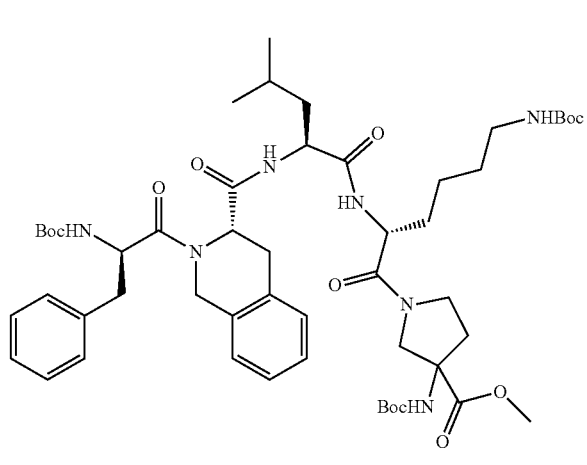

145

Into a reaction flask under nitrogen was added compound (144) (0.20 g, 0.26 mmol, 1 eq) and DMF (4.3 mL) under nitrogen. The resulting reaction mixture was cooled to 0° C. in ice bath. To the cooled reaction mixture was added HOBt.H₂O (48 mg, 0.31 mmol, 1.2 eq) and EDCI (60 mg, 0.31 mmol, 1.2 eq). After stirring for 30 minutes in ice bath, methyl 3-(tert-butoxycarbonylamino)pyrrolidine-3-carboxylate (24) (76 mg, 0.31 mmol, 1.2 eq) and N-methylmorpholine (NMM) (72 mg, 0.62 mmol, 2.4 eq) were added. The reaction mixture was stirred at 0° C. for 1 hours, then stirred at room temperature until HPLC analysis indicated the reaction was completed. The reaction was added dropwise into water (12 mL) under stirring; plenty of precipitate formed; the mixture stood for one hour; then the solid was collected and washed with water (20 mL×3). The solid was then dried in vacuum (30° C.); it provided a white solid (145), 170 mg; LCMS: m/z=993.2 [M+H]⁺.

Example 188: Synthesis of Compound 146

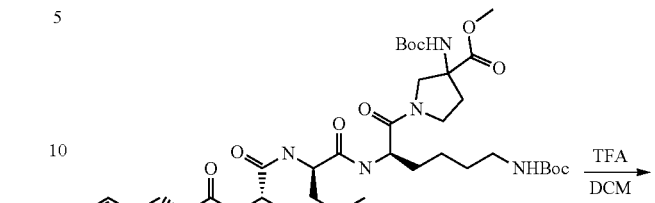

145

146

3CF3COOH

The compound (145) (100 mg, 0.101 mmol, 1.0 eq) was placed into a reaction flask under nitrogen; to the flask was added dichloromethane (2 mL); the resulting solution was cooled to 0° C. for 10 minutes; then to the cooled reaction was added dropwise a mixture of TFA (2 mL) and dichloromethane (4 mL). The resulting solution was stirred at 0° C. for 4 hours, then 2 hours at room temperature until HPLC analysis indicated the reaction was completed. The volatiles were removed on rotavapor. To the residue was added dichloromethane (10 mL); the resulting solution was evaporated on rotavapor; the dissolving/evaporating with dichloromethane was repeat three times; to the residue was added methanol (10 mL), the resulting solution was evaporated on rotavapor; the dissolving/evaporation with methanol was repeated twice; to the residue was added ether (10 mL) under vigorously stirring; plenty of white precipitates formed; the volatile were removed on rotavapor; the solid was further dried in vacuum (30° C.); it provided a white solid (146), 67.7 mg; LCMS: MS m/z=692.4 [M+H]⁺.

Example 189: Synthesis of Compound 147

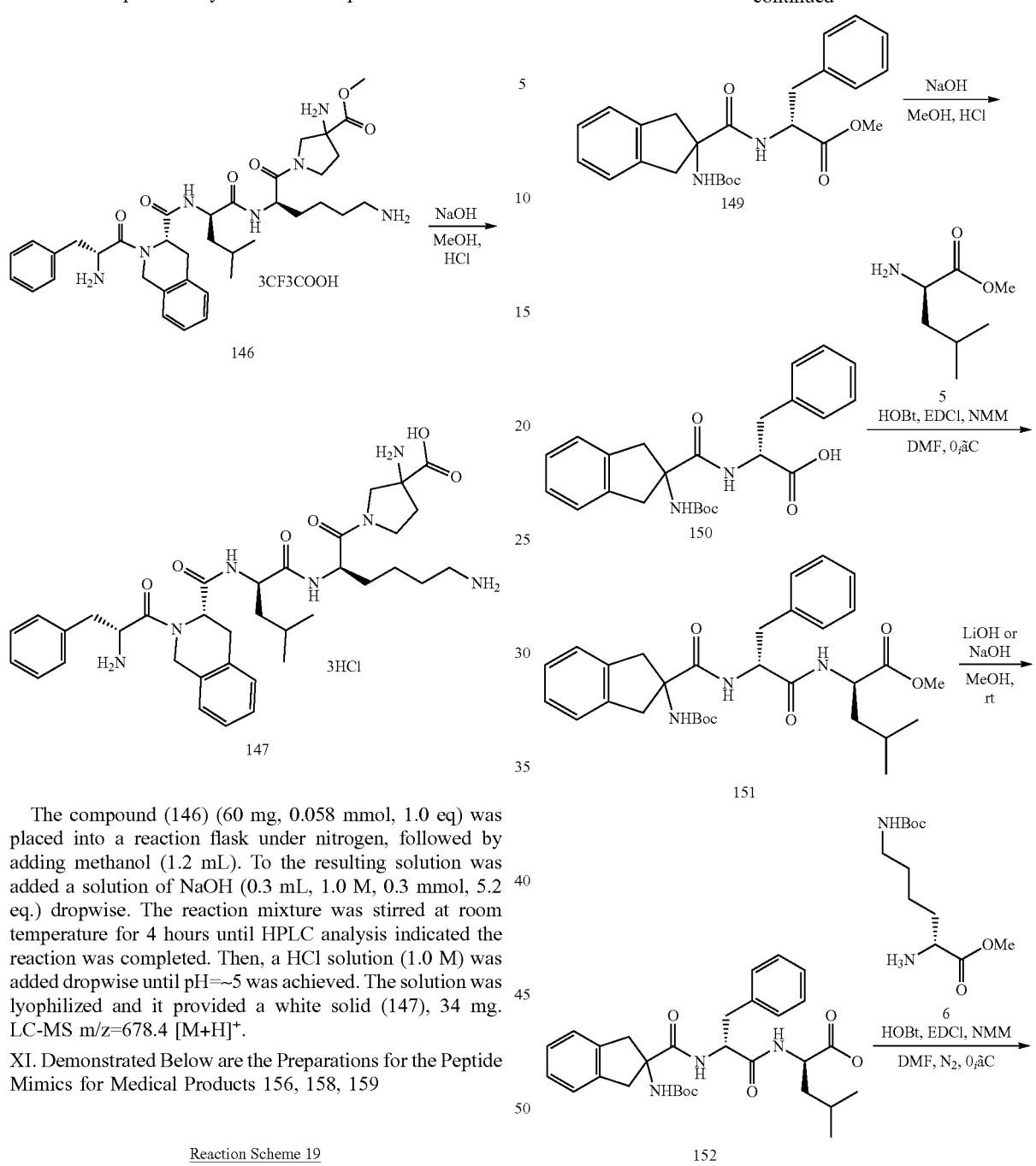

The compound (146) (60 mg, 0.058 mmol, 1.0 eq) was placed into a reaction flask under nitrogen, followed by adding methanol (1.2 mL). To the resulting solution was added a solution of NaOH (0.3 mL, 1.0 M, 0.3 mmol, 5.2 eq.) dropwise. The reaction mixture was stirred at room temperature for 4 hours until HPLC analysis indicated the reaction was completed. Then, a HCl solution (1.0 M) was added dropwise until pH=~5 was achieved. The solution was lyophilized and it provided a white solid (147), 34 mg. LC-MS m/z=678.4 [M+H]$^+$.

XI. Demonstrated Below are the Preparations for the Peptide Mimics for Medical Products 156, 158, 159

Reaction Scheme 19

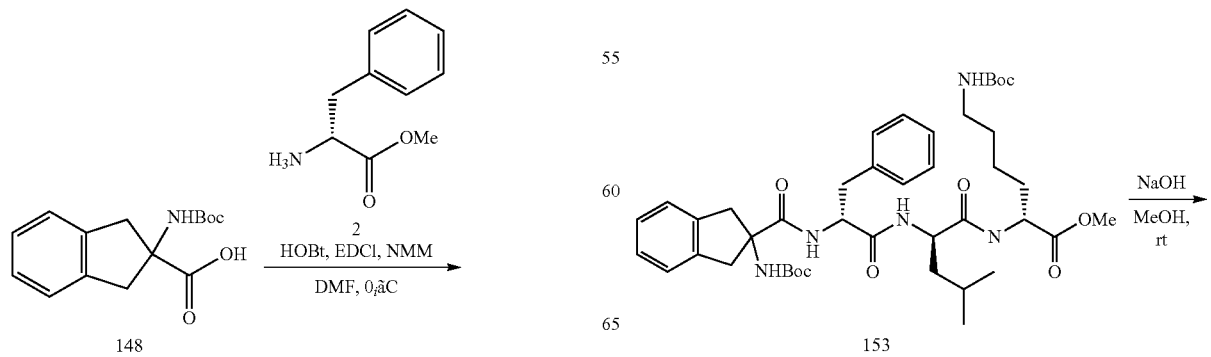

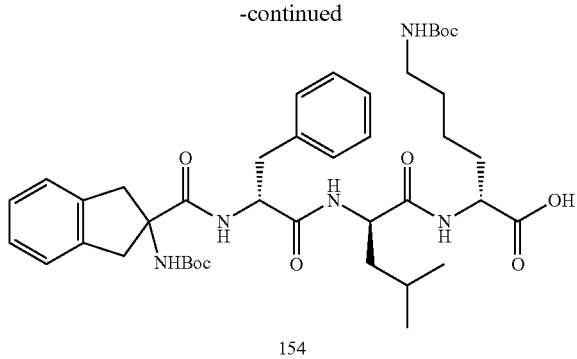

154

Example 190: Synthesis of Compound 149

Into a reaction flask under nitrogen was added 2-(tert-butoxycarbonylamino) indane-2-carboxylic acid (148) (10 g, 36.1 mmol, 1 eq) and DMF (212 mL) under nitrogen. The resulting reaction mixture was cooled to 0° C. in ice bath. To the cooled reaction mixture was added HOBt. $H_2O$ (5.36 g, 39.7 mmol, 1.1 eq) and EDCI (7.60 g, 39.7 mmol, 1.1 eq). After stirring for 30 minutes in ice bath, H-D-Phe-OMe·HCl (2) (8.56 g, 39.7 mmol, 1.1 eq) and N-methylmorpholine (NMM) (7.66 g, 75.7 mmol, 2.1 eq) were added. The reaction mixture was stirred at 0° C. for 1 hours, then stirred at room temperature until HPLC analysis indicated the reaction was completed. The reaction was added dropwise into water (600 mL) under stirring; plenty of precipitate formed; the mixture stood for one hour; then the solid was collected and washed with water (400 mL×3). The solid was then dried in vacuum (30° C.); it provided a white solid (149), 14.23 g; LCMS: m/z=439.5 $[M+H]^+$.

Example 191: Synthesis of Compound 150

The compound (149) (10 g, 22.8 mmol, 1.0 eq) was placed into a reaction flask under nitrogen, followed by adding methanol (200 mL). To the resulting solution was added a solution of NaOH (50 mL, 1.0 M, 50 mmol, 2.2 eq.) dropwise. The reaction mixture was stirred at room temperature for 2 hours until HPLC analysis indicated the reaction was completed. Then, a HCl solution (1.0 M) was added dropwise until pH=2-2.5 was achieved. To the mixture was added water (400 mL) under stirring; the mixture was then standing for one hours; the solid was collected by filtration and washed with water (265 mL×3). The collected solid was dried in vacuum (30° C.); it provided a white solid, 9.04 g (150). LC-MS m/z=425.5 $[M+H]^+$.

Example 192: Synthesis of Compound 151

Into a reaction flask under nitrogen was added compound (150) (9 g, 21.2 mmol, 1 eq) and DMF (191 mL) under nitrogen. The resulting reaction mixture was cooled to 0° C. in ice bath. To the cooled reaction mixture was added HOBt. $H_2O$ (3.15 g, 23.3 mmol, 1.1 eq) and EDCI (4.47 g, 23.3 mmol, 1.1 eq). After stirring for 30 minutes in ice bath, H-D-Leu-OMe·HCl (5) (4.24 g, 23.3 mmol, 1.1 eq) and N-methylmorpholine (NMM) (4.50 g, 44.5 mmol, 2.1 eq) were added. The reaction mixture was stirred at 0° C. for 1 hours, then stirred at room temperature until HPLC analysis indicated the reaction was completed. The reaction was added dropwise into water (540 mL) under stirring; plenty of precipitate formed; the mixture stood for one hour; then the solid was collected and washed with water (360 mL×3). The solid was then dried in vacuum (30° C.); it provided a white solid (151), 10.5 g; LCMS: m/z=552.7 $[M+H]^+$.

Example 193: Synthesis of Compound 152

The compound (151) (8.0 g, 14.5 mmol, 1.0 eq) was placed into a reaction flask under nitrogen, followed by adding methanol (160 mL). To the resulting solution was added a solution of NaOH (40 mL, 1.0 M, 40 mmol, 2.8 eq.) dropwise. The reaction mixture was stirred at room temperature for 2 hours until HPLC analysis indicated the reaction was completed. Then, a HCl solution (1.0 M) was added dropwise until pH=2-2.5 was achieved. To the mixture was added water (320 mL) under stirring; the mixture was then standing for one hours; the solid was collected by filtration and washed with water (210 mL×3). The collected solid was dried in vacuum (30° C.); it provided a white solid, 6.96 g (152). LC-MS m/z=538.6 $[M+H]^+$.

Example 194: Synthesis of Compound 153

Into a reaction flask under nitrogen was added compound (152) (6.0 g, 11.2 mmol, 1 eq) and DMF (128 mL) under nitrogen. The resulting reaction mixture was cooled to 0° C. in ice bath. To the cooled reaction mixture was added HOBt. $H_2O$ (1.81 g, 13.4 mmol, 1.1 eq) and EDCI (2.57 g, 13.4 mmol, 1.2 eq). After stirring for 30 minutes in ice bath, H-D-Lys(Boc)-OMe·HCl (6) (3.97 g, 13.4 mmol, 1.1 eq) and N-methylmorpholine (NMM) (2.37 g, 23.4 mmol, 2.1 eq) were added. The reaction mixture was stirred at 0° C. for 1 hours, then stirred at room temperature until HPLC analysis indicated the reaction was completed. The reaction was added dropwise into water (360 mL) under stirring; plenty of precipitate formed; the mixture stood for one hour; then the solid was collected and washed with water (240 mL×3). The solid was then dried in vacuum (30° C.); it provided a white solid (153), 7.32 g; LCMS: m/z=781.0 $[M+H]^+$.

Example 195: Synthesis of Compound 154

The compound (153) (5.0 g, 6.41 mmol, 1.0 eq) was placed into a reaction flask under nitrogen, followed by adding methanol (100 mL). To the resulting solution was added a solution of NaOH (25 mL, 1.0 M, 25 mmol, 3.9 eq.) dropwise. The reaction mixture was stirred at room temperature for 2 hours until HPLC analysis indicated the reaction was completed. Then, a HCl solution (1.0 M) was added dropwise until pH=2-2.5 was achieved. To the mixture was added water (200 mL) under stirring; the mixture was then standing for one hours; the solid was collected by filtration and washed with water (130 mL×3). The collected solid was dried in vacuum (30° C.); it provided a white solid (154), 4.52 g, LC-MS m/z=766.5 $[M+H]^+$.

Synthesis of Peptide Analogue

Example 196: Synthesis of Compound 155

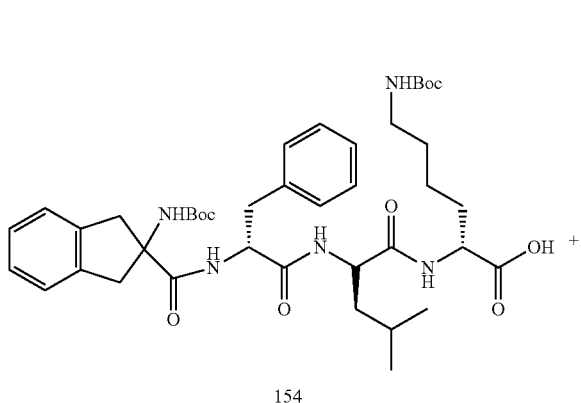

154

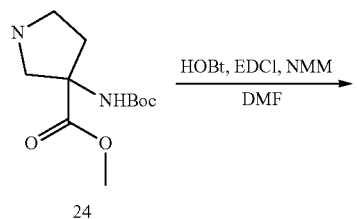

24

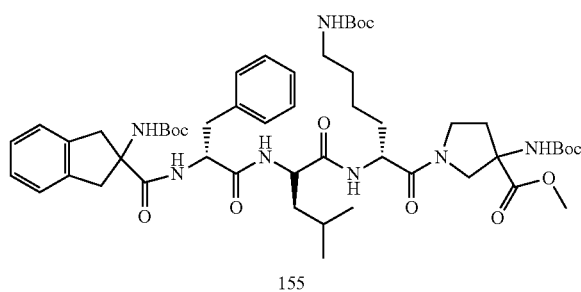

155

Into a reaction flask under nitrogen was added compound (154) (1.0 g, 1.31 mmol, 1 eq) and DMF (21.2 mL) under nitrogen. The resulting reaction mixture was cooled to 0° C. in ice bath. To the cooled reaction mixture was added HOBt.H$_2$O (211.7 mg, 1.57 mmol, 1.2 eq) and EDCI (300.3 mg, 1.57 mmol, 1.2 eq). After stirring for 30 minutes in ice bath, methyl 3-(tert-butoxycarbonylamino)pyrrolidine-3-carboxylate (24) (383 mg, 1.57 mmol, 1.1 eq) and N-methylmorpholine (NMM) (277 mg, 2.74 mmol, 2.1 eq) were added. The reaction mixture was stirred at 0° C. for 1 hours, then stirred at room temperature until HPLC analysis indicated the reaction was completed. The reaction was added dropwise into water (60 mL) under stirring; plenty of precipitate formed; the mixture stood for one hour; then the solid was collected and washed with water (40 mL×3). The solid was then dried in vacuum (30° C.); it provided a white solid (155), 1.12 g; LCMS: m/z=993.2 [M+H]$^+$.

Example 197: Synthesis of Compound 156

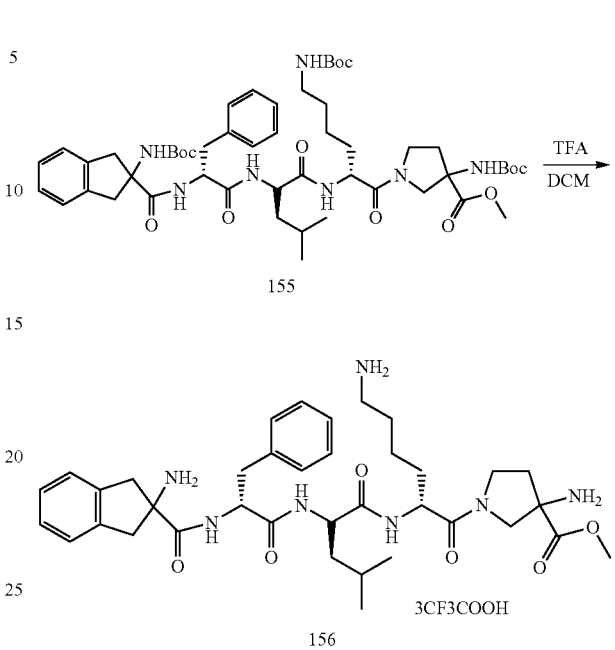

155

156

The compound (155) (200 mg, 0.201 mmol, 1.0 eq) was placed into a reaction flask under nitrogen; to the flask was added dichloromethane (4 mL); the resulting solution was cooled to 0° C. for 10 minutes; then to the cooled reaction was added dropwise a mixture of TFA (4 mL) and dichloromethane (8 mL). The resulting solution was stirred at −10° C. for one hour, then 2 hours at room temperature until HPLC analysis indicated the reaction was completed. The volatiles were removed on rotavapor. To the residue was added dichloromethane (4 mL); the resulting solution was evaporated on rotavapor; the dissolving/evaporating with dichloromethane was repeat three times; to the residue was added methanol (4 mL), the resulting solution was evaporated on rotavapor; the dissolving/evaporation with methanol was repeated twice; the residue was further purified on reverse phase HPLC; the collected fraction was lyophilized and it provided a white solid, (156), 117.2 mg; LCMS: MS m/z=692.4 [M+H]$^+$.

Example 198: Synthesis of Compound 157

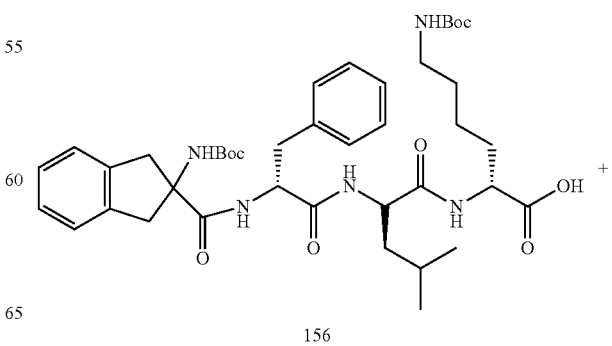

156

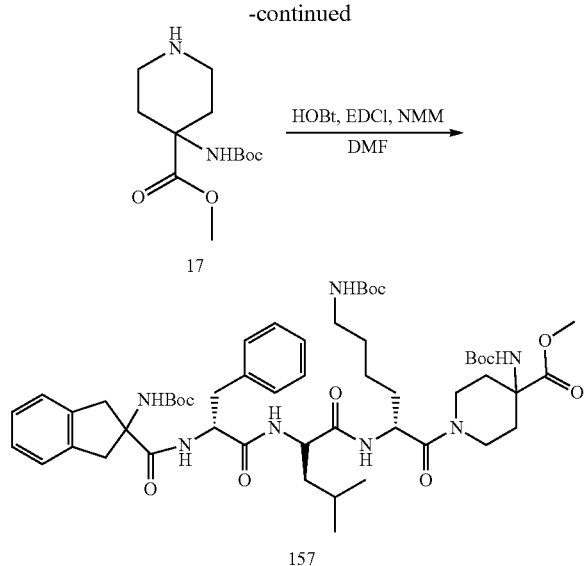

Into a reaction flask under nitrogen was added compound (156) (1.0 g, 1.31 mmol, 1 eq) and DMF (21.2 mL) under nitrogen. The resulting reaction mixture was cooled to 0° C. in ice bath. To the cooled reaction mixture was added HOBt.H$_2$O (211.7 mg, 1.57 mmol, 1.2 eq) and EDCI (300.3 mg, 1.57 mmol, 1.2 eq). After stirring for 30 minutes in ice bath, methyl 4-(tert-butoxycarbonylamino)piperidine-4-carboxylate (17) (405.6 mg, 1.57 mmol, 1.2 eq) and N-methylmorpholine (NMM) (277 mg, 2.74 mmol, 2.1 eq) were added. The reaction mixture was stirred at 0° C. for 1 hours, then stirred at room temperature until HPLC analysis indicated the reaction was completed. The reaction was added dropwise into water (60 mL) under stirring; plenty of precipitate formed; the mixture stood for one hour; then the solid was collected and washed with water (40 mL×3). The solid was then dried in vacuum (30° C.); it provided a white solid (157), 1.15 g; LCMS: m/z=1006.6 [M+H]$^+$.

Example 199: Synthesis of Compound 158

The compound (157) (500 mg, 0.497 mmol, 1.0 eq) was placed into a reaction flask under nitrogen; to the flask was added dichloromethane (10 mL); the resulting solution was cooled to 0° C. for 10 minutes; then to the cooled reaction was added dropwise a mixture of TFA (10 mL) and dichloromethane (20 mL). The resulting solution was stirred at −10° C. for one hour, then 2 hours at room temperature until HPLC analysis indicated the reaction was completed. The volatiles were removed on rotavapor. To the residue was added dichloromethane (10 mL); the resulting solution was evaporated on rotavapor; the dissolving/evaporating with dichloromethane was repeat three times; to the residue was added methanol (10 mL), the resulting solution was evaporated on rotavapor; the dissolving/evaporation with methanol was repeated twice; the residue was further purified on reverse phase HPLC; the collected fraction was lyophilized and it provided a white solid, (158), 442.6 mg; LCMS: MS m/z=706.4 [M+H]$^+$.

Example 200: Synthesis of Compound 159

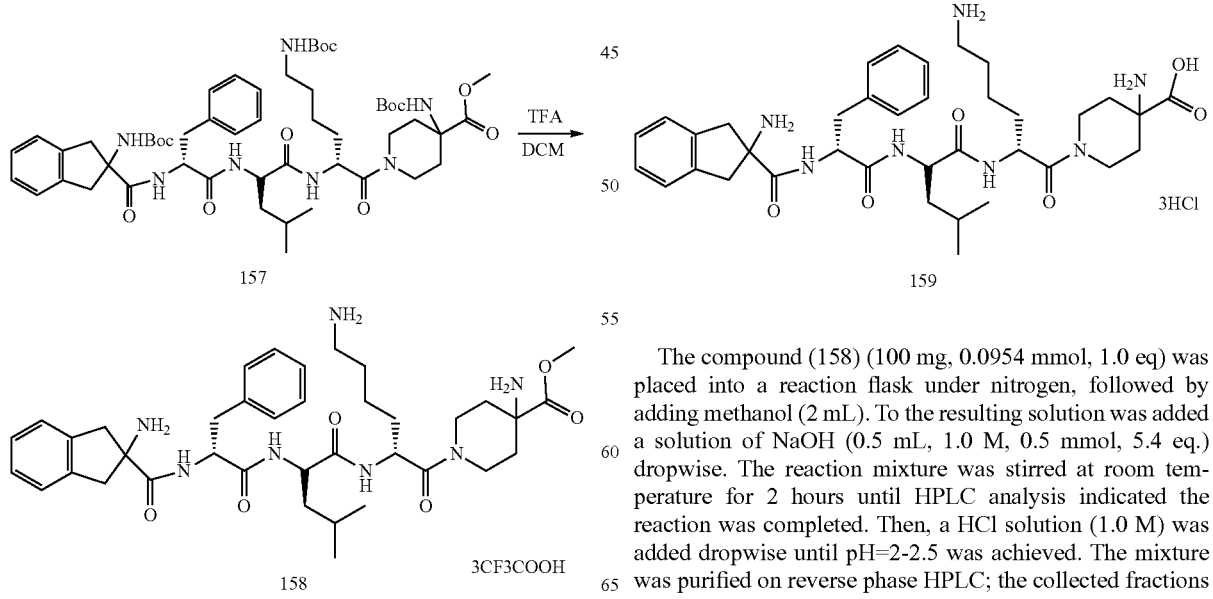

The compound (158) (100 mg, 0.0954 mmol, 1.0 eq) was placed into a reaction flask under nitrogen, followed by adding methanol (2 mL). To the resulting solution was added a solution of NaOH (0.5 mL, 1.0 M, 0.5 mmol, 5.4 eq.) dropwise. The reaction mixture was stirred at room temperature for 2 hours until HPLC analysis indicated the reaction was completed. Then, a HCl solution (1.0 M) was added dropwise until pH=2-2.5 was achieved. The mixture was purified on reverse phase HPLC; the collected fractions were lyphollized and it provided a white solid (159), 45.9 mg, LC-MS m/z=692.4 [M+H]$^+$.

XIIII. Demonstrated Below are the Preparations for the Peptide Mimics for Medical Products 168, 169, 171, 172

Reaction Scheme 20

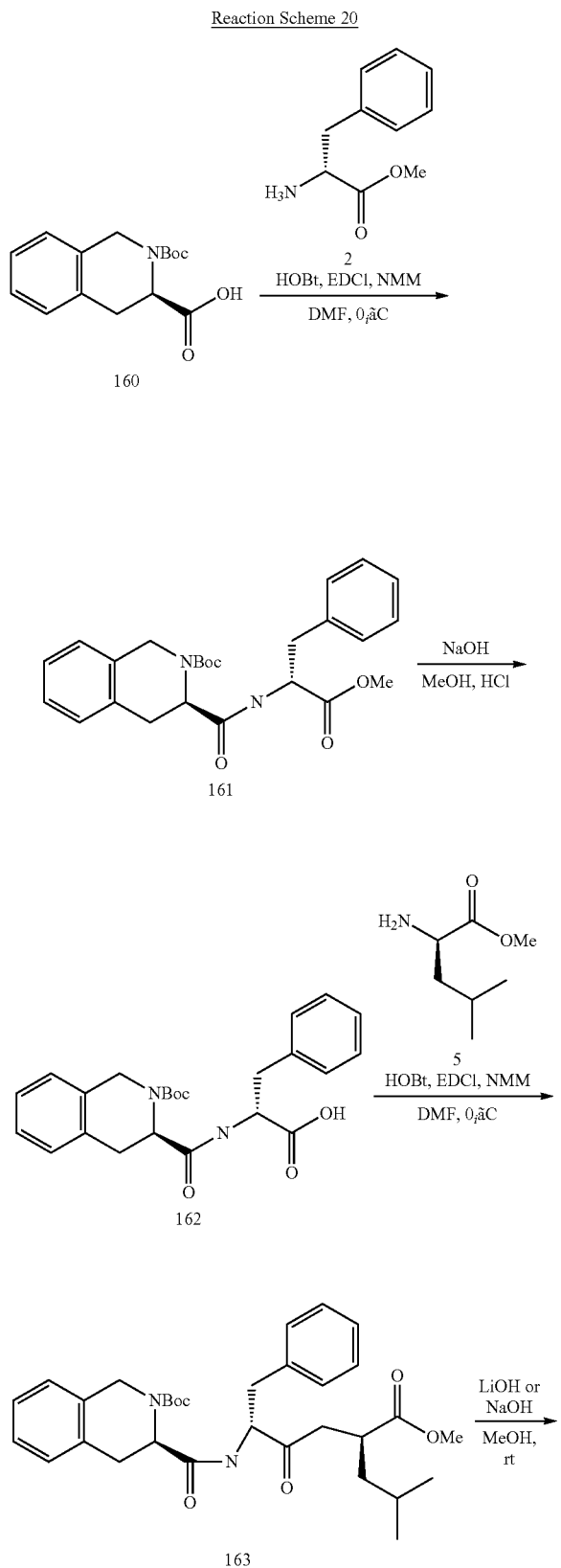

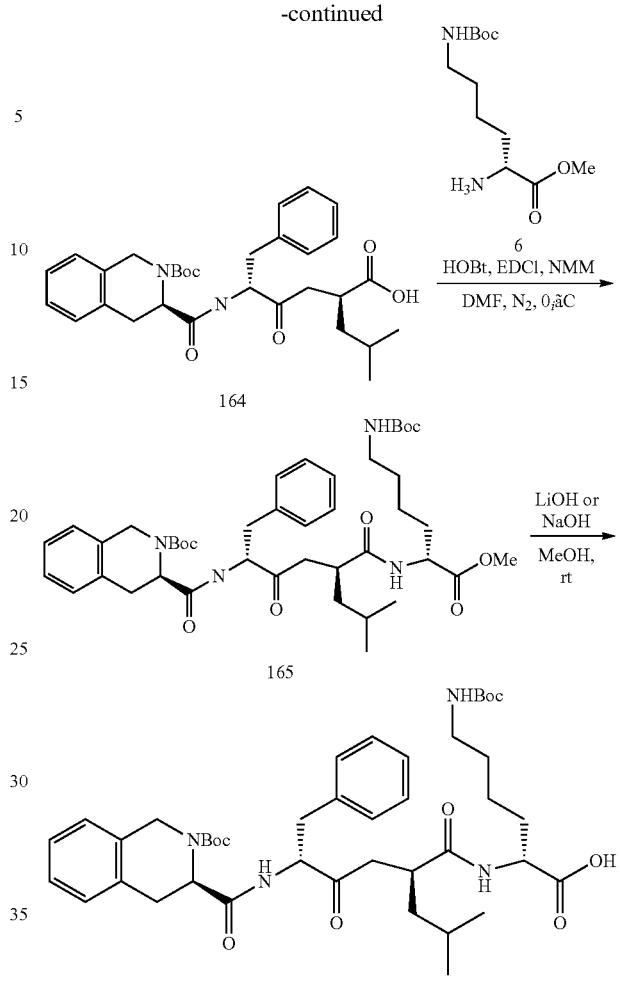

Example 201: Synthesis of Compound 161

Into a reaction flask under nitrogen was added (3R)-2-tert-butoxycarbonyl-3,4-dihydro-1H-isoquinoline-3-carboxylic acid (160) (10.0 g, 36.1 mmol, 1 eq) and DMF (212 mL) under nitrogen. The resulting reaction mixture was cooled to 0° C. in ice bath. To the cooled reaction mixture was added HOBt. H$_2$O (5.36 g, 39.7 mmol, 1.1 eq) and EDCI (7.61 g, 39.7 mmol, 1.1 eq). After stirring for 30 minutes in ice bath, H-D-Phe-OMe·HCl (2) (8.56 g, 39.7 mmol, 1.1 eq) and N-methylmorpholine (NMM) (7.66 g, 75.7 mmol, 2.1 eq) were added. The reaction mixture was stirred at 0° C. for 1 hours, then stirred at room temperature until HPLC analysis indicated the reaction was completed. The reaction was added dropwise into water (600 mL) under stirring; plenty of precipitate formed; the mixture stood for one hour; then the solid was collected and washed with water (400 mL×3). The solid was then dried in vacuum (30° C.); it provided a white solid (161), 14.0 g; LCMS: m/z=439.5 [M+H]$^+$.

Example 202: Synthesis of Compound 162

The compound (161) (10.0 g, 22.8 mmol, 1.0 eq) was placed into a reaction flask under nitrogen, followed by adding methanol (200 mL). To the resulting solution was added a solution of NaOH (50 mL, 1.0 M, 50 mmol, 2.2 eq.) dropwise. The reaction mixture was stirred at room temperature for 2 hours until HPLC analysis indicated the reaction was completed. Then, a HCl solution (1.0 M) was added dropwise until pH=2-2.5 was achieved. To the reaction was then added dropwise water (400 mL); plenty of precipitate were formed; the suspension stood for one hour; the solid was collected by filtration and washed with water (260 mL×3); the solid was then dried in vacuum (30° C.); it provided a white solid (162), 7.74 g, LC-MS m/z=425.5 [M+H]$^+$.

Example 203: Synthesis of Compound 163

Into a reaction flask under nitrogen was added compound (162) (8.0 g, 18.8 mmol, 1 eq) and DMF (170 mL) under nitrogen. The resulting reaction mixture was cooled to 0° C. in ice bath. To the cooled reaction mixture was added HOBt. H$_2$O (2.79 g, 20.6 mmol, 1.1 eq) and EDCI (3.96 g, 20.5 mmol, 1.1 eq). After stirring for 30 minutes in ice bath, methyl (D)-leucine ester hydrochloride (5) (3.75 g, 20.6 mmol, 1.1 eq) and N-methylmorpholine (NMM) (3.98 g, 39.4 mmol, 2.1 eq) were added. The reaction mixture was stirred at 0° C. for 1 hours, then stirred at room temperature until HPLC analysis indicated the reaction was completed. The reaction was added dropwise into water (360 mL) under stirring; plenty of precipitate formed; the mixture stood for one hour; then the solid was collected and washed with water (240 mL×3). The solid was then dried in vacuum (30° C.); it provided a white solid (163), 9.0 g; LCMS: m/z=552.7 [M+H]$^+$.

Example 204: Synthesis of Compound 164

The compound (163) (8.0 g, 14.5 mmol, 1.0 eq) was placed into a reaction flask under nitrogen, followed by adding methanol (160 mL). To the resulting solution was added a solution of NaOH (40 mL, 1.0 M, 40 mmol, 2.8 eq.) dropwise. The reaction mixture was stirred at room temperature for 2 hours until HPLC analysis indicated the reaction was completed. Then, HCl solution (1.0 M) was added dropwise until pH=2~2.5 was achieved. To the reaction was then added dropwise water (320 mL); plenty of precipitate were formed; the suspension stood for one hour; the solid was collected by filtration and washed with water (210 mL×3); the solid was then dried in vacuum (30° C.); it provided a white solid (164), 6.53 g, LC-MS m/z=538.6 [M+H]$^+$.

Example 205: Synthesis of Compound 165

Into a reaction flask under nitrogen was added compound (164) (5.0 g, 9.30 mmol, 1 eq) and DMF (106 mL) under nitrogen. The resulting reaction mixture was cooled to 0° C. in ice bath. To the cooled reaction mixture was added HOBt. H$_2$O (1.51 g, 11.2 mmol, 1.2 eq) and EDCI (2.14 g, 11.2 mmol, 1.2 eq). After stirring for 30 minutes in ice bath, H-D-Lys(Boc)-OMe·HCl (3.31 g, 11.2 mmol, 1.2 eq) and N-methylmorpholine (NMM) (1.97 g, 19.5 mmol, 2.1 eq) were added. The reaction mixture was stirred at 0° C. for 1 hours, then stirred at room temperature until HPLC analysis indicated the reaction was completed. The reaction was added dropwise into water (300 mL) under stirring; plenty of precipitate formed; the mixture stood for one hour; then the solid was collected and washed with water (200 mL×3). The solid was then dried in vacuum (30° C.); it provided a white solid (165), 6.68 g; LCMS: m/z=781.0 [M+H]$^+$.

Example 206: Synthesis of Compound 166

The compound (165) (5.0 g, 6.41 mmol, 1.0 eq) was placed into a reaction flask under nitrogen, followed by adding methanol (100 mL). To the resulting solution was added a solution of NaOH (25 mL, 1.0 M, 25 mmol, 3.9 eq.) dropwise. The reaction mixture was stirred at room temperature for 2 hours until HPLC analysis indicated the reaction was completed. Then, a HCl solution (1.0 M) was added dropwise until pH=2-2.5 was achieved. To the reaction was then added dropwise water (200 mL); plenty of precipitate were formed; the suspension stood for one hour; the solid was collected by filtration and washed with water (130 mL×3); the solid was then dried in vacuum (30° C.); it provided a white solid (166), 4.44 g, LC-MS m/z=767.0 [M+H]$^+$.

Synthesis of Peptide Analogues

Example 207: Synthesis of Compound 167

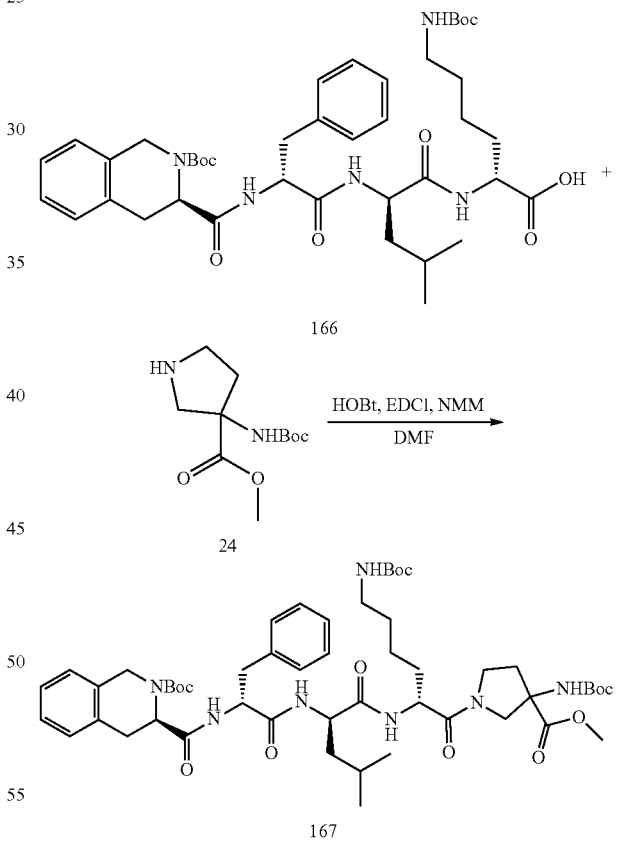

Into a reaction flask under nitrogen was added compound (166) (1.0 g, 1.30 mmol, 1 eq) and DMF (21.2 mL) under nitrogen. The resulting reaction mixture was cooled to 0° C. in ice bath. To the cooled reaction mixture was added HOBt. H$_2$O (210.8 mg, 1.56 mmol, 1.2 eq) and EDCI (299 mg, 1.56 mmol, 1.2 eq). After stirring for 30 minutes in ice bath, Methy-3-(Boc-NH)pyrrolidine-3-carboxylate (24) (381.1 mg, 1.56 mmol, 1.2 eq) and N-methylmorpholine (NMM) (276.1 mg, 2.73 mmol, 2.1 eq) were added. The reaction mixture was stirred at 0° C. for 1 hours, then stirred at room temperature until HPLC analysis indicated the reaction was completed. The reaction was added dropwise into water (60 mL) under stirring; plenty of precipitate formed; the mixture stood for one hour; then the solid was collected and washed with water (40 mL×3). The solid was then dried in vacuum (30° C.); it provided a white solid (167), 1.03 g; LCMS: m/z=993.2 [M+H]⁺.

Example 208: Synthesis of Peptide Product 168

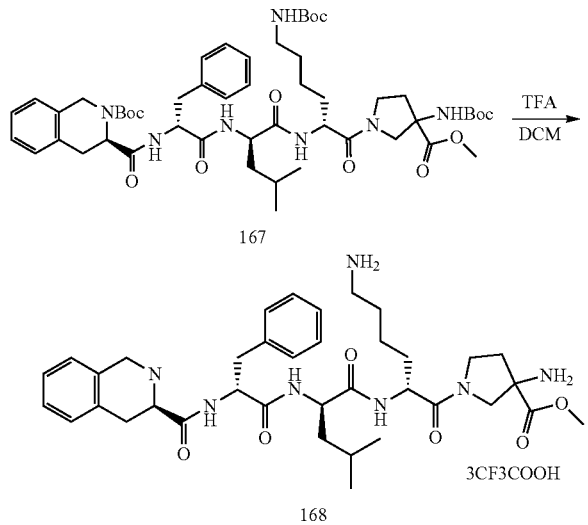

The compound (167) (200 mg, 0.201 mmol, 1.0 eq) was placed into a reaction flask under nitrogen; to the flask was added dichloromethane (4 mL); the resulting solution was cooled to 0° C. for 10 minutes; then to the cooled reaction was added dropwise a mixture of TFA (4 mL) and dichloromethane (8 mL). The resulting solution was stirred at −10° C. for one hour, then 2 hours at room temperature until HPLC analysis indicated the reaction was completed. The volatiles were removed on rotavapor. To the residue was added dichloromethane (4 mL); the resulting solution was evaporated on rotavapor; the dissolving/evaporating with dichloromethane was repeat three times; to the residue was added methanol (4 mL), the resulting solution was evaporated on rotavapor; the dissolving/evaporation with methanol was repeated twice; the residue was further purified on reverse phase HPLC; the collected fraction was lyophilized and it provided a white solid, (168), 166.7 mg; LCMS: MS m/z=692.5 [M+H]⁺.

Example 209: Synthesis of Compound 169

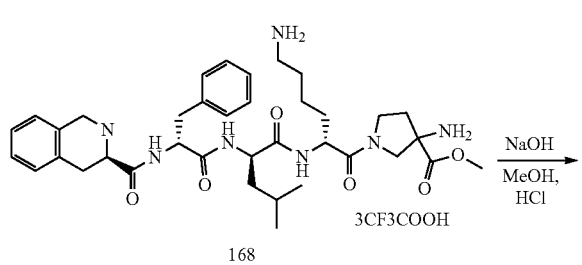

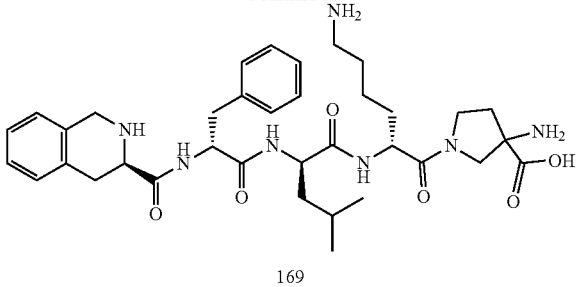

The compound (168) (100 mg, 0.0967 mmol, 1.0 eq) was placed into a reaction flask under nitrogen, followed by adding methanol (2 mL). To the resulting solution was added a solution of NaOH (0.5 mL, 1.0 M, 0.5 mmol, 5.2 eq.) dropwise. The reaction mixture was stirred at room temperature for 2 hours until HPLC analysis indicated the reaction was completed. Then, HCl solution (1.0 M) was added dropwise until pH=2~2.5 was achieved. The reaction mixture was then purified on reverse phase HPLC; the collected fractions were lyophilized and it provided a white solid, (169), 60 mg, LC-MS m/z=678.8 [M+H]⁺.

Example 210: Synthesis of Compound 170

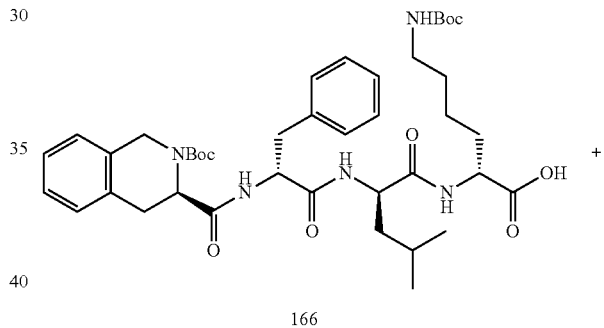

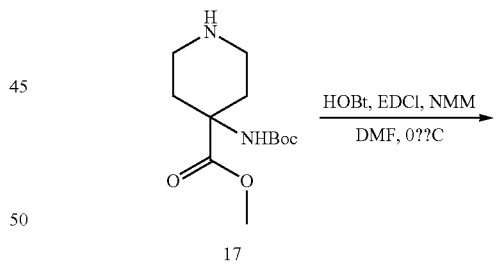

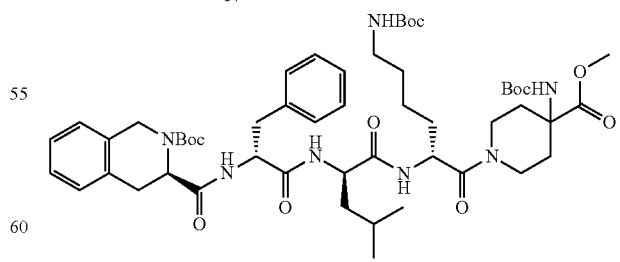

Into a reaction flask under nitrogen was added compound (166) (1.0 g, 1.30 mmol, 1 eq) and DMF (21.2 mL) under nitrogen. The resulting reaction mixture was cooled to 0° C.

in ice bath. To the cooled reaction mixture was added HOBt. H₂O (210.8 mg, 1.56 mmol, 1.2 eq) and EDCI (299 mg, 1.56 mmol, 1.2 eq). After stirring for 30 minutes in ice bath, methy-4-(Boc-NH) piperidine-4-carboxylate (17) (402.9 mg, 1.56 mmol, 1.2 eq) and N-methylmorpholine (NMM) (276.1 mg, 2.73 mmol, 2.1 eq) were added. The reaction mixture was stirred at 0° C. for 1 hours, then stirred at room temperature until HPLC analysis indicated the reaction was completed. The reaction was added dropwise into water (60 mL) under stirring; plenty of precipitate formed; the mixture stood for one hour; then the solid was collected and washed with water (40 mL×3). The solid was then dried in vacuum (30° C.); it provided a white solid (170), 1.19 g; LCMS: m/z=1007.3 [M+H]⁺.

Example 211: Synthesis of Compound 171

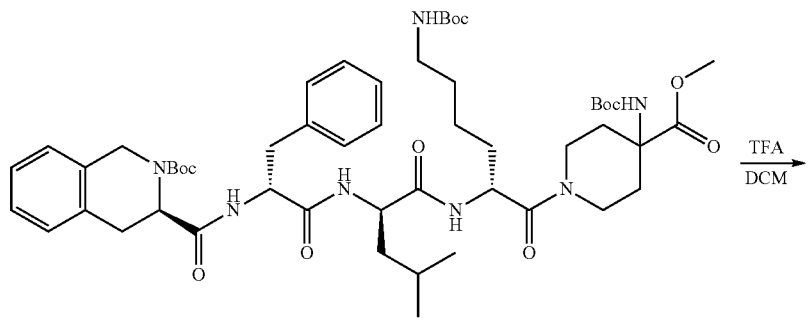

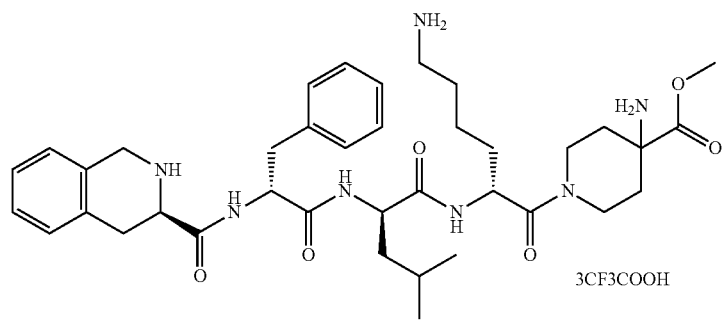

The compound (170) (500 mg, 0.496 mmol, 1.0 eq) was placed into a reaction flask under nitrogen; to the flask was added dichloromethane (10 mL); the resulting solution was cooled to −10° C. for 10 minutes; then to the cooled reaction was added dropwise a mixture of TFA (10 mL) and dichloromethane (20 mL). The resulting solution was stirred at −10° C. for one hour, then 2 hours at room temperature until HPLC analysis indicated the reaction was completed. The volatiles were removed on rotavapor. To the residue was added dichloromethane (10 mL); the resulting solution was evaporated on rotavapor; the dissolving/evaporating with dichloromethane was repeat three times; to the residue was added methanol (10 mL), the resulting solution was evaporated on rotavapor; the dissolving/evaporation with methanol was repeated twice; the residue was further purified on reverse phase HPLC; the collected fraction was lyophilized and it provided a white solid, (171), 442.6 mg; LCMS: MS m/z=706.4 [M+H]$^+$.

Example 212: Synthesis of Compound 172

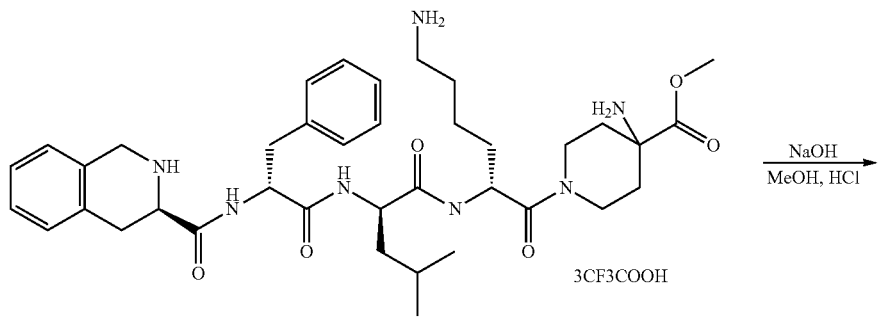

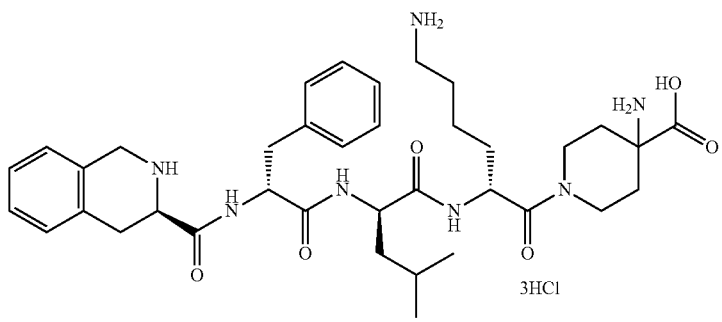

The compound (171) (100 mg, 0.0954 mmol, 1.0 eq) was placed into a reaction flask under nitrogen, followed by adding methanol (2 mL). To the resulting solution was added a solution of NaOH (0.5 mL, 1.0 M, 0.5 mmol, 5.2 eq.) dropwise. The reaction mixture was stirred at room temperature for 2 hours until HPLC analysis indicated the reaction was completed. Then, a HCl solution (1.0 M) was added dropwise until pH=2-2.5 was achieved. The reaction mixture was then purified on reverse phase HPLC; the collected fractions were lyophilized and it provided a white solid, (172), 45.9 mg, LC-MS m/z=692.9 [M+H]$^+$.

XII. Demonstrated Below are the Preparations for the Peptide Mimics for Medical Products 181, 182, 184, 185

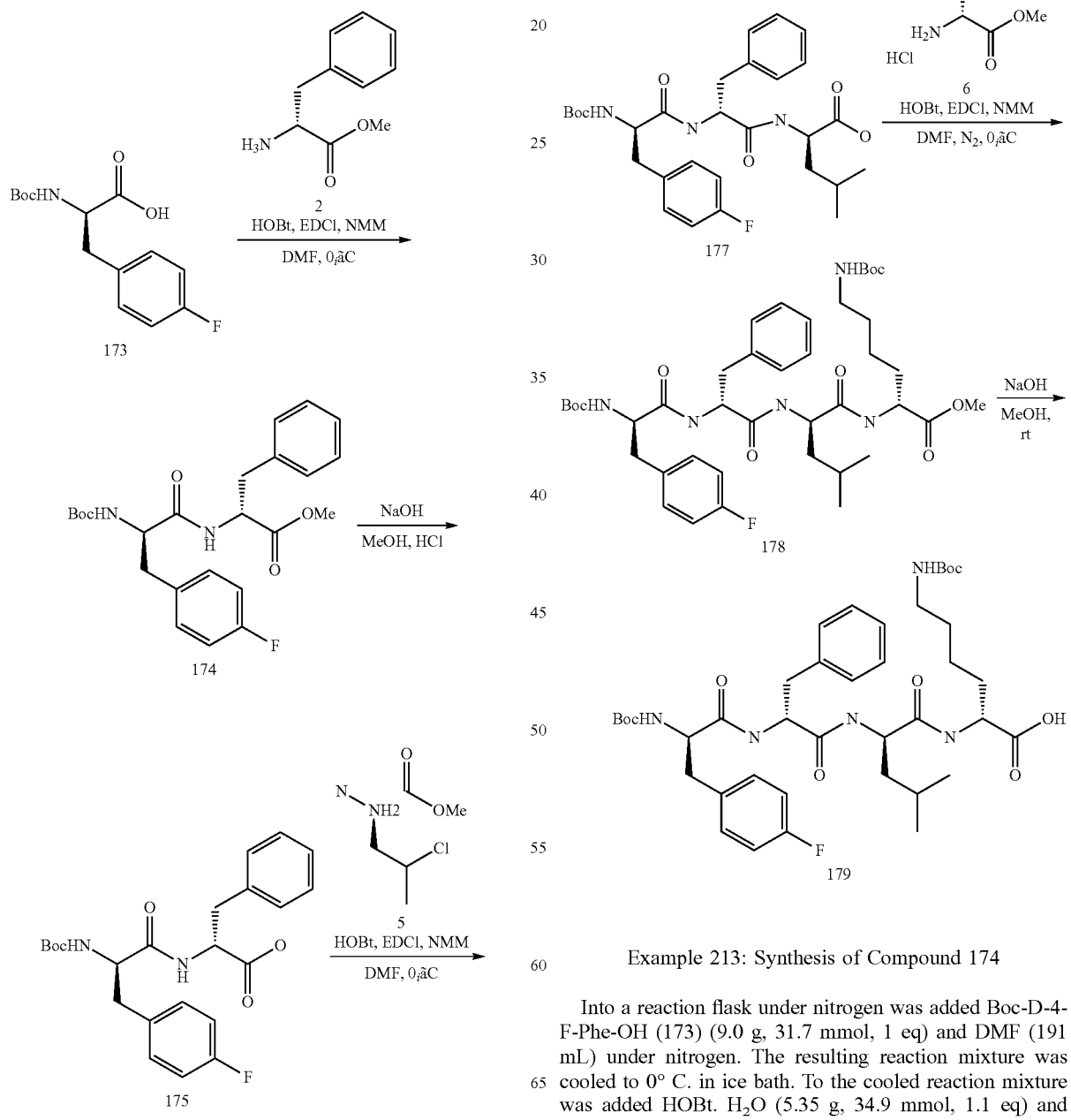

Example 213: Synthesis of Compound 174

Into a reaction flask under nitrogen was added Boc-D-4-F-Phe-OH (173) (9.0 g, 31.7 mmol, 1 eq) and DMF (191 mL) under nitrogen. The resulting reaction mixture was cooled to 0° C. in ice bath. To the cooled reaction mixture was added HOBt. H$_2$O (5.35 g, 34.9 mmol, 1.1 eq) and EDCI (6.70 g, 34.9 mmol, 1.1 eq). After stirring for 30 minutes in ice bath, H-D-Phe-OMe·HCl (2) 7.51 g, 34.9 mmol, 1.1 eq) and N-methylmorpholine (NMM) (6.73 g, 66.57 mmol, 2.1 eq) were added. The reaction mixture was stirred at 0° C. for 1 hours, then stirred at room temperature until HPLC analysis indicated the reaction was completed. The reaction was added dropwise into water (540 mL) under stirring; plenty of precipitate formed; the mixture stood for one hour; then the solid was collected and washed with water (360 mL×3). The solid was then dried in vacuum (30° C.); it provided a white solid (174), 12.13 g; LCMS: m/z=445.5 [M+H]$^+$.

Example 214: Synthesis of Compound 175

The compound (174) (10.0 g, 22.5 mmol, 1.0 eq) was placed into a reaction flask under nitrogen, followed by adding methanol (200 mL). To the resulting solution was added a solution of NaOH (50 mL, 1.0 M, 50 mmol, 2.2 eq.) dropwise. The reaction mixture was stirred at room temperature for 2 hours until HPLC analysis indicated the reaction was completed. Then, a HCl solution (1.0 M) was added dropwise until pH=2~2.5 was achieved. The reaction mixture was added dropwise into water (400 mL) under stirring; the resulting suspension stood for one hour; the solid was collected by filtration and washed with water (260 mL×3), then dried in vacuum (30° C.); it provided a white solid (175), 9.0 g; LC-MS m/z=431.5 [M+H]$^+$.

Example 215: Synthesis of Compound 176

Into a reaction flask under nitrogen was added compound (175) (9.0 g, 20.9 mmol, 1 eq) and DMF (191 mL) under nitrogen. The resulting reaction mixture was cooled to 0° C. in ice bath. To the cooled reaction mixture was added HOBt. H$_2$O (3.52 g, 23.0 mmol, 1.1 eq) and EDCI (4.41 g, 23.0 mmol, 1.1 eq). After stirring for 30 minutes in ice bath, H-D-Leu-OMe·HCl (5) (4.18 g, 23.0 mmol, 1.1 eq) and N-methylmorpholine (NMM) (4.44 g, 43.9 mmol, 2.1 eq) were added. The reaction mixture was stirred at 0° C. for 1 hours, then stirred at room temperature until HPLC analysis indicated the reaction was completed. The reaction was added dropwise into water (540 mL) under stirring; plenty of precipitate formed; the mixture stood for one hour; then the solid was collected and washed with water (360 mL×3), then dried in vacuum (30° C.); it provided a white solid compound (176), 11.21 g. LC-MS m/z=558.6 [M+H]$^+$.

Example 216: Synthesis of Compound 177

The compound (176) (10.0 g, 17.9 mmol, 1.0 eq) was placed into a reaction flask under nitrogen, followed by adding methanol (200 mL). To the resulting solution was added a solution of NaOH (50 mL, 1.0 M, 50 mmol, 2.2 eq.) dropwise. The reaction mixture was stirred at room temperature for 2 hours until HPLC analysis indicated the reaction was completed. Then, a HCl solution (1.0 M) was added dropwise until pH=2-2.5 was achieved. The reaction mixture was added dropwise into water (400 mL) under stirring; the resulting suspension stood for one hour; the solid was collected by filtration and washed with water (260 mL×3), then dried in vacuum (30° C.); it provided a white solid (177), 9.48 g; LC-MS m/z=544.3 [M+H]$^+$.

Example 217: Synthesis of Compound 178

Into a reaction flask under nitrogen was added compound (177) (9.0 g, 16.2 mmol, 1.0 eq) and DMF (191 mL) under nitrogen. The resulting reaction mixture was cooled to 0° C. in ice bath. To the cooled reaction mixture was added HOBt. H$_2$O (2.98 g, 19.5 mmol, 1.2 eq) and EDCI (3.74 g, 19.5 mmol, 1.2 eq). After stirring for 30 minutes in ice bath, H-D-Lys(Boc)-OMe·HCl (6) (5.78 g, 19.5 mmol, 1.2 eq) and N-methylmorpholine (NMM) (3.46 g, 34.1 mmol, 2.1 eq) were added. The reaction mixture was stirred at 0° C. for 1 hours, then stirred at room temperature until HPLC analysis indicated the reaction was completed. The reaction was added dropwise into water (540 mL) under stirring; plenty of precipitate formed; the mixture stood for one hour; then the solid was collected and washed with water (360 mL×3), then dried in vacuum (30° C.); it provided a white solid compound (178), 12.33 g. LC-MS m/z=787.4 [M+H]$^+$.

Example 218: Synthesis of Compound 179

The compound (178) (5.0 g, 6.47 mmol, 1.0 eq) was placed into a reaction flask under nitrogen, followed by adding methanol (100 mL). To the resulting solution was added a solution of NaOH (25 mL, 1.0 M, 25 mmol, 3.9 eq.) dropwise. The reaction mixture was stirred at room temperature for 2 hours until HPLC analysis indicated the reaction was completed. Then, a HCl solution (1.0 M) was added dropwise until pH=2-2.5 was achieved. The reaction mixture was added dropwise into water (200 mL) under stirring; the resulting suspension stood for one hour; the solid was collected by filtration and washed with water (130 mL×3), then dried in vacuum (30° C.); it provided a white solid (179), 4.19 g; LC-MS m/z=773.4 [M+H]$^+$.

Synthesis of Peptide Analogues

Example 219: Synthesis of Compound 180

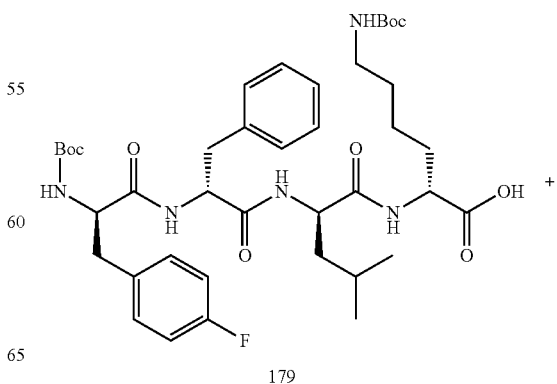

179

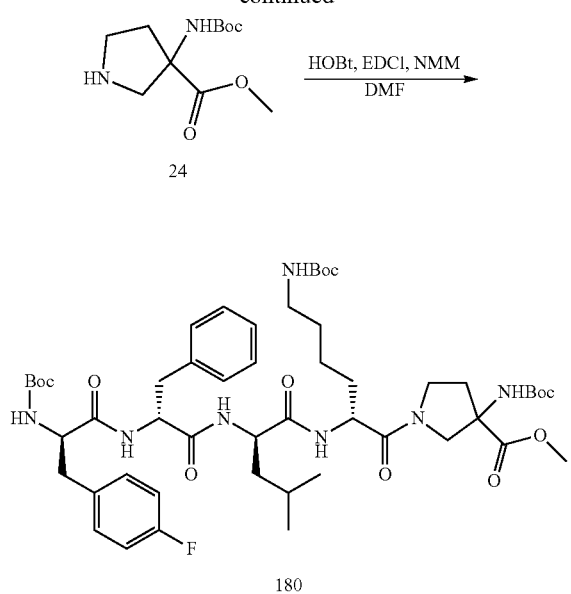

Into a reaction flask under nitrogen was added compound (179) (1.0 g, 1.29 mmol, 1.0 eq) and DMF (21.2 mL) under nitrogen. The resulting reaction mixture was cooled to 0° C. in ice bath. To the cooled reaction mixture was added HOBt.H$_2$O (237.6 mg, 1.55 mmol, 1.2 eq) and EDCI (297.4 mg, 1.55 mmol, 1.2 eq). After stirring for 30 minutes in ice bath, methyl 3-(boc-NH)pyrrolidine-3-carboxylate (24) (378.8 mg, 1.55 mmol, 1.2 eq) and N-methylmorpholine (NMM) (274.6 g, 2.72 mmol, 2.1 eq) were added. The reaction mixture was stirred at 0° C. for 1 hours, then stirred at room temperature until HPLC analysis indicated the reaction was completed. The reaction was added dropwise into water (60 mL) under stirring; plenty of precipitate formed; the mixture stood for one hour; then the solid was collected and washed with water (40 mL×3), then dried in vacuum (30° C.); it provided a white solid compound (180), 1.07 g. LC-MS m/z=999.5 [M+H]$^+$.

Example 220: Synthesis of Compound 181

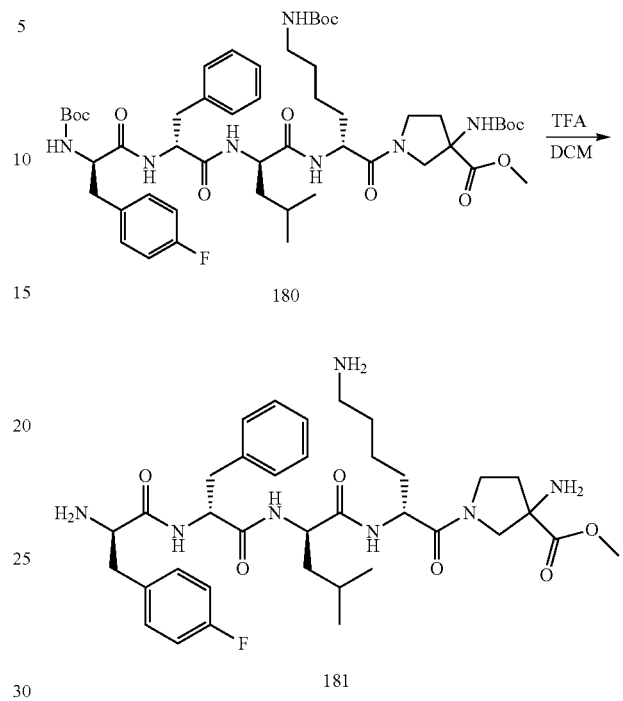

The compound (180) (200 mg, 0.20 mmol, 1.0 eq) was placed into a reaction flask under nitrogen; to the flask was added dichloromethane (4 mL); the resulting solution was cooled to −10° C. for 10 minutes; then to the cooled reaction was added dropwise a mixture of TFA (4 mL) and dichloromethane (8 mL). The resulting solution was stirred at −10° C. for one hour, then 2 hours at room temperature until HPLC analysis indicated the reaction was completed. The volatiles were removed on rotavapor. To the residue was added dichloromethane (4 mL); the resulting solution was evaporated on rotavapor; the dissolving/evaporating with dichloromethane was repeat three times; to the residue was added methanol (4 mL), the resulting solution was evaporated on rotavapor; the dissolving/evaporation with methanol was repeated twice; the residue was further purified on reverse phase HPLC; the collected fraction was lyophilized and it provided a white solid, (181), 40.0 mg; LCMS: MS m/z=699.4 [M+H]$^+$.

Example 221: Synthesis of Compound 182

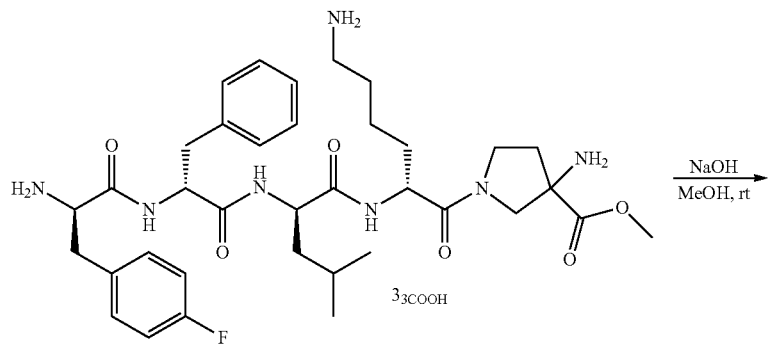

-continued

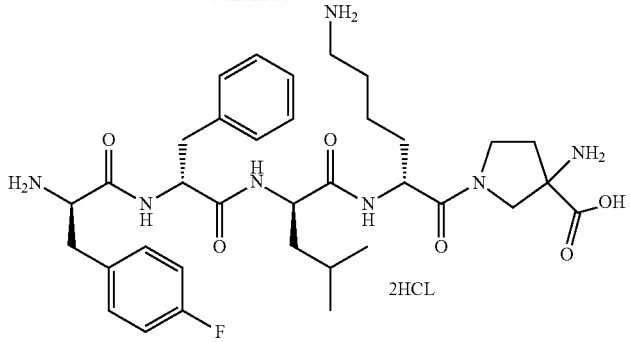

182

The compound (181) (20 mg, 0.0189 mmol, 1.0 eq) was placed into a reaction flask under nitrogen, followed by adding methanol (1.0 mL). To the resulting solution was added a solution of NaOH (0.2 mL, 1.0 M, 0.2 mmol, 10.6 eq.) dropwise. The reaction mixture was stirred at room temperature for 2 hours until HPLC analysis indicated the reaction was completed. Then, a HCl solution (1.0 M) was added dropwise until pH=2-2.5 was achieved. The reaction mixture was purified on reverse phase HPLC; the collected fractions were lyophilized into a white solid compound (182), 2.37 mg; LC-MS m/z=685.4 [M+H]+.

Example 222: Synthesis of Compound 183

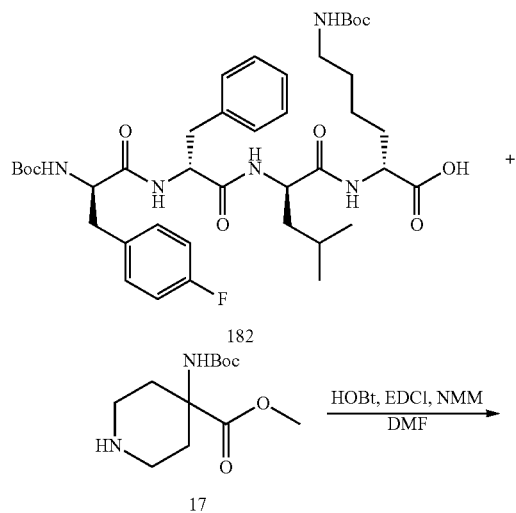

-continued

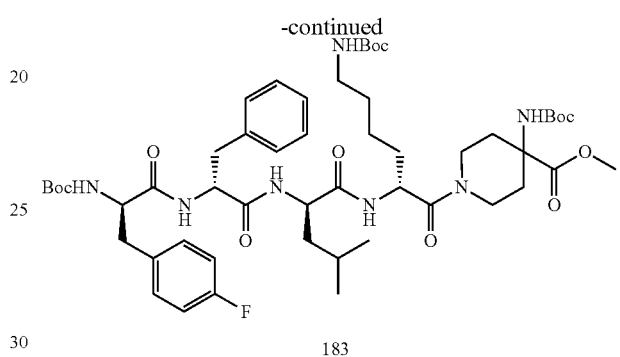

183

Into a reaction flask under nitrogen was added compound (182) (1.0 g, 1.29 mmol, 1.0 eq) and DMF (21.2 mL) under nitrogen. The resulting reaction mixture was cooled to 0° C. in ice bath. To the cooled reaction mixture was added HOBt. H$_2$O (237.6 mg, 1.55 mmol, 1.2 eq) and EDCI (297.4 mg, 1.55 mmol, 1.2 eq). After stirring for 30 minutes in ice bath, methyl 4-(Boc-NH)piperidine-4-carboxylate (17) (400.1 mg, 1.55 mmol, 1.2 eq) and N-methylmorpholine (NMM) (274.6 mg, 2.72 mmol, 2.1 eq) were added. The reaction mixture was stirred at 0° C. for 1 hours, then stirred at room temperature until HPLC analysis indicated the reaction was completed. The reaction was added dropwise into water (60 mL) under stirring; plenty of precipitate formed; the mixture stood for one hour; then the solid was collected and washed with water (40 mL×3), then dried in vacuum (30° C.); it provided a white solid compound (183), 1.14 g. LC-MS m/z=1012.6 [M+H]+.

Example 223: Synthesis of Compound 184

183

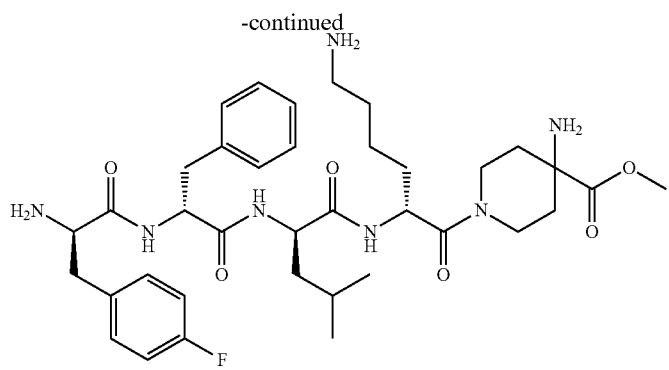

184

The compound (183) (200 mg, 0.19 mmol, 1.0 eq) was placed into a reaction flask under nitrogen; to the flask was added dichloromethane (4 mL); the resulting solution was cooled to −10° C. for 10 minutes; then to the cooled reaction was added dropwise a mixture of TFA (4 mL) and dichloromethane (8 mL). The resulting solution was stirred at −10° C. for one hour, then 2 hours at room temperature until HPLC analysis indicated the reaction was completed. The volatiles were removed on rotavapor. To the residue was added dichloromethane (4 mL); the resulting solution was evaporated on rotavapor; the dissolving/evaporating with dichloromethane was repeat three times; to the residue was added methanol (4 mL), the resulting solution was evaporated on rotavapor; the dissolving/evaporation with methanol was repeated twice; the residue was further purified on reverse phase HPLC; the collected fraction was lyophilized and it provided a white solid, (184), 30.0 mg; LCMS: MS m/z=712.4 [M+H]⁺.

Example 224: Synthesis of Compound 185

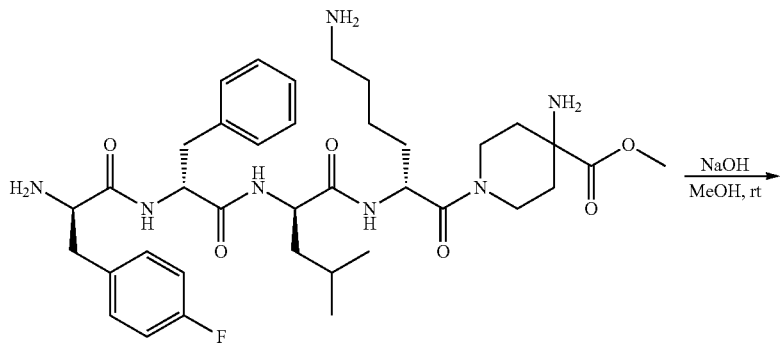

184

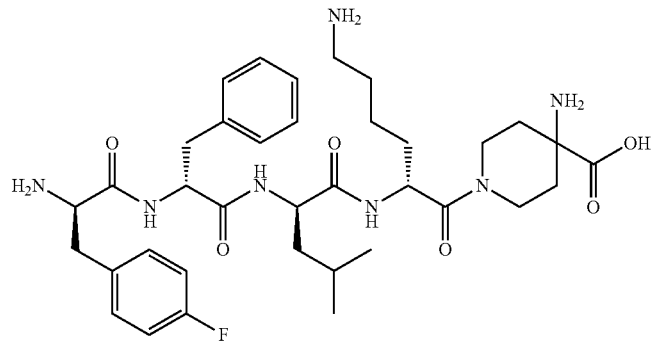

185

The compound (184) (20 mg, 0.0189 mmol, 1.0 eq) was placed into a reaction flask under nitrogen, followed by adding methanol (1.0 mL). To the resulting solution was added a solution of NaOH (0.2 mL, 1.0 M, 0.2 mmol, 10.6 eq.) dropwise. The reaction mixture was stirred at room temperature for 2 hours until HPLC analysis indicated the reaction was completed. Then, a HCl solution (1.0 M) was added dropwise until pH=2-2.5 was achieved. The reaction mixture was purified on reverse phase HPLC; the collected fractions were lyophilized into a white solid compound (185), 3.24 mg; LC-MS m/z=687.4 [M+H]$^+$.

XIII. Demonstrated Below are the Preparations for the Peptide Mimics for Medical Products 194 and 196

Reaction Scheme 22

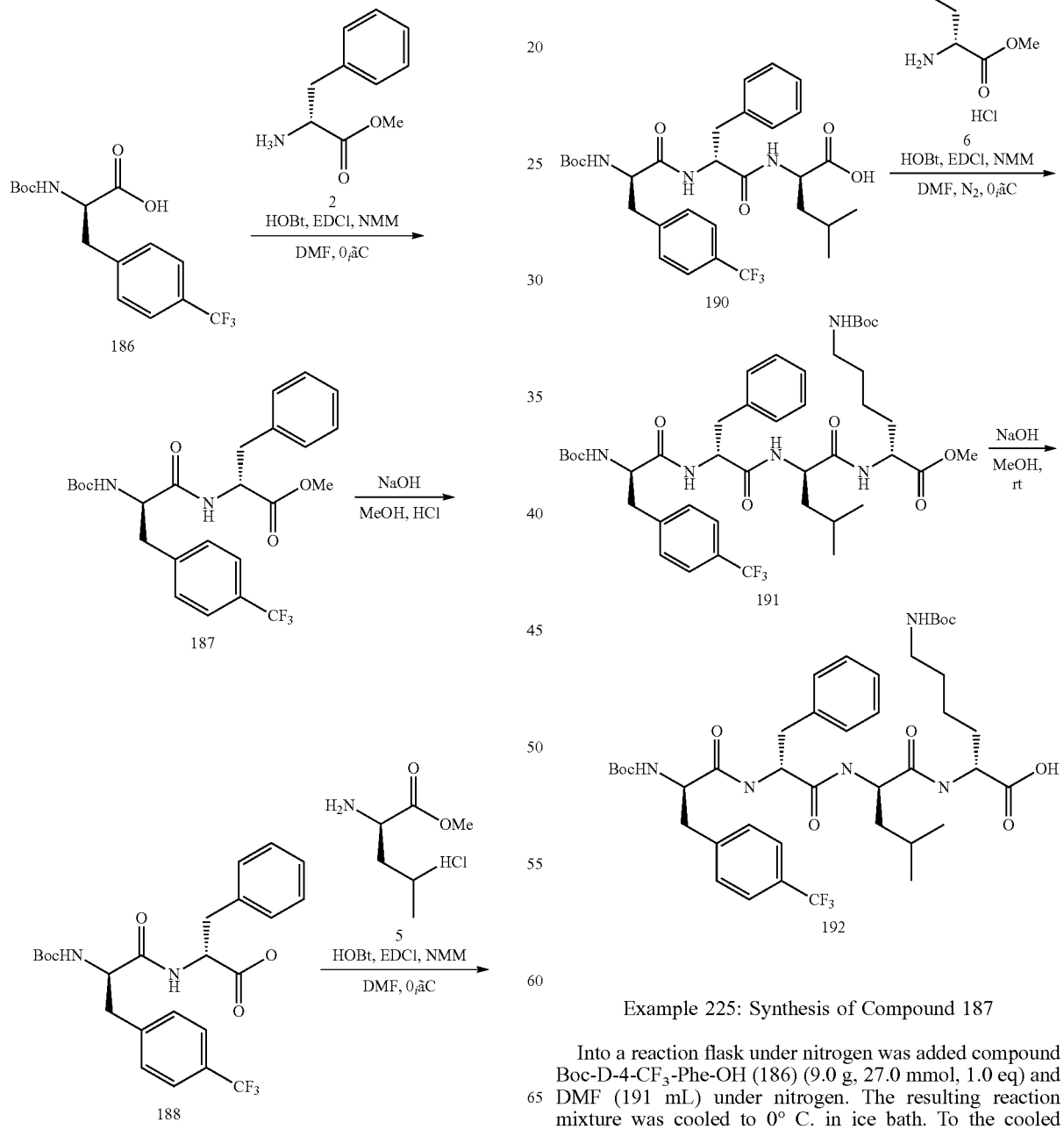

Example 225: Synthesis of Compound 187

Into a reaction flask under nitrogen was added compound Boc-D-4-CF$_3$-Phe-OH (186) (9.0 g, 27.0 mmol, 1.0 eq) and DMF (191 mL) under nitrogen. The resulting reaction mixture was cooled to 0° C. in ice bath. To the cooled reaction mixture was added HOBt. H$_2$O (4.55 g, 29.7 mmol, 1.1 eq) and EDCI (5.69 g, 29.7 mmol, 1.1 eq). After stirring for 30 minutes in ice bath, H-D-Phe-OMe·HCl (2) (6.40 g, 29.7 mmol, 1.1 eq) and N-methylmorpholine (NMM) (6.32 g, 56.7 mmol, 2.1 eq) were added. The reaction mixture was stirred at 0° C. for 1 hours, then stirred at room temperature until HPLC analysis indicated the reaction was completed. The reaction was added dropwise into water (540 mL) under stirring; plenty of precipitate formed; the mixture stood for one hour; then the solid was collected and washed with water (360 mL×3), then dried in vacuum (30° C.); it provided a white solid compound (187), 12.0 g. LC-MS m/z=495.2 [M+H]$^+$.

Example 226: Synthesis of Compound 188

The compound (187) (10.0 g, 22.2 mmol, 1.0 eq) was placed into a reaction flask under nitrogen, followed by adding methanol (200 mL). To the resulting solution was added a solution of NaOH (50 mL, 1.0 M, 50 mmol, 2.3 eq.) dropwise. The reaction mixture was stirred at room temperature for 2 hours until HPLC analysis indicated the reaction was completed. Then, a HCl solution (1.0 M) was added dropwise until pH=2~2.5 was achieved. To the reaction was added dropwise water (400 mL) under stirring; then the resulting suspension stood for one hour; the solid was collected by filtration and washed with water (265 mL×3). The solid was then dried in vacuum (30° C.); it provided a white solid compound (188), 9.50 g; LC-MS m/z=481.5 [M+H]$^+$.

Example 227: Synthesis of Compound 189

Into a reaction flask under nitrogen was added compound (188) (9.0 g, 18.73 mmol, 1.0 eq) and DMF (191 mL) under nitrogen. The resulting reaction mixture was cooled to 0° C. in ice bath. To the cooled reaction mixture was added HOBt. H$_2$O (3.16 g, 20.6 mmol, 1.1 eq) and EDCI (3.95 g, 20.6 mmol, 1.1 eq). After stirring for 30 minutes in ice bath, H-D-Leu-OMe·HCl (5) (3.74 g, 20.6 mmol, 1.1 eq) and N-methylmorpholine (NMM) (3.99 g, 39.34 mmol, 2.1 eq) were added. The reaction mixture was stirred at 0° C. for 1 hours, then stirred at room temperature until HPLC analysis indicated the reaction was completed. The reaction was added dropwise into water (540 mL) under stirring; plenty of precipitate formed; the mixture stood for one hour; then the solid was collected and washed with water (360 mL×3), then dried in vacuum (30° C.); it provided a white solid compound (189), 10.86 g. LC-MS m/z=608.6 [M+H]$^+$.

Example 228: Synthesis of Compound 190

The compound (189) (10.0 g, 16.9 mmol, 1.0 eq) was placed into a reaction flask under nitrogen, followed by adding methanol (200 mL). To the resulting solution was added a solution of NaOH (50 mL, 1.0 M, 50 mmol, 2.96 eq.) dropwise. The reaction mixture was stirred at room temperature for 2 hours until HPLC analysis indicated the reaction was completed. Then, a HCl solution (1.0 M) was added dropwise until pH=2~2.5 was achieved. To the reaction was added dropwise water (400 mL) under stirring; then the resulting suspension stood for one hour; the solid was collected by filtration and washed with water (190 mL×3). The solid was then dried in vacuum (30° C.); it provided a white solid compound (190), 9.21 g; LC-MS m/z=594.6 [M+H]$^+$.

Example 229: Synthesis of Compound 191

Into a reaction flask under nitrogen was added compound (190) (9.0 g, 15.2 mmol, 1.0 eq) and DMF (191 mL) under nitrogen. The resulting reaction mixture was cooled to 0° C. in ice bath. To the cooled reaction mixture was added HOBt. H$_2$O (2.79 g, 18.2 mmol, 1.2 eq) and EDCI (3.49 g, 18.2 mmol, 1.2 eq). After stirring for 30 minutes in ice bath, H-D-Lys(Boc)-OMe·HCl (6) (5.4 g, 18.2 mmol, 1.2 eq) and N-methylmorpholine (NMM) (3.23 g, 31.8 mmol, 2.1 eq) were added. The reaction mixture was stirred at 0° C. for 1 hours, then stirred at room temperature until HPLC analysis indicated the reaction was completed. The reaction was added dropwise into water (540 mL) under stirring; plenty of precipitate formed; the mixture stood for one hour; then the solid was collected and washed with water (360 mL×3), then dried in vacuum (30° C.); it provided a white solid compound (191), 11.73 g. LC-MS m/z=837.4 [M+H]$^+$.

Example 230: Synthesis of Compound 192

The compound (191) (5.0 g, 5.97 mmol, 1.0 eq) was placed into a reaction flask under nitrogen, followed by adding methanol (100 mL). To the resulting solution was added a solution of NaOH (25 mL, 1.0 M, 25 mmol, 4.2 eq.) dropwise. The reaction mixture was stirred at room temperature for 2 hours until HPLC analysis indicated the reaction was completed. Then, a HCl solution (1.0 M) was added dropwise until pH=2-2.5 was achieved. To the reaction was added dropwise water (200 mL) under stirring; then the resulting suspension stood for one hour; the solid was collected by filtration and washed with water (130 mL×3). The solid was then dried in vacuum (30° C.); it provided a white solid compound (192), 3.46 g; LC-MS m/z=823.1 [M+H]$^+$.

Synthesis of Peptide Analogues

Example 231: Synthesis of Compound 193

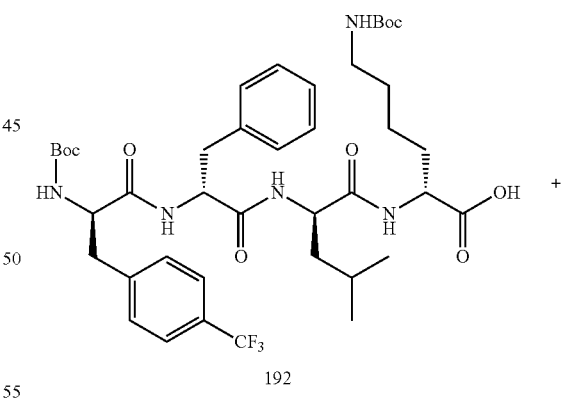

192

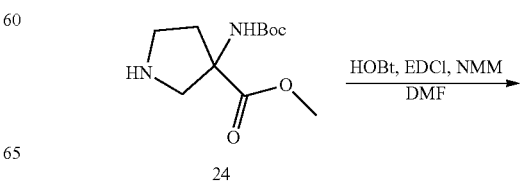

24

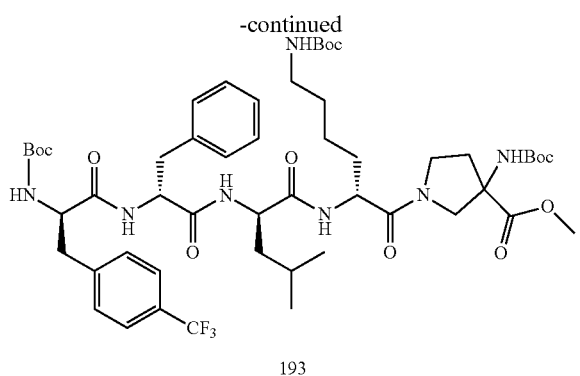

193

Into a reaction flask under nitrogen was added compound (192) (1.0 g, 1.22 mmol, 1.0 eq) and DMF (21.2 mL) under nitrogen. The resulting reaction mixture was cooled to 0° C. in ice bath. To the cooled reaction mixture was added HOBt.H$_2$O (223.3 mg, 1.46 mmol, 1.1 eq) and EDCI (279.5 mg, 1.46 mmol, 1.2 eq). After stirring for 30 minutes in ice bath, methyl 3-(Boc-NH)pyrrolidine-3-carboxylate (24) (357.6 mg, 1.55 mmol, 1.2 eq) and N-methylmorpholine (NMM) (258.7 mg, 2.55 mmol, 2.1 eq) were added. The reaction mixture was stirred at 0° C. for 1 hours, then stirred at room temperature until HPLC analysis indicated the reaction was completed. The reaction was added dropwise into water (60 mL) under stirring; plenty of precipitate formed; the mixture stood for one hour; then the solid was collected and washed with water (40 mL×3), then dried in vacuum (30° C.); it provided a white solid compound (193), 45 mg. LC-MS m/z=1049.3 [M+H]$^+$.

Example 232: Synthesis of Compound 194

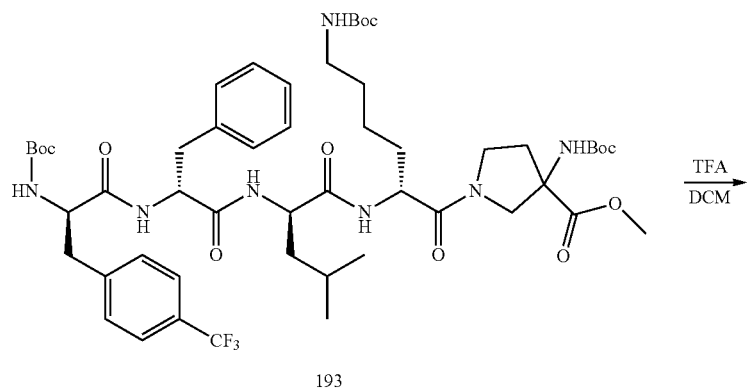

193

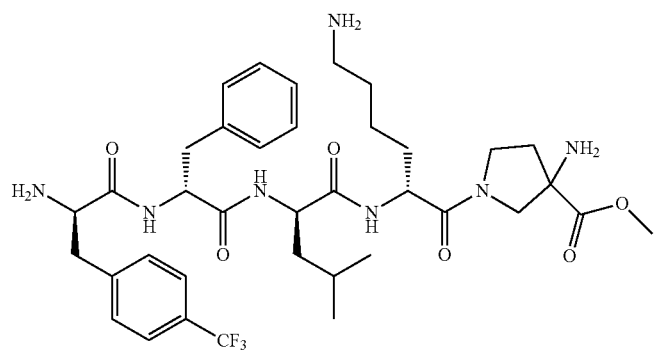

194

The compound (193) (45 mg, 0.043 mmol, 1.0 eq) was placed into a reaction flask under nitrogen; to the flask was added dichloromethane (0.9 mL); the resulting solution was cooled to −10° C. for 10 minutes; then to the cooled reaction was added dropwise a mixture of TFA (0.9 mL) and dichloromethane (1.8 mL). The resulting solution was stirred at −10° C. for one hour, then 2 hours at room temperature until HPLC analysis indicated the reaction was completed. The volatiles were removed on rotavapor. To the residue was added dichloromethane (0.9 mL); the resulting solution was concentrated on rotavapor; the dissolving/evaporating with dichloromethane was repeat three times; to the residue was added methanol (0.9 mL), the resulting solution was evaporated on rotavapor; the dissolving/evaporation with methanol was repeated twice; the residue was further purified on reverse phase HPLC; the collected fraction was lyophilized and it provided a white solid, (194), 2.96 mg; LCMS: MS m/z=749.4 [M+H]$^+$.

Example 233: Synthesis of Compound 195

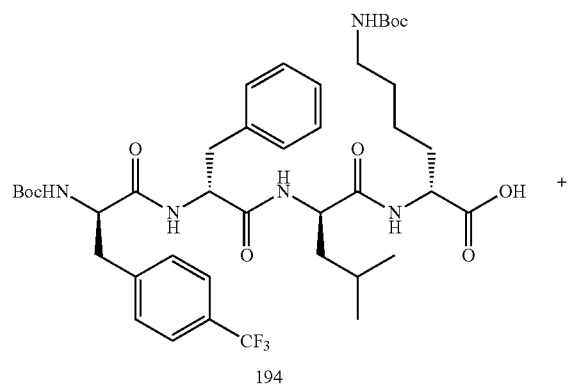

194

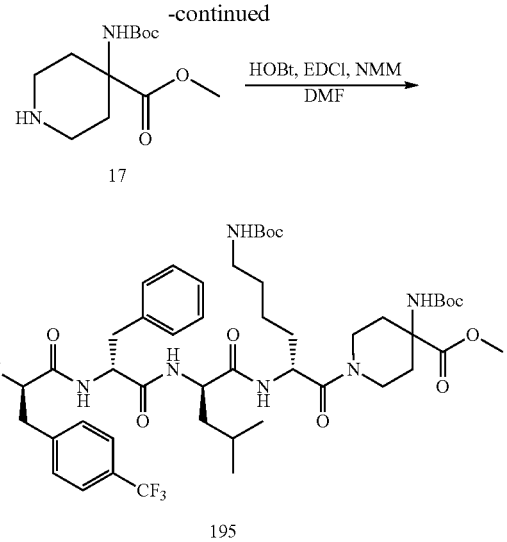

17

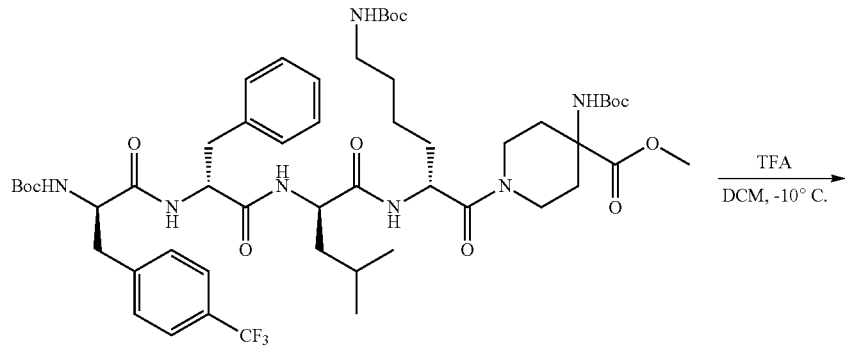

195

Into a reaction flask under nitrogen was added compound (194) (1.0 g, 1.22 mmol, 1.0 eq) and DMF (21.2 mL) under nitrogen. The resulting reaction mixture was cooled to 0° C. in ice bath. To the cooled reaction mixture was added HOBt. H$_2$O (223.3 mg, 1.46 mmol, 1.1 eq) and EDCI (279.5 mg, 1.46 mmol, 1.2 eq). After stirring for 30 minutes in ice bath, methyl 4-(Boc-NH)piperidine-4-carboxylate (377.9 mg, 1.46 mmol, 1.2 eq) and N-methylmorpholine (NMM) (258.7 mg, 2.55 mmol, 2.1 eq) were added. The reaction mixture was stirred at 0° C. for 1 hours, then stirred at room temperature until HPLC analysis indicated the reaction was completed. The reaction was added dropwise into water (60 mL) under stirring; plenty of precipitate formed; the mixture stood for one hour; then the solid was collected and washed with water (40 mL×3), then dried in vacuum (30° C.); it provided a white solid compound (195), 50 mg. LC-MS m/z=1062.6 [M+H]$^+$.

Example 234: Synthesis of Compound 196

195

-continued

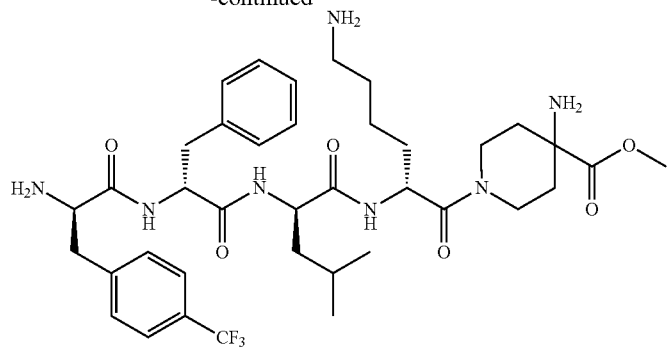

196

The compound (195) (50 mg, 0.047 mmol, 1.0 eq) was placed into a reaction flask under nitrogen; to the flask was added dichloromethane (1.0 mL); the resulting solution was cooled to −10° C. for 10 minutes; then to the cooled reaction was added dropwise a mixture of TFA (1.0 mL) and dichloromethane (2.0 mL). The resulting solution was stirred at −10° C. for one hour, then at room temperature until HPLC analysis indicated the reaction was completed. The volatiles were removed on rotavapor. To the residue was added dichloromethane (1 mL); the resulting solution was concentrated on rotavapor; the dissolving/evaporating with dichloromethane was repeat three times; then to the residue was added methanol (1 mL), the resulting solution was concentrated on rotavapor; the dissolving/evaporation with methanol was repeated three times; the residue was further purified on reverse phase HPLC; the collected fraction was lyophilized and it provided a white solid, (196), 2.56 mg; LCMS: MS m/z=762.4 [M+H]$^+$.

Example 235: Opioid Receptor Binding Assay

The measurement of opioid receptor binding affinity was conducted using a radioligand binding assay on cell membranes prepared from HEK293 cells (human embryonic kidney cell line) that were heterologously expressing recombinant human mu (MOR), delta (DOR), or kappa (KOR) opioid receptors.

The assay buffers used for opioid receptor binding studies were 50 mM Tris HCl (pH 7.4) for KOR, 50 mM Tris HCl (pH 7.4) with 5 mM $MgCl_2$ for MOR, and 50 mM Tris HCl (pH 7.4) with 10 mM $MgCl_2$ plus 1 mM EDTA for DOR. Wash buffer contained 50 mM Tris HCl at pH 7.4.

The opioid receptor binding affinity were compared to three known standards: Naltrindole, U-50488 (trans-(+)-3,4-dichloro-N-methyl-N-[2-(1-pyrrolidinyl)cyclohexyl]phenylacetamide (Doi et al., Acta Cryst. 1990, C46, 676-678), and DAMGO [D-Ala2 MePhe4,Gly(ol)5] encephalin (Allan et al., J Biol Chem, 1997, 272(2): 782-790).

The radio ligands were prepared at the final concentration of 0.5 nM for [$^3$H]DAMGO, 0.5 nM for [$^3$H]diprenorphine, and 0.5 nM for [$^3$H] DADLE, which were used as the competing radioligands for mu, kappa and delta receptors, respectively.

Cell membrane of HEK293 cells transfected with opioid receptors was prepared in the amount of 20 ug of MOR, 6.7 ug of KOR and 6.7 ug of DOR per each well respectively. These membranes containing the receptor of interest were incubated with increasing concentrations of test compound in the presence of a single concentration of radio ligand. The fixed concentration of the radio ligand was used and serial dilutions of the test compound were prepared.

Testing was started at 10 uM of testing compound to 4-fold serial dilution for 8-points detection. Transfer 1 µl of compounds/high control/low control to the 96 well plates according to the plate map, then dispensed 100 µl of membrane stock solution into the plate, add 100 µl of radio ligand solution. Incubation was carried out for 1 hour at room temperature with 300 rpm gentle agitation. Then, soaked the Unifilter-96 GF/C filter plates with 50 µl of 0.3% Poly ethyleneimine per well for at least 0.5 hour at room temperature, and filtered the reaction mixture through the plates using FilterMate™ harvester. Each plate was washed four times with cold wash buffer. The filter plates are then dried for 1 hour at 50° C. After drying, the filter was sealed in polyethylene and 50 µl of Perkin Elmer Microscint 20 cocktail was added and the radioactivity counted in a Perkin Elmer MicroBeta2 counter.

Specific binding is determined by subtraction of the Bound CPM values in the presence of 50-100× excess of cold ligand. Data was fitted using the saturation analysis non-linear curve fitting routines in Prism®. Inhibition was calculated using following equation:

% Inhibition=(1-(Assay well-Average_$LC$)/(Average_$HC$-Average_$LC$))*100%

Binding data were analyzed using GraphPad Prism 5.0 and $IC_{50}$ is generated by non-linear regression from dose response curves. Used the model "log (inhibitor) vs. response—Variable slope" to fit the data. These data are shown in Table

TABLE 1

Binding Affinity of Peptide Ligands on Recombinant Human Opioid receptors

| # | Sample ID | KOR, $IC_{50}$ (nM) | MOR, $IC_{50}$ (nM) | DOR, $IC_{50}$ (nM) |
|---|---|---|---|---|
|  | U-50488 | 7.804 |  |  |
|  | DAMGO |  | 0.4262 |  |
|  | Naltrindole |  |  | 0.1833 |
| 1 | 13-1 | 1.96 | 2075 | >10000 |
| 2 | 13-2 | 1.37 | >10000 | >10000 |
| 3 | 13-3 | 28.15 | >10000 | >10000 |
| 4 | 13-4 | 2.80 | >10000 | >10000 |
| 5 | 13-5 | 5.92 | >10000 | >10000 |
| 6 | 13-6 | 9.45 | >10000 | >10000 |
| 7 | 13-7 | 11.41 | >10000 | >10000 |
| 8 | 13-8 | 6.04 | >10000 | >10000 |

TABLE 1-continued

Binding Affinity of Peptide Ligands on Recombinant Human Opioid receptors

| # | Sample ID | KOR, IC$_{50}$ (nM) | MOR, IC$_{50}$ (nM) | DOR, IC$_{50}$ (nM) |
|---|---|---|---|---|
| 9 | 13-9 | 0.41 | >10000 | >10000 |
| 10 | 13-10 | 0.67 | >10000 | >10000 |
| 11 | 13-11 | 0.91 | >10000 | >10000 |
| 12 | 13-12 | 6.60 | >10000 | >10000 |
| 13 | 13-13 | 16.06 | >10000 | >10000 |
| 14 | 13-14 | 0.21 | >10000 | >10000 |
| 15 | 13-15 | 0.41 | >10000 | >10000 |
| 16 | 13-16 | 0.37 | 214.8 | 2414 |
| 17 | 13-17 | 23.44 | >10000 | >10000 |
| 18 | 13-18 | 2.00 | >10000 | >10000 |
| 19 | 13-19 | 0.33 | >726.8 | >10000 |
| 20 | 13-20 | 1.44 | >10000 | >10000 |
| 21 | 13-22 | 0.096 | >10000 | >10000 |
| 22 | 13-23 | 0.79 | 318.1 | >10000 |
| 23 | 13-24 | 0.52 | 7993 | >10000 |
| 24 | 13-25 | 5.56 | >10000 | >10000 |
| 25 | 13-26 | 1.83 | >10000 | >10000 |
| 26 | 13-27 | 0.53 | >10000 | >10000 |
| 27 | 13-28 | 0.26 | >10000 | >10000 |
| 28 | 13-29 | 0.29 | 6.86 | >10000 |
| 29 | 13-30 | 0.15 | >10000 | >10000 |
| 30 | 13-31 | 0.28 | 171.5 | >10000 |
| 31 | 13-32 | 8.49 | 7110 | >10000 |
| 32 | 13-33 | 0.54 | >10000 | >10000 |
| 33 | 13-34 | 3.33 | 2980 | >10000 |
| 34 | 13-35 | 0.31 | 8429 | >10000 |
| 35 | 13-36 | 0.49 | >10000 | >10000 |
| 36 | 13-37 | 10.98 | 9293 | >10000 |
| 37 | 13-38 | 0.30 | >10000 | >10000 |
| 38 | 13-39 | 0.23 | >10000 | >10000 |
| 39 | 13-40 | 0.30 | 6391 | >10000 |
| 40 | 13-41 | 0.21 | 8217 | >10000 |
| 41 | 13-42 | 0.48 | >10000 | >10000 |
| 42 | 13-43 | 0.33 | >10000 | >10000 |
| 43 | 13-44 | 0.46 | >10000 | >10000 |
| 44 | 13-45 | 0.43 | >10000 | >10000 |
| 45 | 13-46 | 0.31 | >10000 | >10000 |
| 46 | 13-47 | 0.27 | >10000 | >10000 |
| 47 | 13-48 | 0.36 | >10000 | >10000 |
| 48 | 13-49 | 0.46 | >10000 | >10000 |
| 49 | 13-50 | 0.37 | 1108 | >10000 |
| 50 | 13-51 | 0.27 | 349.1 | >10000 |
| 51 | 13-52 | 1.02 | >10000 | >10000 |
| 52 | 13-53 | 2.01 | 8755 | >10000 |
| 53 | 13-54 | 0.21 | 1531 | >10000 |
| 54 | 13-55 | 0.35 | >10000 | >10000 |
| 55 | 13-56 | 0.35 | >10000 | >10000 |
| 56 | 13-57 | 0.70 | 4995 | >10000 |
| 57 | 13-58 | 0.29 | >10000 | >10000 |
| 58 | 13-59 | 0.36 | >10000 | >10000 |
| 59 | 13-60 | 0.42 | >10000 | >10000 |
| 60 | 13-62 | 0.20 | >10000 | >10000 |
| 61 | 13-63 | 1.81 | >10000 | >10000 |
| 62 | 13-64 | 0.47 | >10000 | >10000 |
| 63 | 13-65 | 0.45 | >10000 | >10000 |
| 64 | 22 | 200 | 5065 | >10000 |
| 65 | 28 | >200 | >10000 | >10000 |
| 66 | 35 | 0.19 | 8175 | >10000 |
| 67 | 40 | 0.41 | >10000 | >1000 |
| 68 | 45 | 0.33 | 7369 | >10000 |
| 69 | 50 | 0.39 | 7528 | >10000 |
| 70 | 55 | 0.45 | 8534 | >10000 |
| 71 | 60 | 0.94 | >10000 | >10000 |
| 72 | 66 | 20.89 | 307.4 | >10000 |
| 73 | 67 | 24.84 | 5146 | >10000 |
| 74 | 70 | 0.17 | >10000 | >10000 |
| 75 | 71 | 0.16 | >10000 | >10000 |
| 76 | 79 | 5.73 | 9747 | >10000 |
| 77 | 82 | 42.55 | 5174 | >10000 |
| 78 | 89 | >200 | >10000 | >10000 |
| 79 | 92 | 32.96 | >10000 | >10000 |
| 80 | 100 | 12.96 | >10000 | >10000 |
| 81 | 103 | 14.42 | >10000 | >10000 |
| 82 | 112 | 1.00 | 15.17 | >10000 |
| 83 | 118 | 0.33 | >10000 | >10000 |
| 84 | 119 | 2.36 | NA | NA |
| 85 | 126 | 0.36 | 3033 | >10000 |
| 86 | 127 | 0.10 | 1023 | >10000 |
| 87 | 133 | 1.30 | >10000 | >10000 |
| 88 | 134 | 2.35 | NA | NA |
| 89 | 144 | 123 | >10000 | >10000 |
| 90 | 146 | 163.9 | >10000 | >10000 |
| 91 | 156 | 2.30 | 5366 | >10000 |
| 92 | 158 | 0.90 | 5366 | >10000 |
| 93 | 159 | 16.92 | >10000 | >10000 |
| 94 | 168 | 4.23 | 2406 | >10000 |
| 95 | 169 | 88.78 | NA | NA |
| 96 | 171 | 0.83 | >10000 | >10000 |
| 97 | 172 | 4.02 | >10000 | >10000 |
| 98 | 181 | 0.40 | >10000 | >10000 |
| 99 | 184 | 0.25 | 8087 | >10000 |
| 100 | 185 | 0.85 | >10000 | >10000 |
| 101 | 194 | 4.07 | 7338 | >10000 |

Example 236: FLIPR Calcium Assay in Whole Cells

The FLIPR Calcium Assay was used to measure the ability of an opioid ligand to induce a functional response upon receptor binding. The opioid mu receptors (MORs), delta receptors (DORs) and kappa receptors (KORs) are G-protein coupled receptors (GPCRs) which play an important role in cell signaling. The receptor was activated by a ligand then triggering G-protein activation inside the cell. An activated G-protein induces various cascades of intracellular messengers including calcium flux. The functional cell-based assays were evaluated the changes of intracellular calcium level which were detected through use of fluorescent calcium-sensitive reporter dyes. The basic system of performing a calcium mobilization assay includes the FLIPR Calcium Assay Kit and the FLIPR Tetra® System, which were used to observe changes in intracellular calcium levels and determine the dose-response in HEK293 cells transfected with recombinant human mu, delta or kappa opioid receptors.

The cells used in the assay were grown in the culture medium of 88% DMEM (Need the chemical compound) which contains 10% FBS, 300 ug/mL G418, 2 ug/mL Blasticidin, 1% GlutaMax and 1% Penicillin/Streptomycin (Hyclone-SV30010). Seeded 20000 cells in 20 uL medium to each well of assay plate (Greiner-781946), and the cells were maintained at 37° C. in an incubator with 5% CO$_2$ for 20 hours. The compound was then prepared at 5-fold serial dilution to get 10 doses and 500 nL of each concentration was transferred to compound plate. Then 30 uL assay buffer (20 mM HEPES and 1×HBSS) was added to each well of compound plate. The plate was spun at 1500 rpm for 15 seconds. Then 20 uL of 2× Fluo-4 Direct™ No-wash Loading Buffer ((Invitrogen-F10471) was gently dispensed to each well of assay plate and was spun at 1000 rpm for 15 s, followed by incubation at 37° C. for 50 min. The assay plate was removed from the incubator and placed at room temperature for 10 min. Then, the assay plate, compound plate and tip box were placed directly into the FLIPR Tetra® System. 10 uL Compound was transferred from compound plate to the assay plate in FLIPR Tetra Fluorometric Imaging Plate Reader and the plate was read. Then, the calculated the "Max-Min" starting from Read 1 to 140 was performed to generate the final signal for % Effect calculation. The data was analyzed using Prism, curve fitting equation "log (agonist) vs. response—Variable slope". Table 2 shows the results of these assays.

TABLE 2

Activities of Some Peptide Opioid Kappa Receptor Agonists in FLIPR ASSAY

| Sample # | Sample ID | $EC_{50}$ (nM) |
|---|---|---|
|  | U69593 | 56.63 |
|  | nor-Binaltorphimine dihydrochloride | >720 |
| 1 | 13-1 | 42.25 |
| 2 | 13-2 | 8.310 |
| 3 | 13-4 | 13.48 |
| 4 | 13-5 | 15.75 |
| 5 | 13-6 | 30.54 |
| 6 | 13-7 | 24.73 |
| 7 | 13-8 | 14.65 |
| 8 | 13-9 | 18.08 |
| 9 | 13-10 | 23.13 |
| 10 | 13-12 | 7.07 |
| 11 | 13-13 | 88.43 |
| 12 | 13-14 | 12.94 |
| 13 | 13-15 | 51.53 |
| 14 | 13-16 | 19.41 |
| 15 | 13-17 | 21.99 |
| 16 | 13-18 | 39.35 |
| 17 | 13-19 | 75.85 |
| 18 | 13-20 | 18.03 |
| 19 | 13-22 | 24.79 |
| 20 | 13-23 | 8.58 |
| 21 | 13-24 | 31.48 |
| 22 | 13-26 | 10.23 |
| 23 | 13-27 | 12.05 |
| 24 | 13-28 | 20.84 |
| 25 | 13-29 | 15.52 |
| 26 | 13-30 | 4.77 |
| 27 | 13-31 | 17.93 |
| 28 | 13-32 | 26.47 |
| 29 | 13-33 | 39.51 |
| 30 | 13-34 | 20.24 |
| 31 | 13-35 | 10.77 |
| 32 | 13-36 | 37.70 |
| 33 | 13-38 | 6.08 |
| 34 | 13-39 | 14.74 |
| 35 | 13-40 | 7.48 |
| 36 | 13-41 | 9.12 |
| 37 | 13-42 | 8.43 |
| 38 | 13-43 | 8.70 |
| 39 | 13-44 | 4.75 |
| 40 | 13-45 | 1.53 |
| 41 | 13-46 | 1.58 |
| 42 | 13-47 | 4.84 |
| 43 | 13-48 | 5.69 |
| 44 | 13-49 | 25.48 |
| 45 | 13-50 | 12.21 |
| 46 | 13-51 | 5.15 |
| 47 | 13-52 | 12.14 |
| 48 | 13-53 | 12.60 |
| 48 | 13-54 | 15.09 |
| 49 | 13-55 | 20.38 |
| 50 | 13-56 | 16.75 |
| 51 | 13-57 | 29.47 |
| 52 | 13-58 | 10.77 |
| 53 | 13-59 | 14.28 |
| 54 | 13-60 | 14.28 |
| 55 | 13-62 | 2.96 |
| 56 | 13-63 | 5.20 |
| 57 | 13-64 | 2.91 |
| 58 | 13-65 | 1.68 |
| 59 | 35 | 11.66 |
| 60 | 40 | 11.93 |
| 61 | 45 | 30.22 |
| 62 | 50 | 9.07 |
| 63 | 55 | 9.36 |
| 64 | 60 | 7.19 |
| 66 | 66 | 12.94 |
| 67 | 67 | 51.53 |
| 68 | 70 | 3.57 |
| 69 | 71 | 5.40 |
| 70 | 112 | 5.95 |
| 71 | 118 | 9.31 |
| 72 | 119 | 23.12 |
| 73 | 126 | 6.81 |
| 74 | 127 | 14.77 |
| 75 | 133 | 9.64 |
| 76 | 134 | 12.64 |
| 77 | 156 | 28.05 |
| 78 | 158 | 28.35 |
| 79 | 169 | 167 |
| 80 | 181 | 8.70 |
| 81 | 184 | 6.26 |
| 82 | 185 | 12.98 |

In most of the tested compounds as compared to the controls, the FLIPR Assay showed a better $EC_{50}$ than U69593 or nor-binaltorphimine dihydrochloride.

What is claimed is:

1. A kappa opioid receptor peptide ligand of Formula (I) or a salt thereof:

$$A_1\text{-}A_2\text{-}A_3\text{-}A_4\text{-}B \qquad \text{Formula (I),}$$

wherein $A_1$ is D-phenylalanine, $A_2$ is D-phenylalanine, $A_3$ is D-leucine, $A_4$ is D-lysine, and B is selected from the group consisting of:

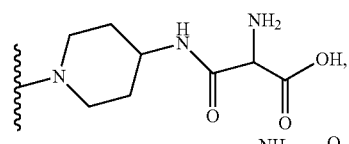

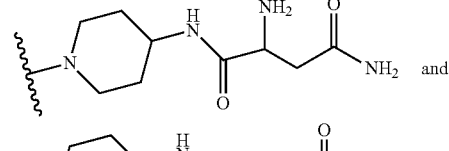 and

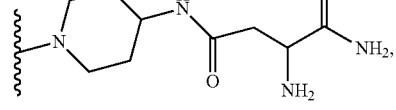

wherein ⸝ represents the connection to $A_4$.

2. A composition comprising: the kappa opioid receptor peptide ligand of claim 1 and at least one pharmaceutically acceptable excipient.

* * * * *